(12) United States Patent
Nezu et al.

(10) Patent No.: US 11,066,483 B2
(45) Date of Patent: *Jul. 20, 2021

(54) CYTOTOXICITY-INDUCING THERAPEUTIC AGENT

(75) Inventors: Junichi Nezu, Shizuoka (JP); Takahiro Ishiguro, Kanagawa (JP); Atsushi Narita, Shizuoka (JP); Akihisa Sakamoto, Shizuoka (JP); Yumiko Kawai, Kanagawa (JP); Tomoyuki Igawa, Shizuoka (JP); Taichi Kuramochi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 385 days.

This patent is subject to a terminal disclaimer.

(21) Appl. No.: 13/990,088

(22) PCT Filed: Nov. 30, 2011

(86) PCT No.: PCT/JP2011/077603
§ 371 (c)(1),
(2), (4) Date: Dec. 19, 2013

(87) PCT Pub. No.: WO2012/073985
PCT Pub. Date: Jun. 7, 2012

(65) Prior Publication Data
US 2014/0112914 A1 Apr. 24, 2014

(30) Foreign Application Priority Data

Nov. 30, 2010 (JP) .................................. 2010-266760
May 31, 2011 (JP) .................................. 2011-121771
Oct. 31, 2011 (JP) .................................. 2011-238818

(51) Int. Cl.
*C07K 16/46* (2006.01)
*C07K 16/30* (2006.01)
*C07K 16/28* (2006.01)
*A61K 39/00* (2006.01)

(52) U.S. Cl.
CPC .......... *C07K 16/46* (2013.01); *C07K 16/2809* (2013.01); *C07K 16/2863* (2013.01); *C07K 16/30* (2013.01); *C07K 16/303* (2013.01); *A61K 2039/505* (2013.01); *C07K 2317/31* (2013.01); *C07K 2317/35* (2013.01); *C07K 2317/41* (2013.01); *C07K 2317/52* (2013.01); *C07K 2317/55* (2013.01); *C07K 2317/56* (2013.01); *C07K 2317/60* (2013.01); *C07K 2317/622* (2013.01); *C07K 2317/64* (2013.01); *C07K 2317/71* (2013.01); *C07K 2317/73* (2013.01); *C07K 2317/94* (2013.01); *C07K 2319/00* (2013.01); *C07K 2319/30* (2013.01)

(58) Field of Classification Search
CPC .... C07K 16/46; C07K 16/30; C07K 2317/71; C07K 16/2809

USPC ............................................ 424/133.1, 178.1
See application file for complete search history.

(56) References Cited

U.S. PATENT DOCUMENTS

| | | | |
|---|---|---|---|
| 5,585,097 | A | 12/1996 | Bolt et al. |
| 5,595,756 | A | 1/1997 | Bally et al. |
| 5,601,819 | A | 2/1997 | Wong et al. |
| 5,624,821 | A | 4/1997 | Winter et al. |
| 5,648,260 | A | 7/1997 | Winter et al. |
| 5,859,205 | A | 1/1999 | Adair et al. |
| 5,945,311 | A | 8/1999 | Lindhofer et al. |
| 6,025,165 | A | 2/2000 | Whitlow et al. |
| 6,129,914 | A | 10/2000 | Weiner |
| 6,143,297 | A | 11/2000 | Bluestone |
| 8,735,545 | B2 | 5/2014 | Lazar et al. |
| 9,096,651 | B2 | 5/2015 | Igawa et al. |
| 9,315,567 | B2 | 4/2016 | Chang et al. |
| 9,670,269 | B2 | 6/2017 | Igawa et al. |
| 9,975,966 | B2 * | 5/2018 | Nezu ........................ A61P 43/00 |
| 10,435,458 | B2 | 10/2019 | Kuramochi et al. |
| 10,759,870 | B2 * | 9/2020 | Teranishi ................ C07K 16/46 |
| 10,934,344 | B2 | 3/2021 | Igawa |
| 2002/0102278 | A1 | 8/2002 | Guo |
| 2002/0164668 | A1 | 11/2002 | Durham et al. |
| 2003/0078385 | A1 | 4/2003 | Arathoon et al. |
| 2003/0190311 | A1 | 10/2003 | Dall'Aqua et al. |
| 2003/0207346 | A1 | 11/2003 | Arathoon et al. |
| 2003/0232049 | A1 | 12/2003 | Jung |
| 2004/0002587 | A1 | 1/2004 | Watkins et al. |
| 2004/0236080 | A1 | 11/2004 | Aburatani et al. |
| 2005/0118174 | A1 | 6/2005 | Presta |
| 2005/0130224 | A1 | 6/2005 | Saito et al. |
| 2005/0191293 | A1 | 9/2005 | Deshpande et al. |
| 2006/0134709 | A1 | 6/2006 | Stavenhagen et al. |

(Continued)

FOREIGN PATENT DOCUMENTS

| | | |
|---|---|---|
| CA | 2819530 | 6/2012 |
| CA | 2830972 | 10/2012 |

(Continued)

OTHER PUBLICATIONS

Ward et al. (Nature 341:544-546 (1989)).*

(Continued)

*Primary Examiner* — Lynn A Bristol

(74) *Attorney, Agent, or Firm* — Fish & Richardson P.C.

(57) ABSTRACT

By replacing the antigen-binding domain, the present inventors discovered novel polypeptide complexes that retain BiTE's strong anti-tumor activity and excellent safety properties, as well as have long half-life in blood and can damage various different target cells.

48 Claims, 26 Drawing Sheets

Specification includes a Sequence Listing.

(56) References Cited

U.S. PATENT DOCUMENTS

| | | |
|---|---|---|
| 2006/0134805 A1 | 6/2006 | Berg et al. |
| 2006/0159673 A1 | 7/2006 | Kojima et al. |
| 2006/0160184 A1 | 7/2006 | Hoogenboom et al. |
| 2006/0177896 A1 | 8/2006 | Mach et al. |
| 2006/0204493 A1 | 9/2006 | Huang et al. |
| 2006/0235208 A1 | 10/2006 | Lazar et al. |
| 2007/0054354 A1 | 3/2007 | Humphreys et al. |
| 2007/0110757 A1 | 5/2007 | Wei et al. |
| 2007/0178092 A1 | 8/2007 | Bolt et al. |
| 2007/0224188 A1 | 9/2007 | Allan et al. |
| 2007/0231329 A1 | 10/2007 | Lazar et al. |
| 2007/0254831 A1 | 11/2007 | Mezo et al. |
| 2008/0025979 A1 | 1/2008 | Honjo et al. |
| 2008/0095755 A1 | 4/2008 | Kink et al. |
| 2008/0220000 A1 | 9/2008 | Moore et al. |
| 2008/0317758 A9 | 12/2008 | Presta |
| 2010/0015133 A1 | 1/2010 | Igawa et al. |
| 2010/0178298 A1 | 7/2010 | Lindhofer et al. |
| 2010/0221252 A1 | 9/2010 | Bigler et al. |
| 2010/0298542 A1 | 11/2010 | Igawa et al. |
| 2010/0322935 A1 | 12/2010 | Croasdale et al. |
| 2011/0081354 A1 | 4/2011 | Korman et al. |
| 2011/0150892 A1 | 6/2011 | Thudium et al. |
| 2011/0236374 A1 | 9/2011 | Shitara et al. |
| 2012/0021409 A1 | 1/2012 | McWhirter et al. |
| 2012/0034228 A1 | 2/2012 | Kufer et al. |
| 2012/0100140 A1 | 4/2012 | Reyes et al. |
| 2012/0184718 A1 | 7/2012 | Peter et al. |
| 2012/0213781 A1 | 8/2012 | Hilbert |
| 2012/0269826 A1 | 10/2012 | McKee et al. |
| 2013/0018174 A1 | 1/2013 | Igawa et al. |
| 2013/0058937 A1 | 3/2013 | Auer et al. |
| 2013/0129730 A1 | 5/2013 | Kufer et al. |
| 2014/0051833 A1 | 2/2014 | Fischer et al. |
| 2014/0154270 A1 | 6/2014 | Wang et al. |
| 2014/0294759 A1 | 10/2014 | Chu et al. |
| 2014/0348832 A1 | 11/2014 | Zhu et al. |
| 2014/0370020 A1* | 12/2014 | Kuramochi ........ C07K 16/2866 424/136.1 |
| 2014/0377253 A1 | 12/2014 | Harding et al. |
| 2015/0166661 A1 | 6/2015 | Chen et al. |
| 2015/0337053 A1 | 11/2015 | McCarthy et al. |
| 2016/0024147 A1 | 1/2016 | Tustian et al. |
| 2016/0152722 A1 | 6/2016 | Sharp et al. |
| 2016/0168259 A1 | 6/2016 | Igawa et al. |
| 2016/0229915 A1 | 8/2016 | Igawa et al. |
| 2016/0333095 A1 | 11/2016 | Van et al. |
| 2017/0022287 A1 | 1/2017 | Igawa et al. |
| 2017/0260271 A1 | 9/2017 | Igawa et al. |
| 2017/0267783 A1* | 9/2017 | Nezu ..................... C07K 16/46 |
| 2017/0275332 A1 | 9/2017 | Igawa et al. |
| 2018/0162902 A1 | 6/2018 | Igawa et al. |
| 2018/0192623 A1 | 7/2018 | Jishage et al. |
| 2018/0244805 A1* | 8/2018 | Nezu ..................... C12N 15/09 |
| 2019/0330268 A1 | 10/2019 | Tanaka et al. |
| 2019/0352334 A1 | 11/2019 | Igawa et al. |
| 2019/0352421 A1 | 11/2019 | Adams et al. |
| 2020/0087380 A1* | 3/2020 | Kuramochi ............. A61P 43/00 |
| 2020/0123256 A1* | 4/2020 | Hoshino ............ C07K 16/2809 |
| 2020/0207805 A1 | 7/2020 | Igawa et al. |
| 2020/0223940 A1* | 7/2020 | Teranishi ................. C12N 5/10 |
| 2020/0354473 A1* | 11/2020 | Teranishi ................. C12N 5/10 |
| 2021/0040147 A1 | 2/2021 | Igawa et al. |

FOREIGN PATENT DOCUMENTS

| | | |
|---|---|---|
| CN | 1842540 | 10/2006 |
| CN | 101198698 | 6/2008 |
| CN | 102471378 | 5/2012 |
| CN | 102574921 | 7/2012 |
| CN | 103429737 | 12/2013 |
| CN | 103833852 | 6/2014 |
| EP | 0 637 593 | 2/1995 |
| EP | 1 378 520 | 1/2004 |
| EP | 1 510 943 | 3/2005 |
| EP | 1 605 058 A | 12/2005 |
| EP | 1 674 111 | 6/2006 |
| EP | 1 870 459 | 12/2007 |
| EP | 1 876 236 | 1/2008 |
| EP | 2 009 101 | 12/2008 |
| EP | 2 107 115 | 10/2009 |
| EP | 2 194 006 | 6/2010 |
| EP | 2194066 | 6/2010 |
| EP | 2 270 051 | 1/2011 |
| EP | 2 445 936 | 5/2012 |
| EP | 2 522 724 | 11/2012 |
| EP | 2 543 730 A | 1/2013 |
| EP | 2 576 621 | 4/2013 |
| EP | 2 644 698 | 10/2013 |
| EP | 2 647 707 | 10/2013 |
| EP | 2 698 431 A | 2/2014 |
| EP | 3 199 628 | 8/2017 |
| EP | 3 378 488 | 9/2018 |
| JP | H09-506001 | 6/1997 |
| JP | 2002-521053 | 7/2002 |
| JP | 2002-540771 | 12/2002 |
| JP | 2004-508036 | 3/2004 |
| JP | 2004-321100 | 11/2004 |
| JP | 2005-537009 | 12/2005 |
| JP | 2007-532095 | 11/2007 |
| JP | 2008-523783 | 7/2008 |
| JP | 2009-526823 | 7/2009 |
| JP | 2009-527499 | 7/2009 |
| JP | 2010-532369 | 10/2010 |
| JP | 2010-266760 | 11/2010 |
| JP | 2011-508604 | 3/2011 |
| JP | 2012-504970 | 3/2012 |
| JP | 2012-515556 | 7/2012 |
| JP | 2015-515160 | 7/2012 |
| JP | 2012-224631 | 11/2012 |
| JP | 2012-528092 | 11/2012 |
| JP | 2013-505732 | 2/2013 |
| JP | 2013-508392 | 3/2013 |
| JP | 2013-528569 | 7/2013 |
| JP | 2015-535828 | 12/2015 |
| JP | 5912436 | 4/2016 |
| JP | 2016-538275 | 12/2016 |
| JP | 2017-504314 | 2/2017 |
| JP | 2017-513011 | 5/2017 |
| KR | 2008/0013875 | 2/2008 |
| KR | 2009/0107091 | 10/2009 |
| KR | 2010/0056467 | 5/2010 |
| KR | 2012/0123055 | 11/2012 |
| KR | 2013/0130765 | 12/2013 |
| KR | 2014/0084249 | 7/2014 |
| MX | 2016/02132 | 7/2014 |
| MX | 349057 | 7/2017 |
| RU | 94028282 | 7/1996 |
| RU | 2006/104842 | 8/2007 |
| RU | 2355705 | 5/2009 |
| RU | 2009/149451 | 7/2011 |
| RU | 2012/112067 | 10/2013 |
| SG | 11201701119 R | 3/2017 |
| TW | 2012/49872 | 12/2012 |
| TW | 2016/19193 | 6/2016 |
| WO | WO 95/33844 | 12/1995 |
| WO | WO 96/27011 | 9/1996 |
| WO | WO 98/50431 | 11/1998 |
| WO | WO 99/58572 | 11/1999 |
| WO | WO 99/61057 | 12/1999 |
| WO | WO 00/06605 | 2/2000 |
| WO | WO 00/18806 | 4/2000 |
| WO | WO 01/90192 | 11/2001 |
| WO | WO 02/20615 | 3/2002 |
| WO | WO 03/035835 | 5/2003 |
| WO | WO 2004/020579 | 3/2004 |
| WO | WO 2004/035607 | 4/2004 |
| WO | WO 2004/003019 * | 6/2004 |
| WO | WO 2004/065611 | 8/2004 |
| WO | WO 2005/000900 | 1/2005 |
| WO | WO 2005/035584 | 4/2005 |
| WO | WO 2005/061547 | 7/2005 |
| WO | WO 2005/063815 | 7/2005 |

(56) References Cited

FOREIGN PATENT DOCUMENTS

| | | |
|---|---|---|
| WO | WO 2005/092927 | 10/2005 |
| WO | WO 2005/115451 | 12/2005 |
| WO | WO 2005/118635 | 12/2005 |
| WO | WO 2006/020114 | 2/2006 |
| WO | WO 2006/105338 | 10/2006 |
| WO | WO 2006/106905 | 10/2006 |
| WO | WO 2006/109592 | 10/2006 |
| WO | WO 2006/113767 | 10/2006 |
| WO | WO 2007/093630 | 8/2007 |
| WO | WO 2007/110205 | 10/2007 |
| WO | WO 2007/114325 | 10/2007 |
| WO | WO 2007/145941 | 12/2007 |
| WO | WO 2007/147901 | 12/2007 |
| WO | WO 2008/090960 | 7/2008 |
| WO | WO 2008/118970 | 10/2008 |
| WO | WO 2009/012394 | 1/2009 |
| WO | WO 2009/041613 | 4/2009 |
| WO | WO 2009/053368 | 4/2009 |
| WO | WO 2009/080252 | 7/2009 |
| WO | WO 2009/080253 | 7/2009 |
| WO | WO 2009/089004 | 7/2009 |
| WO | WO 2009/095478 | 8/2009 |
| WO | WO 2009/120922 | 10/2009 |
| WO | WO 2009/134776 | 11/2009 |
| WO | WO 2010/034441 | 4/2010 |
| WO | WO 2010/042904 | 4/2010 |
| WO | WO 2010/080065 | 7/2010 |
| WO | WO 2010/085682 | 7/2010 |
| WO | WO 2010/102251 | 9/2010 |
| WO | WO 2010/120561 | 10/2010 |
| WO | WO 2010/129304 | 11/2010 |
| WO | WO 2010/136172 | 12/2010 |
| WO | WO 2010/151792 | 12/2010 |
| WO | WO 2011/025964 | 3/2011 |
| WO | WO 2011/039126 | 4/2011 |
| WO | WO 2011/050106 | 4/2011 |
| WO | WO 2011/078332 | 6/2011 |
| WO | WO 2011/108714 | 9/2011 |
| WO | WO 2011/121110 | 10/2011 |
| WO | WO 2011/147986 | 12/2011 |
| WO | WO 2012/067176 | 5/2012 |
| WO | WO 2012/073985 | 6/2012 |
| WO | WO 2012/095412 | 7/2012 |
| WO | WO 2012/115241 | 8/2012 |
| WO | WO 2012/131555 | 10/2012 |
| WO | WO 2012/145183 | 10/2012 |
| WO | WO 2012/175751 | 12/2012 |
| WO | WO 2013/026833 | 2/2013 |
| WO | WO 2013/065708 | 5/2013 |
| WO | WO 2013/070468 | 5/2013 |
| WO | WO 2013/072523 | 5/2013 |
| WO | WO 2013/092001 | 6/2013 |
| WO | WO 2013/158856 | 10/2013 |
| WO | WO 2013/181543 | 12/2013 |
| WO | WO 2014/047231 | 3/2014 |
| WO | WO 2014/051433 | 4/2014 |
| WO | WO 2014/089113 | 6/2014 |
| WO | WO 2014/108483 | 7/2014 |
| WO | WO 2014/116846 | 7/2014 |
| WO | WO 2014/138306 | 9/2014 |
| WO | WO 2014/145907 | 9/2014 |
| WO | WO 2014/165818 | 10/2014 |
| WO | WO 2015/046467 | 4/2015 |
| WO | WO 2015/046554 | 4/2015 |
| WO | WO 2015/095392 | 6/2015 |
| WO | WO 2015/124715 | 8/2015 |
| WO | WO 2015/149077 | 10/2015 |
| WO | WO 2015/156268 | 10/2015 |
| WO | WO 2015/164392 | 10/2015 |
| WO | WO 2015/174439 | 11/2015 |
| WO | WO 2016/047722 | 3/2016 |
| WO | WO 2016/179003 | 11/2016 |
| WO | WO 2016/194992 | 12/2016 |
| WO | WO 2017/086367 | 5/2017 |
| WO | WO 2017/086419 | 5/2017 |
| WO | WO 2017/115773 | 7/2017 |
| WO | WO 2017/159287 | 9/2017 |
| WO | WO 2018/203567 | 11/2018 |
| WO | WO 2019/131988 | 7/2019 |

OTHER PUBLICATIONS

Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Salfeld (Nature Biotech. 25(12): 1369-1372 (2007)).*
Dall'Acqua (J. Immunol. 177:1129-1138 (2006)).*
Asano et al. JBC 282: 27659-27665 (Jul. 19, 2007).*
Asano et al. J Immunother. Oct. 2008;31(8):752-61 (Abstract).*
Ishiguro et al (Science Translational Medicine (9, eaal4291 or pp. 1-13 (Oct. 4, 2017).*
Yu et al. (Can. Biol.Ther. Jul. 2, 2020;21(7):597-603. doi: 10.1080/15384047.2020.1743158. Epub Apr. 2, 2020; abstract).*
Harada et al. (Toxicol In Vitro. Aug. 2020;66:104841. doi: 10.1016/j.tiv.2020.104841. Epub Apr. 1, 2020).*
Szoor et al. (Mol Ther Oncolytics. Jul. 28, 2017;6:69-79. doi: 10.1016/j.omto.2017.07.002. eCollection Sep. 15, 2017).*
Waaijer et al. (J Immunother Cancer. Mar. 2020;8(1):e000548. doi: 10.1136/jitc-2020-000548).*
Iwata et al (Toxicol Appl Pharmacol. Sep. 15, 2019;379:114657. doi: 10.1016/j.taap.2019.114657. Epub Jul. 19, 2019).*
Bi et al. (Oncotarget. May 16, 2017;8(32):52866-52876. doi: 10.18632/oncotarget.17905. eCollection Aug. 8, 2017).*
Shiraiwa et al. (Methods. Feb. 1, 2019;154:10-20. doi: 10.1016/j.ymeth.2018.10.005. Epub Oct. 13, 2018).*
Jain et al., "Engineering antibodies for clinical applications," *Trends Biotechnol.*, 25(7):307-16 (2007).
Kufer et al., "A revival of bispecific antibodies," *Trends Biotechnol.*, 22(5):238-44 (2004).
Hombach et al., "A CD16/CD30 bispecific monoclonal antibody induces lysis of Hodgkin's cells by unstimulated natural killer cells in vitro and in vivo," *Int J Cancer*, 55:830-6 (1993).
Roguska et al., "Humanization of murine monoclonal antibodies through variable domain resurfacing," *Proc Natl Acad Sci U.S.A.*, 91:969-73 (1994).
Staerz et al., "Hybrid hybridoma producing a bispecific monoclonal antibody that can focus effector T-cell activity," *Proc Natl Acad Sci U.S.A.*, 83:1453-7 (1986).
Amann et al., "Therapeutic window of an EpCAM/CD3-specific BiTE antibody in mice is determined by a subpopulation of EpCAM-expressing lymphocytes that is absent in humans," *Cancer Immunol Immunother.* 58(1):95-109 (2009). Epub Jul. 2, 2008.
Armour et al., "Recombinant human IgG molecules lacking Fcgamma receptor I binding and monocyte triggering activities," *Eur J Immunol.*, 29(8):2613-2624 (1999).
Bargou et al., "Tumor regression in cancer patients by very low doses of a T cell-engaging antibody," *Science*, 321(5891):974-977 (2008).
Bokemeyer, "Catumaxomab—trifunctional anti-EpCAM antibody used to treat malignant ascites," *Expert Opin Biol Ther.*, 10(8):1259-1269 (2010).
Campoli et al., "Immunotherapy of malignant disease with tumor antigen-specific monoclonal antibodies," *Clin Cancer Res.*, 16(1):11-20 (2010). Epub Dec. 22, 2009.
Kumagai et al., "Humanized bispecific antibodies that recognize lymphocytes and cancer cells," *Drug Delivery System*, 23(5):518-525 (2008) (English translation).
Mack et al., "A small bispecific antibody construct expressed as a functional single-chain molecule with high tumor cell cytotoxicity," *Proc Natl Acad Sci U S A.*, 92(15):7021-7205 (1995).
Mcearchern et al., "Engineered anti-CD70 antibody with multiple effector functions exhibits in vitro and in vivo antitumor activities," *Blood*, 109(3):1185-1192 (2007). Epub Oct. 12, 2006.
Merchant et al., "An efficient route to human bispecific IgG," *Nat Biotechnol.*, 16(7):677-681 (1998).
Mezzanzanica et al., "Human ovarian carcinoma lysis by cytotoxic T cells targeted by bispecific monoclonal antibodies: analysis of the antibody components," *Int J Cancer*, 41(4):609-615 (1988).

(56) References Cited

OTHER PUBLICATIONS

Molhoj et al., "CD19-/CD3-bispecific antibody of the BiTE class is far superior to tandem diabody with respect to redirected tumor cell lysis," *Mol Immunol.*, 44(8):1935-1943 (2007). Epub Nov. 2, 2006.
Nakano et al., "Anti-glypican 3 antibodies cause ADCC against human hepatocellular carcinoma cells," *Biochem Biophys Res Commun.*, 378(2):279-284 (2009). doi: 10.1016/j.bbrc.2008.11.033. Epub Nov. 18, 2008.
Natsume et al., "Improving effector functions of antibodies for cancer treatment: Enhancing ADCC and CDC," *Drug Des Devel Ther.*, 3:7-16 (2009).
Presta, "Molecular engineering and design of therapeutic antibodies," *Curr Opin Immunol.*, 20(4):460-470 (2008). doi: 10.1016/j.coi.2008.06.012.
Schlereth et al., "T-cell activation and B-cell depletion in chimpanzees treated with a bispecific anti-CD19/anti-CD3 single-chain antibody construct," *Cancer Immunol Immunother.*, 55(5):503-514 (2006). Epub Jul. 20, 2005.
Sebastian et al., "Treatment of non-small cell lung cancer patients with the trifunctional monoclonal antibody catumaxomab (anti-EpCAM x anti-CD3): a phase I study," *Cancer Immunol Immunother.*, 56(10):1637-1644 (2007).
Segal et al., "Bispecific antibodies in cancer therapy," *Curr Opin Immunol.*, 11(5):558-562 (1999).
Seimetz et al., "Development and approval of the trifunctional antibody catumaxomab (anti-EpCAM x anti-CD3) as a targeted cancer immunotherapy," *Cancer Treat Rev.*, 36(6):458-467 (2010).
Staerz et al., "Hybrid antibodies can target sites for attack by T cells," *Nature*, 314(6012):628-631 (1985).
Stroehlein et al., "Induction of anti-tumor immunity by trifunctional antibodies in patients with peritoneal carcinomatosis," *J Exp Clin Cancer Res.*, 28:18 (2009). doi: 10.1186/1756-9966-28-18.
Suzuki, "Research and Development of Antibody Pharmaceuticals," *NIBS Letter*, 56(4):45-51 (2010) (English translation).
Teerinen et al., "Structure-based stability engineering of the mouse IgG1 Fab fragment by modifying constant domains," *J Mol Biol.*, 361(4):687-97 (2006).
Thakur et al., "Cancer therapy with bispecific antibodies: Clinical experience," *Curr Opin Mol Ther.*, 12(3):340-349 (2010).
Wolf et al., "BiTEs: bispecific antibody constructs with unique anti-tumor activity," *Drug Discov Today*, 10(18):1237-1244 (2005).
International Search Report for App. Ser. No. PCT/JP2011/077603, dated Mar. 13, 2012, 8 pages.
Bowie et al., "Deciphering the Message in Protein Sequences: Tolerance to Amino Acid Substitutions," *Science*, Mar. 16, 1990;247:1306-1310.
Burgess, "Possible dissociation of the heparin-binding and mitogenic activities of heparin-binding (acidic fibroblast) growth factor-1 from its receptor-binding activities by site-directed mutagenesis of a single lysine residue," J. Cell. Biol., 1990;111:2129-2138.
Lazar et al., "Transforming growth factor alpha: mutation of aspartic acid 47 and leucine 48 results in different biological activities," Mol. Cell Biol., 1988;8:1247-1252.
Medesan et al., "Delineation of the amino acid residues involved in transcytosis and catabolism of mouse IgG1," J Immunol., Mar. 1, 1997;158(5):2211-7.
Pan et al., "Blocking neuropilin-1 function has an additive effect with anti-VEGF to inhibit tumor growth," Cancer Cell, Jan. 2007;11(1):53-67.
Singer et al., Genes & Genomes, 1991;67-69.
Singer et al., Genes & Genomes, 1998;1:63-64.
Mack et al., "A small bispecific antibody construct expressed as a functional single-chain molecule with high tumor cell cytotoxicity," *Proc Natl Acad Sci U S A.*, 92(15):7021-7025 (1995).
Edelman et al., "The covalent structure of an entire gammaG immunoglobulin molecule," *Proc Natl Acad Sci U S A.*, May 1969;63(1):78-85.
Johnson et al., "Kabat database and its applications: 30 years after the first variability plot," *Nucleic Acids Res.*, Jan. 1, 2000;28(1):214-8.

Zhu et al., "Remodeling domain interfaces to enhance heterodimer formation," *Protein Sci.*, Apr. 1997;6(4):781-8.
Jackman et al., "Development of a two-part strategy to identify a therapeutic human bispecific antibody that inhibits IgE receptor signaling," *J Biol Chem.*, Jul. 2, 2010;285(27): 20850-9. doi: 10.1074/jbc.M110.113910. Epub May 5, 2010.
Padlan et al., "Antibody Fab assembly: the interface residues between CH1 and CL," *Mol Immunol.*, 23(9):951-60 (1986).
Ridgway et al., "'Knobs-into-holes' engineering of antibody CH3 domains for heavy chain heterodimerization," *Protein Eng.*, 9(7):617-21 (1996).
Rothlisberger et al., "Domain interactions in the Fab fragment: a comparative evaluation of the single-chain Fv and Fab format engineered with variable domains of different stability," *J Mol Biol.*, 347(4):773-89 (2005).
Spiess et al., "Bispecific antibodies with natural architecture produced by co-culture of bacteria expressing two distinct half-antibodies," *Nat Biotechnol.*, Aug. 2013; 31(8):753-8. doi: 10.1038/nbt.2621. Epub Jul. 7, 2013.
International Search Report for App. Ser. No. PCT/JP2012/078103, dated Jan. 22, 2013, 6 pages.
International Preliminary Report on Patentability for App. Ser. No. PCT/JP2012/078103, dated May 6, 2014, 6 pages.
Allard et al., "Antigen binding properties of highly purified bispecific antibodies," *Mol Immunol.*, Oct. 1992;29(10):1219-27.
Haagen et al., "Unprimed CD4+ and CD8+ T cells can be rapidly activated by a CD3 x CD19 bispecific antibody to proliferate and become cytotoxic," *Cancer Immunol Immunother.*, Dec. 1994;39(6):391-6.
IMGT Scientific charts depicting the correspondence between Eu and Kabat numberings for the human IgG constant region, created May 17, 2001 and last updated Aug. 13, 2014.
Lloyd et al., "The production of a bispecific anti-CEA, anti-hapten (4-amino-phthalate) hybrid-hybridoma," *J Natl Med Assoc.*, Oct. 1991;83(10):901-4.
Manzke et al., "Single-step purification of bispecific monoclonal antibodies for immunotherapeutic use by hydrophobic interaction chromatography," *J. Immunol. Methods*, 1997;208:65-73.
Suresh et al., "Bispecific monoclonal antibodies from hybrid hybridomas," *Methods Enzymol.*, 1986;121:210-228.
Chinese Search Report for App. Ser. No. 201180068471.0, dated May 13, 2014, 2 pages.
Hinton et al., "An engineered human IgG1 antibody with longer serum half-life," *J. Immunol.*, Jan. 1, 2006;176:346-56.
Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.
Kim et al., "Mapping the site on human IgG for binding of the MHC class I-related receptor, FcRn," *Eur. J. Immunol.*, Sep. 1999;29(9):2819-25.
Lebégue et al., "Production and characterization of hybrid monoclonal antibodies with IgG1/IgG3 double isotype," *C R Acad Sci III.*, 1990;310(9):377-82.
Michaelsen et al., "A mutant human IgG molecule with only one C1q binding site can activate complement and induce lysis of target cells," *Eur J Immunol.*, Jan. 2006;36(1):129-38.
Klein et al., "Progress in overcoming the chain association issue in bispecific heterodimeric IgG antibodies," *MAbs.*, Nov.-Dec. 2012;4(6):653-63. doi: 10.4161/mabs.21379. Epub Aug. 27, 2012.
Male et al., "Antibodies" *Immunology*, 7th Edition (2006), published by Elsevier Ltd., pp. 59-86.
Roitt et al., *Immunology, M., Mir*, 5th Edition (2000), pp. 97-113.
Dumont et al., "Monomeric Fc fusions: impact on pharmacokinetic and biological activity of protein therapeutics," *BioDrugs.*, 20(3):151-60 (2006).
Jendeberg et al., "Engineering of Fc(1) and Fc(3) from human immunoglobulin G to analyse subclass specificity for staphylococcal protein A," *J. Immunol. Methods.*, 201(1):25-34 (1997).
Van Loghem et al., "Staphylococcal protein A and human IgG subclasses and allotypes," *Scand. J. Immunol.*, 15(3):275-8 (1982).
Abe et al., "Purification of monoclonal antibodies with light-chain heterogeneity produced by mouse hybridomas raised with NS-1

(56) References Cited

OTHER PUBLICATIONS myelomas: application of hydrophobic interaction high-performance liquid chromatography," J Biochem Biophys Methods., Oct. 1993;27(3):215-27.
Amersham Biosciences, "Protein Purification Handbook," Edition AD., 137:16-18 (2002).
Branden et al., "Recognition of Foreign Molecules by the Immune System," Introduction to Protein Structure 2nd Edition, 1999;299-323.
Burges et al., "Effective relief of malignant ascites in patients with advanced ovarian cancer by a trifunctional anti-EpCAM × anti-CD3 antibody: a phase I/II study," Clin Cancer Res., Jul. 1, 2007;13(13):3899-905.
Carter, "Bispecific human IgG by design," J Immunol Methods., Feb. 1, 2001;248(1-2):7-15.
Chamow et al., "A humanized, bispecific immunoadhesin-antibody that retargets CD3+ effectors to kill HIV-1-infected cells," J Immunol., Nov. 1, 1994;153(9):4268-80.
Gupta et al., "Affinity chromatography and co-chromatography of bispecific monoclonal antibody immunoconjugates," J Biochem Biophys Methods, May 31, 2002;51(3):203-16.
Kranenborg et al., "Development and characterization of anti-renal cell carcinoma × antichelate bispecific monoclonal antibodies for two-phase targeting of renal cell carcinoma," Cancer Res., Dec. 1, 1995;55(23 Suppl):5864s-5867s.
Kreutz et al., "Efficient bispecific monoclonal antibody purification using gradient thiophilic affinity chromatography," J Chromatogr B Biomed Sci Appl., Sep. 4, 1998;714(2):161-70.
Lansdorp et al., "Purification and analysis of bispecific tetrameric antibody complexes," Mol Immunol., Jul. 1990;27(7):659-66.
Lindhofer et al., "Preferential species-restricted heavy/light chain pairing in rat/mouse quadromas. Implications for a single-step purification of bispecific antibodies," J Immunol., Jul. 1, 1995;155(1):219-25.
Marvin et al., "Recombinant approaches to IgG-like bispecific antibodies," Acta Pharmacol Sin., Jun. 2005;26(6):649-58.
Marvin et al., "Redesigning an antibody fragment for faster association with its antigen," Biochemistry, Jun. 17, 2003;42(23):7077-83.
Morimoto et al., "Single-step purification of F(ab')2 fragments of mouse monoclonal antibodies (immunoglobulins G1) by hydrophobic interaction high performance liquid chromatography using TSKgel Phenyl-5PW," J Biochem Biophys Methods., Mar. 1992;24(1-2):107-17.
Morell et al., "Metabolic properties of IgG subclasses in man," J Clin Invest., Apr. 1970;49(4):673-80.
Queen et al., "A humanized antibody that binds to the interleukin 2 receptor," Proc Natl Acad Sci U.S.A., Dec. 1989;86(24):10029-33.
Ruf et al., "Pharmacokinetics in in vivo stability of intraperitoneally administered therapeutic antibody catumaxomab," J Clin Oncol., 2008 ASCO Annual Meeting Proceedings (Post-Meeting Edition). vol. 25, No. 15S (May 20 Supplement), 2008; 14006.
Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt. 1):29-34.
Salfeld, "Isotype selection in antibody engineering," Nat Biotechnol. Dec. 2007;25(12):1369-72.
Shaul et al., "Exploring the charge space of protein-protein association: a proteomic study," Proteins, Aug. 15, 2005;60(3):341-52.
Tarditi et al., "Selective high-performance liquid chromatographic purification of bispecific monoclonal antibodies," J Chromatogr., May 22, 1992;599(1-2):13-20.
Warnaar et al., "Purification of bispecific F(ab')2 from murine trinoma OC/TR with specificity for CD3 and ovarian cancer," Hybridoma, Dec. 1994;13(6):519-26.
Ruf et al., "Induction of a long-lasting antitumor immunity by a trifunctional bispecific antibody," *Blood*, Oct. 15, 2001;98(8):2526-34.

Manz et al., Bioanalytical Chemistry, World Scientific Publishing Co. (2003).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Smans et al., "Bispecific antibody-mediated lysis of primary cultures of ovarian carcinoma cells using multiple target antigens," *Int. J. Cancer*, 83:270-277 (1999).
USPTO Non-Final Office Action in U.S. Appl. No. 12/295,075, dated Jun. 7, 2013, 17 pages.
International Preliminary Report on Patentability for App. Ser. No. PCT/JP2011/077603, dated Jun. 4, 2013, 10 pages.
Ibragimova et al., "Stability of the beta-sheet of the WW domain: A molecular dynamics simulation study," *Biophys J.*, Oct. 1999;77(4):2191-8.
Lin et al., "Structure-function relationships in glucagon: properties of highly purified des-His-1-, monoiodo-, and (des-Asn-28, Thr-29)(homoserine lactone-27)-glucagon," *Biochemistry*, Apr. 22, 1975;14(8):1559-63.
Paul et al., "Immunologiya", M.:Mir, 1987-1988, vol. 1, p. 231 (with English translation).
Pritsch et al., "Can Immunoglobulin CH1 Constant Region Domain Modulate Antigen Binding Affinity of Antibodies?," J Clin Invest. Nov. 15, 1996;98(10):2235-43.
Schwartz et al., "A superactive insulin: [B10-aspartic acid]insulin(human)," *Proc Natl Acad Sci U S A.*, Sep. 1987;84(18):6408-11.
U.S. Appl. No. 15/467,654, filed Mar. 23, 2017, Nezu et al.
U.S. Appl. No. 15/490,936, filed Apr. 19, 2017, Igawa et al.
Buque et al., "Trial Watch: Immunomodulatory monoclonal antibodies for oncological indications," Oncoimmunology, Mar. 2, 2015;4(4):e1008814. eCollection 2015.
Chan et al., "Therapeutic antibodies for autoimmunity and inflammation," Nat Rev Immunol. May 2010;10(5):301-16. doi:10.1038/nri2761.
Hess et al., "Cancer therapy with trifunctional antibodies: linking innate and adaptive immunity," Future Oncol., Jan. 2012: 8(1):73-85. doi:10.2217/fon.11.138.
Iwai et al., "Therapeutic Agents for Gastric Cancer," Igan Chiryoyaku, Yakkyoku, Jan. 5, 2016:67(1)138-41 (with English translation).
Jefferis et al., "Interaction sites on human IgG-Fc for FcγR: current models," Immunol. Lett., Jun. 3, 2002:82(1-2):57-65.
Jones et al., "Growth factor receptor interplay and resistance in cancer," Endocr. Relat. Cancer, Dec. 2006:13 Suppl 1:S45-51.
Klinger et al., "Harnessing T cells to fight cancer with BiTE((R)) antibody constructs—past developments and future directions," Immunol. Rev., Mar. 2016:270(1):193-208. doi:10.1111/imr.12393.
Kontermann, "Dual targeting strategies with bispecific antibodies," MAbs. Mar.-Apr. 2012;4(2):182-97. doi:10.4161/mabs.4.2.19000. Epub Mar. 1, 2012.
Larkin et al., "Combined Nivolumab and Ipilimumab or Monotherapy in Untreated Melanoma," N. Engl. J. Med., Jul. 2, 2015:373(1):23-34. doi:10.1056/NEJMoa1504030. Epub May 31, 2015.
Muller et al., "A Novel Antibody-4-1BBL Fusion Protein for Targeted Costimulation in Cancer Immunotherapy," J. Immunother., Oct. 2008;31(8):714-22. doi: 10.1097/CJI.0b013e31818353e9.
Nimmerjahn et al., "Fcγ receptors as regulators of immune responses," Nat. Rev. Immunol., Jan. 2008;8(1):34-47.
Pastor et al., "Targeting 4-1BB Costimulation to Disseminated Tumor Lesions With Bi-specific Oligonucleotide Aptamers," Mol. Ther., Oct. 2011;19(10):1878-86. doi:10.1038/mt.2011.145. Epub Aug. 9, 2011.
Pavlou et al., "The therapeutic antibodies market to 2008," Eur. J. Pharm. Biopharm., 59:389-396 (Apr. 2005).
Radaev et al., "The Structure of a Human Type III Fcγ Receptor in Complex with Fc," J. Biol. Chem., May 11, 2001;276(19):16469-77. Epub Jan. 31, 2001.
Reichert et al., "Monoclonal antibody successes in the clinic," Nat. Biotechnol., 23:1073-78 (Sep. 2005).
Riechelmann et al., "Adoptive therapy of head and neck squamous cell carcinoma with antibody coated immune cells: a pilot clinical trial," Cancer Immunol. Immunother., Sep. 2007:56(9):1397-406. Epub Feb. 2, 2007.

(56) References Cited

OTHER PUBLICATIONS

Rothe et al., Recombinant proteins in rheumatology—recent advances, New Biotechnol., Sep. 2011;28(5):502-10. doi:10.1016/j.nbt.2011.03.019. Epub Apr. 5, 2011.
Sampei et al., "Identification and multidimensional optimization of an asymmetric bispecific IgG antibody mimicking the function of factor VIII cofactor activity," PLoS One, Feb. 2013;8(2):e57479. doi:10.1371/journal.pone.0057479. Epub Feb. 28, 2013.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (Mar. 2001) (Epub Nov. 28, 2000).
Unkeless et al., "Structure and Function of Human and Murine Receptors for IgG," Annu. Rev. Immunol., Jan. 1988:6:251-81.
Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A," J Immunol. May 15, 2000;164(10):5313-8.
Wozniak-Knopp et al., "Introducing antigen-binding sites in structural loops of immunoglobulin constant domains: Fc fragments with engineered HER2/neu-binding sites and antibody properties," Protein Eng. Des. Sel., Apr. 2010;23(4):289-97. doi:10.1093/protein/gzq005. Epub Feb. 11, 2010.
Zeidler et al., "Simultaneous Activation of T Cells and Accessory Cells by a New Class of Intact Bispecific Antibody Results in Efficient Tumor Cell Killing," J. Immunol., Aug. 1, 1999;163(3):1246-52.
U.S. Appl. No. 13/518,861, Igawa et al., filed Oct. 4, 2012.
U.S. Appl. No. 15/617,008, Igawa et al., filed Jun. 8, 2017.
U.S. Appl. No. 15/875,847, Igawa et al., filed Jan. 19, 2018.
U.S. Appl. No. 15/467,654, Nezu et al., filed Mar. 23, 2017.
U.S. Appl. No. 15/578,931, filed Dec. 1, 2017, Taniguchi et al.
U.S. Appl. No. 15/617,008, filed Jun. 8, 2017, Igawa et al.
U.S. Appl. No. 15/776,541, filed May 16, 2018, Igawa.
U.S. Appl. No. 15/776,587, filed May 16, 2018, Tsunenari et al.
U.S. Appl. No. 15/875,847, filed Jan. 19, 2018, Igawa et al.
U.S. Appl. No. 15/963,221, filed Apr. 26, 2018, Nezu et al.
U.S. Appl. No. 16/061,454, filed Jun. 12, 2018, Tanaka et al.
Ascierto et al., "Clinical Experiences With Anti-CD137 and Anti-PD1 Therapeutic Antibodies," Semin. Oncol., Oct. 2010, 37(5):508-16.
Barach et al., "T cell coinhibition in prostate cancer: new immune evasion pathways and emerging therapeutics," Trends Mol Med., Jan. 2011, 17(1):47-55. doi: 10.1016/j.molmed.2010.09.006.
Bastid et al., "ENTPD1/CD39 is a promising therapeutic target in oncology," Oncogene, Apr. 4, 2013, 32(14):1743-51. doi: 10.1038/onc. 2012. 269. Epub Jul. 2, 2012.
Bates et al., "Quantification of Regulatory T Cells Enables the Identification of High-Risk Breast Cancer Patients and Those at Risk of Late Relapse," J. Clin. Oncol., Dec. 1, 2006;24(34):5373-80.
Bekeredjian-Ding et al., "Toll-like receptors—sentries in the B-cell response," Immunology, Nov. 2009, 128(3):311-23. doi: 10.1111/j.1365-2567.2009.03173.x.
Bendig, "Humanization of Rodent Monoclonal Antibodies by CDR Grafting," Methods: A Companion to Methods in Enzymology, 1995, 8:83-93.
Bhatia et al., "CTLA4 Blockade Enhances the Anti-Tumor Activity of Therapy with an Anti-CD3-Based Bispecific Antibody," J. Investig. Med., Sep. 1997, 45(7):346A.
Borch, et al., "Reorienting the immune system in the treatment of cancer by using anti-PD-1 and anti-PD-L1 antibodies," Drug Discov Today, Sep. 2015, 20(9):1127-34. doi: 10.1016/j.drudis.2015.07.003. Epub Jul. 17, 2015.
Brandl et al., "The effect of dexamethasone on polyclonal T cell activation and redirected target cell lysis as induced by a CD19/CD3-bispecific single-chain antibody construct," Cancer Immunol. Immunother., Oct. 2007, 56(10):1551-63. Epub Feb. 20, 2007.
Buszko et al., "Differential depletion of total T cells and regulatory T cells and prolonged allotransplant survival in CD3ε humanized mice treated with polyclonal anti human thymocyte globulin," PLoS One, Mar. 3, 2017, 12(3):e0173088. doi: 10 .1371/journal. pone. 0173088. eCollection 2017.
Curiel et al., "Specific recruitment of regulatory T cells in ovarian carcinoma fosters immune privilege and predicts reduced survival," Nat. Med., Sep. 2004, 10(9):942-9. Epub Aug. 22, 2004.
D'Arena et al., "Regulatory T-cell number is increased in chronic lymphocytic leukemia patients and correlates with progressive disease," Leuk. Res., Mar. 2011, 35(3):363-8. doi: 10.1016/j.leukres. 2010.08.010. Epub Sep. 28, 2010.
Deluca et al., "Fine-tuning of dendritic cell biology by the TNF superfamily," Nat. Rev. Immunol., Apr. 10, 2012, 12(5):339-51.
De Vos Van Steenwijk et al., "Tumor-infiltrating CD14-positive myeloid cells and CD8-positive T-cells prolong survival in patients with cervical carcinoma," Int. J. Cancer., Dec. 15, 2013, 133(12):2884-94. doi: 10.1002/ijc.28309. Epub Jul. 5, 2013.
Drake, "Combined Immune Checkpoint Blockage," Semin Oncol., Aug. 2015, 42(4):656-62. doi: 10.1053/j.seminoncol.2015.05.002. Epub Jun. 3, 2015.
Dubrot et al., "Treatment with anti-CD137 mAbs causes intense accumulations of liver T cells without selective antitumor immunotherapeutic effects in this organ," Cancer Immunol. Immunother., Aug. 2010, 59(8):1223-33.
El Andaloussi et al., "Prolongation of survival following depletion of $CD4^+CD25^+$ regulatory T cells in mice with experimental brain tumors." J. Neurosurg., Sep. 2006, 105(3):430-7.
Filmus et al., "Glypicans," J. Clin. Invest., Aug. 2001, 108(4):497-501.
French et al., "Tumor-Associated Lymphocytes and Increased $FoxP3^+$ Regulatory T Cell Frequency Correlate with More Aggressive Papillary Thyroid Cancer," J. Clin. Endocrinol. Metab., May 2010, 95(5):2325-33. doi: 10.1210/jc.2009-2564. Epub Mar. 5, 2010.
Furness et al., Impact of tumour microenvironment and Fc receptors on the activity of immunomodulatory antibodies, Trends Immunol., Jul. 2014, 35(7):290-8. doi:10.1016/j.it.2014.05.002. Epub Jun. 18, 2014.
Gajewski et al., "Innate and adaptive immune cells in the tumor microenvironment," Nat. Immunol., Oct. 2013, 14(10):1014-22. doi: 10.1038/ni.2703.
Gerber et al., "High expression of $FOXP_3$ in primary melanoma is associated with tumour progression," Br. J. Dermatol., Jan. 2014, 170(1):103-9. doi: 10.1111/bjd.12641.
Gobert et al., "Regulatory T Cells Recruited through CCL22/CCR4 Are Selectively Activated in Lymphoid Infiltrates Surrounding Primary Breast Tumors and Lead to an Adverse Clinical Outcome," Cancer Res., Mar. 1, 2009, 69(5):2000-9. doi: 10.1158/0008-5472. CAN-08-2360. Epub Feb. 24, 2009.
Goldstein et al., "Adoptive Cell Therapy for Lymphoma with CD4 T Cells Depleted of CD137—Expressing Regulatory T Cells," Cancer Res., Mar. 1, 2012:72(5):1239-47. doi: 10. 1158/0008-5472. CAN-11-3375. Epub Jan. 9, 2012.
Guo et al., "Extracellular domain of 4-1BBL enhanced the antitumoral efficacy of peripheral blood lymphocytes mediated by anti-CD3 × anti-Pgp bispecific diabody against human multidrug-resistant leukemia," Cell Immunol., Feb. 2008, 251(2):102-8. doi: 10.1016/j.cellimm.2008.04.006. Epub May 14, 2008.
Hamid et al., "Anti-programmed death-1 and anti-programmed death-ligand 1 antibodies in cancer therapy," Expert Opin Biol Ther., Jun. 2013, 13(6):847-61 doi:10.1517/14712598.2013. 770836. Epub Feb. 19, 2013.
Hanahan et al., "Hallmarks of Cancer: The Next Generation," Cell., Mar. 4, 2011, 144(5):646-74. doi: 10.1016/j.cell.2011.02.013.
Hiraoka et al., "Prevalence of $FOXP3^+$ Regulatory T Cells Increases During the Progression of Pancreatic Ductal Adenocarcinoma and Its Premalignant Lesions," Clin. Cancer Res., Sep. 15, 2006, 12(18):5423-34.
Houot et al., "Therapeutic effect of CD137 immunomodulation in lymphoma and its enhancement by Treg depletion," Blood, Oct. 15, 2009, 114(16):3431-8.

(56) References Cited

OTHER PUBLICATIONS

Hornig et al., "Evaluating combinations of costimulatory antibody-ligand fusion proteins for targeted cancer immunotherapy," Cancer Immunol Immunother., Aug. 2013, 62(8): 1369-80. doi: 10.1007/s00262-013 1441-7. Epub May 30, 2013.
Hornig et al., "Combination of a Bispecific Antibody and Costimulatory Antibody-Ligand Fusion Proteins for Targeted Cancer Immunotherapy," J Immunother., Jun. 2012, 35(5):418-29. doi: 10.1097/CJI.O Ь 013e3182594387.
Jacobs et al., "Dendritic Cell Vaccination in Combination with Anti-CD25 Monoclonal Antibody Treatment: A Phase 1/11 Study in Metastatic Melanoma Patients," Clin Cancer Res., Oct. 15, 2010, 16(20):5067-78. doi: 10.1158/1078-0432.CCR-10-1757. Epub Aug. 2010.
Jaeger, "Clinical Immunology and Allergology," 2nd edition, M.: Medicina, 1990, 2:484-5 (with English translation).
Jure-Kunkel, et al., "Synergy between chemotherapeutic agents and CTLA-4 blockade in preclinical tumor models," Cancer Immunol Immunother., Sep. 2013, 62(9):1533-45. doi: 10.1007/s00262-013-1451-5. Epub Jul. 20, 2013.
Kabat et al., "Sequences of Proteins of Immunological Interest," J Immunol, Sep. 1, 1991, 147(5):1709-19.
Kawaida et al., "Distribution of CD4(+)CD25$^{high}$ regulatory T-cells in tumor-draining lymph nodes in patients with gastric cancer," J. Surg. Res., Mar. 2005, 124(1):151-7.
Khan et al., "Tumor infiltrating regulatory T cells: tractable targets for immunotherapy," Int. Rev. Immunol., Oct. 2010, 29(5):461-84. doi: 10.3109/08830185.2010.508854.
Kim et al., "Anti-CD137 mAb Deletes Both Donor $CD4^+$ and $CD8^+$ T Cells in Acute Graft-versus-host Disease," Immune Netw., Dec. 2011, 11(6):428-30. doi: 10. 4110/in. 2011. 11. 6. 428. Epub Dec. 31, 2011.
Kim et al., "Antibody light chain variable domains and their biophysically improved versions for human immunotherapy," mAbs, Jan.-Feb. 2014, 6(1):219-35 doi: 10.4161/mabs 26844.
Kobayashi et al., "$FOXP3^+$ Regulatory T Cells Affect the Development and Progression of Hepatocarcinogenesis," Clin Cancer Res , Feb. 1, 2007;13(3):902-11.
Kono et al., "CD4(+)CD25$^{high}$ regulatory T cells increase with tumor stage in patients with gastric and esophageal cancers," Cancer Immunol. Immunother., Sep. 2006, 55(9):1064-71. Epub Nov. 23, 2005.
Koriskta et al., "Retargeting of Human Regulatory T Cells by Single-Chain Bispecific Antibodies," J. Immunol., Feb. 1, 2012, 188(3):1551-8. doi:10.4049/jimmuno1.1101760. Epub Dec. 19, 2011.
Li et al., "Framework selection can influence pharmacokinetics of a humanized therapeutic antibody through differences in molecule charge," mAbs, Sep./Oct. 2014, 6(5):1255-64 doi:10.4161/mabs 29809 Epub Oct. 30, 2014.
Li et al., "Antitumor activities of agonistic anti-TNFR antibodies require differential FcγRIIB coengagement in vivo," Proc. Natl. Acad. Sci. USA., Nov. 26, 2013, 110(48):19501-6. doi: 10.1073/pnas.1319502110. Epub Nov. 11, 2013.
Li et al., "Phosphorylated ERM Is Responsible for Increased T Cell Polarization, Adhesion, and Migration in Patients with Systemic Lupus Erythematosus," J. Immunol., Feb. 1, 2007, 178:1938-1947.
Liu et al., "Efficient Inhibition of Human B-cell Lymphoma in SCID Mice by Synergistic Antitumor Effect of Human 4-1BB Ligand/Anti-CD20 Fusion Proteins and Anti-CD3/Anti-CD20 Diabodies," J Immunother., Jun. 2010, 33(5):500-9. doi: 10.1097/CJI.Ob013e3181d75c20.
Liotta et al., "Frequency of regulatory T cells in peripheral blood and in tumour-infiltrating lymphocytes correlates with poor prognosis in renal cell carcinoma," BJU Int., May 2011, 107(9):1500-6. doi: 10.1111/j.1464-410X.2010.09555.x. Epub Aug. 24, 2010.
McDermott et al., "PD-1 as a potential target in cancer therapy," Cancer Med., Oct. 2013, 2(5):662-73. doi: 10.1002/cam4.106. Epub Jul. 21, 2013.

Nishikawa et al., Inflammation & Immunology, Jan. 2013, 21(1):66-72 (with English Translation).
Paul, Fundamental Immunology, 3rd Edition, 1993, 292-295.
Percival-Alwyn et al., "Generation of potent mouse monoclonal antibodies to self-proteins using T-cell epitope 'tags'", mAbs., Jan./Feb. 2015, 7(1):129-37. doi: 10.4161/19420862.2014.985489.
Pere et al., "Comprehensive analysis of current approaches to inhibit regulatory T cells in cancer," Oncoimmunology, May 1, 2012, 1(3):326-333.
Prieto et al., "CTLA-4 Blockade with Ipilimumab: Long-term Follow-up of 177 Patients with Metastatic Melanoma," Clin. Cancer Res., Apr. 1, 2012, 18(7):2039-47.
Porter et al., "Chimeric Antigen Receptor-Modified T Cells in Chronic Lymphoid Leukemia," N Engl J Med., Aug. 25, 2011, 365(8):725-33. doi.1056/NEJMoa1103849. Epub Aug. 10, 2011.
Postow et al., "Nivolumab and ipilimumab versus ipilimumab in untreated melanoma," N Engl J Med., May 21, 2015, 372(21):2006-17. doi: 10.1056/NEJMoa1414428. Epub Apr. 20, 2015.
Remer et al., "Abstract B046: Therapeutic mechanisms of anti-4-1BB antibodies in cancer: agonism versus regulatory T cell depletion," Cancer Immunol. Res., Nov. 2016, 4(11 Suppl) (Abstract only).
Roitt et al., Immunology, M., Mir, 2000, pp. 110, 150, and 537-9 (with English translation).
Sandin et al., "Local CTLA4 blockade effectively restrains experimental pancreatic adenocarcinoma growth in vivo," Oncoimmunology, Jan. 1, 2014, 3(1):e27614. Epub Jan. 16, 2014.
Sato et al., "Intraepithelial $CD8^+$ tumor-infiltrating lymphocytes and a high $CD8^+$/regulatory T cell ratio are associated with favorable prognosis in ovarian cancer," Proc. Natl. Acad. Sci. USA, Dec. 20, 2005, 102(51):18538-43. Epub Dec. 12, 2005.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-22. doi: 10.1016/j.vaccine.2009.09.127. Epub Oct. 29, 2009.
Selby et al., "Anti-CTLA-4 Antibodies of IgG2a Isotype Enhance Antitumor Activity, through Reduction of Intratumoral Regulatory T Cells," Cancer Immunol. Res., Jul. 2013, 1(1):32-42. doi: 10.1158/2326-6066.CIR-13-0013. Epub Apr. 7, 2013.
Simpson et al., "Fc-dependent depletion of tumor-infiltrating regulatory T cells co-defines the efficacy of anti-CTLA-4 therapy against melanoma," J. Exp. Med., Aug. 26, 2013, 210(9):1695-710. doi: 10.1084/jem.20130579. Epub Jul. 29, 2013.
Son et al., "Humanization of agonistic anti-human 4-1BB monoclonal antibody using a phage-displayed combinatorial library," J Immunol Methods., Mar. 2004, 286(1-2):187-201.
Sugiyama et al., "Anti-CCR4 mAb selectively depletes effector-type $FoxP3^+CD4^+$ regulatory T cells, evoking antitumor immune responses in humans," Proc Natl Acad Sci USA, Oct. 29, 2013, 110(44):17945-50. doi: A15210.1073/pnas.1316796110. Epub Oct. 14, 2013.
Teschner et al., "In Vitro Stimulation and Expansion of Human Tumour-Reactive $CD8^+$ Cytotoxic T Lymphocytes by Anti-CD3/CD28/CD137 Magnetic Beads," Scand. J. Immunol., Aug. 2011, 74(2):155-64. doi: 10. 1111/j. 1365-3083. 2011. 02564. x.
Tosti et al., "Anti-cytotoxic T lymphocyte antigen-4 antibodies in melanoma," Clin. Cosmet. Investig. Dermatol., Oct. 17, 2013, 6:245-56. doi: 10.2147/CCID.S24246.
Viardot et al., "Treatment of Patients With Non-Hodgkin Lymphoma With CD19/CD3 Bispecific Antibody Blinautumomab (MT103)," Internet Citation, Dec. 6, 2010 (Dec. 6, 2010), 1 page (http://www.bloodjournal.org/content/116/21/2880?sso-checked=true).
Vinay et al., "TNF superfamily: costimulation and clinical applications," Cell Biol. Int., Apr. 2009, 33(4):453-65.
Vinay et al., "4-1BB signaling beyond T cells," Cell Mol. Immunol., Jul. 2011, 8(4):281-4 doi: 10.1038/cmi.2010.82 Epub Jan. 10, 2011.
Wainwright et al., "Targeting Tregs in malignant brain cancer: overcoming IDO," Front Immunol., May 15, 2013, 4:116. doi: 10.3389/fimmu.2013.00116. eCollection 2013.
Wang et al., "The variation of CD4+CD25+ regulatory T cells in the periphery blood and tumor microenvironment of non-small cell lung

(56) References Cited

OTHER PUBLICATIONS cancer patients and the downregulation effects induced by CpG ODN," Target Oncol., Sep. 2011, 6(3):147-54. doi: 10.1007/s11523-011-0182-9. Epub May 25, 2011.
Weiner et al., "Monoclonal antibodies: versatile platforms for cancer immunotherapy," Nat. Rev. Immunol., May 2010, 10(5):317-27. doi: 10.1038/nri2744.
Wherry et al., "T cell exhaustion," Nat. Immunol., Jun. 2011, 12(6):492-9.
Yamauchi et al., "The glypican 3 oncofetal protein is a promising diagnostic marker for hepatocellular carcinoma," Mod. Pathol., Dec. 2005, 18(12):1591-8.
Yang et al., "Attenuation of $CD8^+$ T-Cell Function by $CD4^+CD25^+$ Regulatory T Cells in B-Cell Non-Hodgkin's Lymphoma," Cancer Res., Oct. 15, 2006, 66(20):10145-52.
Yang et al., "Intratumoral $CD4^+CD25^+$ regulatory T-cell-mediated suppression of infiltrating CD4+ T cells in B-cell non-Hodgkin lymphoma," Blood, May 1, 2006, 107(9):3639-46. Epub Jan. 10, 2006.
Yang et al., "Anti-CD3 scFv-B7.1 fusion protein expressed on the surface of HeLa cells provokes potent T-lymphocyte activation and cytotoxicity," Biochem. Cell Biol., Apr. 2007, 85(2):196-202.
Yarilin, "Immunology Basics", M:Medicina, 1999, pp. 169-174 (with English translation), 14 pages.
Yonezawa et al., "Boosting Cancer Immunotherapy with Anti-CD137 Antibody Therapy," Clin Cancer Res., Jul. 15, 2015, 21(14):3113-20 doi 10.1158/1078-0432.CCR-15-0263 Epub Apr. 23, 2015.
Yorita et al., "Prognostic significance of circumferential cell surface immunoreactivity of glypican-3 in hepatocellular carcinoma," Liver Int., Jan. 2011, 31(1):120-31.Epub Oct. 21, 2010.
Yu et al., "Simultaneous inhibition of two regulatory T-cell subsets enhanced Interleukin-15 efficacy in a prostate tumor model," Proc. Natl. Acad. Sci. USA, Apr. 17, 2012, 109(16):6187-92. doi: 10.1073/pnas.1203479109. Epub Apr. 2, 2012.
Zalevsky et al., "The impact of Fc engineering on an anti-CD 19 antibody: increased Fcγ receptor affinity enhances B-cell clearing in nonhuman primates," Blood, Apr. 16, 2009, 113(16):3735-43. Epub Dec. 24, 2008.
Zheng et al., "YB-1 immunization combined with regulatory T-cell depletion induces specific T-cell responses that protect against neuroblastoma in the early stage," Acta. Biochim. Biophys. Sin. (Shanghai), Dec. 2012, 44(12):1006-14. doi:10.1093/abbs/gms089.
Zhu et al., "Enhanced glypican-3 expression differentiates the majority of hepatocellular carcinomas from benign hepatic disorders," Gut., Apr. 2001, 48(4):558-64.
International Search Report for App. Ser. No. PCT/JP2016/066331, dated Jul. 19, 2016, 2 pages.
USPTO Restriction Requirement in U.S. Appl. No. 14/351,654, dated Apr. 29, 2015, 14 pages.
USPTO Non-Final Office Action in U.S. Appl. No. 14/351,654, dated Sep. 8, 2015, 9 pages.
USPTO Final Office Action in U.S. Appl. No. 14/351,654, dated Apr. 14, 2016, 12 pages.
USPTO Non-Final Office Action in U.S. Appl. No. 14/351,654, dated Nov. 9, 2016, 15 pages.
USPTO Non-Final Office Action in U.S. Appl. No. 14/351,654, dated Aug. 22, 2017, 9 pages.
USPTO Final Office Action in U.S. Appl. No. 14/351,654, dated May 11, 2018, 12 pages.
De Gast et al., "CD8 T cell activation after intravenous administration of CD3 × CD19 bispecific antibody in patients with non-Hodgkin lymphoma," Cancer Immunol Immunother, Jun. 1995, 40(6):390-6.
Lazar et al., "Engineered antibody Fc variants with enhanced effector function," Proc Natl Acad Sci USA, Mar. 14, 2006, 103(11):4005-10. Epub Mar. 6, 2006.
Wang et al., "A new recombinant single chain trispecific antibody recruits T lymphocytes to kill CEA (carcinoma embryonic antigen) positive tumor cells in vitro efficiently," J Biochem, Apr. 2004, 135(4):555-65.

Zeidler et al., "The Fc-region of a new class of intact bispecific antibody mediates activation of accessory cells and NK cells and induces direct phagocytosis of tumour cells," Br J Cancer, Jul. 2000, 83(2):261-6.
Dreier et al., "Extremely Potent, Rapid and Costimulation-Independent Cytotoxic T-Cell Response Against Lymphoma Cells Catalyzed by a Single-Chain Bispecific Antibody," Int J Cancer, Aug. 20, 2002, 100(6):690-7.
U.S. Appl. No. 16/605,556, filed Oct. 16, 2019, Hoshino et al.
U.S. Appl. No. 16/692,676, filed Nov. 22, 2019, Kuramochi et al.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Koo et al., "Tumour suppressor RNF43 is a stem-cell E3 ligase that induces endocytosis of Wnt receptors," Nature, Aug. 30, 2012, 488(7413):665-9. doi: 10.1038/nature11308.
Lloyd et al., "Modelling the human immune response: performance of a $10^{11}$ human antibody repertoire against a broad panel of therapeutically relevant antigens," Protein Eng Des Sel, Mar. 2009, 22(3):159-68. doi: 10.1093/protein/gzn058. Epub Oct. 29, 2008.
Niu et al., "RNF43 Inhibits Cancer Cell Proliferation and Could be a Potential Prognostic Factor for Human Gastric Carcinoma," Cell Physiol Biochem, Jul. 13, 2015, 36(5):1835-46.
Sakamoto et al., "Clinicopathological significance of somatic RNF43 mutation and aberrant expression of ring finger protein 43 in intraductal papillary mucinous neoplasms of the Pancreas," Mod Pathol, Feb. 2015, 28(2):261-7. doi: 10.1038/modpathol.2014.98. Epub Aug. 1, 2014.
Taniguchi et al., "Phase 1 study of OCV-C02, a peptide vaccine consisting of two peptide epitopes for refractory metastatic colorectal cancer," Cancer Sci, May 2017, 108(5):1013-1021. doi: 10.1111/cas.13227. Epub May 11, 2017.
Wang et al., The ubiquitin ligase RNF43 downregulation increases membrane expression of frizzled receptor in pancreatic ductal adenocarcinoma, Tumour Biol, Jan. 2016, 37(1):627-31. doi: 10.1007/s13277-015-3499-7. Epub Aug. 5, 2015.
Xing et al., "Reversing Effect of Ring Finger Protein 43 Inhibition on Malignant Phenotypes of human Hepatocellular Carcinoma," Mol Cancer Ther, Jan. 2013, 12(1):94-103. doi: 10.1158/1535-7163. MCT-12-0672. Epub Nov. 6, 2012.
Yagyu et al., "A novel oncoprotein RNF43 functions in an autocrine manner in colorectal cancer," Int J Oncol, Nov. 2004, 25(5):1343-8.
U.S. Appl. No. 15/490,936, Igawa et al., filed Apr. 19, 2017.
U.S. Appl. No. 16/448,088, Igawa et al., filed Jun. 21, 2019.
U.S. Appl. No. 16/448,088, filed Jun. 21, 2019, Igawa et al.
Auerbach et al., "Angiogenesis assays: Problems and pitfalls," Cancer Metastasis Rev, Jun. 2000, 19(1-2):167-72.
Baeuerle et al., "Bispecific T-Cell Engaging Antibodies for Cancer Therapy," Cancer Res, Jun. 15, 2009, 69(12):4941-4. doi: 10.1158/0008-5472.CAN-09-0547. Epub Jun. 9, 2009.
Bodelon et al, "Immunoglobulin domains in *Escherichia coli* and other enterobacteria: from pathogenesis to applications in antibody technologies," FEMS Microbiol Rev, Mar. 2013, 37(2):204-50. doi: 10.1111/j.1574-6976.2012.00347.x. Epub Jul. 23, 2012.
Brown et al., "Tolerance to Single, but not Multiple, Amino Acid Replacements in Antibody $V_H$ CDR2," J Immunol, May 1, 1996, 156(9):3285-91.
Chen et al., "Bispecific antibodies in cancer immunotherapy," Hum Vaccin Immunother, Oct. 2, 2016, 12(10):2491-2500. doi:10.1080/21645515.2016.1187802. Epub Jun. 1, 2016.
Christiansen et al., "Biological impediments to monoclonal antibody—based cancer immunotherapy," Mol Cancer Ther, Nov. 2004, 3(11):1493-501.
Clayton et al., "Unligated Epidermal Growth Factor Receptor Forms Higher Order Oligomers within Microclusters on A431 Cells That Are Sensitive to Tyrosine Kinase Inhibitor Binding," Biochemistry, Apr. 17, 2007, 46(15):4589-97. Epub Mar. 24, 2007.
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.

(56) References Cited

OTHER PUBLICATIONS

Feige et al., "An Unfolded $C_H1$ Domain Controls the Assembly and Secretion of IgG Antibodies," Mol Cell, Jun. 12, 2009, 34(5):569-79. doi: 10.1016/j.molcel.2009.04.028.
Gura, "Cancer Models—Systems for Identifying New Drugs Are Often Faulty," Science, Nov. 7, 1997, 278(5340):1041-2.
Hausler et al., "Anti-CD39 and anti-CD73 antibodies Al and 7G2 improve targeted therapy in ovarian cancer by blocking adenosine-dependent immune evasion," Am J Transl Res, Jan. 2014, 6(2):129-139.
Horne et al., "Noncovalent Association of Heavy and Light Chains of Human Immunoglobulins," J Immunol, Aug. 1982, 129(2):660-4.
InvivoGen, "Review: Immunoglobulin G," 2011, 1 page (downloaded on Jul. 1, 2019 from www.invivogen.com/sites/default/files/invivogen/old/docs/reviews/review-ImmunoglobulinG-invivogen.pdf).
Jain, Barriers to Drug Delivery in Solid Tumors, Sci Am, Jul. 1994, 271(1):58-65.
Kabat et al., "Heavy Constant Chains CH2 Region," Sequences of proteins of immunological interest, $5^{th}$ ed., 1991, pp. 647-652 and 661-669.
Loffler et al., "A recombinant bispecific single-chain antibody, CD19 × CD3, induces rapid and high lymphoma-directed cytotoxicity in unstimulated T lymphocytes," Blood, Mar. 15, 2000, 95(6):2098-103.
Mariuzza, "The Structural Basis of Antigen-Antibody Recognition," Annu Rev, Biophys Chem, Jun. 1987, 16:139-159.
Melero et al., "Agonist antibodies to TNFR molecules that costimulate T and NK cells," Clin Cancer Res, Mar. 1, 2013, 19(5):1044-53. doi: 10.1158/1078-0432.CCR-12-2065.
Moiseenko, "Monoclonal Antibodies in the Treatment of Malignant Tumors," Practical Oncology, 2003, 4(3):148-56 (with English translation).
Muller et al., "The first constant domain ($C_H1$ and $C_L$) of an antibody used as heterodimerization domain for bispecific miniantibodies," FEBS Lett, Jan. 30, 1998, 422(2):259-64.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Palazon et al., "The HIF-1α Hypoxia Response in Tumor-Infiltrating T Lymphocytes Induces Functional CD137 (4-1BB) for Immunotherapy," Cancer Discov, Jul. 2012, 2(7):608-23. doi: 10.1158/2159-8290.CD-11-0314. Epub Jun. 19, 2012.
Rudikoff et al., "Single amino acid substitution altering antigen-binding specificity," Proc Natl Acad Sci USA, Mar. 1982, 79(6):1979-83.
Sporn et al., "Chemoprevention of cancer," Carcinogenesis, Mar. 2000, 21(3):525-3.
Topp et al., "Antibody transport in cultured tumor cell layers," J Control Release, Apr. 30, 1998, 53(1-3):15-23.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-28.
Yano et al., "Ipilimumab augments antitumor activity of bispecific antibody-armed T cells," Journal of Translational Medicine, Jul. 2014, 12(1):191.
USPTO Notice of Allowance in U.S. Appl. No. 14/351,654, dated Jul. 10, 2019, 10 pages.
USPTO Applicant-Initiated Interview Summary in U.S. Appl. No. 14/351,654, dated May 24, 2019, 4 pages.
USPTO Notice of Allowance in U.S. Appl. No. 14/351,654, dated Sep. 30, 2019, 15 pages.
Chandramohan et al., "Antibody, T-cell and dendritic cell immunotherapy for malignant brain tumors," Future Oncol, Jul. 2013, 9(7):977-90. doi: 10.2217/fon.13.47.
Fischer et al., "Bispecific Antibodies: Molecules That Enable Novel Therapeutic Strategies," Pathobiology, Jan. 2007, 74(1):3-14.
Li et al., "Construction and characterization of a humanized anti-human CD3 monoclonal antibody 12F6 with effective immunoregulation functions," Immunology, Dec. 2005, 116(4):487-98.
Wing et al., "Mechanism of First-Dose Cytokine-Release Syndrome by CAMPATH 1-H: Involvement of CD16 (FcγRIII) and CD11a/CD18 (LFA-1) on NK Cells," J Clin Invest, Dec. 15, 1996, 98(12):2819-26.
Alignment of Fc domain sequences of catumaxomab and SEQ ID Nos. 23, 24, 25 and 26 (cited in oppositions filed against European Patent No. 2 647 707 on May 31, 2019 and Jun. 12, 2019), 2 pages.
An et al., "IgG2m4, an engineered antibody isotype with reduced Fc function," mAbs, Nov.-Dec. 2009, 1(6):572-9.
Aschermann et al., "The other side of immunoglobulin G: suppressor of inflammation," Clin Exp Immunol, May 2010, 160(2):161-7. doi: 10.1111/j.1365-2249.2009.04081.x. Epub Dec. 16, 2009.
Brennan et al., "Safety and immunotoxicity assessment of immunomodulatory monoclonal antibodies," mAbs, May-Jun. 2010, 2(3):233-55. Epub May 23, 2010.
Chelius et al., "Structural and functional characterization of the trifunctional antibody catumaxomab," mAbs, May-Jun. 2010, 2(3):309-19. Epub May 16, 2010.
Annex 1, submitted by the patentee during examination proceedings on Sep. 18, 2015 (cited in oppositions filed against European Patent No. 2 647 707 on May 31, 2019 and Jun. 12, 2019), 5 pages.
Das et al., "Producing Bispecific and Bifunctional Antibodies," Methods Mol Med, 2005, 109:329-46.
Demanet et al., "Treatment of murine B cell lymphoma with bispecific monoclonal antibodies (anti-idiotype x anti-CD3)," J Immunol, Aug. 1, 1991, 147(3):1091-7.
English translation of EP 11845786 as filed (cited in oppositions filed against European Patent No. 2 647 707 on May 31, 2019 and Jun. 12, 2019), 123 pages.
Graca, The Immune Synapse as a Novel Target for Therapy, 2008, pp. 59-61.
Haagen et al., "Evaluation of Fcγ receptor mediated T-cell activation by two purified CD3 × CD19 bispecific monoclonal antibodies with hybrid Fc domains," Ther Immunol, Oct. 1994, 1(5):279-87.
Haagen et al., "Interaction of human monocyte Fc gamma receptors with rat IgG2b. A new indicator for the Fc gamma RIIa (R-H131) polymorphism," J Immunol, Feb. 15, 1995, 154(4):1852-60.
Hezareh et al., "Effector Function Activities of a Panel of Mutants of a Broadly Neutralizing Antibody against Human Immunodeficiency Virus Type 1," J Virol, Dec. 2001, 75(24):12161-8.
Hoseini et al., "Immunotherapy of hepatocellular carcinoma using chimeric antigen receptors and bispecific antibodies," Cancer Lett, Jul. 28, 2017;399:44-52. doi: 10.1016/j.canlet.2017.04.013. Epub Apr. 17, 2017.
Ishiguro et al., "An anti-glypican 3/CD3 bispecific T cell-redirecting antibody for treatment of solid tumors," Sci Transl Med, Oct. 4, 2017, 9(410). pii: eaal4291. doi:10.1126/scitranslmed.aa14291.
Kasthuri et al., "Role of Tissue Factor in Cancer," J Clin Oncol, Oct. 10, 2009, 27(29):4834-8. doi: 10.1200/JCO.2009.22.6324. Epub Sep. 8, 2009.
King, Applications and Engineering of Monoclonal Antibodies, 2005, pp. 146-147.
Kontermann, "The Role of the Fc Region," Bispecific Antibodies, 2011, 296-8.
Link et al., "Anti-CD-3-Based Bispecific Antibody Designed for Therapy of Human B-Cell Malignancy Can Induce T-Cell Activation by Antigen-Dependent and Antigen-Independent Mechanisms," Int J Cancer, Jul. 17, 1998, 77(2):251-6.
Little, Recombinant Antibodies for Immunotherapy, 2009, pp. 133-134.
Matzku et al., Antibodies in Diagnosis and Therapy; Technologies, Mechanisms and Clinical Data, 1999, p. 7.
Milstein et al., "Hybrid hybridomas and their use in immunohistochemistry," Nature, Oct. 6-12, 1983, 305(5934):537-40.
Nelson et al., "5.2 Complementary Interactions between Proteins and Ligands: The Immune System and Immunoglobulins," Lehninger, Principles of Biochemistry, 5th Ed., 2008, p. 171.

(56) References Cited

OTHER PUBLICATIONS

Nitta et al., "Bispecific F(ab')₂ monomer prepared with anti-CD3 and anti-tumor monoclonal antibodies is most potent in induction of cytolysis of human T cells," Eur J Immunol, Aug. 1989, 19(8):1437-41.

Oganesyan et al., "Structural characterization of a human Fc fragment engineered for lack of effector functions," Acta Crystallogr D Biol Crystallogr, Jun. 2008, 64(Pt 6):700-4. doi: 10.1107/S0907444908007877. Epub May 14, 2008.

Parren et al., "Induction of T-cell proliferation by recombinant mouse and chimeric mouse/human anti-CD3 monoclonal antibodies," Res Immunol, Nov.-Dec. 1991, 142(9):749-63.

Ravetch et al., "Fc Receptors," Annu Rev Immunol, Apr. 1991, 9:457-92.

Routledge et al., "A humanized monovalent CD3 antibody which can activate homologous complement," Eur J Immunol, Nov. 1991, 21(11):2717-25.

Salnikov et al., "Targeting of cancer stem cell marker EpCAM by bispecific antibody EpCAMxCD3 inhibits pancreatic carcinoma," J Cell Mol Med, Sep. 2009, 13(9B):4023-33. doi: 10.1111/j.1582-4934.2009.00723.x.

Segal et al., "Production of Bispecific Antibodies," Current Protocols in Immunology, 1995, Unit 2.13.1-2.13.16.

Sequence Alignments (cited in oppositions filed against European Patent No. 2 647 707 on May 31, 2019 and Jun. 12, 2019), 6 pages.

Strauss et al., "Without Prior Stimulation, Tumor-associated Lymphocytes from Malignant Effusions Lyse Autologous Tumor Cells in the Presence of Bispecific Antibody HEA125xOKT3," Clin Cancer Res, Jan. 1999, 5(1):171-80.

Strohl, "Optimization of Fc-mediated effector functions of monoclonal antibodies," Curr Opin Biotechnol, Dec. 2009, 20(6):685-91. doi: 10.1016/j.copbio.2009.10.011. Epub Nov. 4, 2009.

Xu et al., "In Vitro Characterization of Five Humanized OKT3 Effector Function Variant Antibodies," Cell Immunol, Feb. 25, 2000, 200(1):16-26.

U.S. Appl. No. 12/295,075, filed Apr. 20, 2009.
U.S. Appl. No. 13/518,861, filed Oct. 4, 2012.
Examiner Lynn Anne Bristol, USPTO Non-Final Office Action in U.S. Appl. No. 14/351,654, dated Apr. 16, 2020, 11 pages.
U.S. Pat. No. 9,670,269, Igawa et al., filed Jun. 6, 2017.
U.S. Appl. No. 16/815,089, Igawa et al., filed Mar. 11, 2020.
U.S. Appl. No. 15/578,931, Taniguchi et al., filed Dec. 1, 2017.
U.S. Pat. No. 9,975,966, Nezu et al., filed May 22, 2018.
U.S. Appl. No. 61/467,727, Blein et al. filed Mar. 25, 2011.
Annex I. Analysis of the Examples of EP 2 787 078, 3 pages (document submitted in opposition of EP 2 787 078 dated Feb. 28, 2020).

Arguments filed Oct. 12, 2016 in U.S. Appl. No. 14/351,654, 10 pages (document submitted in opposition of EP 2 787 078 dated Feb. 28, 2020).

Claims filed Sep. 5, 2018 in U.S. Appl. No. 14/351,654, 7 pages (document submitted in opposition of EP 2 787 078 dated Feb. 28, 2020).

Schneider et al., "In vitro and in vivo properties of a dimeric bispecific single-chain antibody IgG-fusion protein for depletion of CCR2+ target cells in mice," Eur J Immunol, Feb. 22, 2005, 35:987-995 <https://onlinelibrary.wiley.com/doi/full/10.1002/eji.200425512>.

Examiner Lynn Anne Bristol, USPTO Notice of Allowance in U.S. Appl. No. 14/351,654, dated Jan. 29, 2020, 9 pages.

Dall'Acqua et al., "Increasing the Affinity of a Human IgG1 for the Neonatal Fc Receptor: Biological Consequences," J Immunol, Nov. 1, 2002, 169(9):5171-80.

Examination report 18192844.1, dated Dec. 5, 2019, 6 pages (submitted by Opponent 3 dated Mar. 26, 2020 in Opposition of EP 2 647 707).

Mueller et al., "Humanized Porcine VCAM-Specific Monoclonal Antibodies with Chimeric IgG2/G4 Constant Regions Block Human Leukocyte Binding to Porcine Endothelial Cells," Mol Immunol, Apr. 1997, 34(6):441-52.

Nissim et al., "Historical Development of Monoclonal Antibody Therapeutics," in Therapeutic Antibodies, ed. Chernajovsky et al., Springer-Verlag (2008), pp. 3-7.

Beckman et al., "Antibody Constructs in Cancer Therapy—Protein Engineering Strategies to Improve Exposure in Solid Tumors," Cancer, Jan. 15, 2007, 109(2):170-179. doi:10.1002/cncr.22402.

Carpenter et al., "Non-Fc Receptor-Binding Humanized Anti-CD3 Antibodies Induce Apoptosis of Activated Human T Cells," J Immunol, 2000, 165(11):6205-6213. doi:10.4049/jimmuno1.165.11.6205.

Cespedes et al., "Mouse models in oncogenesis and cancer therapy," Clin Transl Oncol, May 2006, 8(5):318-329. doi:10.1007/s12094-006-0177-7.

Dennis, "Cancer: Off by a whisker," Nature, Aug. 17, 2006, 442(7104):739-741. doi:10.1038/442739a.

EPO opposition preliminary decision in opposition of EP 2 647 707 (dated May 13, 2020), 23 pages.

Feucht et al., "T-cell responses against CD19⁺pediatric acute lymphoblastic leukemia mediated by bispecific T-cell engager (BiTE) are regulated contrarily by PD-L1 and CD80/CD86 on leukemic blasts," Oncotarget, Sep. 30, 2016, 7(47):76902-76919.

Filmus et al., "Protein family review—Glypicans," Genome Biol, May 22, 2008, 9(5):224. doi:10.1186/gb-2008-9-5-224.

Fujimori et al., "A Modeling Analysis of Monoclonal Antibody Percolation Through Tumors: A Binding-Site Barrier," J Nucl Med, Jul. 1990, 31(7):1191-1198.

Huang et al., "Recombinant immunotherapeutics: feasibility and market," Appl Microbiol current state and perspectives regarding the Biotechnol, Jun. 2010, 87(2):401-410. doi:10.1007/s00253-010-2590-7.

Kohnke et al., "Increase of PD-L1 expressing B-precursor ALL cells in a patient resistant to the CD19/CD3-bispecific T cell engager antibody blinatumomab," J Hematol Oncol, Oct. 8, 2015, 8:111, 5 pages. doi:10.1186/s13045-015-0213-6.

Lejeune et al., "Bispecific, T-Cell-Recruiting Antibodies in B-Cell Malignancies," Frontiers in Immunology, May 7, 2020, 11:762, 20 pages.

Rudnick et al., "Affinity and Avidity in Antibody-Based Tumor Targeting," Cancer Biother Radiopharm, Apr. 2009, 24(2):155-161. doi:10.1089/cbr.2009.0627.

Runcie et al., "Bi-specific and tri-specific antibodies—the next big thing in solid tumor therapeutics," Molecular Medicine, 2018, 24:50, 15 pages.

Singer et al., Chapter 1.3 "Structure of Proteins," Genes & Genomes, 1998, 1:63-64 (with what are believed to be the corresponding pp. from an English version of Genes & Genomes).

Talmadge et al., "Murine Models to Evaluate Novel and Conventional Therapeutic Strategies for Cancer," Am J Pathol, Mar. 2007, 170(3):793-804. doi:10.2353/ajpath.2007.060929.

Thurber et al., "Antibody tumor penetration: Transport opposed by systemic and antigen-mediated clearance," Adv Drug Deliv Rev, Sep. 2008, 60(12):1421-1434. doi:10.1016/j.addr.2008.04.012.

Voskoglou-Nomikos et al., "Clinical Predictive Value of the in Vitro Cell Line, Human Xenograft, and Mouse Allograft Preclinical Cancer Models," Clin Cancer Res, Sep. 15, 2003,9(11):4227-4239.

Witte et al., "Monoclonal antibodies targeting the VEGF receptor-2 (Flkl/KDR) as an anti-angiogenic therapeutic strategy," Cancer Metastasis Rev, Jun. 1998, 17(2):155-161.

Yu et al., "Interaction between Bevacizumab and Murine VEGF-A: A Reassessment," Invest Ophthalmol Vis Sci, Feb. 2008, 49(2):522-527. doi: 10.1167/iovs.07-1175.

Yu et al., "T cell-redirecting bispecific antibodies in cancer immunotherapy: recent advances," J. Cancer Research and Clinical Oncology, Feb. 23, 2019, 145:941-956.

Bolt et al., "The generation of a humanized, non-mitogenic CD3 monoclonal antibody which. etains in vitro immunosuppressive properties," Eur J Immunol, Feb. 1993, 23(2):403-411.

Brischwein et al.,"MT110: A novel bispecific single-chain antibody construct with high efficacy in eradicating established tumors," Mol Immunol, Mar. 2006, 43(8):1129-1143. doi: 10.1016/j.molimm.2005.07.034. Epub Sep. 1, 2005.

(56) References Cited

OTHER PUBLICATIONS

Hammond et al., "Selective Targeting and Potent Control of Tumor Growth Using an EphA2/CD3-Bispecific Single-Chain Antibody Construct," Cancer Res, Apr. 15, 2007, 67(8):39273935. doi: 10.1158/0008-5472.CAN-06-2760.
Lutterbuese et al., "Conversion of Cetuximab and Trastuzumab into T cell-engaging BiTE antibodies creates novel drug candidates with superior anti-tumor activity," Proc Am Assoc Cancer Res., from 99th AACR Annual Meeting, May 2008, vol. 68, Issue 9, Abstract 2402.
Representative abstracts allegedly showing long-term administration of a variety of anti-cancer antibodies in the prior art, 5 pages (document submitted by the Opponents in the Opposition Proceedings of EP 2 647 707 and reported in the EPO Communication dated Jan. 20, 2021; the document cites publication dates of the abstracts ranging from May 2006 to Feb. 2010).
Rother et al., "Discovery and development of the complement inhibitor eculizumab for the treatment of paroxysmal nocturnal hemoglobinuria," Nat Biotechnol, Nov. 25, 2007(11):1256-1264.
U.S. Appl. No. 9,670,269, Igawa et al., dated Jun. 6, 2017.
U.S. Appl. No. 10,934,344, Igawa et al., dated Mar. 2, 2021.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020.
U.S. Appl. No. 14/351,654, Kuramochi et al., filed Apr. 14, 2014.
U.S. Appl. No. 16/692,676, Kuramochi et al., filed Nov. 22, 2019.
U.S. Appl. No. 16/061,454, Tanaka et al., filed Jun. 12, 2018.
U.S. Appl. No. 16/605,556, Hoshino et al., filed Oct. 16, 2019.
U.S. Appl. No. 15/302,439, Igawa et al., filed Oct. 6, 2016.
U.S. Appl. No. 15/578,931, Taniguchi et al., filed Dec. 1, 2017 (abandoned).
U.S. Appl. No. 15/310,162, Igawa et al., filed Nov. 10, 2016.
U.S. Appl. No. 15/776,541, Igawa, filed May 16, 2018.
U.S. Appl. No. 15/776,587, Tsunenari et al., filed May 16, 2018.
U.S. Pat. No. 9,975,966, Nezu et al., dated May 22, 2018.
U.S. Appl. No. 15/963,221, Nezu et al., filed Apr. 26, 2018.
U.S. Appl. No. 16/083,975, Kinoshita et al., filed Sep. 11, 2018.
Brezski et al., "The origins, specificity, and potential biological relevance of human anti-IgG hinge autoantibodies," Scientific World Journal, May 26, 2011, 11:1153-1167.
Curriculum vitae of Dr. K. Philipp Holliger, 12 pages (submitted by opponent in opposition of EP Patent 2 787 078 on Mar. 4, 2021).
Declaration of Dr. K. Philipp Holliger, 15 pages (submitted by opponent in opposition of EP Patent 2 787 078 on Mar. 4, 2021).
EPO Opposition Division, Consolidated List of cited references submitted in opposition of EP Patent 2 647 707, dated Feb. 18, 2021 ( 5 pages).
EPO Opposition Division, Grounds for Decision and Minutes of Oral Proceedings in opposition of EP Patent 2 647 707, dated Apr. 1, 2021 (51 pages).
Feng et al., "Glypican-3 antibodies: A new therapeutic target for liver cancer," FEBS Lett, Jan. 10, 2014, 588(2):377-382. doi: 10.1016/j.febslet.2013.10.002. Epub Oct. 15, 2013.
Gao et al., "Ring finger protein 43 associates with gastric cancer progression and attenuates the stemness of gastric cancer stem-like cells via the Wnt-ß/catenin signaling pathaway," Stem Cell Res Ther, Apr. 26, 2017 8(1):98, 11 pages.
Ho et al., "Glypican-3: A new target for cancer immunotherapy," Eur J Cancer, Feb. 2011, 47(3):333-338. doi: 10.10166/j.ejca.2010.10.024. Epub Nov. 26, 2010.

Lutterguese et al., "T cell-engaging BiTe antibodies specific for EGFR potently eliminate KRAS-and BRAF-mutated colorectal cancer cells," Proc Natl Acad Sci USA, Jul. 13, 2010 107(28):1260-12610. doi: 10.1073/pnas.1000976107. Epub Jun. 28, 2010.
Santos et al., "Development of more efficacious antibodies for medical therapy and diagnosis," Pro Nucleic Acid Res Mol Biol, 1998, 60:169-194.
Sequence Alignments (comparison of heavy chain constant region), 1 page (submitted by the patentee (Chugai Seiyaku Kabushiki Kaisha) in opposition of EP Patent 2 647 707 on Dec. 23, 2020).
Shahabuddin et al., "Lymphoctye subset reference ranges in healthy Saudi Arabian Children," Pediatr Allergy Immunol, Feb. 9, 1998 9(1):44-48.
Shirakawa et al., "Glypican-3 is a useful diagnostic marker for a component of a hepatocellular carinoma in human liver cancer," Int J Oncol, Mar. 2009, 34(3):649-656.
Wang et al., "Evidence for Segregation of Heterlogous GPI-anchored Proteins into Separate Lipid Rafts within the Plasma Membrane," J Membr Biol, Sep. 1, 2002, 189(1):35-43. doi: 10.1007/s00232-002-1002-z. PMID:12202950.
Examiner Lynn Anne Bristol, USPTO Final Office Action in U.S. Appl. No. 14/351,654, dated Dec. 1, 2020, 13 pages.
Baeuerle et al., "BiTE: Teaching antibodies to engage T-cells for cancer therapy," Curr Opin Mol Ther, Feb. 2009, 11(1):22-30.
Bolt et al., "The generation of humanized, non-mitogenic CD3 monoclonal antibody which retains in vitro immunosuppressive properties," Eur J Immunol, Feb. 23, 1993, 23(2):403-411.
Brischwein et al., "MT110: A novel bispecific single-chain antibody construct with high efficacy in eradicating established tumor," Mol Immunol, Mar. 2006, 43(8):1129-1143. doi: 10.1016/k.molimm.2005.07.034. Epub Sep. 1, 2005.
Bugelski et al., "Monoclonal antibody-induced cytokine-release syndrome," Expert Rev Clin Immunol, Sep. 2009, 5(5):499-521.
Carter et al., "Potent antibody therapeutics by design," Nat Rev Immunol, May 2006, 6(5):343-357.
Hammond et al., "Selective Targeting and Potent Control of Tumor Growth Using an EphA2/CD3-Bisepecific Single-Chain Antibody Construct," Cancer Res, Apr. 15, 2007, 67(8):3927-3935. doi: 10.1158/0008-5472.CAN-066-2760.
Kontermann, "Recombinant bispecific antibodies for cancer therapy," Acta Pharmacol Sin, Jan. 2005, 26(1):1-9.
Kontermann, "Strategies to Extend Plasma Half-Lives of Recombinant Antibodies," BioDrugs, 2009, 23(2):93-109. doi: 10.2165/00063030-200923020-00003.
Lutterbuese et al., "Potent tumor killing and inhibition of tumor growth by CEA/CD3-bispecific single chain antibodies that are resistant to inhibition by soluble CEA," Proc Am Assoc Cancer Res, from 98th AACR Annual Meeting, May 2007, vol. 67, Issue 9, Abstract 4106.
Lutterbuese et al., "Conversion of Cetuximab and Trastuzumab into T cell-engaging BiTE antibodies create novel drug candidates with superior anti-tumor activity," Proc Am Assoc Cancer Res., from 99th AACR Annual Meeting, May 2008, vol. 68, Issue 9, Abstract 2402.
Representative abstracts allegedly showing long-term administration of a variety of anti-cancer antibodies in the prior art, 5 pages (document submitted by the Opponents in the Opposition Proceeding of EP 2 647 707 and reported in the EPO Communication dated Jan. 20 2021; the document cites publication dates of the abstracts ranging from May 2006 to Feb. 2010).
Rother et al., "Discovery and development of the complement inhibitor eculizumab for the treatment of paroxysmal nocturnal hemoglobinuria," Nat Biotechnol, Nov. 2007, 25(11):1256-1264.
Saunders et al., "Conceptual Approaches to Modulating Antibody Effector Functions and Circulation Half-Life," Front Immunol, Jun. 7, 2019, 10(1296):1-20.
Thomas et al., "A Cell-Based Artificial Antigen-Presenting Cell Coated with Anti-CD3 and CD28 Antibodies Enables Rapid Expansion and Long-Term Growth of CD4 T Lymphocytes," Clin Immunol, Dec. 2002, 105(3):259-272.
Weiner et al., "The Role of T Cell Activation in Anti-CD3 x Antitumor Bispecific Antibody Therapy," J Immunol, Mar. 1, 1994, 152(5):2385-2392.

(56) References Cited

OTHER PUBLICATIONS

Zhao et al., "Targeting CD37-positive lymphoid malignancies with a novel engineered small modular immunopharmaceutical," Blood, Oct. 1, 2007, 110(7):2569-2577.

Form posted on EPO website and dated Mar. 2, 2021, disclosing that EP patent No. 2647707B1 was revoked in an oral proceeding that occurred on Feb. 25 and 26, 2021 (1 page).

* cited by examiner

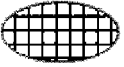 ANTI-CANCER ANTIGEN (GPC3, EpCAM, EGFR) ANTIBODY H-CHAIN VARIABLE REGION
 ANTI-CANCER ANTIGEN (GPC3, EpCAM, EGFR) ANTIBODY L-CHAIN VARIABLE REGION
 ANTI-CD3 ANTIBODY H-CHAIN VARIABLE REGION
 ANTI-CD3 ANTIBODY L-CHAIN VARIABLE REGION
 ANTIBODY CONSTANT REGION
 SILENT Fc MUTATION
 HETERO Fc ASSOCIATING MUTATION
FIG. 16

```
Kabat     1
EU index  1-2----------3----------4----------5----------6----------7----------8----------9----------2----------1----------2
          8-0----------0----------0----------0----------0----------0----------0----------0----------0----------0----------0
IgG1      ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCD-
IgG2      ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK--CC
IgG3      ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRVELKTPLG
IgG4      ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYG--

Kabat     2
EU index  2----------3----------4----------5----------6----------7----------8
          2----------8----------0----------0----------0----------0----------0
IgG1      -KTHTCPP------------------CPAPELLGGPSVFLFPPKPKDTLMISRTPEVTCVVVDVSHEDPEVKFNWYVD
IgG2      -V-E-CPP------------------CPAPPVA-GPSVFLFPPKPKDTLMISRTPEVTCVVVDVSHEDPEVQFNWYVD
IgG3      DTTHTCPRCPEPKSCDTPPPCPRCPEPKSCDTPPPCPRCPAPELLGGPSVFLFPPKPKDTLMISRTPEVTCVVVDVSHEDPEVQFKWYVD
IgG4      ---PPCPS------------------CPAPEFLGGPSVFLFPPKPKDTLMISRTPEVTCVVVDVSQEDPEVQFNWYVD Kabat              3
EU index  2----------9----------1----------2----------3----------4----------5----------6----------7----------8
          8----------0----------0----------0----------0----------0----------0----------0----------0----------0
IgG1      GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNG
IgG2      GVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNG
IgG3      GVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSG
IgG4      GVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNG Kabat     3               4
EU index  8----------9----------0----------1----------2----------3----------4
          6----------0----------0----------0----------0----------0----------7
IgG1      QPENNYKTTPPVLDSDGSFFLYSKLTVDKSRWQQGNVFSCSVMHEALHNHYTQKSLSLSPGK (SEQ ID NO: 23)
IgG2      QPENNYKTTPPMLDSDGSFFLYSKLTVDKSRWQQGNVFSCSVMHEALHNHYTQKSLSLSPGK (SEQ ID NO: 24)
IgG3      QPENNYNTTPPMLDSDGSFFLYSKLTVDKSRWQQGNIFSCSVMHEALHNRFTQKSLSLSPGK (SEQ ID NO: 25)
IgG4      QPENNYKTTPPVLDSDGSFFLYSRLTVDKSRWQEGNVFSCSVMHEALHNHYTQKSLSLSLGK (SEQ ID NO: 26)
```

FIG. 18

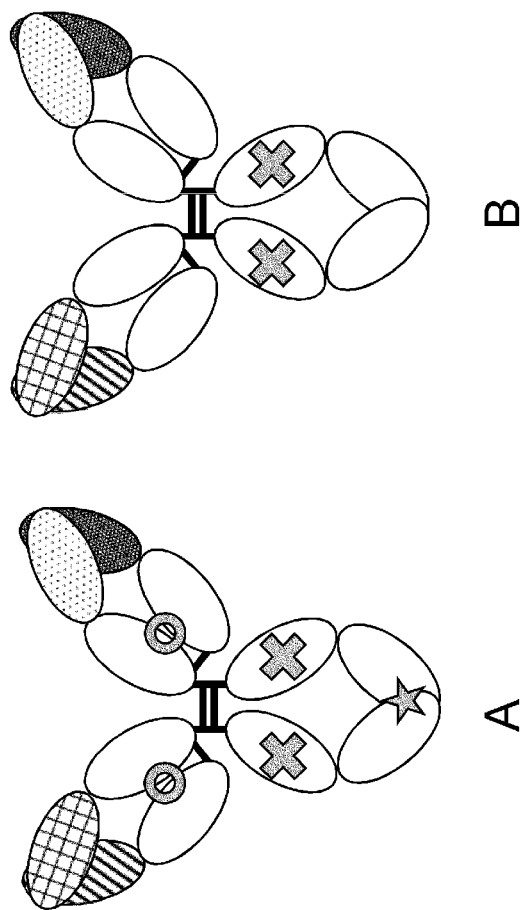
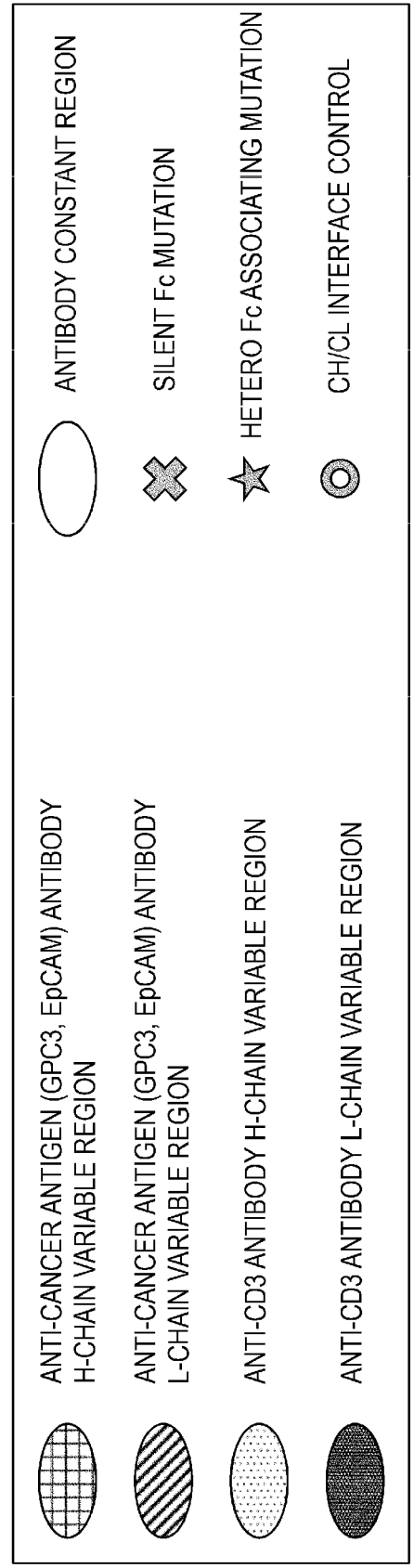
FIG. 24

CYTOTOXICITY-INDUCING THERAPEUTIC AGENT

CROSS-REFERENCE TO RELATED APPLICATIONS

This application is the National Stage of International Patent Application Serial No. PCT/JP2011/077603, filed on Nov. 30, 2011, which claims the benefit of Japanese Patent Application Serial No. 2010-266760, filed on Nov. 30, 2010, Japanese Patent Application Serial No. 2011-121771, filed on May 31, 2011, and Japanese Patent Application Serial No. 2011-238818, filed on Oct. 31, 2011.

TECHNICAL FIELD

The present invention relates to polypeptide complexes that enable cancer treatment by having T cells close to target cancer cells and using the cytotoxic activity of T cells against the target cancer cells, methods for producing the polypeptide complexes, and therapeutic agents that contain such a polypeptide complex as an active ingredient for inducing cellular cytotoxicity. The present invention also relates to pharmaceutical compositions for treating or preventing various cancers, which contain an above-mentioned therapeutic agent for inducing cellular cytotoxicity as an active ingredient, and therapeutic methods using such pharmaceutical compositions.

BACKGROUND ART

To date, multiple therapeutic antibodies having an excellent anti-tumor effect have been developed as pharmaceuticals for treating cancer (Non-patent Document 1). These therapeutic antibodies are known to exert their anti-tumor effect on cancer cells through inhibition of signals essential for cancer cell growth, induction of cell death signals, antibody dependent cell-mediated cytotoxicity (ADCC), or complement dependent cytotoxicity (CDC) (Non-patent Document 2). ADCC is a cytotoxicity exerted by effector cells such as NK cells and macrophages against antibody-bound target cancer cells when the Fc region of an antibody binds to an Fc receptor on the effector cells. Meanwhile, a complement complex binds to the complement-binding site in an antibody structure. CDC is cytotoxicity that occurs when a complement component in the complex forms a pore through the cell membrane of an antibody-bound cell, enhancing water or ion influx into the cell. Although conventional therapeutic antibodies show excellent activities, to date administration of such antibodies led to only unsatisfactory therapeutic outcomes. Thus, it is desirable to develop therapeutic antibodies that exert a greater cell-killing activity against cancer.

In addition to the above-mentioned antibodies which adopt ADCC as their anti-tumor mechanism by recruiting NK cells or macrophages as effector cells, T cell-recruiting antibodies (TR antibodies) which adopt cytotoxicity as their anti-tumor mechanism by recruiting T cells as effector cells have been known since the 1980s (Non-patent Documents 3 to 5). A TR antibody is a bispecific antibody that contains an antibody against any one of the subunits forming a T-cell receptor (TCR) complex on T cells, in particular an antibody that binds to the CD3 epsilon chain, and an antibody that binds to an antigen on target cancer cells. A T cell gets near a cancer cell when the TR antibody binds to both the CD3 epsilon chain and cancer antigen at the same time, and this causes an anti-tumor effect against the cancer cell due to the cytotoxic activity of the T cell.

An antibody called "trifunctional antibody" is also known as a TR antibody (Non-patent Documents 6 and 7). A trifunctional antibody is a whole IgG-type bispecific antibody in which one arm contains an Fab that binds to a cancer antigen and the other arm contains an Fab that binds to the CD3 epsilon chain. Therapeutic effect against malignant ascites has been demonstrated by administering catumaxomab, which is a trifunctional antibody against EpCAM, into the peritoneal cavities of malignant ascites patients having EpCAM expression-positive cancer cells. The use of catumaxomab has been approved in the EU for the above treatment.

Furthermore, a TR antibody called "bispecific T-cell engager (BiTE)" has been recently found to exhibit a strong anti-tumor effect (Non-patent Documents 8 and 9). BiTE is a TR antibody with a molecular form in which the scFv of an antibody against a cancer antigen is linked to the scFv of an antibody against the CD3 epsilon chain via a short polypeptide linker. BiTE has been reported to have an anti-tumor activity superior to those of the various known TR antibodies (Non-patent Documents 9 and 10). Specifically, as compared to other TR antibodies, BiTE exerts an anti-tumor effect even at a significantly lower concentration and lower effector cell/cancer cell ratio (ET ratio). It has been also demonstrated that the effect can be exerted without the need to activate effector cells using IL-2, a CD28 agonistic antibody or such in advance. Blinatumomab (MT103), which is a BiTE against CD19, exhibits a much stronger cytotoxic activity against cancer cells in vitro than that of Rituxan which is known to produce an excellent clinical effect. Furthermore, blinatumomab has been reported to show an extremely superior anti-tumor effect in phase I and II clinical trials conducted recently (Non-patent Document 11).

The fact that catumaxomab has been approved as a therapeutic agent that demonstrates clinical drug effect, and that multiple BiTEs including blinatumomab exert a strong anti-tumor effect, suggests that TR antibodies that recruit T cells as effector cells have a significantly higher potential as an anti-tumor agent as compared to conventional antibodies that use ADCC as their mechanism of action.

However, it is known that a trifunctional antibody binds to both a T cell and a cell such as an NK cell or macrophage at the same time in a cancer antigen-independent manner, and as a result receptors expressed on the cells are cross-linked, and expression of various cytokines is induced in a cancer antigen-independent manner. Systemic administration of a trifunctional antibody is thought to cause cytokine storm-like side effects as a result of such induction of cytokine expression. In fact, it has been reported that, in the phase I clinical trial, a very low dose of 5 μg/body was the maximum tolerance dose for systemic administration of catumaxomab to patients with non-small cell lung cancer, and that administration of a higher dose causes various severe side effects (Non-patent Document 12). When administered at such a low dose, catumaxomab can never reach the effective blood level. That is, the expected anti-tumor effect cannot be achieved by administrating catumaxomab at such a low dose.

Meanwhile, unlike catumaxomab, BiTE has no Fcγ receptor-binding site, and therefore it does not cross-link the receptors expressed on T cells and cells such as NK cells and macrophages in a cancer antigen-dependent manner. Thus, it has been demonstrated that BiTE does not cause cancer antigen-independent cytokine induction which is observed when catumaxomab is administered. However, since BiTE is a modified low-molecular-weight antibody molecule without an Fc region, the problem is that its blood half-life after administration to a patient is significantly shorter than IgG-type antibodies conventionally used as therapeutic antibodies. In fact, the blood half-life of BiTE administered in vivo has been reported to be about several hours (Non-patent Documents 13 and 14). In the clinical trials of blinatumomab, it is administered by continuous intravenous infusion using a minipump. This administration method is not only extremely inconvenient for patients but also has the potential risk of medical accidents due to device malfunction or the like. Thus, it cannot be said that such an administration method is desirable.

PRIOR ART DOCUMENTS

Non-Patent Documents

[Non-patent Document 1] Clin Cancer Res. (2010) 16 (1), 11-20
[Non-patent Document 2] Drug Des Devel Ther (2009) 3, 7-16
[Non-patent Document 3] Nature (1985) 314 (6012), 628-31
[Non-patent Document 4] Int J Cancer (1988) 41 (4), 609-15
[Non-patent Document 5] Proc Natl Acad Sci USA (1986) 83 (5), 1453-7
[Non-patent Document 6] Cancer Treat Rev. (2010) 36 (6), 458-67
[Non-patent Document 7] Expert Opin Biol Ther (2010) 10 (8), 1259-69
[Non-patent Document 8] Proc Natl Acad Sci USA. (1995) 92 (15), 7021-5
[Non-patent Document 9] Drug Discov Today (2005), 10 (18), 1237-44
[Non-patent Document 10] Trends Biotechnol (2004) 22 (5), 238-44
[Non-patent Document 11] Science (2008), 321 (5891), 974-7
[Non-patent Document 12] Cancer Immunol Immunother (2007) 56 (10), 1637-44
[Non-patent Document 13] Cancer Immunol Immunother. (2006) 55 (5), 503-14
[Non-patent Document 14] Cancer Immunol Immunother. (2009) 58 (1), 95-109

SUMMARY OF THE INVENTION

Problems to be Solved by the Invention

The present invention was achieved in view of the above circumstances. An objective of the present invention is to provide polypeptide complexes that enable cancer treatment by having T cells close to target cancer cells and using the cytotoxicity of T cells against the target cancer cells, methods for producing the polypeptide complexes, and therapeutic agents containing such a polypeptide complex as an active ingredient for inducing cellular cytotoxicity. Another objective of the present invention is to provide pharmaceutical compositions for treating or preventing various cancers, which comprise an above-mentioned therapeutic agent for inducing cellular cytotoxicity as an active ingredient, and therapeutic methods using the pharmaceutical compositions.

Means for Solving the Problems

The present inventors discovered novel polypeptide complexes that retain the strong anti-tumor activity possessed by BiTE and have a long half-life in blood, as well as excellent safety properties that result in no induction of cancer antigen-independent cytokine storm or such. The present inventors also found that the polypeptide complexes can damage various target cells when antigen-binding domains of the polypeptide complexes are substituted. Based on the above findings, the present inventors demonstrated that the polypeptide complexes of the present invention damage cancer cells. The present inventors also revealed that more efficient cellular cytotoxicity is achieved by regulating the CH1/CL interface association and introducing Knobs-into-Holes (KiH) modifications into the polypeptide complexes. In addition, the present inventors demonstrated that various cancers can be treated or prevented using therapeutic agents for inducing cellular cytotoxicity comprising a polypeptide complex of the present invention as an active ingredient.

More specifically, the present invention provides the following:

[1] a polypeptide complex which comprises:
(1) an antigen-binding domain;
(2) a domain comprising an Fc region that has reduced Fcγ receptor-binding activity; and
(3) a T cell receptor complex-binding domain;
[2] the polypeptide complex of [1], wherein the T cell receptor complex-binding domain is a T cell receptor-binding domain;
[3] the polypeptide complex of [1], wherein the T cell receptor complex-binding domain is a CD3-binding domain;
[4] the polypeptide complex of any one of [1] to [3], wherein the antigen-binding domain is a bivalent antigen-binding domain;
[5] the polypeptide complex of [4], wherein the bivalent antigen-binding domain is a domain having an F(ab')2 structure;
[6] the polypeptide complex of [5], in which two polypeptides forming a heavy chain constant region of the domain having the F(ab')2 structure are individually linked to either of the two polypeptides forming an Fc domain;
[7] the polypeptide complex of [6], in which a CD3-binding domain is linked to either or both of the two CH3s forming the Fc domain;
[8] the polypeptide complex of [7], in which a heavy chain Fv fragment forming the CD3-binding domain is linked to one of the CH3s forming the Fc domain and a light chain Fv fragment forming the CD3-binding domain is linked to the other CH3 forming the Fc domain;
[9] the polypeptide complex of [8], in which an antibody CH1 domain is linked to the heavy chain Fv fragment forming the CD3-binding domain and an antibody CL domain is linked to the light chain Fv fragment;
[10] the polypeptide complex of [6], in which the CD3-binding domain is linked to either or both of the two CLs forming the F(ab')2;
[11] the polypeptide complex of [6], in which the CD3-binding domain is linked to either or both of the two VHs forming the F(ab')2;
[12] the polypeptide complex of [6], in which the CD3-binding domain is linked to either or both of the two VLs forming the F(ab')2;
[13] the polypeptide complex of any one of [1] to [12], wherein the CD3-binding domain is Fv;
[14] the polypeptide complex of any one of [1] to [7] and [10] to [12], wherein the CD3-binding domain is Fab;
[15] the polypeptide complex of any one of [1] to [7] and [10] to [12], wherein the CD3-binding domain is scFv;
[16] the polypeptide complex of any one of [1] to [15], wherein the CD3-binding domain is monovalent;

[17] the polypeptide complex of any one of [1] to [3], wherein the antigen-binding domain is a monovalent scFv and a monovalent Fab;

[18] the polypeptide complex of [17], in which the monovalent scFv is linked to one of the polypeptides forming the Fc domain via the scFv that forms the CD3-binding domain; the heavy chain Fv fragment of the monovalent Fab is linked to one of the polypeptides forming the Fc domain via a CH1 domain; and the light chain Fv fragment of the Fab is linked to the CL domain;

[19] the polypeptide complex of any one of [1] to [3], wherein the antigen-binding domain is a bivalent scFv;

[20] the polypeptide complex of [19], in which one monovalent scFv is linked to one of the polypeptides forming the Fc domain via the heavy chain Fv fragment forming the CD3-binding domain, and the other monovalent scFv is linked to the other polypeptide forming the Fc domain via the light chain Fv fragment forming the CD3-binding domain;

[21] the polypeptide complex of [19], wherein one monovalent scFv is linked to one of the polypeptides forming the Fc domain via the scFv forming the CD3-binding domain, and the other monovalent scFv is linked to the other polypeptide forming the Fc domain;

[22] the polypeptide complex of any one of [1] to [3], wherein the antigen-binding domain and T cell receptor complex-binding domain are each a monovalent Fab;

[23] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the heavy chain Fv fragment of Fab forming the T cell receptor-binding domain is linked to the other polypeptide forming the Fc domain via a CH1 domain and the light chain Fv fragment of the Fab is linked to a CL domain;

[24] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the light chain Fv fragment of Fab forming the T cell receptor-binding domain is linked to the other polypeptide forming the Fc domain via a CH1 domain and the heavy chain Fv fragment of the Fab is linked to a CL domain;

[25] the polypeptide complex of [22], in which the heavy chain Fv fragment of a monovalent Fab forming the antigen-binding domain is linked to one of the polypeptides forming the Fc domain via a CH1 domain and the light chain Fv fragment of the Fab is linked to a CL domain; and the heavy chain Fv fragment of the Fab forming the T cell receptor-binding domain is linked to the other polypeptide forming the Fc domain via a CL domain and the light chain Fv fragment of the Fab is linked to a CH1 domain;

[26] the polypeptide complex of [22], in which the heavy chain Fv fragment of a monovalent Fab forming the T cell receptor-binding domain is linked to one of the polypeptides forming the Fc domain via a CH1 domain and the light chain Fv fragment of the Fab is linked to a CL domain; and the light chain Fv fragment of Fab forming the antigen-binding domain is linked to the other polypeptide forming the Fc domain via a CH1 domain and the heavy chain Fv fragment of the Fab is linked to a CL domain;

[27] the polypeptide complex of [22], in which the heavy chain Fv fragment of a monovalent Fab forming the T cell receptor-binding domain is linked to one of the polypeptide forming the Fc domain via a CH1 domain and the light chain Fv fragment of the Fab is linked to a CL domain; and the heavy chain Fv fragment of the Fab forming the antigen-binding domain to the other polypeptide forming the Fc domain via a CL domain and the light chain Fv fragment of the Fab is linked to a CH1 domain;

[28] the polypeptide complex of [22] comprising:
(1) an antigen-binding domain in which the heavy chain Fv fragment of a monovalent Fab structure that binds to an antigen is linked via a CH1 domain to one of the polypeptides forming the Fc domain, and the light chain Fv fragment of the Fab structure is linked to a CL domain; and
(2) a T cell receptor complex-binding domain in which the heavy chain Fv fragment of a monovalent Fab structure that binds to a T cell receptor complex is linked via a CH1 domain to the other polypeptide forming the Fc domain, and the light chain Fv fragment of the Fab structure is linked to a CL domain;
wherein electric charges of the CH1 and CL domains are controlled so that the heavy chain Fv fragment of the antigen-binding domain assembles with the light chain Fv fragment of the antigen-binding domain, or the heavy chain Fv fragment of the T cell receptor-binding domain assembles with the light chain Fv fragment of the T cell receptor-binding domain;

[29] the polypeptide complex of [28], wherein an amino acid residue in the CH1 domain linked to the heavy chain Fv fragment of the T cell receptor complex-binding domain has the same type of electric charge as an amino acid residue in the CL domain linked to the light chain Fv fragment of the antigen-binding domain;

[30] the polypeptide complex of [28], wherein an amino acid residue in the CH1 domain linked to the heavy chain Fv fragment of the antigen-binding domain has the same type of electric charge as an amino acid residue in the CL domain linked to the light chain Fv fragment of the T cell receptor complex-binding domain;

[31] the polypeptide complex of [28], wherein an amino acid residue in the CH1 domain linked to the heavy chain Fv fragment of the T cell receptor complex-binding domain has the same type of electric charge as an amino acid in the CL domain linked to the light chain Fv fragment of the antigen-binding domain, and an amino acid residue in the CH1 domain linked to the heavy chain Fv fragment of the antigen-binding domain has the same type of electric charge as an amino acid in the CL domain linked to the light chain Fv fragment of the T cell receptor complex-binding domain;

[32] the polypeptide complex of [29] or [31], wherein an amino acid residue in the CH1 domain linked to the heavy chain Fv fragment of the T cell receptor complex-binding domain has an electric charge opposite to that of an amino acid residue in the CL domain linked to the light chain Fv fragment of the T cell receptor-binding domain;

[33] the polypeptide complex of [30] or [31], wherein an amino acid residue in the CH1 domain linked to the heavy chain Fv fragment of the antigen-binding domain has an electric charge opposite to that of an amino acid residue in the CL domain linked to the light chain Fv fragment of the antigen-binding domain;

[34] the polypeptide complex of any one of [22] to [33], wherein the T cell receptor complex-binding domain is a T cell receptor-binding domain;

[35] the polypeptide complex of [34], wherein the T cell receptor-binding domain is a CD3-binding domain;

[36] the polypeptide complex of [32] or [33], wherein the amino acid residues in the CH1 and CL domains are one, two, or more combinations of amino acid residues selected from the group consisting of the combinations of:

(a) the amino acid residue at position 147 (EU numbering) in the CH1 domain, and the amino acid residue at position 180 (EU numbering) in the CL domain;
(b) the amino acid residue at position 147 (EU numbering) in the CH1 domain, and the amino acid residue at position 131 (EU numbering) in the CL domain;
(c) the amino acid residue at position 147 (EU numbering) in the CH1 domain, and the amino acid residue at position 164 (EU numbering) in the CL domain;
(d) the amino acid residue at position 147 (EU numbering) in the CH1 domain, and the amino acid residue at position 138 (EU numbering) in the CL domain;
(e) the amino acid residue at position 147 (EU numbering) in the CH1 domain, and the amino acid residue at position 123 (EU numbering) in the CL domain; and
(f) the amino acid residue at position 175 (EU numbering) in the CH1 domain, and the amino acid residue at position 160 (EU numbering) in the CL domain;
and in which the amino acid residue in the CH1 domain has an electric charge opposite to that of the amino acid residue in the CL domain;
[37] the polypeptide complex of [36], wherein the amino acid residues are selected from the group additionally comprising the combination of amino acid residues:
(g) the amino acid residue at position 213 (EU numbering) in the CH1 domain, and the amino acid residue at position 123 (EU numbering) in the CL domain;
[38] the polypeptide complex of [36] or [37], wherein the amino acid residue having an opposite electric charge is selected from an amino acid residue in either group:
(X) glutamic acid (E) and aspartic acid (D); or
(Y) lysine (K), arginine (R), and histidine (H);
[39] the polypeptide complex of any one of [36] to [38], wherein the amino acid residues having an opposite electric charge are:
Lys at position 175 (EU numbering) in the CH1 domain, and Glu at positions 131, 160, and 180 (EU numbering) in the CL domain;
[40] the polypeptide complex of any one of [36] to [38], wherein the amino acid residues having an opposite electric charge are:
Glu at positions 147 and 175 (EU numbering) in the CH1 domain, and Lys at positions 131, 160, and 180 (EU numbering) in the CL domain;
[41] the polypeptide complex of [40], wherein the amino acid residue at position 213 (EU numbering) in the CH1 domain is Glu, and the amino acid residue of position 123 (EU numbering) in the CL domain is Lys;
[42] the polypeptide complex of any one of [1] to [41], wherein the Fc domain exhibits impaired Fcγ receptor-binding activity to FcγI, FcγIIA, FcγIIB, FcγIIIA, and/or FcγIIIB;
[43] the polypeptide complex of any one of [1] to [42], wherein the Fc domain is any one of the Fc domains of SEQ ID NOs: 23, 24, 25, and 26 in which an amino acid(s) forming the Fc domain is mutated;
[44] the polypeptide complex of [43], wherein the Fc domain comprises any one of the amino acids below:
the amino acid sequence of positions 118 to 260 (EU numbering) is the sequence of SEQ ID NO: 24; or
the amino acid sequence at positions 261 to 447 (EU numbering) is the sequence of SEQ ID NO: 26;
[45] the polypeptide complex of [43], wherein the amino acids forming the Fc domain comprises a mutation at any one of the following positions:
220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 (EU numbering);
[46] the polypeptide complex of [45], wherein the Fc domain comprises a mutation in the amino acids of SEQ ID NO: 23 forming the Fc domain;
[47] the polypeptide complex of [46], wherein the Fc domain is an Fc domain comprising a substitution of the amino acid at position 233, 234, 235, 236, 237, 327, 330, or 331 (EU numbering) by the amino acid at a corresponding position (EU numbering) in the corresponding IgG2 or IgG4;
[48] the polypeptide complex of [46], wherein the Fc domain comprises an amino acid mutation at position 234, 235, or 297 (EU numbering);
[49] the polypeptide complex of [48], in which the amino acid(s) at position 234, 235, and/or 297 is substituted with alanine;
[50] the polypeptide complex of any one of [43] to [49], wherein the sequences of two polypeptides forming the Fc domain are different from each other;
[51] the polypeptide complex of any one of [1] to [50], wherein the amino acid at position 349 is substituted with cysteine and the amino acid at position 366 (EU numbering) is substituted with tryptophan among the amino acid residues of one of the two polypeptides forming the Fc domain; and wherein the amino acid at position 356 is substituted with cysteine, the amino acid at position 366 is substituted with serine, the amino acid at position 368 is substituted with alanine, and the amino acid at position 407 (EU numbering) is substituted with valine among the amino acid residues of the other polypeptide;
[52] the polypeptide complex of any one of [1] to [50], wherein the amino acid at position 356 (EU numbering) is substituted with lysine among the amino acid residues of one of the two polypeptides forming the Fc domain; the amino acid at position 439 (EU numbering) is substituted with glutamic acid in the other polypeptide; and the amino acid at position 435 (EU numbering) is substituted with arginine among the amino acid residues of either of the two polypeptides;
[53] the polypeptide complex of [51] or [52], wherein the sequence GK is deleted from the carboxyl termini of two polypeptides forming the Fc domain;
[54] the polypeptide complex of any one of [1] to [53], wherein the antigen-binding domains bind to the same epitope;
[55] the polypeptide complex of [54], wherein the same epitope is present in a protein comprising the amino acid sequence of SEQ ID NO: 2;
[56] the polypeptide complex of [54], wherein the same epitope is present in a protein comprising the amino acid sequence of SEQ ID NO: 4;
[57] the polypeptide complex of any one of [1] to [53], wherein the antigen-binding domains each bind to a different epitope;
[58] the polypeptide complex of [57], wherein the different epitope is present in a protein comprising the amino acid sequence of SEQ ID NO: 2;
[59] the polypeptide complex of [57], wherein the different epitope is present in a protein comprising the amino acid sequence of SEQ ID NO: 4;
[60] a polynucleotide encoding the polypeptide complex of any one of [1] to [59];
[61] a vector comprising the polynucleotide of [60];
[62] a cell comprising the vector of [61];

[63] a method for producing a polypeptide complex, which comprises culturing the cell of [62] and isolating the polypeptide complex from the culture supernatant;
[64] a therapeutic agent for inducing cellular cytotoxicity, which comprises as an active ingredient the polypeptide complex of any one of [1] to [59];
[65] the therapeutic agent of [64], wherein the therapeutic agent for inducing cellular cytotoxicity is a therapeutic agent for cancer;
[66] the therapeutic agent of [65], wherein the cancer is liver cancer or lung cancer;
[67] a method for treating or preventing cancer, in which the polypeptide complex of any one of [1] to [59] is administered to a patient in need thereof; and
[68] the therapeutic or preventive method of [67], wherein the cancer is liver cancer or lung cancer.

The present invention also relates to kits for use in a method of the present invention, which contain a polypeptide complex of the present invention or a polypeptide complex produced by a method of the present invention. The present invention also relates to use of a polypeptide complex of the present invention or a polypeptide complex produced by a method of the present invention in producing a therapeutic agent for inducing cellular cytotoxicity. The present invention also relates to polypeptide complexes of the present invention or polypeptide complexes produced by methods of the present invention for use in a method of the present invention.

Effects of the Invention

The present invention provides novel polypeptide complexes that retain the strong anti-tumor activity of BiTE and have a long half-life in blood, as well as excellent safety properties that result in no induction of cancer antigen-independent cytokine storm or such. When the antigen-binding domain of a polypeptide complex of the present invention is substituted, therapeutic agents that comprise the polypeptide complex as an active ingredient for inducing cellular cytotoxicity can target and damage various cells including cancer cells. Thus, various cancers can be treated or prevented. This allows desirable treatments that are highly safe and convenient, and reduce the physical burden for patients.

BRIEF DESCRIPTION OF THE DRAWINGS

FIG. 16 shows diagrams that represent domains forming the following polypeptide complexes described in the Examples herein: GPC3 BiTE, GPC3 ERY2, GPC3 ERY5, GPC3 ERY6, GPC3 ERY7, GPC3 ERY8-2, GPC3 ERY9-1, GPC3 ERY 10-1, GPC3 ERY15, GPC3 ERY18, and GPC3 ERY19-3. The domain with cross-hatched lines represents the H-chain variable region of the anti-cancer antigen (GPC3, EpCAM, EGFR) antibody; the domain with diagonal lines represents the L-chain variable region of the anti-cancer antigen (GPC3, EpCAM, EGFR) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; and the star represents a mutation promoting heteromeric Fc association.

FIG. 18 shows the amino acid residues forming the Fc domains of IgG1, IgG2, IgG3, and IgG4 and their Kabat EU numbering (herein, also called "EU INDEX").

FIG. 24 shows diagrams that represent domains forming the following polypeptide complexes described in the Examples herein: GM1, GM2, and GM0. "A" shows a polypeptide complex in which the CH1/CL interface association is regulated, and Knobs-into-Holes (KiH) modifications are introduced. "B" shows a polypeptide complex that has no regulation of the CH1/CL interface association or introduction of KiH modifications. The domain with cross-hatched lines represents the H-chain variable region of the anti-cancer antigen (GPC3 or EpCAM) antibody; the domain with diagonal lines represents the L-chain variable region of the anti-cancer antigen (GPC3 or EpCAM) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; the star represents a mutation promoting heteromeric Fc association; and the doughnut-shaped symbol represents a mutation regulating the CH1/CL interface interaction.

MODE FOR CARRYING OUT THE INVENTION

Figure 1:
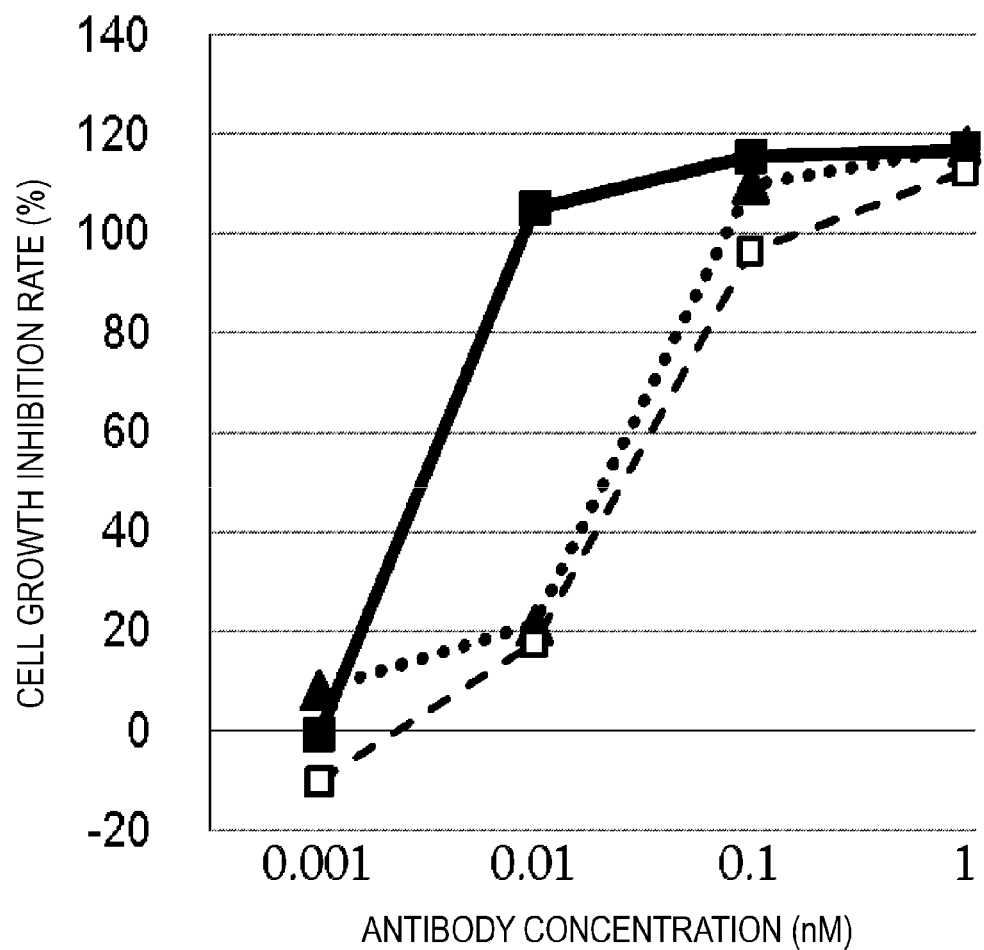
FIG. 1 is a graph showing comparison of the cytotoxic activities of GPC3 ERY1 (GPC3 BiTE), GPC3 ERY2, and an IgG-type anti-GPC3 antibody. Closed square (■), closed triangle (♦), and open square (□) represent the cytotoxic activities of GPC3 ERY1 (GPC3 BiTE), GPC3 ERY2, the IgG-type anti-GPC3 antibody, respectively.

The definitions below are provided to aid understanding of the present invention.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is an example that describes a method for producing an antibody (anti-GPC3 antibody) that binds to GPC3, which belongs to the GPI-anchored receptor family (Int J. Cancer. (2003) 103(4), 455-65). Antibodies that bind to an antigen other than GPC3 can also be produced according to the example described below.

Anti-GPC3 antibodies can be obtained as polyclonal or monoclonal antibodies using known methods. The anti-GPC3 antibodies preferably produced are monoclonal antibodies derived from mammals. Such mammal-derived monoclonal antibodies include antibodies produced by hybridomas or host cells transformed with an expression vector carrying an antibody gene by genetic engineering techniques.

Monoclonal antibody-producing hybridomas can be produced using known techniques, for example, as described below. Specifically, mammals are immunized by conventional immunization methods using a GPC3 protein as a sensitizing antigen. Resulting immune cells are fused with known parental cells by conventional cell fusion methods. Then, hybridomas producing an anti-GPC3 antibody can be selected by screening for monoclonal antibody-producing cells using conventional screening methods.

Specifically, monoclonal antibodies are prepared as mentioned below. First, the GPC3 gene whose nucleotide sequence is disclosed in RefSeq accession number NM_001164617.1 (SEQ ID NO: 1) can be expressed to produce a GPC3 protein shown in RefSeq accession number NP_001158089.1 (SEQ ID NO: 2), which will be used as a sensitizing antigen for antibody preparation. That is, a gene sequence encoding GPC3 is inserted into a known expression vector, and appropriate host cells are transformed with this vector. The desired human GPC3 protein is purified from the host cells or their culture supernatants by known methods. For example, to prepare soluble GPC3 from culture supernatants, amino acids at positions 564 to 580 that form the hydrophobic region corresponding to the GPI-anchor sequence used to anchor GPC3 on the cell membrane are deleted from the GPC3 polypeptide sequence of SEQ ID NO: 2, and then the resulting protein is expressed instead of the GPC3 protein of SEQ ID NO: 2. Alternatively, it is possible to use a purified natural GPC3 protein as a sensitizing antigen.

The purified GPC3 protein can be used as a sensitizing antigen for immunization of mammals. A partial GPC3 peptide may also be used as a sensitizing antigen. In this case, a partial peptide can be prepared by chemical synthesis based on the amino acid sequence of human GPC3, or by inserting a partial GPC3 gene into an expression vector for expression. Alternatively, a partial peptide can be produced by degrading a GPC3 protein with a protease. The length and region of the partial GPC3 peptide are not limited to particular embodiments. A preferred region can be arbitrarily selected from the amino acid sequence at amino acid positions 564 to 580 in the amino acid sequence of SEQ ID NO: 2. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the GPC3 protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing GPC3 to be used as a sensitizing antigen, and immunization methods using GPC3 are specifically described in WO 2003/000883, WO 2004/022754, and WO 2006/006693.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as GPC3; and there is no need to purify the antigen for immunization.

In order to prepare a monoclonal antibody of the present invention using DNA immunization, first, a DNA expressing a GPC3 protein is administered to an animal to be immunized. The GPC3-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized GPC3 can also be produced by the methods described in WO 2003/104453.

After immunizing a mammal as described above, an increase in the titer of a GPC3-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immunocyte. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:
P3(P3x63Ag8.653) (J. Immunol. (1979) 123 (4), 1548-1550);
P3x63Ag8U.1 (Current Topics in Microbiology and Immunology (1978)81, 1-7);
NS-1 (C. Eur. J. Immunol. (1976)6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);

S194/5.XX0.BU.1 (J. Exp. Med. (1978) 148 (1), 313-323); R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, a GPC3-binding monoclonal antibody can bind to GPC3 expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, GPC3-expressing cells are first prepared. Cells preferably used for screening are mammalian cells in which GPC3 is forcedly expressed. As control, the activity of an antibody to bind to cell-surface GPC3 can be selectively detected using non-transformed mammalian cells as host cells. Specifically, hybridomas producing an anti-GPC3 monoclonal antibody can be isolated by selecting hybridomas that produce an antibody which binds to cells forced to express GPC3, but not to host cells.

Alternatively, the activity of an antibody to bind to immobilized GPC3-expressing cells can be assessed based on the principle of ELISA. For example, GPC3-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-GPC3 antibody is prepared from hybridoma cells expressing the anti-GPC3 antibody. For this purpose, total RNA is first extracted from hybridomas. Methods used for extracting mRNAs from cells include, for example:

the guanidine ultracentrifugation method (Biochemistry (1979) 18(24), 5294-5299), and the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ, light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the GPC3-binding activity of a reshaped immunoglobulin as an indicator. For example, when the objective is to isolate an antibody against GPC3, it is more preferred that the binding of the antibody to GPC3 is specific. A GPC3-binding antibody can be screened, for example, by the following steps:
(1) contacting a GPC3-expressing cell with an antibody comprising the V region encoded by a cDNA isolated from a hybridoma;
(2) detecting the binding of the antibody to the GPC3-expressing cell; and
(3) selecting an antibody that binds to the GPC3-expressing cell.

Methods for detecting the binding of an antibody to GPC3-expressing cells are known. Specifically, the binding of an antibody to GPC3-expressing cells can be detected by the above-described techniques such as FACS Immobilized samples of GPC3-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain FIT (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-GPC3 antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-GPC3 antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-GPC3 monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described below, a peptide having the amino acid sequence MGWSCIILFLVATATGVHS (SEQ ID NO: 72) is used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-GPC3 antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 94/11523).

There are various known host cell/expression vector combinations for antibody preparation by introducing isolated antibody genes into appropriate hosts. All of these expression systems are applicable to isolation of the antigen-binding domains and CD3-binding domains of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, TnS, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
yeasts: the *Saccharomyces* genus such as *Saccharomyces cerevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli cells, Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When a polypeptide complex described herein is administered to human, an antigen-binding domain derived from a genetically recombinant antibody that has been artificially modified to reduce the heterologous antigenicity against human and such, can be appropriately used as the antigen-binding domain of the complex. Such genetically recombinant antibodies include, for example, humanized antibodies. These modified antibodies are appropriately produced by known methods.

An antibody variable region used to produce the antigen-binding domain of a polypeptide complex described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

Antigen-Binding Domain

Herein, "antigen-binding domain" refers to an antibody portion which comprises a region that specifically binds and is complementary to the whole or a portion of an antigen. When the molecular weight of an antigen is large, an antibody can only bind to a particular portion of the antigen. The particular portion is called "epitope". An antigen-binding domain can be provided from one or more antibody variable domains. Preferably, the antigen-binding domains contain both the antibody light chain variable region (VL) and antibody heavy chain variable region (VH). Such preferable antigen-binding domains include, for example, "single-chain Fv (scFv)", "single-chain antibody", "Fv", "single-chain Fv2 (scFv2)", "Fab", and "F (ab')2".

The antigen-binding domains of polypeptide complexes of the present invention may bind to the same epitope. The epitope can be present in a protein comprising the amino acid sequence of SEQ ID NO: 2 or 4. Alternatively, the antigen-binding domains of polypeptide complexes of the present invention may individually bind to different epitopes. The epitope can be present in a protein comprising the amino acid sequence of SEQ ID NO: 2 or 4.

Specificity

"Specific" means that a molecule that binds specifically to one or more binding partners does not show any significant binding to molecules other than the partners. Furthermore, "specific" is also used when an antigen-binding domain is specific to a particular epitope of multiple epitopes contained in an antigen. When an epitope bound by an antigen-binding domain is contained in multiple different antigens, a polypeptide complex containing the antigen-binding domain can bind to various antigens that have the epitope.

Antigen

Herein, there is no particular limitation on the antigen, and it is possible to use any antigen except for CD3. Such antigens include, for example, receptors, cancer antigens, MHC antigens, and differentiation antigens. The receptors include, for example, those belonging to the hematopoietic growth factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Receptors belonging to these receptor families and their characteristics are described in various documents, for example, reviews such as Cooke B A., King R J B., van der Molen H J. ed. New Comprehensive Biochemistry Vol. 18B "Hormones and their Actions Part II" pp. 1-46 (1988) Elsevier Science Publishers BV; and SAIBO KOGAKU (Cell Technology) Supplementary Volume Handbook Series "Secchaku Inshi Handbook (Handbook for Adhesion factors)" M. Miyasaka Ed. (1994) Shujunsha, Tokyo, Japan; and Patthy (Cell (1990) 61(1), 13-14); Ullrich et al., (Cell (1990) 61(2), 203-212); Massague (Cell (1992) 69(6), 1067-1070); Miyajima et al., (Annu. Rev. Immunol. (1992) 10, 295-331); Taga et al., (FASEB J. (1992) 6, 3387-3396); Fantl et al., (Annu. Rev. Biochem. (1993), 62, 453-481), Smith et al., (Cell (1994) 76(6) 959-962), Flower D R. Biochim. Biophys. Acta, Flower (Biochim. Biophys. Acta (1999) 1422(3) 207-234.

Specifically, receptors belonging to the above receptor families preferably include, for example, human and mouse erythropoietin (EPO) receptors (Blood (1990) 76(1), 31-35; Cell (1989) 57(2), 277-285), human and mouse granulocyte colony stimulating factor (G-CSF) receptors (Proc. Natl. Acad. Sci. USA. (1990) 87(22), 8702-8706; mG-CSFR, Cell (1990) 61(2), 341-350), human and mouse thrombopoietin (TPO) receptors (Proc. Natl. Acad. Sci. USA (1992) 89(12), 5640-5644; EMBO J. (1993) 12(7), 2645-53), human and mouse insulin receptors (Nature (1985) 313(6005), 756-761), human and mouse Flt-3 ligand receptors (Proc. Natl. Acad. Sci. USA (1994) 91(2), 459-463), human and mouse platelet-derived growth factor (PDGF) receptors (Proc. Natl. Acad. Sci. USA. (1988) 85(10), 3435-3439), human and mouse interferon (IFN)-α and -β receptors (Cell (1990) 60(2), 225-234; and Cell (1994) 77(3), 391-400), human and mouse leptin receptors, human and mouse growth hormone (GH) receptors, human and mouse interleukin (IL)-10 receptors, human and mouse insulin-like growth factor (IGF)-I receptors, human and mouse leukemia inhibitory factor (LIF) receptors, and human and mouse ciliary neurotrophic factor (CNTF) receptors.

Cancer antigens are antigens expressed as cells become malignant, and are also called "tumor-specific antigens". Furthermore, abnormal sugar chains that are expressed on cell surface or protein molecules when the cells become cancerous are also cancer antigens, and are called "cancer-associated carbohydrate antigen". Such cancer antigens include, for example, GPC3 (Int J. Cancer. (2003) 103(4), 455-65), EpCAM (Proc. Natl. Acad. Sci. USA. (1989) 86(1), 27-31), EGFR, CA19-9, CA15-3, and sialyl SSEA-1 (SLX). GPC3 belongs to the above-mentioned GPI-anchored receptor family and is expressed in several types of cancers including liver cancer. EpCAM is expressed in multiple types of cancers including lung cancer, and its polynucleotide and polypeptide sequences are disclosed in RefSeq accession numbers NM_002354.2 (SEQ ID NO: 3) and NP_002345.2 (SEQ ID NO: 4), respectively).

Generally, MHC antigens are categorized into MHC class I and class II antigens. The MHC class I antigens include HLA-A, -B, -C, -E, -F, -G, and -H, while the MHC class II antigens include HLA-DR, -DQ, and -DP.

Differentiation antigens include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Epitope

"Epitope" means an antigenic determinant in an antigen, and refers to an antigen site to which the antigen-binding domain of a polypeptide complex disclosed herein binds. Thus, for example, the epitope can be defined according to its structure. Alternatively, the epitope may be defined according to the antigen-binding activity of a polypeptide complex that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Examples of a method for assessing the epitope binding by a test polypeptide complex containing a GPC3 antigen-binding domain are described below. According to the examples below, methods for assessing the epitope binding by a test polypeptide complex containing an antigen-binding domain for an antigen other than GPC3, can also be appropriately conducted.

For example, whether a test polypeptide complex containing a GPC3 antigen-binding domain recognizes a linear epitope in the GPC3 molecule can be confirmed for example as mentioned below. A linear peptide comprising an amino acid sequence forming the extracellular domain of GPC3 is synthesized for the above purpose. The peptide can be synthesized chemically, or obtained by genetic engineering techniques using a region encoding the amino acid sequence corresponding to the extracellular domain in a GPC3 cDNA. Then, a test polypeptide complex containing a GPC3 antigen-binding domain is assessed for its binding activity towards a linear peptide comprising the amino acid sequence forming the extracellular domain. For example, an immobilized linear peptide can be used as an antigen by ELISA to evaluate the binding activity of the polypeptide complex towards the peptide. Alternatively, the binding activity towards a linear peptide can be assessed based on the level that the linear peptide inhibits the binding of the polypeptide complex to GPC3-expressing cells. These tests can demonstrate the binding activity of the polypeptide complex towards the linear peptide.

Whether a test polypeptide complex containing a GPC3 antigen-binding domain recognizes a conformational epitope can be assessed as follows. GPC3-expressing cells are prepared for the above purpose. A test polypeptide complex containing a GPC3 antigen-binding domain can be determined to recognize a conformational epitope when it strongly binds to GPC3-expressing cells upon contact, but does not substantially bind to an immobilized linear peptide comprising an amino acid sequence forming the extracellular domain of GPC3. Herein, "not substantially bind" means that the binding activity is 80% or less, generally 50% or less, preferably 30% or less, and particularly preferably 15% or less compared to the binding activity towards cells expressing human GPC3.

Methods for assaying the binding activity of a test polypeptide complex containing a GPC3 antigen-binding domain towards GPC3-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using GPC3-expressing cells as antigen.

In the ELISA format, the binding activity of a test polypeptide complex containing a GPC3 antigen-binding domain towards GPC3-expressing cells can be assessed quantitatively by comparing the levels of signal generated by enzymatic reaction. Specifically, a test polypeptide complex is added to an ELISA plate onto which GPC3-expressing cells are immobilized. Then, the test polypeptide complex bound to the cells is detected using an enzyme-labeled antibody that recognizes the test polypeptide complex. Alternatively, when FACS is used, a dilution series of a test polypeptide complex is prepared, and the antibody binding titer for GPC3-expressing cells can be determined to compare the binding activity of the test polypeptide complex towards GPC3-expressing cells.

The binding of a test polypeptide complex towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are Trade Names of Beckman Coulter)

Preferable methods for assaying the binding activity of a test polypeptide complex containing a GPC3 antigen-binding domain towards an antigen include, for example, the following method. First, GPC3-expressing cells are reacted with a test polypeptide complex, and then this is stained with an FITC-labeled secondary antibody that recognizes the polypeptide complex. The test polypeptide complex is appropriately diluted with a suitable buffer to prepare the complex at a desired concentration. For example, the complex can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test polypeptide complex, which is represented by the quantity of the test polypeptide complex bound, can be determined by measuring the Geometric Mean value.

Whether a test polypeptide complex containing a GPC3 antigen-binding domain shares a common epitope with another polypeptide complex can be assessed based on the competition between the two complexes for the same epitope. The competition between polypeptide complexes can be detected by cross-blocking assay or the like. For example, the competitive ELISA assay is a preferred cross-blocking assay.

Specifically, in cross-blocking assay, the GPC3 protein immobilized to the wells of a microtiter plate is pre-incubated in the presence or absence of a candidate competitor polypeptide complex, and then a test polypeptide complex is added thereto. The quantity of test polypeptide complex bound to the GPC3 protein in the wells is indirectly correlated with the binding ability of a candidate competitor polypeptide complex that competes for the binding to the same epitope. That is, the greater the affinity of the competitor polypeptide complex for the same epitope, the lower the binding activity of the test polypeptide complex towards the GPC3 protein-coated wells.

The quantity of the test polypeptide complex bound to the wells via the GPC3 protein can be readily determined by labeling the polypeptide complex in advance. For example, a biotin-labeled polypeptide complex is measured using an avidin/peroxidase conjugate and appropriate substrate. In particular, cross-blocking assay that uses enzyme labels such as peroxidase is called "competitive ELISA assay". The polypeptide complex can also be labeled with other labeling substances that enable detection or measurement. Specifically, radiolabels, fluorescent labels, and such are known.

When the candidate competitor polypeptide complex can block the binding by a test polypeptide complex containing a GPC3 antigen-binding domain by at least 20%, preferably at least 20 to 50%, and more preferably at least 50% compared to the binding activity in a control experiment conducted in the absence of the competitor polypeptide complex, the test polypeptide complex is determined to substantially bind to the same epitope bound by the competitor polypeptide complex, or compete for the binding to the same epitope.

When the structure of an epitope bound by a test polypeptide complex containing a GPC3 antigen-binding domain has already been identified, whether the test and control polypeptide complexes share a common epitope can be assessed by comparing the binding activities of the two polypeptide complexes towards a peptide prepared by introducing amino acid mutations into the peptide forming the epitope.

To measure the above binding activities, for example, the binding activities of test and control polypeptide complexes towards a linear peptide into which a mutation is introduced are compared in the above ELISA format. Besides the ELISA methods, the binding activity towards the mutant peptide bound to a column can be determined by flowing test and control polypeptide complexes in the column, and then quantifying the polypeptide complex eluted in the elution solution. Methods for adsorbing a mutant peptide to a column, for example, in the form of a GST fusion peptide, are known.

Alternatively, when the identified epitope is a conformational epitope, whether test and control polypeptide complexes share a common epitope can be assessed by the following method. First, GPC3-expressing cells and cells expressing GPC3 with a mutation introduced into the epitope are prepared. The test and control polypeptide complexes are added to a cell suspension prepared by suspending these cells in an appropriate buffer such as PBS. Then, the cell suspensions are appropriately washed with a buffer, and an FITC-labeled antibody that recognizes the test and control polypeptide complexes is added thereto. The fluorescence intensity and number of cells stained with the labeled antibody are determined using FACSCalibur (BD). The test and control polypeptide complexes are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control polypeptide complexes, which are represented by the quantity of labeled antibody bound, can be determined by measuring the Geometric Mean value.

In the above method, whether a polypeptide complex does "not substantially bind to cells expressing mutant GPC3" can be assessed, for example, by the following method. First, the test and control polypeptide complexes bound to cells expressing mutant GPC3 are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo-Mean) can be calculated according to the following formula to determine the ratio of increase in fluorescence intensity as a result of the binding by the polypeptide complex.

$$\Delta\text{Geo-Mean}=\text{Geo-Mean (in the presence of the polypeptide complex)}/\text{Geo-Mean (in the absence of the polypeptide complex)}$$

The Geometric Mean comparison value (ΔGeo-Mean value for the mutant GPC3 molecule) determined by the above analysis, which reflects the quantity of a test polypeptide complex bound to cells expressing mutant GPC3, is compared to the ΔGeo-Mean comparison value that reflects the quantity of the test polypeptide complex bound to GPC3-expressing cells. In this case, the concentrations of the test polypeptide complex used to determine the ΔGeo-Mean comparison values for GPC3-expressing cells and cells expressing mutant GPC3 are particularly preferably adjusted to be equal or substantially equal. A polypeptide complex that has been confirmed to recognize an epitope in GPC3 is used as a control polypeptide complex.

If the ΔGeo-Mean comparison value of a test polypeptide complex for cells expressing mutant GPC3 is smaller than the ΔGeo-Mean comparison value of the test polypeptide complex for GPC3-expressing cells by at least 80%, preferably 50%, more preferably 30%, and particularly preferably 15%, then the test polypeptide complex "does not substantially bind to cells expressing mutant GPC3". The formula for determining the Geo-Mean (Geometric Mean) value is described in the CELL QUEST Software User's Guide (BD biosciences). When the comparison shows that the comparison values are substantially equivalent, the epitope for the test and control polypeptide complexes can be determined to be the same.

Variable Fragment (Fv)

Herein, the term "variable fragment (Fv)" refers to the minimum unit of an antibody-derived antigen-binding domain that is composed of a pair of the antibody light chain variable region (VL) and antibody heavy chain variable region (VH). In 1988, Skerra and Pluckthun found that homogeneous and active antibodies can be prepared from the E. coli periplasm fraction by inserting an antibody gene downstream of a bacterial signal sequence and inducing expression of the gene in E. coli (Science (1988) 240(4855), 1038-1041). In the Fv prepared from the periplasm fraction, VH associates with VL in a manner so as to bind to an antigen.

Herein, Fv preferably includes, for example, a pair of Fv which is a polypeptide complex or such comprising:

(1) a bivalent antigen-binding domain which is a bivalent scFv, wherein one monovalent scFv of the bivalent scFv is linked to one polypeptide forming an Fc domain by a heavy-chain Fv fragment forming a CD3-binding domain, and the other monovalent scFv is linked to the other polypeptide forming an Fc domain by a light-chain Fv fragment forming a CD3-binding domain;

(2) a domain comprising an Fc domain that has no Fcγ receptor-binding activity, and which is derived from amino acids forming the Fc domain of IgG1, IgG2a, IgG3, or IgG4; and (3) at least a monovalent CD3-binding domain, wherein the light-chain and heavy-chain Fv fragments associate to form a CD3-binding domain such that it can bind to the CD3 antigen.

scFv, Single-Chain Antibody, and sc(Fv)2

Herein, the terms "scFv", "single-chain antibody", and "sc(Fv)2" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)2 is a single-chain antibody in which four variable regions of two VL and two VH are linked by linkers such as peptide linkers to form a single chain (J. Immunol. Methods (1999) 231(1-2), 177-189). The two VH and two VL may be derived from different monoclonal antibodies. Such sc(Fv)2 preferably includes, for example, a bispecific sc(Fv)2 that recognizes two epitopes present in a single antigen as disclosed in the Journal of Immunology (1994) 152(11), 5368-5374. sc(Fv)2 can be produced by methods known to those skilled in the art. For example, sc(Fv)2 can be produced by linking scFv by a linker such as a peptide linker.

Herein, the form of an antigen-binding domain forming an sc(Fv)2 include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Example order of the form is listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)2 is also described in detail in WO 2006/132352. According to these descriptions, those skilled in the art can appropriately prepare desired sc(Fv)2 to produce the polypeptide complexes disclosed herein.

Furthermore, the polypeptide complexes of the present invention may be conjugated with a carrier polymer such as PEG or an organic compound such as an anticancer agent. Alternatively, a sugar chain addition sequence is preferably inserted into the polypeptide complexes such that the sugar chain produces a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)2 contains three peptide linkers, their length may be all the same or different.

For example, such peptide linkers include:

```
Ser

Gly·Ser

Gly·Gly·Ser

Ser·Gly·Gly (SEQ ID NO: 5)
Gly·Gly·Gly·Ser (SEQ ID NO: 6)
Ser·Gly·Gly·Gly (SEQ ID NO: 7)
Gly·Gly·Gly·Gly·Ser (SEQ ID NO: 8)
Ser·Gly·Gly·Gly·Gly (SEQ ID NO: 9)
Gly·Gly·Gly·Gly·Gly·Ser (SEQ ID NO: 10)
Ser·Gly·Gly·Gly·Gly·Gly (SEQ ID NO: 11)
Gly·Gly·Gly·Gly·Gly·Gly·Ser (SEQ ID NO: 12)
Ser·Gly·Gly·Gly·Gly·Gly·Gly (Gly·Gly·Gly·Gly·Ser (SEQ ID NO: 7))n (Ser·Gly·Gly·Gly·Gly (SEQ ID NO: 8))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS³),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl]sulfone (BSOCOES),
and bis[2-(sulfosuccinimidoxycarbonyloxy)ethyl]sulfone (sulfo-BSOCOES). These crosslinking agents are commercially available.

In general, three linkers are required to link four antibody variable regions together. The linkers to be used may be of the same type or different types.

Fab, F(ab')2, and Fab'

"Fab" consists of a single light chain, and a CH1 domain and variable region from a single heavy chain. The heavy chain of Fab molecule cannot form disulfide bonds with another heavy chain molecule.

"F(ab')2" or "Fab" is produced by treating an immunoglobulin (monoclonal antibody) with a protease such as pepsin and papain, and refers to an antibody fragment generated by digesting an immunoglobulin (monoclonal antibody) at near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CHγ1 (γ1 region in an H-chain constant region) via a disulfide bond at their C-terminal regions. Each of these two homologous antibody fragments is called Fab'.

"F(ab')2" consists of two light chains and two heavy chains comprising the constant region of a CH1 domain and a portion of CH2 domains so that disulfide bonds are formed between the two heavy chains. The F(ab')2 forming a polypeptide complex disclosed herein can be preferably produced as follows. A whole monoclonal antibody or such comprising a desired antigen-binding domain is partially digested with a protease such as pepsin; and Fc fragments are removed by adsorption onto a Protein A column. The protease is not particularly limited, as long as it can cleave the whole antibody in a selective manner to produce F(ab')2 under an appropriate setup enzyme reaction condition such as pH. Such proteases include, for example, pepsin and ficin.

Fc Domain

An Fc domain that forms a polypeptide complex disclosed herein can be preferably produced in the following manner. An antibody such as a monoclonal antibody is partially digested with a protease such as pepsin. Then, the resulting fragment is adsorbed onto a Protein A or Protein G column, and eluted with an appropriate elution buffer. The protease is not particularly limited, as long as it can cleave antibodies such as monoclonal antibodies under an appropriate setup enzyme reaction condition such as pH. Such proteases include, for example, pepsin and ficin.

The polypeptide complexes described herein comprise an Fc domain with reduced Fcγ receptor-binding activity, which includes amino acids forming the Fc domain of IgG1, IgG2, IgG3, or IgG4.

Antibody isotype is determined according to the structure of the constant region. Constant regions of the isotypes IgG1, IgG2, IgG3, and IgG4 are called Cγ1, Cγ2, Cγ3, and Cγ4, respectively. The amino acid sequences of Fc domain polypeptides forming human Cγ1, Cγ2, Cγ3, and Cγ4 are exemplified in SEQ ID NO: 23, 24, 25, and 26, respectively. The relationship between amino acid residues forming each amino acid sequence and Kabat's EU numbering (herein also referred to as EU INDEX) are shown in FIG. 18.

The Fc domain refers to the region besides F(ab')2 which comprises two light chains and two heavy chains comprising a portion of the constant region that comprises a CH1 domain and a region between the CH1 and CH2 domains so that disulfide bonds are formed between the two heavy chains. The Fc domain forming a polypeptide complex disclosed herein can be preferably produced as follows. A monoclonal IgG1, IgG2, IgG3, or IgG4 antibody or the like is partially digested with a protease such as pepsin, followed by elution of the fraction adsorbed onto a Protein A column. The protease is not particularly limited, as long as it can cleave the whole antibody in a selective manner to produce F(ab')2 in an appropriate setup enzyme reaction condition such as pH. Such proteases include, for example, pepsin and ficin.

Fcγ Receptor

Fcγ receptor refers to a receptor capable of binding to the Fc domain of monoclonal IgG1, IgG2, IgG3, or IgG4 antibodies, and includes all members belonging to the family of proteins substantially encoded by an Fcγ receptor gene. In human, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (CD16-2), as well as all unidentified mouse FcγRs, FcγR isoforms, and allotypes thereof. Such preferred Fcγ receptors include, for example, human FcγI (CD64), FcγIIA (CD32), FcγIIB (CD32), FcγIIIA (CD16), and/or FcγIIIB (CD16). The polynucleotide sequence and amino acid sequence of FcγI are shown in SEQ ID NOs: 13 (NM_000566.3) and 14 (NP_000557.1), respectively; the polynucleotide sequence and amino acid sequence of FcγIIA are shown in SEQ ID NOs: 15 (BC020823.1) and 16 (AAH20823.1), respectively; the polynucleotide sequence and amino acid sequence of FcγIIB are shown in SEQ ID NOs: 17 (BC146678.1) and 18 (AAI46679.1), respectively; the polynucleotide sequence and amino acid sequence of FcγIIIA are shown in SEQ ID NOs: 19 (BC033678.1) and 20 (AAH33678.1), respectively; and the polynucleotide sequence and amino acid sequence of FcγIIIB are shown in SEQ ID NOs: 21 (BC128562.1) and 22 (AAI28563.1), respectively (RefSeq accession number is shown in each parentheses). Whether an Fcγ receptor has binding activity to the Fc domain of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, FcγR, FcaR, FccR, FcRn, Clq, and C3, mannan-binding lectin, mannose receptor, *Staphylococcus* Protein A, *Staphylococcus* Protein G, and viral FcγRs. The Fc ligands also include Fc receptor homologs (FcRH) (Davis et al., (2002) Immunological Reviews 190, 123-136), which are a family of Fc receptors homologous to FcγR. The Fc ligands also include unidentified molecules that bind to Fc.

Fcγ Receptor-Binding Activity

The impaired binding activity of Fc domain to any of the Fcγ receptors FcγI, FcγIIA, FcγIIB, FcγIIIA, and/or FcγIIIB can be assessed by using the above-described FACS and ELISA formats as well as ALPHA screen (Amplified Luminescent Proximity Homogeneous Assay) and surface plasmon resonance (SPR)-based BIACORE method (Proc. Natl. Acad. Sci. USA (2006) 103(11), 4005-4010).

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled polypeptide complex is immobilized to the donor beads and glutathione S-transferase (GST)-tagged Fcγ receptor is immobilized to the acceptor beads. In the absence of a polypeptide complex comprising a competitive mutant Fc domain, Fcγ receptor interacts with a polypeptide complex comprising a wild-type Fc domain, inducing a signal of 520 to 620 nm as a result. The polypeptide complex having a non-tagged mutant Fc domain competes with the polypeptide complex comprising a wild-type Fc domain for the interaction with Fcγ receptor. The relative binding affinity can be determined by quantifying the reduction of fluorescence as a result of competition. Methods for biotinylating the polypeptide complexes such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE methods. Examples of such inhibition assay are described in Proc. Natl. Acad. Sci. USA (2006) 103(11), 4005-4010.

Herein, "Fcγ receptor-binding activity is reduced" means, for example, that based on the above-described analysis method the competitive activity of a test polypeptide complex is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control polypeptide complex.

Polypeptide complexes comprising the Fc domain of a monoclonal IgG1, IgG2, IgG3, or IgG4 antibody can be appropriately used as control polypeptide complexes. The Fc domain structures are shown in SEQ ID NOs: 23 (A is added to the N terminus of RefSeq accession number AAC82527.1), 24 (A is added to the N terminus of RefSeq accession number AAB59393.1), 25 (A is added to the N terminus of RefSeq accession number CAA27268.1), and 26 (A is added to the N terminus of RefSeq accession number AAB59394.1). Furthermore, when a polypeptide complex comprising an Fc domain mutant of an antibody of a particular isotype is used as a test substance, the effect of the mutation of the mutant on the Fcγ receptor-binding activity is assessed using as a control a polypeptide complex comprising an Fc domain of the same isotype. As described above, polypeptide complexes comprising an Fc domain mutant whose Fcγ receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1(1), 47-54); C226S, C229S, E233P, L234V, and L235A (Blood (2007) 109, 1185-1192).

Specifically, the preferred polypeptide complexes include those comprising an Fc domain with a substitution of the amino acid at position 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering) in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

The preferred polypeptide complexes include, for example, those comprising an Fc domain which has any one of the substitutions shown below, whose positions are specified according to EU numbering (each number represents the position of an amino acid residue in the EU numbering; and the one-letter amino acid symbol before the number represents the amino acid residue before substitution, while the one-letter amino acid symbol after the number represents the amino acid residue before the substitution) in the amino acids forming the Fc domain of IgG1 antibody:

(a) L234F, L235E, P331S;
(b) C226S, C229S, P238S;
(c) C226S, C229S; or
(d) C226S, C229S, E233P, L234V, L235A;

as well as those having an Fc domain which has a deletion of the amino acid sequence at positions 231 to 238.

Furthermore, the preferred polypeptide complexes also include those comprising an Fc domain that has any one of the substitutions shown below, whose positions are specified according to EU numbering in the amino acids forming the Fc domain of an IgG2 antibody:

(e) H268Q, V309L, A330S, and P331S;
(f) V234A;
(g) G237A;
(h) V234A and G237A;
(i) A235E and G237A; or
(j) V234A, A235E, and G237A. Each number represents the position of an amino acid residue in EU numbering; and the one-letter amino acid symbol before the number represents the amino acid residue before substitution, while the one-letter amino acid symbol after the number represents the amino acid residue before the substitution.

Furthermore, the preferred polypeptide complexes also include those comprising an Fc domain that has any one of the substitutions shown below, whose positions are specified according to EU numbering in the amino acids forming the Fc domain of an IgG3 antibody:

(k) F241A;
(l) D265A; or
(m) V264A. Each number represents the position of an amino acid residue in EU numbering; and the one-letter amino acid symbol before the number represents the amino acid residue before substitution, while the one-letter amino acid symbol after the number represents the amino acid residue before the substitution.

Furthermore, the preferred polypeptide complexes also include those comprising an Fc domain that has any one of the substitutions shown below, whose positions are specified according to EU numbering in the amino acids forming the Fc domain of an IgG4 antibody:

(n) L235A, G237A, and E318A;
(o) L235E; or
(p) F234A and L235A. Each number represents the position of an amino acid residue in EU numbering; and the one-letter amino acid symbol before the number represents the amino acid residue before substitution, while the one-letter amino acid symbol after the number represents the amino acid residue before the substitution.

The other preferred polypeptide complexes include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

The preferred polypeptide complexes also include, for example, those comprising an Fc domain in which any one or more of the amino acids at positions 234, 235, and 297 (EU numbering) in the amino acids forming the Fc domain of an IgG1 antibody is substituted with other amino acids. The type of amino acid after substitution is not particularly limited; however, the polypeptide complexes comprising an Fc domain in which any one or more of the amino acids at positions 234, 235, and 297 are substituted with alanine are particularly preferred.

The preferred polypeptide complexes also include, for example, those comprising an Fc domain in which an amino acid at position 265 (EU numbering) in the amino acids forming the Fc domain of an IgG1 antibody is substituted with another amino acid. The type of amino acid after substitution is not particularly limited; however, polypeptide complexes comprising an Fc domain in which an amino acid at position 265 is substituted with alanine are particularly preferred.

Fc Domain Derived from Bispecific Antibody

Herein, appropriate Fc domains derived from bispecific antibody are also used as an Fc domain with reduced Fcγ receptor-binding activity. A bispecific antibody is an antibody having two different specificities. The IgG-type bispecific antibody can be secreted from hybrid hybridoma (quadroma) produced by fusing two types of IgG antibody-producing hybridomas (Milstein C et al., Nature (1983) 305, 537-540).

Alternatively, the IgG-type bispecific antibody can also be secreted by introducing a total of four genes, genes of the L chains and H chains forming two types of IgGs of interest, into cells and co-expressing them. However, in theory, there are ten combinations of IgG H chains and L chains produced by such methods. It is difficult to purify IgG consisting of a desired combination of H chain and L chain from ten types of IgGs. In addition, in theory the amount of secreted IgG with a desired combination is also significantly reduced, which requires large scale culture. This further increases the production cost.

In this case, an appropriate amino acid substitution can be introduced into the CH3 domain forming an H-chain Fc domain in order to preferentially secrete IgG with a heterologous combination of H chains. Specifically, this method is conducted by substituting an amino acid having a larger side chain (knob (which means "bulge")) for an amino acid in the CH3 domain of one of the H chains, and substituting an amino acid having a smaller side chain (hole (which means "void")) for an amino acid in the CH3 domain of the other H chain so that the knob is placed in the hole. This promotes heteromeric H chain formation and simultaneously inhibits homomeric H chain formation (WO 1996/027011; Ridgway J B et al., Protein Engineering (1996) 9, 617-621; Merchant A M et al., Nature Biotechnology (1998) 16, 677-681).

On the other hand, with respect to the L chain, the L-chain variable region is less polymorphic than the H-chain variable region, and thus obtaining a common L chain that can confer binding ability to both H chains is expected. Efficient expression of a bispecific IgG can be achieved by introducing the genes of such a common L chain and two H chains into cells to express the IgG (Nature Biotechnology (1998) 16, 677-681). However, it is difficult to realize this idea because the probability that two types of antibodies containing the same L chain are randomly selected is low. Thus, a method for selecting a common L chain which shows strong binding ability to any different H chains is proposed (WO 2004/065611).

Furthermore, there are also known techniques for producing a bispecific antibody by applying methods for controlling polypeptide association, or association of polypeptide-formed heteromeric multimers to the association between the two polypeptides that form an Fc domain. Specifically, methods for controlling polypeptide association may be employed to produce a bispecific antibody (WO 2006/106905), in which amino acid residues forming the interface between two polypeptides that form the Fc domain are altered to inhibit the association between Fc domains having the same sequence and to allow the formation of polypeptide complexes formed by two Fc domains of different sequences.

The above-described two polypeptides forming an Fc domain derived from a bispecific antibody can be appropriately used as a domain encompassing an Fc domain of the present invention. More specifically, such preferred two polypeptides forming an Fc domain include those in which amino acids at positions 349 and 366 (EU numbering) in the amino acid sequence of one polypeptide are cysteine and tryptophan, respectively, and amino acids at positions 356, 366, 368, and 407 (EU numbering) in the amino acid sequence of the other polypeptide are cysteine, serine, alanine, and valine, respectively.

In another embodiment, preferred domains encompassing an Fc domain of the present invention include two polypeptides forming an Fc domain, in which amino acid at position 409 (EU numbering) in the amino acid sequence of one polypeptide is aspartic acid, and amino acid at position 399 (EU numbering) in the amino acid sequence of the other polypeptide is lysine. In the above embodiment, amino acid at position 409 may be glutamic acid instead of aspartic acid, while the amino acid at position 399 may be arginine instead of lysine. Furthermore, aspartic acid at position 360 or 392 can also be preferably combined with lysine at position 399.

In another embodiment, preferred domains encompassing an Fc domain of the present invention include two polypeptides forming an Fc domain, in which the amino acid at position 370 (EU numbering) in the amino acid sequence of one polypeptide is glutamic acid, and the amino acid at position 357 (EU numbering) in the amino acid sequence of the other polypeptide is lysine.

In still another embodiment, preferred domains encompassing an Fc domain of the present invention include two polypeptides forming an Fc domain, in which amino acid at position 439 (EU numbering) in the amino acid sequence of one polypeptide is glutamic acid, and amino acid at position 356 (EU numbering) in the amino acid sequence of the other polypeptide is lysine.

In addition, preferred domains encompassing an Fc domain of the present invention include embodiments with a combination thereof:

two polypeptides forming an Fc domain, in which amino acids at positions 409 and 370 (EU numbering) in the amino acid sequence of one polypeptide are aspartic acid and glutamic acid, respectively, and amino acids at positions 399 and 357 (EU numbering) in the amino acid sequence of the other polypeptide are both lysine (in this embodiment, glutamic acid at position 370 may be replaced with aspartic acid, and glutamic acid at position 370 may be replaced with aspartic acid at position 392);

two polypeptides forming an Fc domain, in which amino acids at positions 409 and 439 (EU numbering) in the amino acid sequence of one polypeptide are aspartic acid and glutamic acid, respectively, and amino acids at positions 399 and 356 (EU numbering) in the amino acid sequence of the other polypeptide are both lysine (in this embodiment, glutamic acid at position 439 may be replaced with aspartic acid at position 360, 392, or 439);

two polypeptides forming an Fc domain, in which amino acids at positions 370 and 439 (EU numbering) in the amino acid sequence of one polypeptide are both glutamic acid, and amino acids at positions 357 and 356 (EU numbering) in the amino acid sequence of the other polypeptide are both lysine; and two polypeptides forming an Fc domain, in which amino acids at positions 409, 370, and 439 (EU numbering) in the amino acid sequence of one polypeptide are aspartic acid, glutamic acid, and glutamic acid, respectively, and amino acids at positions 399, 357, and 356 (EU numbering) in the amino acid sequence of the other polypeptide are all lysine (in this embodiment, the amino acid at position 370 may not be substituted with glutamic acid; alternatively, instead of substituting amino acid at position 370 with glutamic acid, glutamic acid at position 439 may be replaced with aspartic acid, or glutamic acid at position 439 may be replaced with aspartic acid at position 392).

In yet another embodiment, preferred domains encompassing an Fc domain of the present invention include two polypeptides forming an Fc domain, in which amino acid at position 356 (EU numbering) in the amino acid sequence of one polypeptide is lysine, and amino acids at positions 435 and 439 (EU numbering) in the amino acid sequence of the other polypeptide are arginine and glutamic acid, respectively.

When the above-described two polypeptides forming an Fc domain derived from a bispecific antibody are used as a domain encompassing an Fc domain of the present invention, antigen-binding domains and/or CD3-binding domains of the present invention can be arranged in a desired combination.

Fc Domain with Reduced C-Terminal Heterogeneity

Herein, Fc domains with improved Fc domain C-terminal heterogeneity in addition to the above-described characteristic are appropriately used as Fc domains with reduced Fcγ receptor-binding activity. More specifically, the present invention provides Fc domains in which glycine and lysine at positions 446 and 447 (EU numbering), respectively, in the amino acid sequences of two polypeptides forming an Fc domain derived from IgG1, IgG2, IgG3, or IgG4 are deleted.

T Cell Receptor Complex-Binding Domain

Herein, "T cell receptor complex-binding domain" refers to a portion of a T cell receptor complex antibody, which comprises a region that specifically binds and is complementary to the whole or a portion of a T cell receptor complex. Such T cell receptor complex may be T cell receptor itself, or an adaptor molecule that together with the T cell receptor forms the T cell receptor complex. A preferred adaptor is CD3.

T Cell Receptor-Binding Domain

Herein, "T cell receptor-binding domain" refers to a portion of a T cell receptor antibody, which comprises a region that specifically binds and is complementary to the whole or a portion of a T cell receptor.

It is possible to use the variable region or constant region of a T cell receptor. However, preferred epitopes to which a CD3-binding domain binds are those located in the constant region. Sequences of the constant region include, for example, those of the T cell receptor α chain (RefSeq accession number CAA26636.1; SEQ ID NO: 67), T cell receptor β chain (RefSeq accession number C25777; SEQ ID NO: 68), T cell receptor γ1 chain (RefSeq accession number A26659; SEQ ID NO: 69), T cell receptor γ2 chain (RefSeq accession number AAB63312.1; SEQ ID NO: 70), and T cell receptor δ chain (RefSeq accession number AAA61033.1; SEQ ID NO: 71).

CD3-Binding Domain

Herein, "CD3-binding domain" refers to a portion of a CD3 antibody, which comprises a region that specifically binds and is complementary to the whole or a portion of CD3. The CD3-binding domain can be derived from one or more antibody variable domains. Preferably, the CD3-binding domain includes both CD3 antibody light chain variable region (VL) and CD3 antibody heavy chain variable region (VH). Such preferred CD3-binding domains include, for example, "single-chain Fv (scFv)", "single chain antibody", "Fv", "single-chain Fv2 (scFv2)", "Fab", and "F(ab')2".

The CD3-binding domain of the present invention may bind to any epitope, as long as the epitope is located within the γ chain, δ chain, or ε chain sequence forming human CD3. In the present invention, preferred CD3-binding domains include those comprising a CD3 antibody light chain variable region (VL) and a CD3 antibody heavy chain variable region (VH), which bind to an epitope in the extracellular domain of the ε chain of a human CD3 complex. Such preferred CD3-binding domains include those comprising a CD3 antibody light chain variable region (VL) and a CD3 antibody heavy chain variable region (VH) of antibody OKT3 (Proc. Natl. Acad. Sci. USA (1980) 77, 4914-4917) or various known CD3 antibodies. Furthermore, such appropriate CD3-binding domains include those derived from a CD3 antibody with desired characteristics, which are obtained by immunizing a desired animal with the γ chain, δ chain, or ε chain forming human CD3 by the above-described methods. Appropriate anti-CD3 antibodies from which a CD3-binding domain is derived include human antibodies and antibodies appropriately humanized as described above. The structures of γ chain, δ chain, and ε chain forming CD3 are shown as polynucleotide sequences in SEQ ID NOs: 27 (NM_000073.2), 29 (NM_000732.4), and 31 (NM_000733.3), respectively, and as polypeptide sequences in SEQ ID NO: 28 (NP_000064.1), 30 (NP_000723.1), and 32 (NP_000724.1), respectively (RefSeq accession number is shown in parentheses).

Polypeptide Complex

The structure of a polypeptide complex of the present invention is not limited, as long as it contains
(1) an antigen-binding domain;
(2) a domain comprising an Fc domain with reduced Fcγ receptor-binding activity; and
(3) a T cell receptor complex-binding domain, as described above.

In the present invention, the preferred T cell receptor complex-binding domain is a T cell receptor-binding domain or CD3-binding domain. Each of the domains described above may be linked directly via peptide linkage. For example, (1) F(ab')2 is used as the antigen-binding domain, and (2) an Fc domain with reduced Fcγ receptor-binding activity is used as the domain comprising an Fc domain with reduced Fcγ receptor-binding activity. In this case, when the antigen-binding domain of (1) is linked via a peptide bond to the domain comprising an Fc domain of (2), the linked polypeptide forms an antibody structure. Such an antibody may be prepared by purifying the culture media of the above-described hybridoma or purifying culture media of desired host cells stably carrying the polynucleotide that encodes the antibody-forming polypeptide.

When the CD3-binding domain of (3) is linked to the antibody structure, the CD3-binding domain may be linked via peptide bond to the C terminus of the constant region of the antibody structure. In another embodiment, the CD3-binding domain is linked via peptide bond to the N terminus of the heavy chain variable region or light chain variable region of the antibody structure. In the other embodiment, the CD3-binding domain may be linked via peptide bond to the C terminus of the light chain constant region of the antibody structure. The CD3-binding domain to be linked may have any desired structure; however, such an appropriate CD3-binding domain includes preferably Fv, and more preferably scFv. The valency of the CD3-binding domain that binds to the antibody structure is not limited. To link a divalent CD3-binding domain to the antibody structure, a monovalent CD3-binding domain may be linked via peptide bond to the respective C termini of two Fc domains forming the constant region of the antibody structure. Alternatively, to link a divalent CD3-binding domain to the antibody structure, a divalent scFv (i.e., sc(Fv)2) may be linked via peptide bond to the C terminus of one of the two Fc domains. In this case, the polypeptide complex in which a divalent scFv (i.e., sc(Fv)2) is linked to the C terminus of only one of the two Fc domains forming the constant region of the antibody structure is efficiently produced by using an above-described Fc domain derived from a bispecific antibody. Alternatively, to link a monovalent CD3-binding domain to the antibody structure, a monovalent scFv may be linked via peptide bond to the C terminus of one of the two Fc domains. In this case, a polypeptide complex of the present invention in which a monovalent scFv is linked to the C terminus of only one of the two Fc domains forming the constant region of the antibody structure is efficiently produced by using an above-described Fc domain derived from a bispecific antibody.

Furthermore, when the CD3-binding domain of (3) is linked via peptide bond to the C terminus of the constant region of the antibody structure, the appropriate polypeptide complexes include those in which the heavy chain Fv fragment forming the CD3-binding domain is linked to the C terminus of one constant region (CH3 domain) forming the Fc domain, and the light chain Fv fragment forming the CD3-binding domain is linked to the C terminus of the other constant region (CH3 domain) forming the Fc domain. In this case, an appropriate linker such as Gly-Gly-Gly-Gly-Ser (SEQ ID NO: 7) is inserted to link the heavy chain or light chain Fv fragment to the C terminus of the constant region (CH3 domain). The number of repeats in the linker is not limited; however, it is selected from 1 to 10, preferably 2 to 8, or more preferably 2 to 6. Specifically, it is possible to insert an appropriate linker in which the number of [Gly-Gly-Gly-Gly-Ser] (SEQ ID NO: 7) repeats is 1, 2, 3, 4, 5, 6, 7, 8, 9, or 10.

Alternatively, when a polypeptide complex is produced in which the heavy chain Fv fragment forming the CD3-binding domain is linked to the C terminus of one constant region (CH3 domain) forming the Fc domain and the light chain Fv fragment of the CD3-binding domain is linked to the C terminus of the other constant region (CH3 domain) forming the Fc domain, appropriate alterations of amino acid residues that allow formation of disulfide bonds between the heavy chain Fv fragment and light chain Fv fragment can be used to enhance the association between the heavy chain Fv fragment and light chain Fv fragment.

In another embodiment, when a polypeptide complex of the present invention in which the heavy chain Fv fragment forming the CD3-binding domain is linked to the C terminus of one constant region (CH3 domain) forming the Fc domain and the light chain Fv fragment forming the CD3-binding domain is linked to the C terminus of the other constant region (CH3 domain) forming the Fc domain is produced, antibody CH1 and CL domains can be linked to each of the heavy chain Fv fragment and light chain Fv fragment to enhance the association between the heavy chain Fv fragment and light chain Fv fragment.

In still another embodiment, in order to link a divalent CD3-binding domain to the antibody structure, a monovalent CD3-binding domain may be linked via peptide bond to the respective C termini of two light chain constant regions or the respective N termini of the light chain variable regions of the antibody structure. Alternatively, in order to link a divalent CD3-binding domain to the antibody structure, a divalent scFv (i.e., sc(Fv)2) may be linked via peptide bond to the respective C termini of two light chain constant regions or the respective N termini of light chain variable regions. In this case, polypeptide complexes in which a divalent scFv (i.e., sc(Fv)2) is linked to the C or N terminus of one of the two light chain variable regions of the antibody structure can be efficiently produced by using an above-described Fc domain derived from a bispecific antibody. Alternatively, in order to link a monovalent CD3-binding domain to the antibody structure, a monovalent scFv may be linked via peptide bond to the C or N terminus of one of the two light chain variable regions. In this case, polypeptide complexes of the present invention in which a monovalent scFv is linked to the N or C terminus of one light chain variable region of the two light chain variable regions of the antibody structure can be efficiently produced by using an above-described Fc domain derived from a bispecific antibody.

In another embodiment, in order to link a divalent CD3-binding domain to the antibody structure, a monovalent CD3-binding domain may be linked via peptide bond to the respective N termini of two heavy chain variable regions of the antibody structure. Alternatively, in order to link a divalent CD3-binding domain to the antibody structure, a divalent scFv (i.e., sc(Fv)2) may be linked via peptide bond to the N terminus of one of the two heavy chain variable regions. In this case, polypeptide complexes in which a divalent scFv (i.e., sc(Fv)2) is linked to the N terminus of only one of two heavy chain variable regions of the antibody structure can be efficiently produced by using an above-described Fc domain derived from bispecific antibody. Alternatively, in order to link a monovalent CD3-binding domain to the antibody structure, a monovalent scFv may be linked via peptide bond to the N terminus of one of the two heavy chain variable regions. In this case, polypeptide complexes of the present invention in which a monovalent scFv is linked to the N terminus of one of the two heavy chain variable regions of the antibody structure can be efficiently produced by using an above-described Fc domain derived from a bispecific antibody.

Furthermore, an above-described polypeptide complex can be produced by linking each domain directly via peptide bond or by peptide binding via a peptide linker. In this case, the linker to be used includes the linker described above as an example and appropriate linkers with a peptide tag, for example, His-tag, HA-tag, myc-tag, or FLAG-tag. In addition, it is preferred to use the property of mutual binding based on hydrogen bonding, disulfide linkage, covalent bonding, or ionic interaction, or a combination thereof. For example, it is possible to employ the affinity between antibody CH1 and CL, or the above-described Fc domains derived from a bispecific antibody may be used for the hetermomeric association of Fc domains. Moreover, inter-domain disulfide bonds can be preferably used as described in the Examples.

In another structure of the polypeptide complex of the present invention, for example, a monovalent Fv and a monovalent Fab are preferably used as (1) the antigen binding domain. In this case, the following structure is used. The heavy chain Fv fragment (VH) or light chain Fv fragment (VL) of monovalent Fv is linked via peptide bond to the heavy chain CH1 domain. The heavy chain CH1 domain is linked via peptide bond to one of (2) the two Fc domains with reduced Fcγ receptor-binding activity which form the polypeptide complex of the present invention. The other VL or VH fragment of the monovalent Fv is linked via peptide bond to the light chain CH domain which is linked via disulfide bond to the heavy chain CH1 domain. Thus, VH and VL respectively linked to the termini of heavy chain CH1 domain and light chain CL domain form an antibody-binding domain. sc(Fv)2 which forms both the (1) antibody-binding domain and (3) CD3-binding domain may be linked via peptide bond to the N terminus of the other Fc domain of the two described above. In this case, a polypeptide complex having a structure in which the heavy chain CH1 domain is linked via peptide bond to one of the two Fc domains forming the polypeptide complex, and sc(Fv)2 is linked via peptide bond to the other Fc domain can be produced by using an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG-tag.

In another preferred structure of the polypeptide complex of the present invention, for example, a divalent scFv is also used as (1) the antigen-binding domain. In an embodiment of the structure, it is also possible to produce a polypeptide complex in which one of the divalent scFvs is linked via peptide bond through VH forming (3) the CD3-binding domain to one of the two (2) Fc domains with reduced Fcγ receptor-binding activity, and the other divalent scFv is linked via peptide bond through VL forming (3) the CD3-binding domain to one of the two (2) Fc domains with reduced Fcγ receptor-binding activity. In this case, it is possible to use an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG-tag.

In another embodiment of the structure where a divalent scFv is used as (1) the antigen-binding domain, it is possible to produce a polypeptide complex in which one of the divalent scFv is linked via peptide bond scFv forming (3) the CD3-binding domain to one of the two (2) Fc domains with reduced Fcγ receptor-binding activity, and the other divalent scFv is linked via peptide bond to the other (2) Fc domain with reduced Fcγ receptor. In this case, a polypeptide complex in which scFv forming the antigen-binding domain is linked via peptide bond through scFv forming the CD3-binding domain to one of the two Fc domains forming the polypeptide complex, and scFv forming the antigen-binding domain is linked via peptide bond to the other Fc domain can be produced by using an above-described Fc domain derived from a bispecific antibody. The above-described polypeptide complex can be produced by linking each domain directly via peptide bond or by peptide binding via a peptide linker. In this case, the linker to be used includes the linkers described above as an example and appropriate linkers with a peptide tag, for example, His-tag, HA-tag, myc-tag, or FLAG-tag.

In another preferred structure of the polypeptide complex of the present invention, for example, both antigen-binding domain and T cell receptor complex-binding domain are each a structure of monovalent Fab. In an embodiment of the structure, it is possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a heavy chain Fv fragment of Fab forming the T cell receptor-binding domain is linked through a CH1 domain to the other polypeptide forming the Fc domain and a light chain Fv fragment of the Fab is linked to a CL domain.

In another embodiment of the structure, it is also possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a light chain Fv fragment of an Fab forming the T cell receptor-binding domain is linked through a CH1 domain to the other polypeptide forming the Fc domain and a heavy chain Fv fragment of the Fab is linked to a CL domain. Alternatively, it is also possible to produce a polypeptide complex in which a heavy chain Fv fragment of monovalent Fab forming the T cell receptor-binding domain is linked through a CH1 domain to one polypeptide forming an Fc domain and a light chain Fv fragment of the Fab is linked to a CL domain, while a light chain Fv fragment of an Fab forming the antigen-binding domain is linked through a CH1 domain to the other polypeptide forming an Fc domain and a heavy chain Fv fragment of the Fab is linked to a CL domain.

In another embodiment of the structure, it is also possible to produce a polypeptide complex in which a heavy chain Fv fragment of a monovalent Fab forming the antigen-binding domain is linked through a CH1 domain to one polypeptide forming an Fc domain and a light chain Fv fragment of the Fab is linked to a CL domain, while a heavy chain Fv fragment of Fab forming the T cell receptor-binding domain is linked through a CL domain to the other polypeptide forming an Fc domain and a light chain Fv fragment of the Fab is linked to a CH1 domain. Alternatively, it is also possible to produce a polypeptide complex in which a heavy chain Fv fragment of a monovalent Fab forming the T cell receptor-binding domain is linked through a CH1 domain to one polypeptide forming an Fc domain and a light chain Fv fragment of the Fab is linked to a CL domain, while a heavy chain Fv fragment of Fab forming the antigen-binding domain is linked through a CL domain to the other polypeptide forming an Fc domain and a light chain Fv fragment of the Fab is linked to a CH1 domain.

In an embodiment of another structure of the polypeptide complex of the present invention in which both antigen-binding domain and T cell receptor complex-binding domain are each a structure of monovalent Fab, the preferred polypeptides of the present invention include those that have:

(1) an antigen-binding domain in which a heavy chain Fv fragment of a monovalent Fab structure that binds to an antigen is linked through a CH1 domain to one of the above-described polypeptides forming an Fc domain and a light chain Fv fragment of the Fab structure is linked to a CL domain; and (2) a T cell receptor complex-binding domain in which a heavy chain Fv fragment of a monovalent Fab structure that binds to an T cell receptor complex is linked through a CH1 domain to the other polypeptide forming an Fc domain and a light chain Fv fragment of the Fab structure is linked to a CL domain;

and in which the electric charges of the CH1 and CL domains are controlled so that the heavy chain Fv fragment of the antigen-binding domain is associated with the light chain Fv fragment of the antigen-binding domain, or the heavy chain Fv fragment of the T cell receptor-binding domain is associated with the light chain Fv fragment of the T cell receptor-binding domain. In this embodiment, the structure (structure with controlled association) of the polypeptide complex is not limited to a particular structure, as long as the electric charges of the CH1 and CL domains are controlled so that the heavy chain Fv fragment of the antigen-binding domain is associated with the light chain Fv fragment of the antigen-binding domain, or the heavy chain Fv fragment of the T cell receptor-binding domain is associated with the light chain Fv fragment of the T cell receptor-binding domain.

In an embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain.

In an embodiment of the structure with controlled association, it is possible to produce a polypeptide complex in which amino acid residues of the CH1 domain linked to the heavy chain Fv fragment of the antigen-binding domain have the same electric charges as amino acid residues of the CL domain linked to the light chain Fv fragment of the T cell receptor complex-binding domain.

In an embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain, and amino acid residues of the CH1 domain linked to the heavy chain Fv fragment of antigen-binding domain have the same electric charges as amino acid residues of the CL domain linked to the light chain Fv fragment of the T cell receptor complex-binding domain.

In another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain, and amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain.

In still another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to the heavy chain Fv fragment of the antigen-binding domain have the same electric charges as amino acid residues of the CL domain linked to the light chain Fv fragment of the T cell receptor complex-binding domain; and amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain.

In yet another embodiment of the structure with controlled association, it is possible to produce a polypeptide complex in which amino acid residues of the CH1 domain linked to the heavy chain Fv fragment of the antigen-binding domain have the same electric charges as amino acid residues of the CL domain linked to the light chain Fv fragment of the T cell receptor complex-binding domain, and amino acid residues of the CH1 domain linked to the heavy chain Fv fragment of the antigen-binding domain have electric charges opposite to those of amino acid residues of the CL domain linked to the light chain Fv fragment of the antigen-binding domain.

In an alternative embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to the heavy chain Fv fragment of the antigen-binding domain have the same electric charges as amino acid residues of the CL domain linked to the light chain Fv fragment of the T cell receptor complex-binding domain; and amino acid residues of the CH1 domain linked to the heavy chain Fv fragment of the antigen-binding domain have electric charges opposite to those of amino acid residues of the CL domain linked to the light chain Fv fragment of the antigen-binding domain.

In still yet another embodiment of the structure with controlled association, it is possible to produce a polypeptide complex in which amino acid residues of the CH1 domain linked to the heavy chain Fv fragment of the T cell receptor complex-binding domain have the same electric charges as amino acid residues of the CL domain linked to the light chain Fv fragment of the antigen-binding domain; amino acid residues of the CH1 domain linked to heavy chain Fv fragment of the antigen-binding domain have the same electric charges as amino acid residues of the CL domain linked to the light chain Fv fragment of the T cell receptor complex-binding domain; amino acid residues of the CH1 domain linked to the heavy chain Fv fragment of the T cell receptor complex-binding domain have electric charges opposite to those of amino acid residues of the CL domain linked to the light chain Fv fragment of the T cell receptor-binding domain; and amino acid residues of the CH1 domain linked to the heavy chain Fv fragment of the antigen-binding domain have electric charges opposite to those of amino acid residues of the CL domain linked to the light chain Fv fragment of the antigen-binding domain.

Control of Electric Charges of CH1 and CL Domains

To obtain a bispecific polypeptide complex that recognizes an epitope of the T cell receptor-binding domain by the heavy and light chains of the T cell receptor-binding domain, and an epitope of an antigen by the heavy and light chains of the antigen-binding domain, theoretically ten types of polypeptide complex molecules are produced if each of the four chains is expressed when producing the polypeptide complex.

Nevertheless, the desired polypeptide complex molecule can be preferentially obtained, for example, by controlling the domains so as to inhibit the association between the heavy chain of the T cell receptor-binding domain and the light chain of the antigen-binding domain, and/or the association between the heavy chain of the antigen-binding domain and the light chain of the T cell receptor-binding domain.

Examples include alterations of amino acid residues that form an interface between the heavy chain CH1 of the T cell receptor-binding domain and the light chain CL of the antigen-binding domain to positively charged amino acid residues, and alterations of amino acid residues that form an interface between the heavy chain CH1 of the antigen-binding domain and the light chain CL of the T cell receptor-binding domain to negatively charged amino acid residues. As a result of such alterations, undesired association between the heavy chain CH1 of the T cell receptor-binding domain and the light chain CL of the antigen-binding domain is inhibited because the electric charges of the amino acid residues that form the interface are both positive, and undesired association between the heavy chain CH1 of the antigen-binding domain and the light chain CL of the T cell receptor-binding domain is also inhibited because the electric charges of the amino acid residues that form the interface are both negative. A desired polypeptide complex of the present invention can be efficiently produced as a result of the desired association between the heavy chain CH1 of T cell receptor-binding domain and the light chain CL of the T cell receptor-binding domain as well as the desired association between the heavy chain CH1 of the antigen-binding domain and the light chain CL of the antigen-binding domain. Furthermore, the desired association between the heavy light chains of the T cell receptor-binding domains is preferably promoted because the amino acid residues that form the interface have opposite electric charges from each other. The desired association between the heavy and light chains of the antigen-binding domains is also preferably promoted because the amino acid residues that form the interface have opposite electric charges from each other. This allows efficient production of a polypeptide complex of the present invention with the desired association.

Furthermore, control of the association in the present invention can also be used to inhibit the association between CH1s (the heavy chains of the T cell receptor-binding domain and antigen-binding domain) or between CLs (the light chains of the T cell receptor-binding domain and antigen-binding domain).

Those skilled in the art can appropriately find in a desired polypeptide complex whose association is controlled according to the present invention the types of amino acid residues locating in close proximity at the CH1/CL interface upon association.

Furthermore, by using public databases or such, those skilled in the art can appropriately find usable antibody CH1 and CL sequences in an organism such as human, monkey, mouse, or rabbit. More specifically, the amino acid sequence information of CH1 and CL can be obtained by methods described below in the Examples.

Specifically, as shown in the Examples described below, specific examples of combinations of amino acid residues locating in close proximity (facing or contacting) at the CH1/CL interface upon association between CH1 and CL which are respectively linked to the VH and VL forming the T cell receptor-binding domain or antigen-binding domain include:

lysine (K) at position 147 (EU numbering) in CH1 (for example, position 147 in the amino acid sequence of SEQ ID NO: 1) and threonine (T) at position 180 (EU numbering) in the facing (contacting) CL;

lysine (K) at position 147 (EU numbering) in CH1 and serine (S) at position 131 (EU numbering) in the facing (contacting) CL;

lysine (K) at position 147 (EU numbering) in CH1 and threonine (T) at position 164 (EU numbering) in the facing (contacting) CL;

lysine (K) at position 147 (EU numbering) in CH1 and asparagine (N) at position 138 (EU numbering) in CL, which face (contact with) each other;

lysine (K) at position 147 (EU numbering) in CH1 and glutamic acid (E) at position 123 (EU numbering) in the facing (contacting) CL;

glutamine (Q) at position 175 (EU numbering) in CH1 and glutamine (Q) at position 160 (EU numbering) in the facing (contacting) CL; or lysine (K) at position 213 (EU numbering) in CH1 and glutamic acid (E) at position 123 (EU numbering) in the facing (contacting) CL.

These positions are numbered according to the document by Kabat et al. (Kabat E A et al., 1991. Sequence of Proteins of Immunological Interest. NIH).

Herein, the numbers indicated by EU numbering are assigned according to EU numbering (Sequences of proteins of immunological interest, NIH Publication No. 91-3242). In the present invention, "amino acid residue at position X (EU numbering)" and "amino acid at position X (EU numbering)" (where X is an arbitrary number) are interchangeable with "amino acid residue corresponding to position X (EU numbering)", "amino acid corresponding to position X (EU numbering)".

As described in the Examples below, a desired polypeptide complex can be preferentially obtained by altering the amino acid residues and conducting the methods of the present invention.

The amino acid residues described above are known to be highly conserved in human and mouse (J. Mol. Recognit. (2003) 16, 113-120). Thus, the association between CH1 and CL in the constant region of a polypeptide complex of the present invention other than the polypeptide complexes described in the Examples can also be controlled by altering amino acid residues corresponding to the above-described amino acid residues.

Specifically, the present invention provides polypeptide complexes with controlled association between the heavy chain and light chain, in which one, two or more pairs selected from the group consisting of the pairs of amino acid residues described in (a) to (f) below have the same electric charges:

(a) the amino acid residue at position 147 (EU numbering) in CH1 and the amino acid residue at position 180 (EU numbering) in CL;

(b) the amino acid residue at position 147 (EU numbering) in CH1 and the amino acid residue at position 131 (EU numbering) in CL;

(c) the amino acid residue at position 147 (EU numbering) in CH1 and the amino acid residue at position 164 (EU numbering) in CL;

(d) the amino acid residue at position 147 (EU numbering) in CH1 and the amino acid residue at position 138 (EU numbering) in CL;

(e) the amino acid residue at position 147 (EU numbering) in CH1 and the amino acid residue at position 123 (EU numbering) in CL; and (f) the amino acid residue at position 175 (EU numbering) in CH1 and the amino acid residue at position 160 (EU numbering) in CL.

Furthermore, in another embodiment, the present invention provides antibodies in which the amino acid residues in the pair of amino acid residues described in (g) below have the same electric charges:

(g) the amino acid residue at position 213 (EU numbering) in CH1 and the amino acid residue at position 123 (EU numbering) in CL.

The amino acid residues in each of the pairs described above are located in close proximity with each other upon association, as described in the EXAMPLES below. By homology modeling or other methods using commercially available software, those skilled in the art can appropriately find in a desired CH1 or CL amino acid positions corresponding to the amino acid residues described in (a) to (g) above, and can appropriately alter amino acid residues at those positions.

Such an "electrically charged amino acid residue" in an above-described antibody is preferably selected, for example, from the amino acid residues belonging to the group (X) or (Y) described below:

(X) glutamic acid (E) and aspartic acid (D); and
(Y) lysine (K), arginine (R) and histidine (H).

In the above-described polypeptide complexes, "has the same electric charge" means that, for example, all of two or more amino acid residues belongs to one of groups (X) and (Y) described above. On the other hand, "has an opposite electric charge" means that, for example, at least one of two or more amino acid residues has an amino acid residue that belongs to one of groups (X) and (Y) described above, while the other amino acid residues have an amino acid residues that belongs to the other group.

Methods of producing the above-described polypeptide complexes and methods of the present invention for controlling the association by altering the amino acid residues in groups (a) to (g) above to amino acid residues having the same electric charge are also preferred embodiments of the present invention.

In the present invention, amino acid residues "to be altered" are not limited to the above-described amino acid residues of the constant region. By homology modeling or other methods using commercially available software, those skilled in the art can appropriately identify amino acid residues that form an interface in a mutant polypeptide or heteromeric multimer and appropriately alter amino acid residues at those positions to control association.

In the techniques for inhibiting undesired association between the heavy chain and light chain by introducing charge repulsion at the interface between the heavy chain and light chain variable regions, amino acid residues in contact with each other at the interface between the heavy chain variable region (VH) and light chain variable region (VL) include, for example, glutamine (Q) at position 39 (for example, position 39 in the amino acid sequence of SEQ ID NO: 6 in WO 2006/106905) in the heavy chain variable region FR2 and glutamine (Q) at position 38 (for example, position 44 in the amino acid sequence of SEQ ID NO: 8 in WO 2006/106905) in the facing (contacting) light chain variable region FR2. Such preferred amino acid residues also include, for example, leucine (L) at position 45 (for example, position 45 in the amino acid sequence of SEQ ID NO: 6 in WO 2006/106905) in the heavy chain variable region FR2 and proline (P) at position 44 (for example, position 44 in the amino acid sequence of SEQ ID NO: 8 in WO 2006/106905) in the facing light chain variable region FR2. These positions are numbered according to the document by Kabat et al. (Kabat E A et al. 1991. Sequence of Proteins of Immunological Interest. NIH).

The amino acid residues described above are known to be highly conserved in human and mouse (J. Mol. Recognit. (2003) 16, 113-120). Thus, the association between VH and VL in antibody variable regions other than the polypeptide complexes described in the Examples can also be controlled by altering amino acid residues corresponding to the above-described amino acid residues.

More specifically, such antibodies having heavy chain and light chain variable regions include those in which the amino acid residues of (1) and (2), or (3) and (4) described below have the same electric charges:
(1) the amino acid residue corresponding to position 39 (EU numbering) in the heavy chain variable region;
(2) the amino acid residue corresponding to position 38 (EU numbering) in the light chain variable region;
(3) the amino acid residue corresponding to position 45 (EU numbering) in the heavy chain variable region;
(4) the amino acid residue corresponding to position 44 (EU numbering) in the light chain variable region.

The amino acid residues of (1) and (2), or (3) and (4) described above are located in close proximity to each other upon association. By homology modeling or other methods using commercially available software, those skilled in the art can appropriately identify in a desired heavy chain or light chain variable region amino acid positions corresponding to the amino acid residues described in (1) to (4) above, and can appropriately alter amino acid residues at those positions.

In an above-described antibody, the "electrically charged amino acid residue" is preferably selected, for example, from the amino acid residues belonging to the group (X) or (Y) below:
(X) glutamic acid (E) and aspartic acid (D); and
(Y) lysine (K), arginine (R), and histidine (H).

In human and mouse, generally, the amino acid residues of (1) to (4) described above are:
(1) glutamine (Q);
(2) glutamine (Q);
(3) leucine (L); and
(4) proline (P), respectively.

In a preferred embodiment of the present invention, the above-described amino acid residues are altered (for example, substitution with a charged amino acid). The types of amino acid residues (1) to (4) described above are not limited to those described above. These amino acids may be any other amino acids corresponding to those described above. For example, in the case of human, an amino acid corresponding to the amino acid at position 38 (EU numbering) in light chain variable region may be histidine (H). By referring to published documents (for example, J. Mol. Recognit. (2003) 16, 113-120) or the like, those skilled in the art can find the type of amino acid residue corresponding to an arbitrary position in the light chain, and thus can appropriately alter the amino acid residue (for example, substitution with a charged amino acid).

In techniques for inhibiting undesired association between the heavy chain and light chain by substituting electrically charged polar amino acids for amino acid residues that form the hydrophobic core at the interface between the heavy chain and light chain variable regions, preferred amino acid residues capable of forming the hydrophobic core at the interface between the heavy chain variable region (VH) and light chain variable region (VL) include, for example, leucine (L) at position 45 in the heavy chain variable region and proline (P) at position 44 in the facing light chain variable region.

In general, a "hydrophobic core" refers to a portion where side chains of hydrophobic amino acids assemble inside the associated polypeptide. Hydrophobic amino acids include, for example, alanine, isoleucine, leucine, methionine, phenylalanine, proline, tryptophan, and valine. Meanwhile, amino acid residues other than the hydrophobic amino acids (for example, tyrosin) can also be involved in the formation of hydrophobic core. Together with the hydrophilic surface from outward exposure of the side chains of hydrophilic amino acids, the hydrophobic core serves as a driving force to promote the association of water-soluble polypeptides. When hydrophobic amino acids of two different domains are present on the molecular surface and exposed to water molecules, the entropy is increased, which results in an increase in the free energy. Therefore, the two domains associate with each other to decrease free energy for stabilization. The hydrophobic amino acids at the interface are buried inside of the molecule to form a hydrophobic core.

It is considered that when the hydrophobic amino acids that form a hydrophobic core in the polypeptide association are altered to polar amino acids with electric charge, the formation of hydrophobic core is inhibited. This results in inhibition of the polypeptide association.

Other known technologies are also applicable to the polypeptide complexes of the present invention. For example, to promote the association of the first VH (VH1) and first VL (VL1), and/or second VH (VH2) and second VL (VL2), in addition to the "alterations" of the present invention, amino acids in one of the H chain variable regions are substituted with those having a larger side chain (knob; bulge) and amino acids in the other H chain variable region are substituted with those having a smaller side chain (hole; void) so that the knob is placed in the hole. This promotes the association of VH1 and VL1, and/or VH2 and VL2, resulting in further inhibition of the association between VH1 and VL2 and/or between VH2 and VL1 polypeptides (WO 1996/027011; Ridgway J B et al., Protein Engineering (1996) 9, 617-621; Merchant A M et al., Nature Biotechnology (1998) 16, 677-681).

In the production of an above-described polypeptide complex, each domain may be linked directly via peptide bond or by peptide binding via a peptide linker. In this case, the linker to be used includes the linker described above as an example and appropriate linkers with a peptide tag, for example, His-tag, HA-tag, myc-tag, or FLAG-tag. In addition, it is preferable to use the property of mutual binding based on hydrogen bonding, disulfide bond, covalent bonding, or ionic interaction, or a combination thereof. For example, it is possible to employ the affinity between antibody CH1 and CL, or the above-described Fc domains derived from a bispecific antibody may be used for heteromeric association of Fc domains. Moreover, interdomain disulfide bonds can be preferably used as described in the EXAMPLES.

Figure 17:
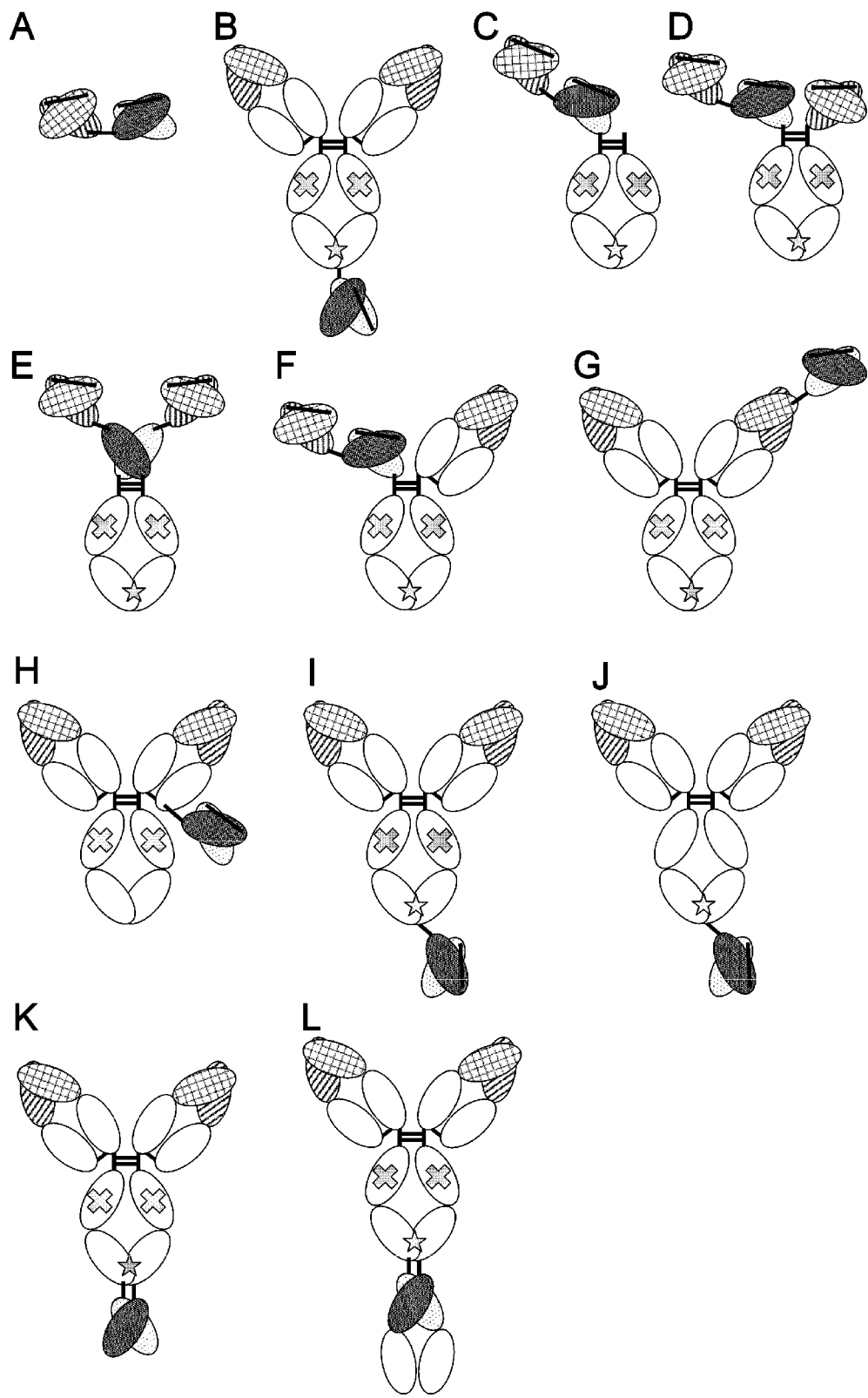
FIG. 17 shows diagrams of GPC3 BiTE (A); GPC3 ERY 10 (B); GPC3 ERY2 (C); GPC3 ERY5 (D); GPC3 ERY6 (E); GPC3 ERY7 (F); GPC3 ERY8-2 (G); GPC3 ERY5-1 (H); GPC3 ERY10-1 (I); GPC3 ERY15 (J); GPC3 ERY18 (K); and GPC3 ERY19-3 (L).
Figure 19:
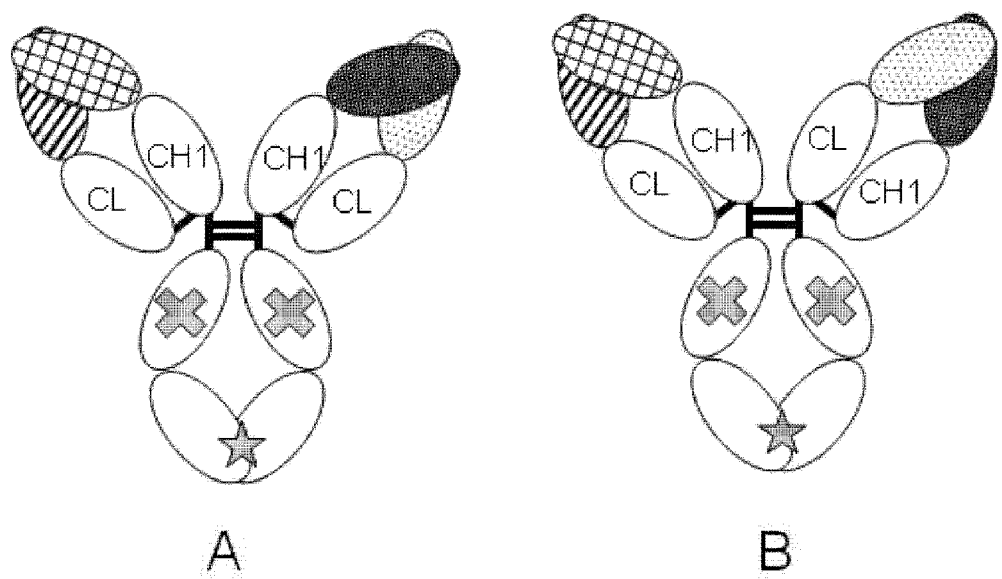
FIG. 19 shows diagrams that represent domains forming the following polypeptide complexes described in the Examples herein: GPC3 ERY17-2, GPC3 ERY17-3, EpCAM ERY17-2, and EpCAM ERY17-3. The domain with cross-hatched lines represents the H-chain variable region of the anti-cancer antigen (GPC3, EpCAM, EGFR) antibody; the domain with diagonal lines represents the L-chain variable region of the anti-cancer antigen (GPC3, EpCAM, EGFR) antibody; the domain with dotted lines represents the H-chain variable region of the anti-CD3 antibody; the closed domain represents the L-chain variable region of the anti-CD3 antibody; the open domain represents the antibody constant region; the cross represents a silent Fc mutation; and the star represents a mutation promoting heteromeric Fc association.

The polypeptide complexes of the present invention include, for example, the embodiments shown in FIGS. 17, 19, and 24.

The polypeptide complexes of the present invention can be produced by the same methods as the above-described methods for producing recombinant antibodies.

Furthermore, the present invention relates to polynucleotides encoding the polypeptide complex of the present invention. A polypeptide complex of the present invention can be inserted into any expression vectors. An appropriate host is transformed with the expression vector to obtain cells expressing the polypeptide complex. The polypeptide complex encoded by the polynucleotide can be obtained by culturing cells expressing the polypeptide complex and collecting the expression product from the culture supernatant. Specifically, the present invention relates to vectors carrying a polynucleotide encoding the polypeptide complex of the present invention, cells containing the vectors, and methods of producing the polypeptide complex of the present invention, in which the cells are cultured and the polypeptide complex is collected from the culture supernatant. Those described above can be obtained by the same technologies described above for the recombinant antibodies.

Pharmaceutical Composition

In another aspect, the present invention provides pharmaceutical compositions which comprise as an active ingredient a polypeptide complex comprising:
(1) an antigen-binding domain;
(2) a domain comprising an Fc domain with reduced Fcγ receptor-binding activity; and
(3) a CD3-binding domain.

The present invention also relates to therapeutic agents to induce cellular cytotoxicity, which comprise the above-described complex as an active ingredient (therapeutic agents for inducing cellular cytotoxicity), cell growth-suppressing agents, and anticancer agents. The pharmaceutical compositions of the present invention can be used as a therapeutic or preventive agent for cancer. The therapeutic agents for inducing cellular cytotoxicity, cell growth-suppressing agents, and anticancer agents of the present invention are preferably administered to subjects with cancer or a likelihood of cancer recurrence.

In the present invention, the therapeutic agents for inducing cellular cytotoxicity, cell growth-suppressing agents, and anticancer agents, which comprise as an active ingredient a polypeptide complex comprising:
(1) an antigen-binding domain;
(2) a domain encompassing an Fc domain with reduced Fcγ receptor-binding activity; and
(3) a CD3-binding domain
may also be described as a method for preventing or treating cancer, which comprises the step of administering the polypeptide complex to a subject, or use of the polypeptide complex in producing therapeutic agents for inducing cellular cytotoxicity, cell growth-suppressing agents, or anticancer agents.

Herein, "comprising as an active ingredient a polypeptide complex comprising:
(1) an antigen-binding domain;
(2) a domain encompassing an Fc domain with reduced Fcγ receptor-binding activity; and
(3) a CD3-binding domain"
means comprising the polypeptide complex as a major active ingredient; however, the content ratio of the polypeptide complex is not limited.

A pharmaceutical composition of the present invention, a therapeutic agent for inducing cellular cytotoxicity, a cell growth-suppressing agent, or an anticancer agent of the present invention may be formulated with different types of polypeptide complexes, if needed. For example, the cytotoxic action against cells expressing an antigen can be enhanced by a cocktail of multiple polypeptide complexes of the present invention that bind to the same antigen. Alternatively, the therapeutic effect can be increased by formulating a polypeptide complex of the present invention comprising an antigen-binding domain that binds to a cancer antigen in combination with other polypeptide complexes of the present invention comprising an antigen-binding domain against a different antigen.

If necessary, the polypeptide complexes of the present invention may be encapsulated in microcapsules (microcapsules made from hydroxymethylcellulose, gelatin, poly[methylmethacrylate], and the like), and made into components of colloidal drug delivery systems (liposomes, albumin microspheres, microemulsions, nano-particles, and nanocapsules) (for example, see "Remington's Pharmaceutical Science 16th edition", Oslo Ed. (1980)). Moreover, methods for preparing agents as sustained-release agents are known, and these can be applied to the polypeptide complexes of the present invention (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, cell growth-suppressing agents, or anticancer agents of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

The present invention also provides methods for damaging cells expressing a cancer antigen or for suppressing the cell growth by contacting the cells expressing the cancer antigen with a polypeptide complex of the present invention that binds to the cancer antigen. Monoclonal antibodies that bind to the cancer antigen are described above as a cancer antigen-binding polypeptide complex of the present invention, which is included in the therapeutic agents for inducing cellular cytotoxicity, cell growth-suppressing agents, and anticancer agents of the present invention. Cells to which a cancer antigen-binding polypeptide complex of the present invention binds are not particularly limited, as long as they express the cancer antigen. Specifically, in the present invention, the preferred cancer antigen-expressing cells include ovary cancer cells, prostate cancer cells, breast cancer cells, uterine cancer cells, liver cancer cells, lung cancer cells, pancreatic cancer cells, stomach cancer cells, urinary bladder cancer cells, and colon cancer cells. When the cancer antigen is GPC3, cells are not limited as long as they are cancer cells expressing GPC3. However, the preferred cancer cells include hepatocarcinoma cells, lung cancer cells, and ovary cancer cells.

In the present invention, "contact" can be carried out, for example, by adding a cancer antigen-binding polypeptide complex of the present invention to culture media of cells expressing the cancer antigen cultured in vitro. In this case, a polypeptide complex to be added can be used in an appropriate form, such as a solution or solid prepared by lyophilization or the like. When the polypeptide complex of the present invention is added as an aqueous solution, the solution may be a pure aqueous solution containing the polypeptide complex alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The added concentration is not particularly limited; however, the final concentration in a culture medium is preferably in a range of 1 pg/ml to 1 g/ml, more preferably 1 ng/ml to 1 mg/ml, and still more preferably 1 µg/ml to 1 mg/ml.

In another embodiment of the present invention, "contact" can also be carried out by administration to nonhuman animals transplanted with cancer antigen-expressing cells in vivo or to animals having cancer cells expressing the cancer antigen endogenously. The administration method may be oral or parenteral. Parenteral administration is particularly preferred. Specifically, the parenteral administration method includes injection, nasal administration, pulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present invention can be administered locally or systemically by injection. Furthermore, an appropriate administration method can be selected according to the age and symptoms of an animal subject. When the polypeptide complex is administered as an aqueous solution, the solution may be a pure aqueous solution containing the polypeptide complex alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The administered dose can be selected, for example, from the range of 0.0001 to 1,000 mg per kg of body weight for each administration. Alternatively, the dose can be selected, for example, from the range of 0.001 to 100,000 mg/body for each patient. However, the dose of a polypeptide complex of the present invention is not limited to these examples.

The methods described below are preferably used as a method for assessing or determining cellular cytotoxicity caused by contacting a polypeptide complex of the present invention with antigen-expressing cells to which the antigen-binding domain forming the polypeptide complex of the present invention binds. The methods for assessing or determining the cytotoxic activity in vitro include methods for determining the activity of cytotoxic T cells or the like. Whether a polypeptide complex of the present invention has the activity of inducing T-cell mediated cellular cytotoxicity can be determined by known methods (see, for example, Current protocols in Immunology, Chapter 7 Immunologic studies in humans, Editor, John E, Coligan et al., John Wiley & Sons, Inc., (1993)). In the cytotoxicity assay, a polypeptide complex whose antigen-binding domain binds to an antigen different from that recognized by the antigen-binding domain of the polypeptide complex of the present invention and which is not expressed in the cells is used as a control polypeptide complex. The control polypeptide complex is assayed in the same manner. Then, the activity is assessed by testing whether a polypeptide complex of the present invention exhibits a stronger cytotoxic activity than that of a control polypeptide complex.

Meanwhile, the in vivo cytotoxic activity is assessed or determined, for example, by the following procedure. Cells expressing the antigen to which the antigen-binding domain forming a polypeptide complex of the present invention binds are transplanted intracutaneously or subcutaneously to a nonhuman animal subject. Then, from the day of transplantation or thereafter, a test polypeptide complex is administered into vein or peritoneal cavity every day or at intervals of several days. The tumor size is measured over time. Difference in the change of tumor size can be defined as the cytotoxic activity. As in an in vitro assay, a control polypeptide complex is administered. The polypeptide complex of the present invention can be judged to have cytotoxic activity when the tumor size is smaller in the group administered with the polypeptide complex of the present invention than in the group administered with the control polypeptide complex.

An MTT method and measurement of isotope-labeled thymidine uptake into cells are preferably used to assess or determine the effect of contact with a polypeptide complex of the present invention to suppress the growth of cells expressing an antigen to which the antigen-binding domain forming the polypeptide complex binds. Meanwhile, the same methods described above for assessing or determining the in vivo cytotoxic activity can be used preferably to assess or determine the activity of suppressing cell growth in vivo.

The present invention also provides kits for use in a method of the present invention, which contain a polypeptide complex of the present invention or a polypeptide complex produced by a method of the present invention. The kits may be packaged with an additional pharmaceutically acceptable carrier or medium, or instruction manual describing how to use the kits, etc.

In addition, the present invention relates to polypeptide complexes of the present invention or polypeptide complexes produced by a method of the present invention for use in a method of the present invention.

All prior-art documents cited herein are incorporated herein by reference.

EXAMPLES

Hereinbelow, the present invention is specifically described with reference to the Examples, but it is not to be construed as being limited thereto.

[Example 1] Construction and Assessment of GPC3 ERY2

(1) Outline

There is a well-known method for prolonging the blood half-life of a protein administered in vivo, which is based on the FcRn-mediated recycling using a protein of interest conjugated to an antibody Fc domain. However, the conjugation of a natural type of Fc to BiTE could lead to induction of various cytokines, since a single molecule would bind to a T cell via the anti-CD3 scFv of its BiTE moiety and simultaneously to the FcgR (Fcγ receptor) on the cellular membrane of, for example, a NK cell or macrophage via its Fc domain, and the resulting cross-linking would activate these cells in a cancer antigen-independent manner. Thus, a molecule termed ERY2, in which a BiTE is linked via a polypeptide linker to an Fc domain having reduced Fcγ receptor-binding activity (silent Fc), was prepared, and the activity of ERY2 was assessed by comparing it to that of the BiTE. The scFv of an anti-CD3 epsilon antibody was linked via a short peptide linker to the scFv of an antibody against Glypican 3 (GPC3), which is a GPI-anchored protein known to be expressed at a high level in liver cancer cells, to produce BiTE against GPC3 (GPC3 BiTE) (FIG. 17A). This was then linked to a silent Fc to produce an ERY2 against GPC3 (GPC3 ERY2) (FIG. 17C). Furthermore, a normal IgG-type anti-GPC3 antibody was constructed for comparison. The IgG-type anti-GPC3 antibody was prepared as an antibody with reduced fucose content in its sugar chain moiety, i.e., a low-fucose antibody, which is known to have an enhanced ADCC activity.

(2) Construction of GPC3 BiTE

By PCR amplification using an expression vector for an anti-GPC3 antibody as a template, cDNAs each encoding an H chain variable region (anti-GPC3 VH) or an L chain variable region (anti-GPC3 VL) were obtained. PCR was performed using primers containing appropriate additional sequences and the above cDNAs as templates to construct a cDNA fragment encoding an anti-GPC3 scFv having an amino acid sequence in which the anti-GPC3 VH and anti-GPC3 VL were linked together via a linker with three repeats of Gly-Gly-Gly-Gly-Ser (SEQ ID NO: 7).

Furthermore, a series of oligonucleotides were prepared each of which had a nucleotide sequence encoding a partial sequence of the H chain variable region (M12 VH) or L chain variable region (M12 VL) of an anti-CD3 antibody (M12), and had complementary sequences at the ends. The oligonucleotides were designed such that they would be linked together via the complementary sequence portions by polymerase reaction to synthesize a polynucleotide corresponding to the H chain variable region (M12 VH) and L chain variable region (M12 VL). The oligonucleotides were mixed and then assembled together by PCR to give two cDNAs encoding the amino acid sequences of respective variable regions. PCR was performed using primers containing appropriate additional sequences and the above cDNAs as templates to produce a cDNA fragment encoding M12 scFv having an amino sequence in which M12 VL and M12 VH were linked together via a linker having three repeats of Gly-Gly-Gly-Gly-Ser (SEQ ID NO: 7).

Next, by PCR using primers containing appropriate additional sequences and the cDNA fragments each encoding anti-GPC3 scFv or M12 scFv as templates, a cDNA fragment was constructed which encoded an amino acid sequence in which anti-GPC3 scFv and M12 scFv were linked together via a linker composed of Gly-Gly-Gly-Gly-Ser (SEQ ID NO: 7) and its C terminus had a His tag (eight histidines) (the sequence of SEQ ID NO: 33 without its amino terminal 19 amino acids).

Using primers containing appropriate additional sequences and as a template the cDNA fragment encoding the amino acid sequence of SEQ ID NO: 33 lacking its amino terminal 19 amino acids, PCR was performed to produce a cDNA fragment in which an EcoRI cleavage sequence, kozac sequence, and a nucleotide sequence encoding a secretion signal sequence were attached to the 5' end of the above cDNA fragment and a NotI cleavage sequence to the 3' end. The resulting cDNA fragment was cleaved with EcoRI and NotI, and inserted into an mammalian cell expression vector to obtain an expression vector for GPC3 BiTE (SEQ ID NO: 33; the mature sequence does not contain the amino terminal 19 amino acids, which serve as a signal sequence).

The vector was introduced into CHO DG44 cells by electroporation. After limiting dilution, the cells were cultured in the presence of 1 mg/ml Geneticin to isolate drug-resistant cell lines. The culture supernatant of the obtained cell lines was analyzed by Western blotting using an anti-His tag antibody to select a cell line expressing GPC3 BiTE.

The culture supernatant obtained by large scale cell culture of the above-described cell line was loaded onto an SP Sepharose FF column (GE Healthcare). After washing the column, a fraction containing GPC3 BiTE was eluted with a NaCl concentration gradient. The fraction was loaded onto a HisTrap HP column (GE Healthcare). After washing the column, a fraction containing GPC3 BiTE was eluted with an imidazole concentration gradient. The fraction was concentrated by ultrafiltration, and then the concentrate was loaded onto a Superdex 200 column (GE Healthcare). Only a monomeric GPC3 BiTE fraction was collected to obtain purified GPC3 BiTE.

(3) Construction of GPC3 ERY2

PCR using primers containing the same appropriate additional sequences as in the above-described method and a method well known to those skilled in the art such as a method using the QuikChange Site-Directed Mutagenesis Kit (Stratagene) were performed to produce expression vectors to which a polynucleotide encoding GPC3 ERY2_Hk (SEQ ID NO: 34; the mature sequence does not contain the amino terminal 19 amino acids, which serve as a signal sequence) or GPC3 ERY2_Hh (SEQ ID NO: 35; the mature sequence does not contain the amino terminal 19 amino acids, which serve as a signal sequence) was inserted.

These expression vectors were co-introduced into FreeStyle293-F cells (Invitrogen) to express GPC3 ERY2 transiently. The resulting culture supernatant was loaded onto an Anti FLAG M2 column (Sigma). After washing, the column was eluted with 0.1 mg/ml FLAG peptide (Sigma). A fraction containing GPC3 ERY2 was loaded onto a HisTrap HP column (GE Healthcare). After washing, the column was eluted with an imidazole concentration gradient. A fraction containing GPC3 ERY2 was concentrated by ultrafiltration, and the concentrate was loaded onto a Superdex 200 column (GE Healthcare). Only a monomeric GPC3 ERY2 fraction was collected from the eluate to obtain purified GPC3 ERY2.

(4) Construction of Low-Fucose Anti-GPC3 Antibody

An expression vector for an anti-GPC3 antibody (that is referred to as humanized GC33 antibody in WO 2006/006693) was introduced into GDP fucose-knockout CHO DXB 11 cells (Cancer Sci. (2010) 101(10), 2227-33) by electroporation. After limiting dilution, the cells were cultured in the presence of 0.5 mg/ml Geneticin to select drug resistant lines, and a cell line expressing a low-fucose anti-GPC3 antibody was obtained. From the culture supernatant obtained by culturing these cells, an antibody fraction was prepared by conventional affinity purification using Hitrap® Protein A (Pharmacia). Then, the antibody fraction was subjected to gel filtration purification using Superdex 20026/60 (Pharmacia). A monomer fraction was collected from the eluate to obtain a low-fucose anti-GPC3 antibody.

(5) Cytotoxicity Assay Using Human Peripheral Blood Mononuclear Cells (5-1) Preparation of Human Peripheral Blood Mononuclear Cell (PBMC) Suspension From healthy volunteers (adult), 50 ml of peripheral blood was collected using syringes to which 100 μl of 1,000 units/ml heparin solution (Novo-Heparin 5000 units for injection; Novo Nordisk) had been added in advance. The peripheral blood was diluted two fold with PBS(−), divided into four equal aliquots, and added to Leucosep lymphocyte separation tubes (Cat. No. 227290; Greiner bio-one) that had been injected with 15 ml of Ficoll-Paque PLUS and centrifuged in advance. After centrifugation (2,150 rpm, 10 minutes, room temperature) of the separation tubes, a mononuclear cell fraction layer was collected. The cells in the mononuclear cell fraction were washed once with Dulbecco's Modified Eagle's Medium (SIGMA) containing 10% FBS (hereinafter referred to as 10% FBS/D-MEM), and then the cell density was adjusted to $4 \times 10^6$ cells/ml using 10% FBS/D-MEM. The cell suspension thus prepared was used as a human PBMC suspension in subsequent experiments.

(5-2) Cytotoxic Activity Assay

The cytotoxic activity was assessed based on the cell growth inhibition rate determined using xCELLigence real-time cell analyzer (Roche Diagnostics). The target cell used was SK− pca13a cell line established by forcedly expressing human GPC3 in SK-HEP-1 cell line. SK− pca13a cells were detached from dishes, and seeded onto an E-Plate 96 (Roche Diagnostics) plate at $1 \times 10^4$ cells/well (100 μl/well). Then viable cell assay was started using xCELLigence real-time cell analyzer. On the following day, the plate was removed from the xCELLigence real-time cell analyzer, and 50 μl of each antibody prepared at various concentrations (0.004, 0.04, 0.4, and 4 nM) was added to the plate. After 15 minutes of reaction at room temperature, 50 μl of human PBMC suspension ($2 \times 10^5$ cells/well) prepared in (5-1) was added. The plate was placed in the xCELLigence real-time cell analyzer again to start viable cell assay. The reaction was carried out under 5% carbon dioxide gas at 37° C. The cell growth inhibition rate (%) was determined according to the formula shown below using the Cell Index value at 72 hours after the addition of human PBMCs. The Cell Index value used in the calculation was normalized such that the Cell Index value immediately before the addition of antibody was taken as 1.

Cell growth inhibition rate $(\%) = (A-B) \times 100/(A-1)$

A denotes the mean Cell Index value for the no-antibody well (the target cell and human PBMC only), while B denotes the mean Cell Index value for each well. The measurement was carried out in triplicate.

The cytotoxic activity of GPC3 BiTE, GPC3 ERY2, and IgG-type anti-GPC3 antibody was measured using PBMCs (peripheral blood mononuclear cells) prepared from human blood as effector cells. GPC3 BiTE showed a very strong activity (FIG. 1). This activity was much stronger than that of the low-fucose anti-GPC3 antibody. Thus, GPC3 BiTE may serve as an excellent cancer therapeutic agent that exceeds the IgG-type antibody. On the other hand, the activity of GPC3 ERY2 was not as strong as that of GPC3 BiTE, although it was greater than that of the IgG-type anti-GPC3 antibody. This suggests that the mere addition of Fc to BiTE does not enable creation of a desired molecule.

[Example 2] Construction and Assessment of GPC3 ERY5, GPC3 ERY6, and GPC3 ERY7

Next, in an attempt to improve the specific activity, the cancer antigen (GPC3)-binding domain was made bivalent to enhance the cancer cell-binding activity. Another anti-GPC3 scFv was added to GPC3 ERY2 to construct GPC3 ERY5 (FIG. 17D). Furthermore, instead of the scFv, a Fab-type GPC3-binding domain was added to produce GPC3 ERY7 (FIG. 17F). In addition, GPC3 ERY6 (FIG. 17E) was also constructed in which the anti-CD3 epsilon scFv of GPC3 ERY5 was split into two arms.

Specifically, a method known to those skilled in the art, such as PCR using primers containing the same appropriate additional sequences as in the above-described method, was performed to produce a series of expression vectors into which a polynucleotide encoding GPC3 ERY5Hh, GPC3 ERY6 Hk, GPC3 ERY6_Hh, GPC3 ERY7 Hh, or GPC3 ERY7_L was inserted.

The following combinations of expression vectors were introduced into FreeStyle293-F cells to express each designed molecule transiently.

A. Designed Molecule: GPC3 ERY5

Polypeptides encoded by polynucleotides inserted in expression vectors: GPC3 ERY5_Hh (SEQ ID NO: 36; the mature sequence does not contain the amino terminal 19 amino acids, which serves as a signal sequence) and GPC3 ERY2_Hk B. Designed Molecule: GPC3 ERY6

Polypeptides encoded by polynucleotides inserted in expression vectors: GPC3 ERY6_Hk (SEQ ID NO: 37; the mature sequence does not contain the amino terminal 19 amino acids, which serves as a signal sequence) and GPC3 ERY6_Hh (SEQ ID NO: 38; the mature sequence does not contain the amino terminal 19 amino acids, which serves as a signal sequence)

C. Designed Molecule: GPC3 ERY7

Polypeptides encoded by polynucleotides inserted in expression vectors: GPC3 ERY7_Hh (SEQ ID NO: 39; the mature sequence does not contain the amino terminal 19 amino acids, which serves as a signal sequence), GPC3 ERY7_L (SEQ ID NO: 40; the mature sequence does not contain the amino terminal 19 amino acids, which serves as a signal sequence), and GPC3 ERY2_Hk The resulting culture supernatant was loaded onto an Anti FLAG M2 column (Sigma). After washing, the column was eluted with 0.1 mg/ml FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultrafiltration. Then, the fraction was loaded onto a Superdex 200 column (GE Healthcare). Only a monomer fraction was collected from the eluate to obtain each purified designed molecule.

Figure 2:
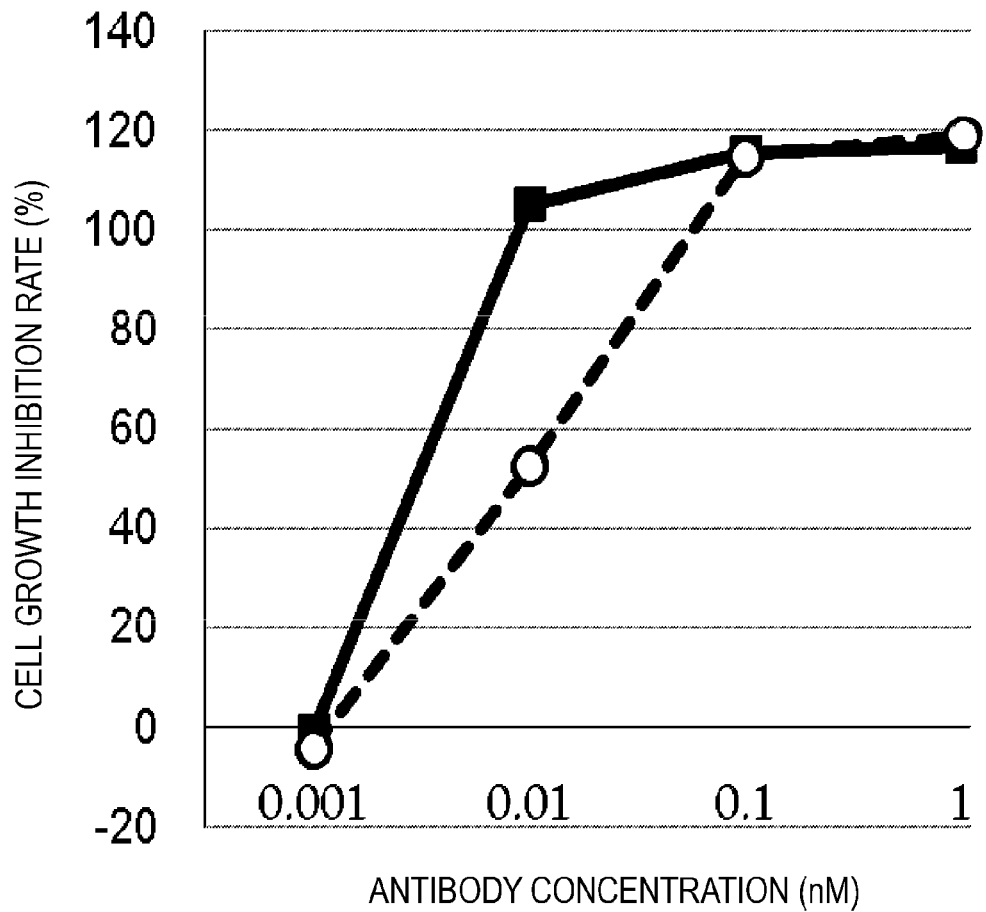
FIG. 2 is a graph showing comparison of the cytotoxic activities of GPC3 BiTE and GPC3 ERY5. Closed square (■) and open circle (○) represent the cytotoxic activities of GPC3 BiTE and GPC3 ERY5, respectively.
Figure 3:
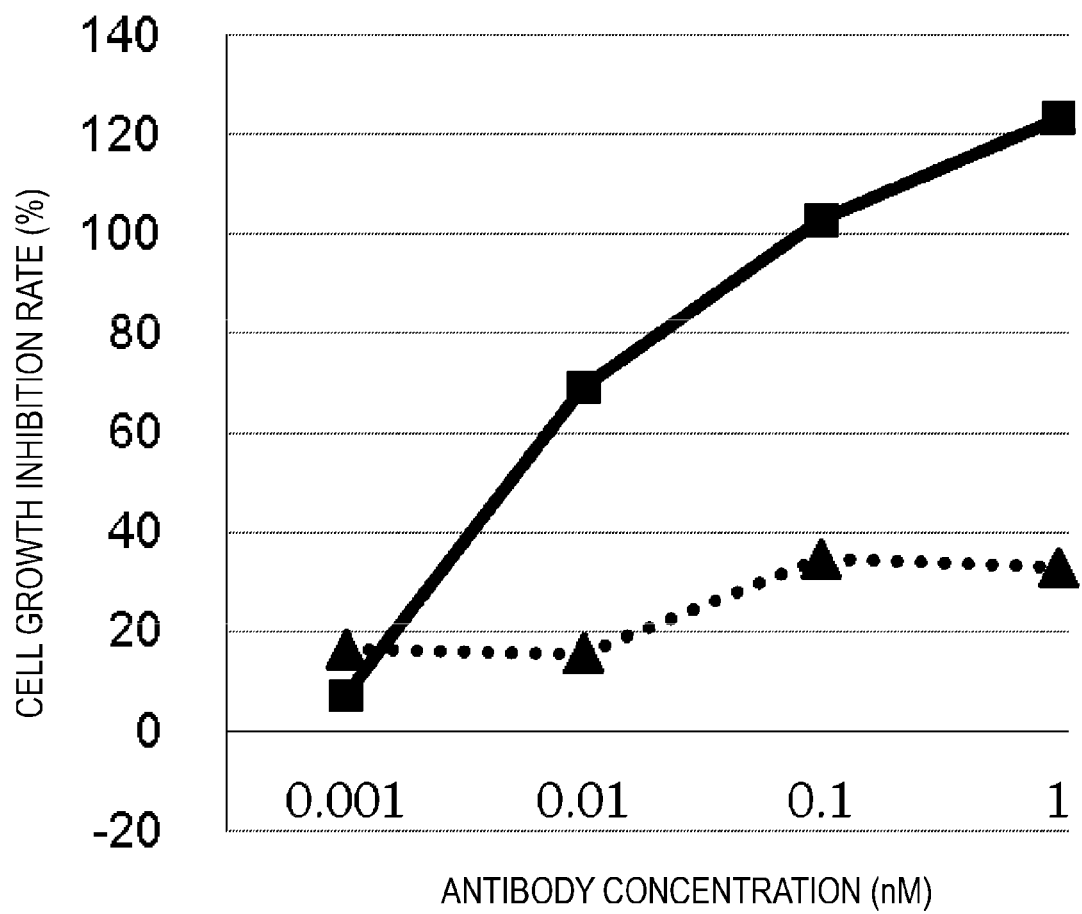
FIG. 3 is a graph showing comparison of the cytotoxic activities of GPC3 BiTE and GPC3 ERY6. Closed square (■) and closed triangle (▲) represent the cytotoxic activities of GPC3 BiTE and GPC3 ERY6, respectively.
Figure 4:
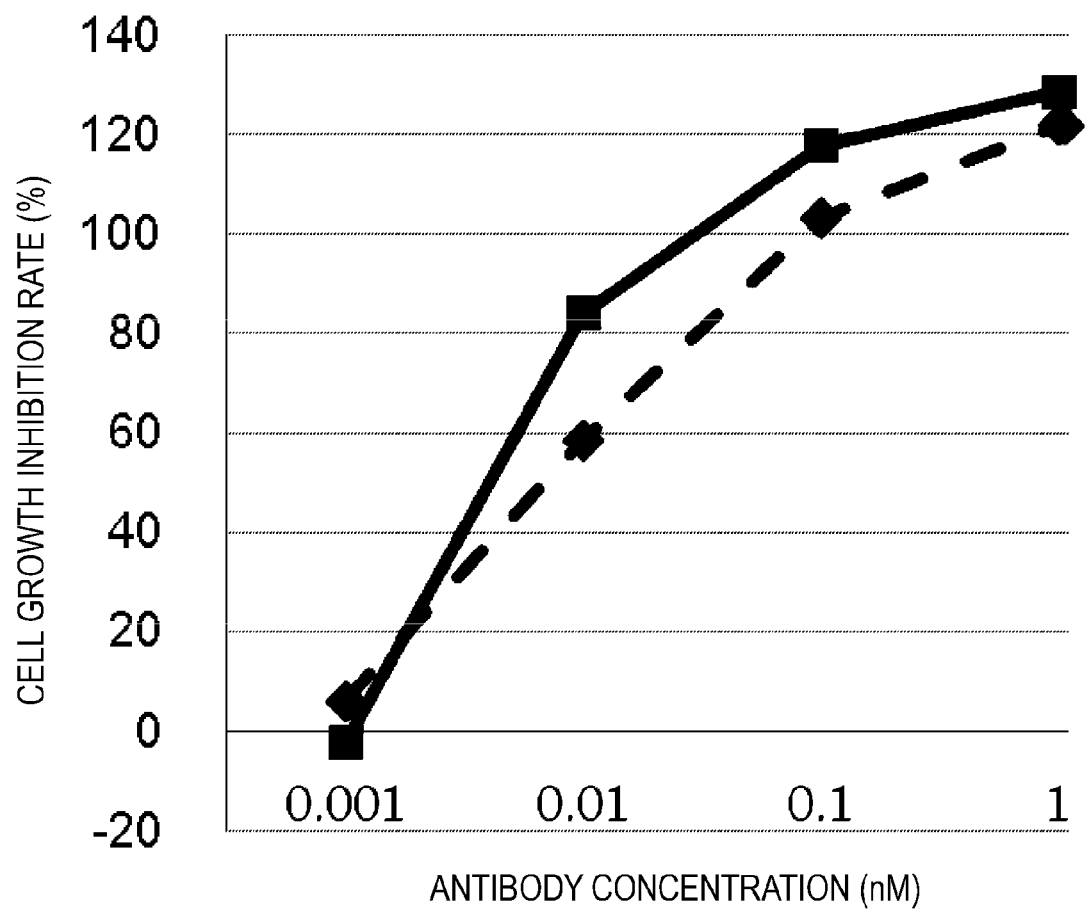
FIG. 4 is a graph showing comparison of the cytotoxic activities of GPC3 BiTE and GPC3 ERY7. Closed square (■) and closed diamond (♦) represent the cytotoxic activities of GPC3 BiTE and GPC3 ERY7, respectively.

These polypeptide complexes were compared to GPC3 BiTE in terms of the cytotoxic activity. The result showed that the cytotoxic activity of these polypeptide complexes was not as much as that of GPC3 BiTE (FIGS. 2 to 4). This finding suggests that the addition of Fc to the BiTE structure or its mimetic structure and the configuration that allows bivalent binding to a cancer antigen do not enable creation of a desired molecule.

[Example 3] Construction and Assessment of GPC3 ERY8-2, GPC3 ERY9-1, and GPC3 ERY10-1

(1) Construction of GPC3 ERY8-2, GPC3 ERY9-1, and GPC3 ERY10-1

Next, molecules having no BiTE structure but possessing the desired activity were designed. An anti-cancer antigen (GPC3) IgG was used as a backbone, and a molecule in which an anti-CD3 epsilon scFv was added to this backbone was constructed. The IgG Fc used as a backbone was a silent Fc having reduced FcgR (Fcγ receptor)-binding activity, as in the above-described cases. GPC3 ERY8-2 (FIG. 17G), GPC3 ERY10-1 (FIG. 17I), and GPC3 ERY9-1 (FIG. 17H) were constructed in which the anti-CD3 epsilon scFv was attached to the N terminus of the H chain, C terminus of the H chain, and C terminus of the L chain of the anti-GPC3 antibody IgG, respectively.

Specifically, by a method known to those skilled in the art, such as PCR using primers containing the same appropriate additional sequences as in the above-described method, a series of expression vectors were constructed into which a polynucleotide encoding GPC3 ERY8-2_Hk (SEQ ID NO: 41; the mature sequence does not contain the amino terminal 19 amino acids, which serve as a signal sequence), GPC3 ERY8-2_Hh (SEQ ID NO: 42; the mature sequence does not contain the amino terminal 19 amino acids, which serve as a signal sequence), GPC3 ERY9-1_H (SEQ ID NO: 43; the mature sequence does not contain the amino terminal 19 amino acids, which serve as a signal sequence), GPC3 ERY9-1_L-His (SEQ ID NO: 44; the mature sequence does not contain the amino terminal 19 amino acids, which serve as a signal sequence), GPC3 ERY9-1 L-FLAG (SEQ ID NO: 45; the mature sequence does not contain the amino terminal 19 amino acids, which serve as a signal sequence), or GPC3 ERY10-1_Hh (SEQ ID NO: 46; the mature sequence does not contain the amino terminal 19 amino acids, which serve as a signal sequence) was inserted.

The following combinations of expression vectors were introduced into FreeStyle293-F cells to express each designed molecule transiently.

D. Designed Molecule: GPC3 ERY8-2

Polypeptides encoded by polynucleotides inserted in expression vectors: GPC3 ERY8-2_Hk (SEQ ID NO: 41; the mature sequence does not contain the amino terminal 19 amino acids, which serve as a signal sequence), GPC3 ERY8-2_Hh (SEQ ID NO: 42; the mature sequence does not contain the amino terminal 19 amino acids, which serve as a signal sequence), and GPC3 ERY7_L E. Designed Molecule: GPC3 ERY9-1

Polypeptides encoded by polynucleotides inserted in expression vectors: GPC3 ERY9-1_H (SEQ ID NO: 43; the mature sequence does not contain the amino terminal 19 amino acids, which serve as a signal sequence), GPC3 ERY9-1_L-His (SEQ ID NO: 44; the mature sequence does not contain the amino terminal 19 amino acids, which serves as a signal sequence), and GPC3 ERY9-1 L-FLAG (SEQ ID NO: 45; the mature sequence does not contain the amino terminal 19 amino acids, which serve as a signal sequence)

F. Designed Molecule: GPC3 ERY10-1

Polypeptides encoded by polynucleotides inserted in expression vectors: GPC3 ERY10-1_Hh (SEQ ID NO: 46; the mature sequence does not contain the amino terminal 19 amino acids, which serve as a signal sequence) and GPC3 ERY8-2_Hk, GPC3 ERY7_L The resulting culture supernatant was loaded onto an Anti FLAG M2 column (Sigma). After washing, the column was eluted with 0.1 mg/ml FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultrafiltration. Then, the fraction was loaded onto a Superdex 200 column (GE Healthcare). Only a monomer fraction was collected from the eluate to obtain each purified designed molecule.

Figure 5:
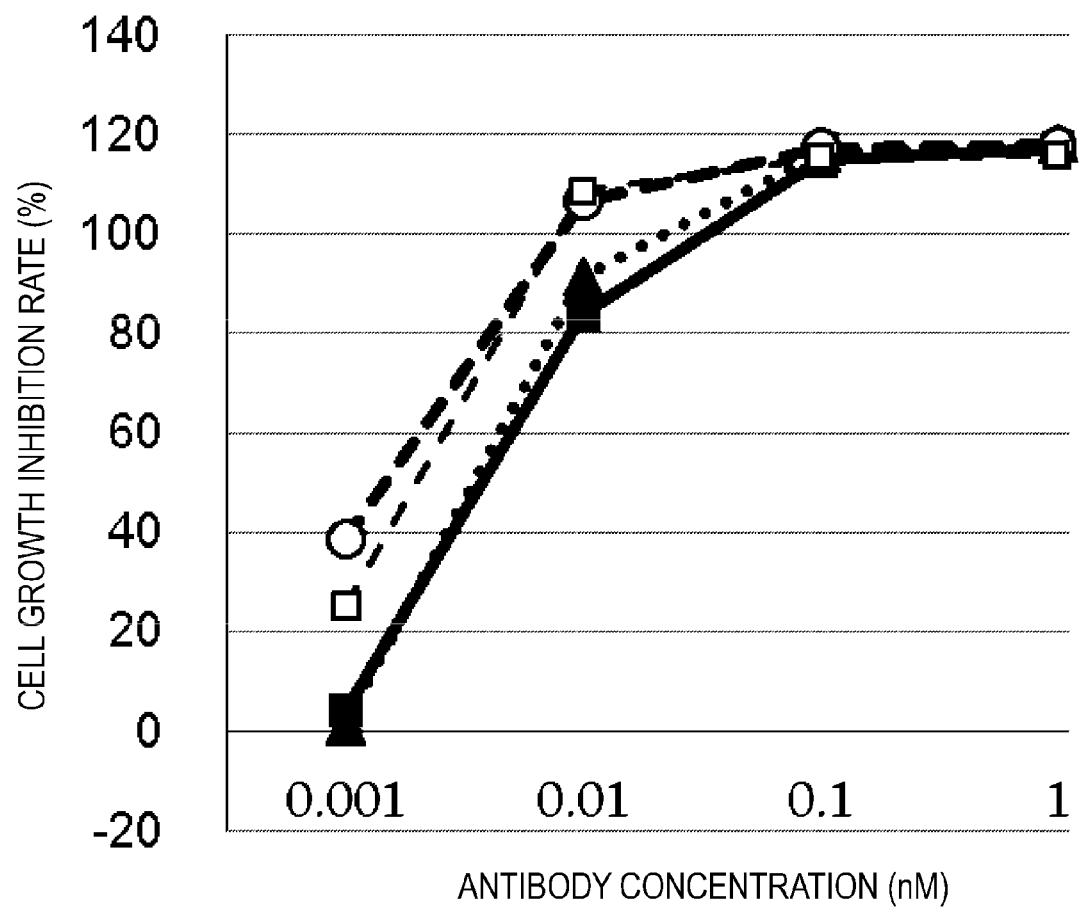
FIG. 5 is a graph showing comparison of the cytotoxic activities of GPC3 BiTE, GPC3 ERY8-2, GPC3 ERY9-1, and GPC3 ERY10-1. Closed square (■), closed triangle (▲), open circle (○), and open square (□) represent the cytotoxic activities of GPC3 BiTE, GPC3 ERY8-2, GPC3 ERY9-1, and GPC3 ERY10-1, respectively.

These molecules were assessed for the in vitro cytotoxic activity. The result revealed that all molecules exhibited a cytotoxic activity comparable to or greater than that of GPC3 BiTE (FIG. 5). In particular, GPC3 ERY9-1 and GPC3 ERY10-1 were found to clearly have a greater cytotoxic activity than GPC3 BiTE. The present invention for the first time demonstrates that molecules made by adding an anti-CD3 epsilon scFv to an anti-cancer antigen IgG also have a cytotoxic activity comparable to or greater than that of BiTE. Particularly, it is surprising that molecules such as GPC3 ERY9-1 and GPC3 ERY10-1 clearly exhibited a greater cytotoxic activity than BiTE although there was a large distance between their cancer antigen-binding domain and CD3 epsilon-binding domain.

(2) Assessment of the In Vivo Efficacy of GPC3 ERY8-2 and GPC3 ERY10-1:

GPC3 ERY8-2 and GPC3 ERY10-1, which were demonstrated to have a cytotoxic activity comparable to or greater than that of GPC3 BiTE in the in vitro assay described in (1), were assessed for the in vivo efficacy. Cells of GPC3-expressing human lung cancer cell line PC-10 were mixed with human PBMCs, and then transplanted to NOD scid mice. The mice were treated by administering GPC3 ERY8-2 or GPC3 ERY10-1 (referred to as pre-mix model).

Specifically, the efficacy test for GPC3 ERY8-2 using the PC-10 pre-mix model was conducted as follows. PBMCs were isolated from blood collected from healthy volunteers. NK cells were removed from the PBMCs using CD56 MicroBeads, human (MCAS Miltenyi biotec). Human lung squamous carcinoma cell line PC-10 (Immuno-Biological Laboratories Co., Ltd.) ($5 \times 10^6$ cells), human PBMCs without NK cells ($4.5 \times 10^6$ cells), and Matrigel Basement Membrane Matrix (BD) were mixed, and then transplanted subcutaneously to the inguinal region of NOD scid mice (CLEA Japan Inc.; female, 7W). The day of transplantation was designated day 0. On the day before transplantation, an anti-asialo GM1 antibody (Wako Pure Chemical Industries) was intraperitoneally administered to the mice at 0.2 mg/head. After two hours of transplantation, GPC ERY8-2 was intraperitoneally administered at 30 μg/head. GPC ERY8-2 was administered five times in total during the period of days 0 to 4.

Furthermore, the efficacy test for GPC3 ERY10-1 using the PC-10 pre-mix model was conducted as follows. PBMCs were isolated from blood collected from healthy volunteers. NK cells were removed from the PBMCs using CD56 MicroBeads, human (MCAS Miltenyi biotec). Human lung squamous carcinoma cell line PC-10 (Immuno-Biological Laboratories Co., Ltd.) (5×10⁶ cells), human PBMCs without NK cells (4.5×10⁶ cells), and Matrigel Basement Membrane Matrix (BD) were mixed, and then transplanted subcutaneously to the inguinal region of NOD scid mice (CLEA Japan Inc.; female, 7W). The day of transplantation was designated day 0. On the day before transplantation, an anti-asialo-GM1 antibody (Wako Pure Chemical Industries) was intraperitoneally administered to the mice at 0.2 mg/head. After two hours of transplantation, GPC ERY10-1 was intraperitoneally administered at 30 µg/head. GPC ERY10-1 was administered 13 times in total during the periods of days 0 to 4, days 7 to 11, and days 14 to 16.

Figure 6:
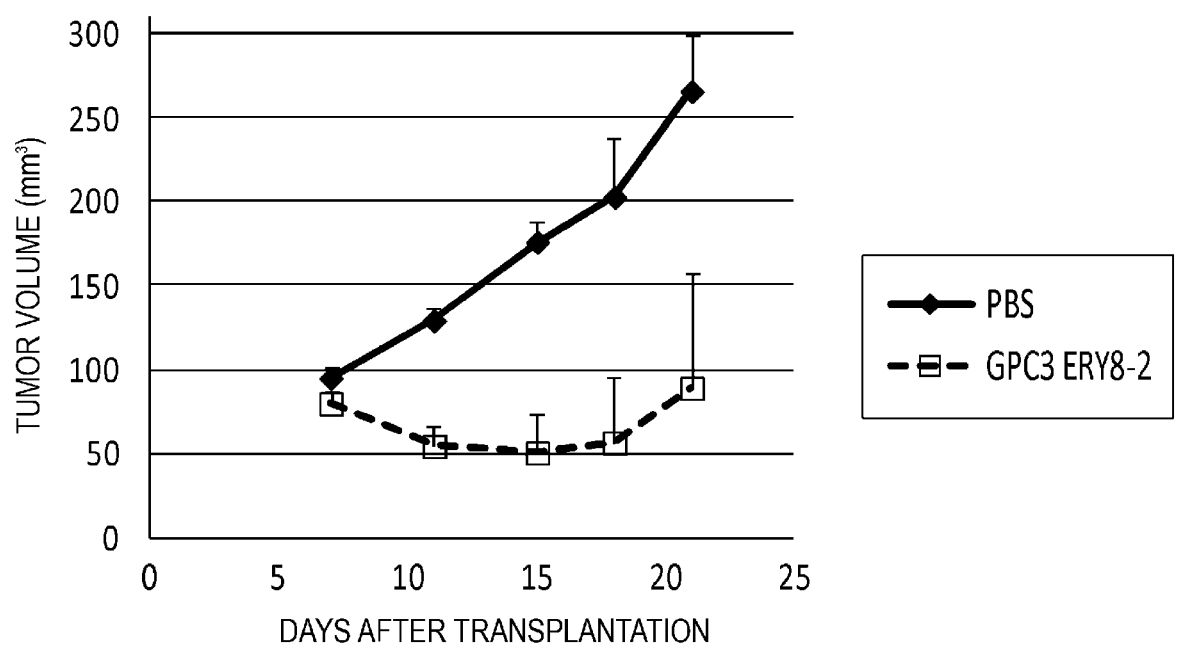
FIG. 6 is a graph showing the in vivo anti-tumor effect of GPC3 ERY8-2 in the PC-10 pre-mix model. Open square (□) and closed diamond (♦) indicate changes in the tumor volume of the GPC3 ERY7 administration group and control (PBS administration) group, respectively.
Figure 7:
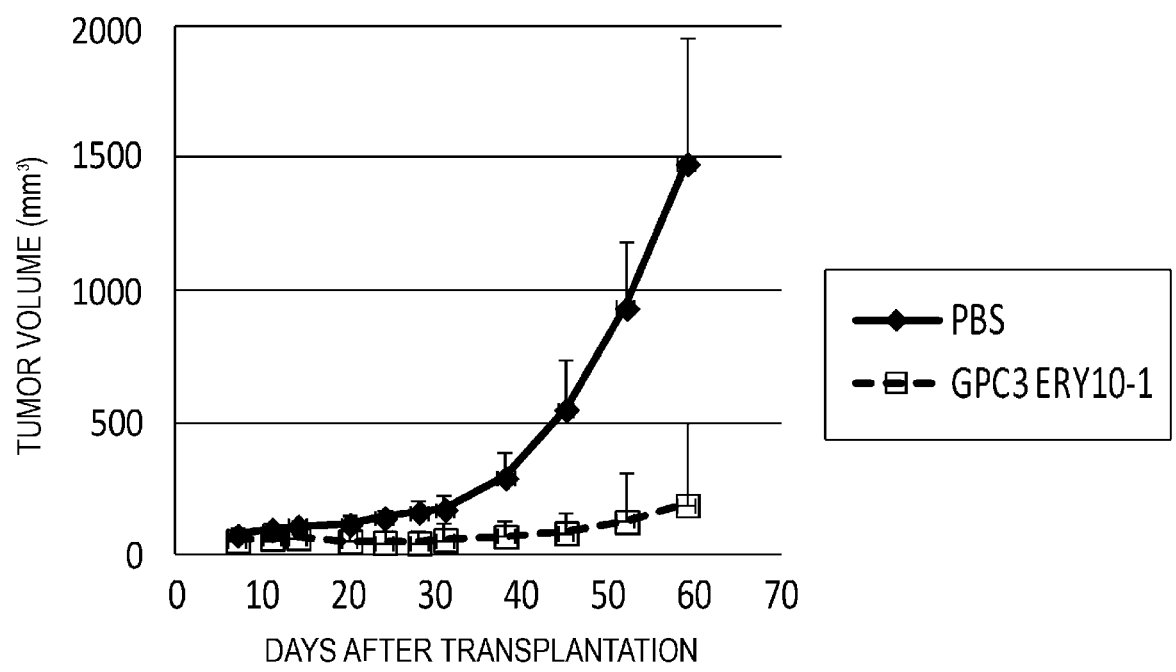
FIG. 7 is a graph showing the in vivo anti-tumor effect of GPC3 ERY10-1 in the PC-10 pre-mix model. Open square (□) and closed diamond (♦) indicate changes in the tumor volume of the GPC3 ERY10-1 administration group and control (PBS administration) group, respectively.

The result showed that in the GPC3 ERY8-2 and GPC3 ERY10-1 administration groups the tumor growth was clearly suppressed as compared to the solvent (PBS) administration group (FIGS. 6 and 7).

Furthermore, GPC3 ERY10-1 was also assessed for the in vivo efficacy using an alternative model. Specifically, T cells were grown by culturing human PBMCs in vitro and then introduced into NOD scid mice which had developed tumors originating from transplanted PC-10. The mice were treated by administering GPC3 ERY10-1 (referred to as T cell transfer model).

Specifically, the efficacy test for GPC3 ERY10-1 using the PC-10 T cell transfer model was conducted as follows. T cell expansion culture was carried out using T cell activation/expansion kit/human (MACS Miltenyi biotec) and PBMCs isolated from blood collected from healthy volunteers. Human lung squamous carcinoma cell line PC-10 cells (Immuno-Biological Laboratories Co., Ltd.) (1×10⁷ cells) were mixed with Matrigel Basement Membrane Matrix (BD), and then transplanted subcutaneously to the inguinal region of NOD scid mice (CLEA Japan Inc.; female, 7W). The day of transplantation was designated day 0. On the day before transplantation and days 6, 8, 12, 16, and 20, an anti-asialo-GM1 antibody (Wako Pure Chemical Industries) was intraperitoneally administered to the mice at 0.2 mg/head. On day 6 of transplantation, the mice were grouped by the tumor size and body weight, and then T cells prepared by expansion culture as described above were transplanted at 1×10⁷ cells/head into the peritoneal cavity. After two hours of transplantation, GPC ERY10-1 was intraperitoneally administered at 30 µg/head. GPC ERY10-1 was administered five times in total on days 7, 8, 12, 16, and 17.

Figure 8:
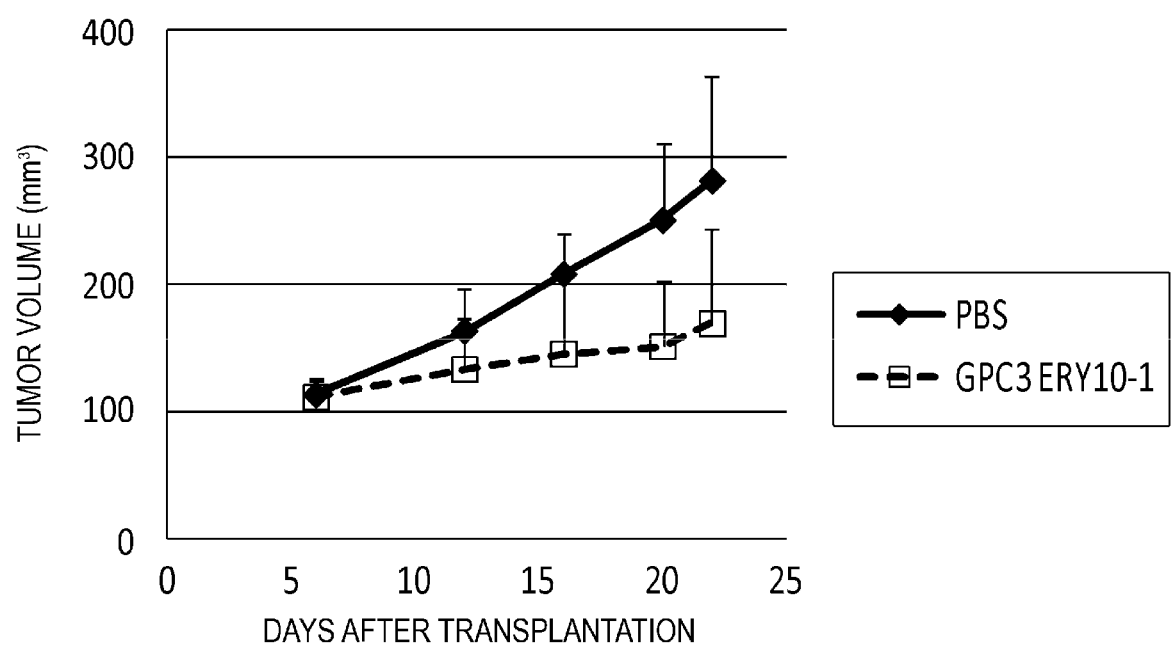
FIG. 8 is a graph showing the in vivo anti-tumor effect of GPC3 ERY10-1 in the PC-10 T cell transfer model. Open square (□) and closed diamond (♦) indicate changes in the tumor volume of the GPC3 ERY10-1 administration group and control (PBS administration) group, respectively.

The result showed that the GPC3 ERY10-1 administration group of this model also exhibited a clear anti-tumor effect as compared to the solvent administration group (FIG. 8).

The finding described above demonstrates that a series of molecules in which one scFv of an anti-CD3 epsilon antibody is added to an IgG backbone having a silent Fc exhibit a clear in vivo anti-tumor effect.

(3) Assessment of Plasma Retention

In order to assess whether molecules such as GPC3 ERY8-2, GPC3 ERY9-1, and GPC3 ERY10-1 have a considerably longer half-life in plasma than GPC3 BiTE, GPC3 ERY9-1 and GPC3 ERY10-1 were administered at 30 µg/head to NOD scid mice to which no cancer cells had been transplanted, and their plasma concentrations were measured over time.

Specifically, PK analysis was carried out in the following manner. GPC3 ERY9-1 and GPC3 ERY10-1 were intraperitoneally administered to NOD scid mice (CLEA Japan Inc.; female, 8W) at 30 µg/head. Blood was collected from the buccal vein of the mice using hematocrit capillaries (Terumo) at 15 minutes, two hours, 1 day, 2 days, and 7 days after administration. Plasma was prepared from the blood.

GPC3 ERY9-1 and GPC3 ERY10-1 were appropriately diluted and added to GPC3-expressing Ba/F3 cells (GPC3/BaF) or human CD3 epsilon-expressing Ba/F3 cells (CD3/BaF) to allow GPC3 ERY9-1 or GPC3 ERY10-1 to react with GPC3/BaF and CD3/BaF. After washing these cells, an FITC-labeled secondary antibody was added for further reaction. After washing the cells, the fluorescent intensity of the label on the cells was measured using Epics XL flow cytometer (Beckman coulter) to prepare a calibration curve for each antibody.

Blood was collected over time from the mice that had been given GPC3 ERY9-1 or GPC3 ERY10-1. Plasma was prepared from the blood and diluted appropriately. In the same manner as for the preparation of calibration curves described above, the plasma samples were reacted with GPC3/BaF or CD3/BaF to determine the amount of plasma GPC3 ERY9-1 and GPC3 ERY10-1 bound to each cell. The plasma concentration of each antibody was calculated using determined values and the calibration curves described above.

Figure 9:
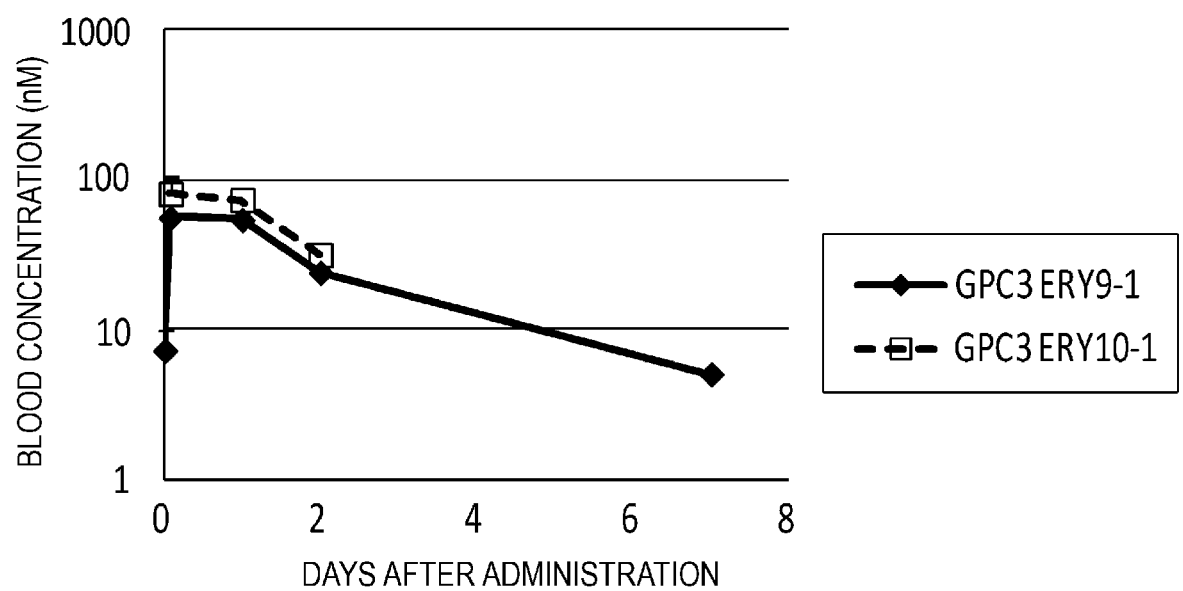
FIG. 9 is a graph showing a time course of the plasma concentrations of GPC3 ERY9-1 and GPC3 ERY10-1 determined using GPC3-expressing Ba/F3 cells. Closed diamond (♦) and open square (□) indicate the plasma concentration time course for GPC3 ERY9-1 and GPC3 ERY10-1, respectively.
Figure 10:
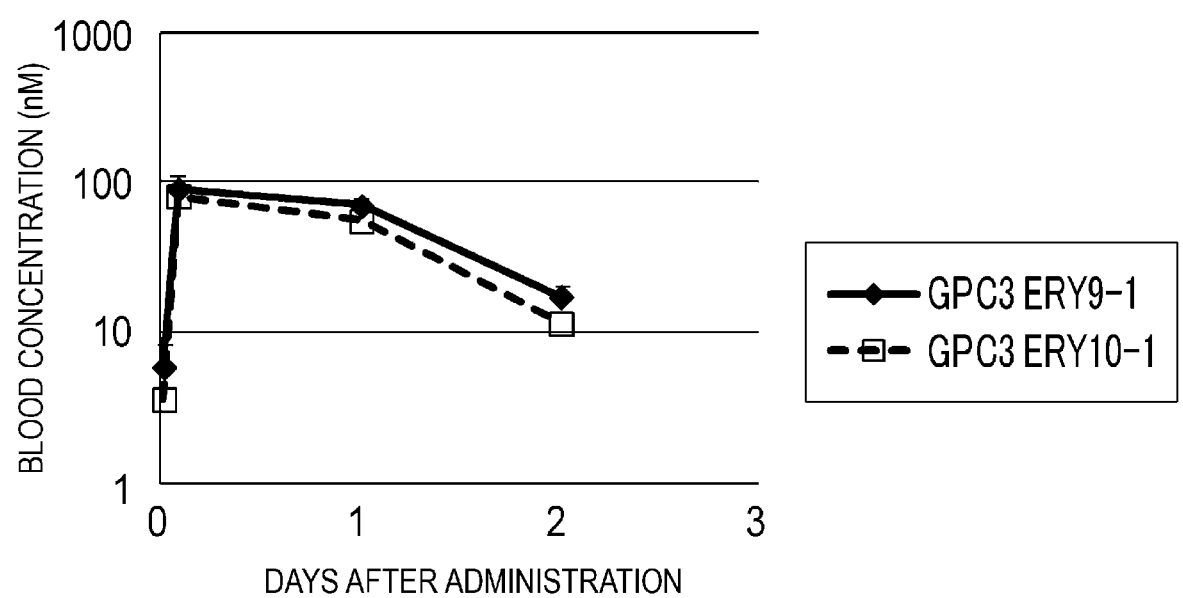
FIG. 10 is a graph showing time course of the plasma concentrations of GPC3 ERY9-1 and GPC3 ERY10-1 determined using CD3-expressing Ba/F3 cells. Closed diamond (♦) and open square (□) indicate the plasma concentration time course for GPC3 ERY9-1 and GPC3 ERY10-1, respectively.

The result showed that the blood concentration of both GPC3 ERY9-1 and GPC3 ERY10-1 remained higher than 10 nM after two days of the administration (FIGS. 9 and 10). This finding demonstrates that molecules such as GPC3 ERY9-1 and GPC3 ERY10-1 have a significantly improved plasma half-life as compared to BiTE.

(4) Effect of Silent Fc on Cancer Antigen-Independent Cytokine Induction (4-1) Construction of GPC3 ERY15-1 having FcgR-binding Fc GPC3 ERY15-1 having an FcgR-binding Fc (FIG. 17J) was constructed to test whether molecules such as GPC3 ERY8-2, GPC3 ERY9-1, and GPC3 ERY10-1 would induce cytokines in a cancer antigen-independent manner.

Specifically, as in the above-described method, PCR using primers containing appropriate additional sequences and a method known to those skilled in the art such as a method using QuikChange Site-Directed Mutagenesis Kit (Stratagene) were performed to construct expression vectors into which a polynucleotide encoding GPC3 ERY15-1_Hh (SEQ ID NO: 47; the mature sequence does not contain the amino terminal 19 amino acids, which serve as a signal sequence) or GPC3 ERY15-1_Hk (SEQ ID NO: 48; the mature sequence does not contain the amino terminal 19 amino acids, which serve as a signal sequence) was inserted.

The expression vectors for GPC3 ERY15-1_Hh (SEQ ID NO: 47; the mature sequence does not contain the amino terminal 19 amino acids, which serve as a signal sequence), GPC3 ERY15-1_Hk (SEQ ID NO: 48; the mature sequence does not contain the amino terminal 19 amino acids, which serve as a signal sequence), and GPC3 ERY7_L were co-introduced into FreeStyle293-F cells to express GPC3 ERY15-1 transiently. The resulting culture supernatant was loaded onto an Anti FLAG M2 column (Sigma). After washing, the column was eluted with 0.1 mg/ml FLAG peptide (Sigma). A fraction containing GPC3 ERY15-1 was loaded onto a HisTrap HP column (GE Healthcare). After washing, the column was eluted with an imidazole concentration gradient. A fraction containing GPC3 ERY15-1 was concentrated by ultrafiltration. Then, the fraction was loaded onto a Superdex 200 column (GE Healthcare). Only a monomeric GPC3 ERY15-1 fraction was collected from the eluate to obtain purified GPC3 ERY15-1.

(4-2) Assay for Cancer Antigen-Independent Cytokine-Inducing Ability

The cancer antigen-independent cytokine-inducing ability of GPC3 ERY15-1 was compared to those of GPC3 BiTE, GPC3 ERY9-1, GPC3 ERY10-1, and catumaxomab. By using the method described above, PBMCs were prepared from blood collected from healthy volunteers. Fifty µl of each antibody adjusted to 40 nM was added to 50 µl of human PBMC suspension (2×10⁵ cells/well), and then 100 µl of 10% FBS/D-MEM was added thereto. The reaction mixture was incubated under 5% carbon dioxide gas at 37° C. After 72 hours of incubation, the culture supernatant was collected, and cytokines secreted in the culture supernatant were quantified by Cytometric Beads Array (CBA) assay using Human Th1/Th2/Th17 Kit (BD). The assay was carried out in triplicate by the method according to the appended protocol.

Figure 11:
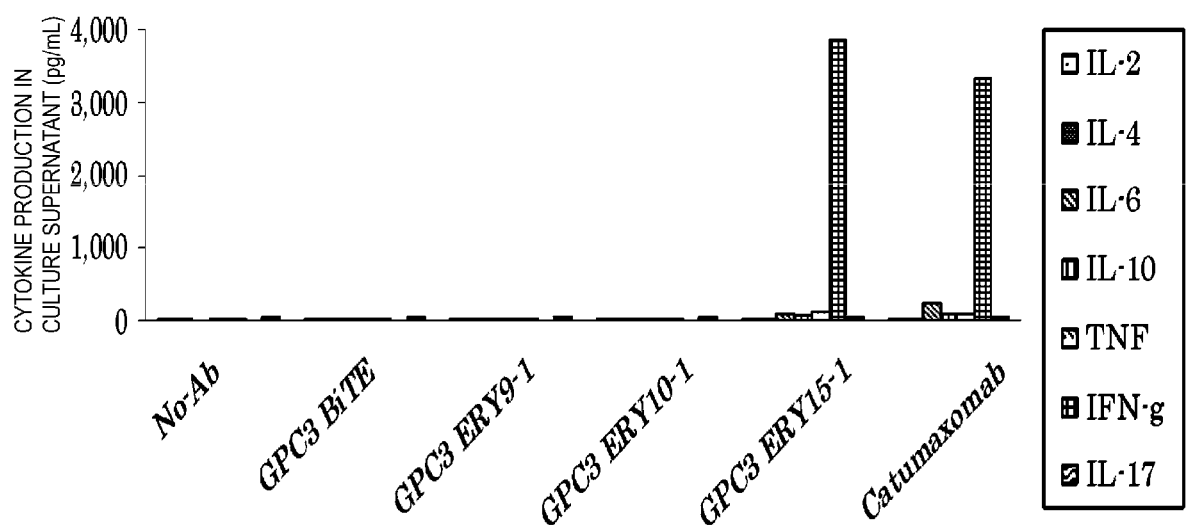
FIG. 11 is a graph showing assessment of GPC3 BiTE, GPC3 ERY9-1, GPC3 ERY10-1, GPC3 ERY15-1, and catumaxomab for their ability to induce cytokines in a cancer antigen-independent manner.

As a result, GPC3 ERY15-1 and catumaxomab, which have a FcgR-binding Fc, showed clear cytokine induction. In contrast, no cytokine induction was observed for GPC3 BiTE, which has no Fc, and GPC3 ERY9-1 and GPC3 ERY10-1, which possess a silent Fc (FIG. 11). This result suggests that molecules having a silent Fc such as GPC3 ERY8-2, GPC3 ERY9-1, and GPC3 ERY10-1 are highly safe molecules which do not induce cytokines in a cancer antigen-independent manner.

[Example 4] Construction and Assessment of GPC3 ERY18 L1, L2, L3, L4, and S1

Molecules having a CD3-binding domain different from the scFv structure were assessed. GPC3 ERY18 (FIG. 17K) was constructed in which the VH and VL domains of an anti-CD3 antibody were linked to the C termini of the two H chains of an anti-cancer antigen (GPC3) IgG. In this construction, a series of molecules (GPC3 ERY18 L1, L2, L3, and L4) having one to four linker units (Gly-Gly-Gly-Gly-Ser) at the junction were produced. At the same time, another molecule (GPC3 ERY18 S1) was constructed in which amino acids at appropriate positions were substituted with Cys to allow introduction of a disulfide bond.

Specifically, a method known to those skilled in the art, such as PCR using primers containing appropriate additional sequences as in the method described above, was performed to construct a series of expression vectors into which a polynucleotide encoding GPC3 ERY18 L1_Hh (SEQ ID NO: 49; the mature sequence does not contain the amino terminal 19 amino acids, which serve as a signal sequence), GPC3 ERY18 µl_Hk (SEQ ID NO: 50; the mature sequence does not contain the amino terminal 19 amino acids, which serve as a signal sequence), GPC3 ERY18 L2 Hh (SEQ ID NO: 51; the mature sequence does not contain the amino terminal 19 amino acids, which serve as a signal sequence), GPC3 ERY18 L2_Hk (SEQ ID NO:52; the mature sequence does not contain the amino terminal 19 amino acids, which serve as a signal sequence), GPC3 ERY18 L3_Hh (SEQ ID NO: 53; the mature sequence does not contain the amino terminal 19 amino acids, which serve as a signal sequence), GPC3 ERY18 L3_Hk (SEQ ID NO: 54; the mature sequence does not contain the amino terminal 19 amino acids, which serve as a signal sequence), GPC3 ERY18 L4_Hh (SEQ ID NO: 55; the mature sequence does not contain the amino terminal 19 amino acids, which serve as a signal sequence), GPC3 ERY18 L4_Hk (SEQ ID NO: 56; the mature sequence does not contain the amino terminal 19 amino acids, which serve as a signal sequence), GPC3 ERY18 S1_Hh (SEQ ID NO: 57; the mature sequence does not contain the amino terminal 19 amino acids, which serve as a signal sequence), or GPC3 ERY18 S1_Hk (SEQ ID NO: 58; the mature sequence does not contain the amino terminal 19 amino acids, which serve as a signal sequence) was inserted.

The following combinations of expression vectors were introduced into FreeStyle293-F cells to express each designed molecule transiently.

G. Designed Molecule: GPC3 ERY18 µl
Expression vectors: GPC3 ERY18 µl_Hh (SEQ ID NO: 49; the mature sequence does not contain the amino terminal 19 amino acids, which serve as a signal sequence), GPC3 ERY18 L1_Hk (SEQ ID NO: 50; the mature sequence does not contain the amino terminal 19 amino acids, which serve as a signal sequence), and GPC3 ERY7 L H. Designed Molecule: GPC3 ERY18 L2
Expression vectors: GPC3 ERY18 L2_Hh (SEQ ID NO: 51; the mature sequence does not contain the amino terminal 19 amino acids, which serve as a signal sequence), GPC3 ERY18 L2_Hk (SEQ ID NO: 52; the mature sequence does not contain the amino terminal 19 amino acids, which serve as a signal sequence), and GPC3 ERY7 L I. Designed Molecule: GPC3 ERY18 L3
Expression vectors: GPC3 ERY18 L3_Hh (SEQ ID NO: 53; the mature sequence does not contain the amino terminal 19 amino acids, which serve as a signal sequence), GPC3 ERY18 L3_Hk (SEQ ID NO: 54; the mature sequence does not contain the amino terminal 19 amino acids, which serve as a signal sequence), and GPC3 ERY7 L J. Designed Molecule: GPC3 ERY18 L4
Expression vectors: GPC3 ERY18 L4_Hh (SEQ ID NO: 55; the mature sequence does not contain the amino terminal 19 amino acids, which serve as a signal sequence), GPC3 ERY18 L4_Hk (SEQ ID NO: 56; the mature sequence does not contain the amino terminal 19 amino acids, which serve as a signal sequence), and GPC3 ERY7 L K. Designed Molecule: GPC3 ERY18 S1
Expression vectors: GPC3 ERY18 S1_Hh (SEQ ID NO: 57; the mature sequence does not contain the amino terminal 19 amino acids, which serve as a signal sequence), GPC3 ERY18 S1_Hk (SEQ ID NO: 58; the mature sequence does not contain the amino terminal 19 amino acids, which serve as a signal sequence), and GPC3 ERY7 L The resulting culture supernatant was loaded onto an Anti FLAG M2 column (Sigma). After washing, the column was eluted with 0.1 mg/ml FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultra-filtration. Then, the fraction was loaded onto a Superdex 200 column (GE Healthcare). Only a monomer fraction was collected from the eluate to obtain each purified designed molecule.

Figure 12:
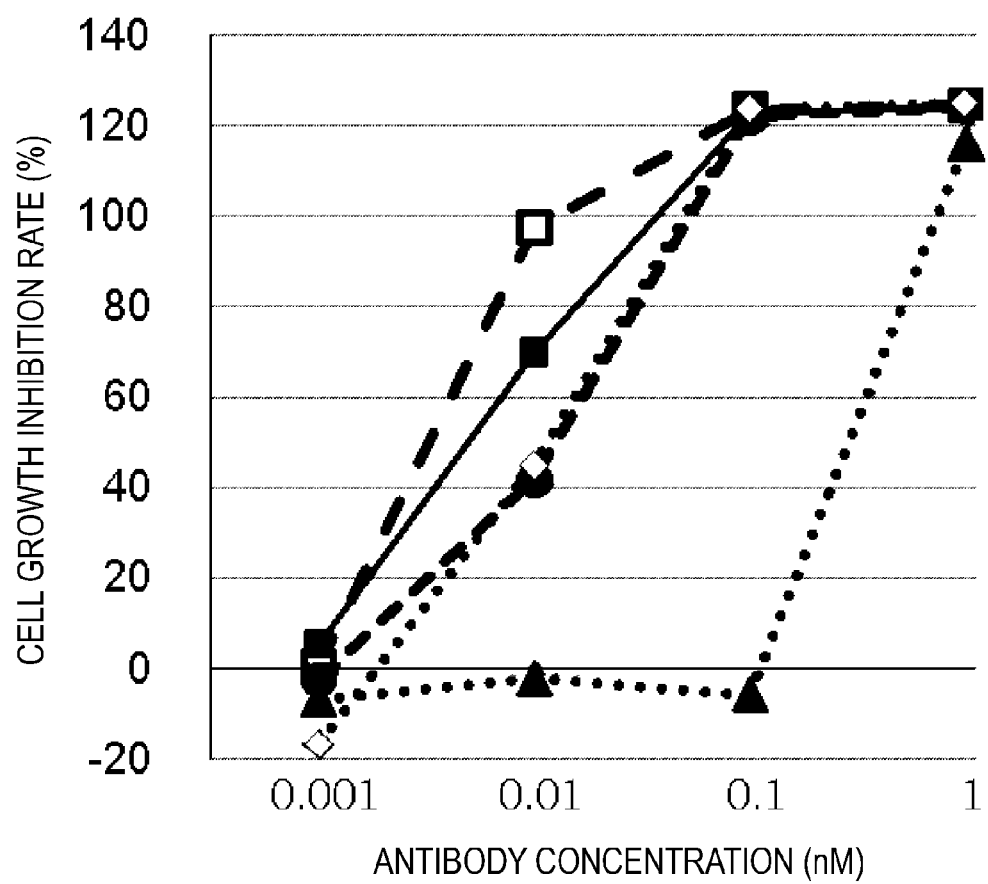
FIG. 12 is a graph showing the in vitro cytotoxicities of GPC3 ERY18 L1, GPC3 ERY18L2, GPC3 ERY18L3, GPC3 ERY18L4, and GPC3 ERY18S1. Closed triangle (▲), closed circle (●), closed square (■), open square (□), and open diamond (◇) represent the cytotoxic activities of GPC3 ERY18 L1, GPC3 ERY18 L2, GPC3 ERY18 L3, GPC3 ERY18 L4, and GPC3 ERY18 S1, respectively.
Figure 13:
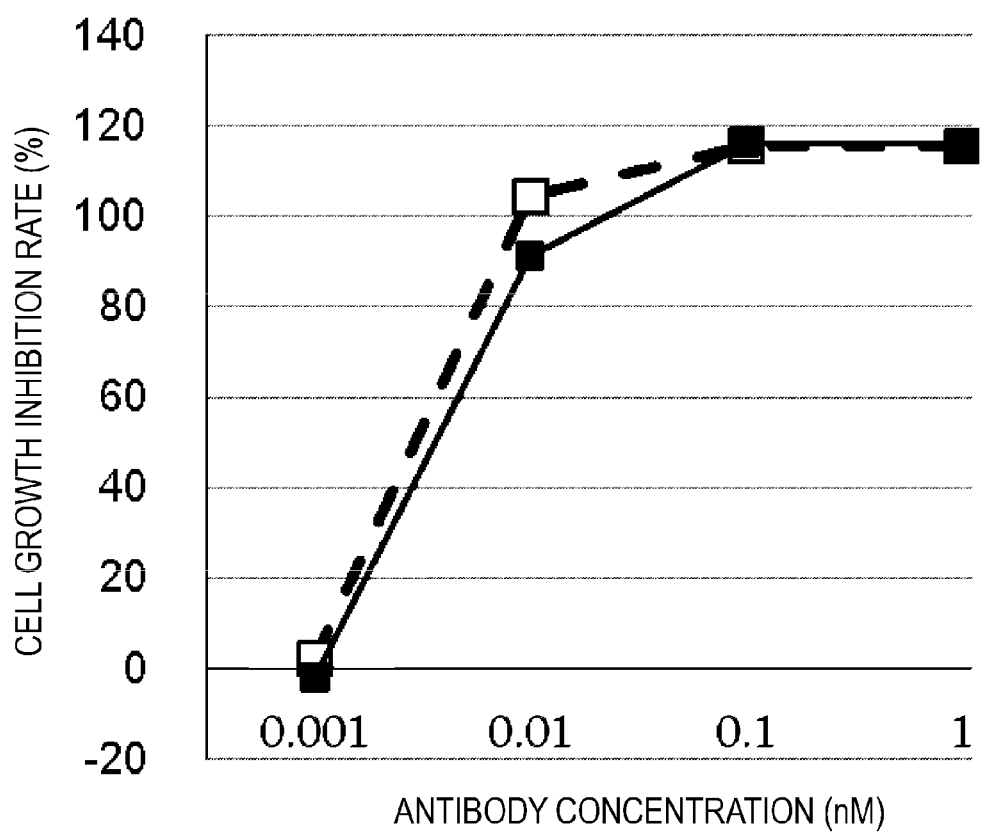
FIG. 13 is a graph showing comparison of the in vitro cytotoxic activities of GPC3 ERY18 L3 and GPC3 ERY10-1. Closed square (■) and open square (□) represent the cytotoxic activities of GPC3 ERY18 L3 and GPC3 ERY10-1, respectively.

GPC3 ERY18 L1, GPC3 ERY18L2, GPC3 ERY18L3, GPC3 ERY18L4, and GPC3 ERY18S1 molecules were each assessed for the in vitro cytotoxic activity (FIGS. 12 and 13). The result showed that all molecules except GPC3 ERY18 L1 had an activity comparable to that of GPC3 ERY10-1. This result demonstrates that molecules having a non-scFv structure have a comparable cytotoxic activity. The structure where the VH and VL domains of CD3 antibody are each linked to the C termini of two H chains of an anti-cancer antigen (GPC3) IgG is expected to contribute to stabilization of the polypeptide complexes of the present invention.

[Example 5] Construction and Assessment of GPC3 ERY19-3

Next, molecules having a Fab-like CD3-binding domain were assessed. GPC3 ERY19-3 (FIG. 17L) was constructed in which the VH and CH1 domains, and VL and CL domains of CD3 antibody were each linked to the C termini of the two H chains of an anti-cancer antigen (GPC3) IgG antibody. Specifically, by a method known to those skilled in the art, such as PCR using primers containing appropriate additional sequences in the same manner as in the method described above, expression vectors were constructed into which a polynucleotide encoding GPC3 ERY19-3_Hh (SEQ ID NO: 59; the mature sequence does not contain the amino terminal 19 amino acids, which serve as a signal sequence) or GPC3 ERY19-3_Hk (SEQ ID NO: 60; the mature sequence does not contain the amino terminal 19 amino acids, which serve as a signal sequence) was inserted.

The expression vectors for GPC3 ERY19-3_Hh (SEQ ID NO: 59; the mature sequence does not contain the amino terminal 19 amino acids, which serve as a signal sequence), GPC3 ERY19-3_Hk (SEQ ID NO: 60; the mature sequence does not contain the amino terminal 19 amino acids, which serve as a signal sequence), and GPC3 ERY7_L were co-introduced into FreeStyle293-F cells to express GPC3 ERY19-3 transiently. The resulting culture supernatant was loaded onto a HiTrap rProtein A FF column (GE Healthcare). After washing, the column was eluted with an acid. A fraction containing GPC3 ERY19-3 was concentrated by ultrafiltration, and then loaded onto a Superdex 200 column (GE Healthcare). Only a monomeric GPC3 ERY19-3 fraction was collected from the eluate to obtain purified GPC3 ERY19-3.

Figure 14:
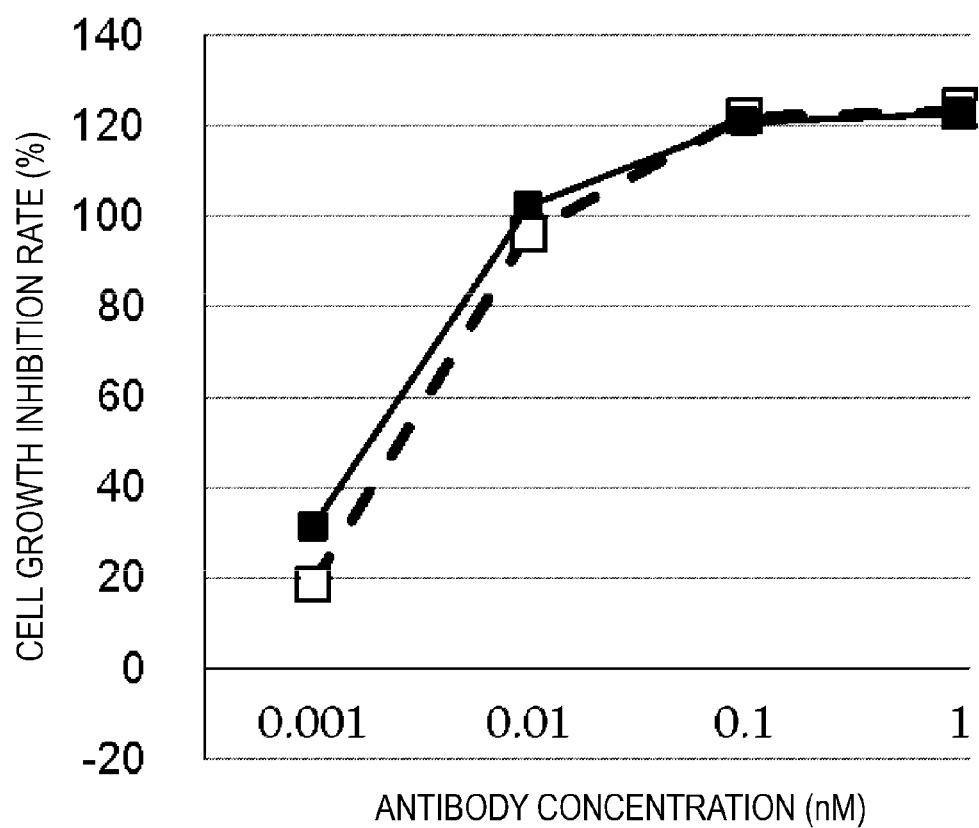
FIG. 14 is a graph showing comparison of the in vitro cytotoxic activities of GPC3 ERY19-3 and GPC3 BiTE. Open square (□) and closed square (■) represent the cytotoxic activities of GPC3 ERY19-3 and GPC3 BiTE, respectively.

The GPC3 ERY19-3 molecule was assessed for the in vitro cytotoxic activity. The result showed that the molecule had an activity comparable to GPC3 BiTE (FIG. 14). The CD3-binding domain with a Fab-like structure is expected to contribute to stabilization of the polypeptide complex molecules of the present invention.

[Example 6] Preparation of Polypeptide Complexes Using a Protein a Purification Step Alone by Introduction of Mutation into the CH3 Domain of GPC3 ERY 10-1

(1) Outline

In GPC3 ERY10-1 prepared in Example 3, the CH3 domain has the knobs-into-holes structure. The desired GPC3 ERY10-1 molecule, in which the two H chains were heteromerically associated together, was purified by two types of affinity purification using the His tag and FLAG tag attached to the C terminus of each H chain. If the GPC3 ERY10-1 molecule is produced as a pharmaceutical, Protein A chromatography is first performed on the culture supernatant of GPC3 ERY10-1-expressing cells to purify a polypeptide complex having a Fc domain. This step has to be followed by an additional chromatographic purification step using His tag affinity chromatography and FLAG tag affinity chromatography. This results in increased costs for the purification process. Thus, this Example examined molecular modifications that enable purification of the desired GPC3 ERY10-1 molecule having the two heteromerically associated H chains by Protein A chromatography only without using a His tag and FLAG tag.

Specifically, modifications to eliminate the Protein A binding in one of the two H chains were examined. As a result of such modifications, when non-Protein A-binding H chains are homomerically associated, the molecule cannot bind to Protein A and therefore passes through Protein A chromatography. On the other hand, a molecule in which a non-Protein A-binding H chain is heteromerically associated with a Protein A-binding H chain, and a molecule in which Protein A-binding H chains are homomerically associated, may be separated using Protein A chromatography based on difference in the affinity for Protein A. However, in the antibody Fc domain, the binding site for Protein A overlaps with the binding site for FcRn, which is crucial for the plasma retention of antibody. Thus, it is necessary to selectively reduce the Protein A-binding activity only, while maintaining the FcRn-binding activity. As such a modification, substitution of His at position 435 (EU numbering) with Arg was discovered. The combination of this mutation with the mutations described in WO 2006/106905 (substituting Asp at position 356 (EU numbering) in one of the H chains with Lys, and Lys at position 439 (EU numbering) in the other H chain with Glu), which promote heteromeric association of the two H chains, was tested as to whether it could enable purification of polypeptide complexes such as GPC3 ERY10-1 using Protein A chromatography only.

(2) Construction of Antibody Gene Expression Vectors and Expression of Respective Antibodies For the antibody H chain variable region, a gene encoding GC33(2)H (anti-human Glypican-3 antibody H chain variable region, SEQ ID NO: 61; the mature sequence does not contain the amino terminal 19 amino acids, which serve as a signal sequence) was constructed by a method known to those skilled in the art. Similarly, for the antibody L chain, a gene encoding GC33-k0 (anti-human Glypican-3 antibody L chain, SEQ ID NO: 62; the mature sequence does not contain the amino terminal 19 amino acids, which serve as a signal sequence) was constructed by a method known to those skilled in the art. Next, for the antibody H chain constant region, the genes described below were constructed by a method known to those skilled in the art.

L. Designed Molecule: LALA-G 1d

LALA-Gld (SEQ ID NO: 63; the mature sequence does not contain the amino terminal 19 amino acids, which serve as a signal sequence), in which Leu at positions 234 and 235 (EU numbering) have been substituted with Ala, Asn at position 297 has been substituted with Ala, and Gly and Lys at the C-terminal have been removed in the sequence of IgG1

M. Designed Molecule: LALA-G1d-CD3

LALA-G1d-CD3 (SEQ ID NO: 64; the mature sequence does not contain the amino terminal 19 amino acids, which serve as a signal sequence), in which a CD3 scFv (anti-human CD3 antibody H chain variable region and anti-human CD3 antibody L chain variable region are linked together via a polypeptide linker) has been linked to the C terminus of LALA-Gld (SEQ ID NO: 63; the mature sequence does not contain the amino terminal 19 amino acids, which serve as a signal sequence)

N. Designed Molecule: LALA-G3S3E-G1d

LALA-G3S3E-Gld (SEQ ID NO: 65; the mature sequence does not contain the amino terminal 19 amino acids, which serve as a signal sequence), in which His at position 435 (EU numbering) has been substituted with Arg, and Lys at position 439 (EU numbering) has been substituted with Glu in the sequence of LALA-G1d (SEQ ID NO: 63; the mature sequence does not contain the amino terminal 19 amino acids, which serve as a signal sequence)

O. Designed Molecule: LALA-S3K-G1d-CD3

LALA-S3K-G1d-CD3 (SEQ ID NO: 66; the mature sequence does not contain the amino terminal 19 amino acids, which serve as a signal sequence), in which Asp at position 356 (EU numbering) has been substituted with Lys in the sequence of LALA-G1d-CD3 (SEQ ID NO: 64; the mature sequence does not contain the amino terminal 19 amino acids, which serve as a signal sequence)

Anti-human GPC3 antibody H chain genes NTA1L and NTA1R were constructed by linking LALA-G1d-CD3 or LALA-G1d downstream of GC33(2)H, respectively. Meanwhile, anti-human GPC3 antibody H chain genes NTA2L and NTA2R were constructed by linking LALA-S3K-G1d-CD3 or LALA-G3S3E-G1d downstream of GC33(2)H, respectively.

Expression vectors for NTA1L, NTA1R, NTA2L, NTA2R(H chains), and GC33-k0 (L chain) were constructed by inserting each gene into an animal cell expression vector. These vectors were combined as shown below and introduced into FreeStyle293 cells (Invitrogen) by a method known to those skilled in the art to transiently express the polypeptide complexes described below. As shown below, the polypeptide complexes are referred to by the names of introduced genes combined in the order of [first H chain/second H chain/L chain].

NTA1L/NTA1R/GC33-k0
NTA2L/NTA2R/GC33-k0

(3) Purification of Expressed Samples and Assessment for Heteromeric Complex Formation Culture supernatant of FreeStyle293 cells (hereinafter referred to as CM) containing a polypeptide complex shown below was used as a sample.

NTA1L/NTA1R/GC33-k0
NTA2L/NTA2R/GC33-k0

CM was filtered through a φ0.22-μm filter and loaded onto a rProtein A Sepharose Fast Flow column (GE Healthcare) equilibrated with D-PBS. Washing steps 1 and 2, and elution step 1 were carried out using the buffers shown in Table 1. The loading amount of CM was adjusted so that the loading amount of antibody was 20 mg/ml resin. Eluted fractions were collected and analyzed by size exclusion chromatography to identify the components in the fractions.

TABLE 1

| EQUILIBRATION | D-PBS |
| --- | --- |
| WASH 1 | 1 mM sodium acetate, 150 mM NaCl, pH 6.5 |
| WASH 2 | 0.3 mM HCl, 150 mM NaCl, pH 3.7 |
| ELUTION 1 | 2 mM HCl, pH 2.7 |

Figure 15:
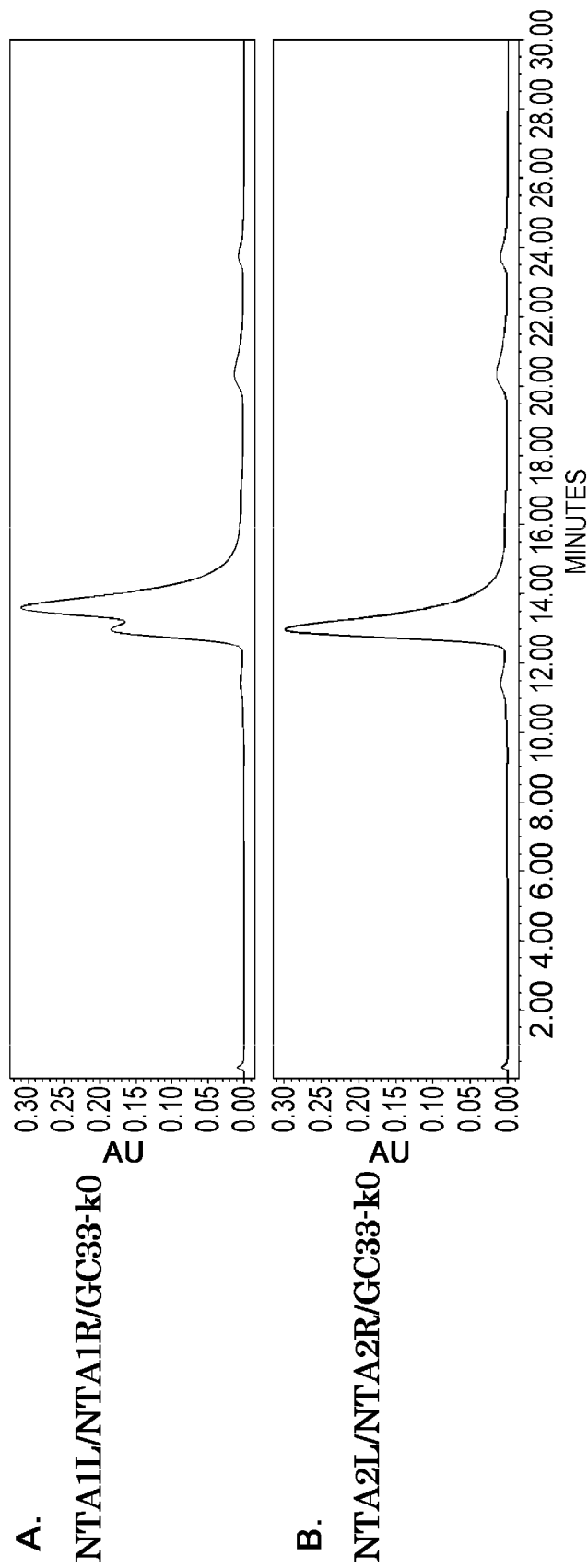
FIG. 15A is a chromatogram showing results of the size exclusion chromatography analysis of CM in which NTA1L/NTA1R/GC33-k0 was expressed.
FIG. 15B is a chromatogram showing results of the size exclusion chromatography analysis of CM in which NTA2L/NTA2R/GC33-k0 was expressed.

The result of size exclusion chromatography analysis of each eluted fraction is shown in FIG. 15 and Table 2. The values indicate percent area of elution peak. When NTA1L/NTA1R/GC33-k0 or NTA2L/NTA2R/GC33-k0 was expressed, the anti-GPC3 homomeric antibody (NTA1L/GC33-k0 or NTA2L/GC33-k0) was almost undetectable in CM. Meanwhile, the anti-GPC3 homomeric antibody (NTA2R/GC33-k0) was only about 2% in CM where NTA2L/NTA2R/GC33-k0 was expressed, whereas it was about 76% in CM where NTA1L/NTA1R/GC33-k0 was expressed. This result demonstrates that, when H is at position 435 (EU numbering) is substituted with Arg and, in order to allow efficient formation of the heteromeric molecule of the respective H chains, Asp at position 356 (EU numbering) in the polypeptide sequence of one of the H chains is substituted with Lys and Lys at position 439 (EU numbering) in the polypeptide sequence of the other H chain is substituted with Glu, heteromeric polypeptide complexes having the same molecular form as GPC3 ERY10-1 can be efficiently purified with a purity of more than 98% by only the purification step using Protein A.

TABLE 2

| | CD3 homomeric antibody | Heteromeric antibody | GPC3 homomeric antibody |
| --- | --- | --- | --- |
| NTA1L/NTA1R/GC33-k0 | 0.7 | 23.5 | 75.8 |
| NTA2L/NTA2R/GC33-k0 | — | 98.2 | 1.8 |

[Example 7] Construction and Assessment of GPC3 ERY 17-2 and GPC3 ERY 17-3

(1) Construction of GPC3 ERY 17-2 and GPC3 ERY 17-3

Next, a molecule was constructed by using an anti-cancer antigen (GPC3) IgG as a backbone and substituting one of the Fabs with a CD3 epsilon-binding domain. As in the above-described cases, the Fc of the backbone IgG was silent Fc having a reduced FcgR (Fcγ receptor)-binding activity. For the CD3 epsilon-binding domains, the VH and VL domains of anti-CD3 epsilon Fab were exchanged to produce GPC3 ERY17-2 (FIG. 19A), and the CH1 and CL domains were exchanged to produce GPC3 ERY17-3 (FIG. 19B).

Specifically, by a method known to those skilled in the art, such as PCR using primers containing the same appropriate additional sequences as in the method described above, a series of expression vectors were constructed into which a polynucleotide encoding ERY17-2_Hh (SEQ ID NO: 73; the mature sequence does not contain the amino terminal 19 amino acids, which serve as a signal sequence), ERY17-2_L (SEQ ID NO: 74; the mature sequence does not contain the amino terminal 19 amino acids, which serve as a signal sequence), ERY17-3_Hh (SEQ ID NO: 75; the mature sequence does not contain the amino terminal 19 amino acids, which serve as a signal sequence), or ERY17-3_L (SEQ ID NO: 76; the mature sequence does not contain the amino terminal 19 amino acids, which serve as a signal sequence) was inserted.

The following combinations of expression vectors were introduced into FreeStyle293-F cells to express each designed molecule transiently.

P. Designed Molecule: GPC3 ERY17-2
Polypeptides encoded by polynucleotides inserted in expression vectors: GPC3 ERY8-2_Hk, GPC3 ERY7_L, ERY17-2_Hh (SEQ ID NO: 73; the mature sequence does not contain the amino terminal 19 amino acids, which serve as a signal sequence), and ERY17-2_L (SEQ ID NO: 74; the mature sequence does not contain the amino terminal 19 amino acids, which serve as a signal sequence)

Q. Designed Molecule: GPC3 ERY17-3
Polypeptides encoded by polynucleotides inserted in expression vectors: GPC3 ERY8-2_Hk, GPC3 ERY7_L, ERY17-3_Hh (SEQ ID NO: 75; the mature sequence does not contain the amino terminal 19 amino acids, which serve as a signal sequence), and ERY17-3_L (SEQ ID NO: 76; the mature sequence does not contain the amino terminal 19 amino acids, which serve as a signal sequence)

(2) Purification of GPC3 ERY 17-2 and GPC3 ERY 17-3

The resulting culture supernatant was loaded onto an Anti FLAG M2 column (Sigma). After washing, the column was eluted with 0.1 mg/ml FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultrafiltration. Then, the fraction was loaded onto a Superdex 200 column (GE Healthcare). Only a monomer fraction was collected from the eluate to obtain each purified designed molecule.

(3) Cytotoxic Activity of GPC3 ERY 17-2 and GPC3 ERY 17-3

Figure 20:
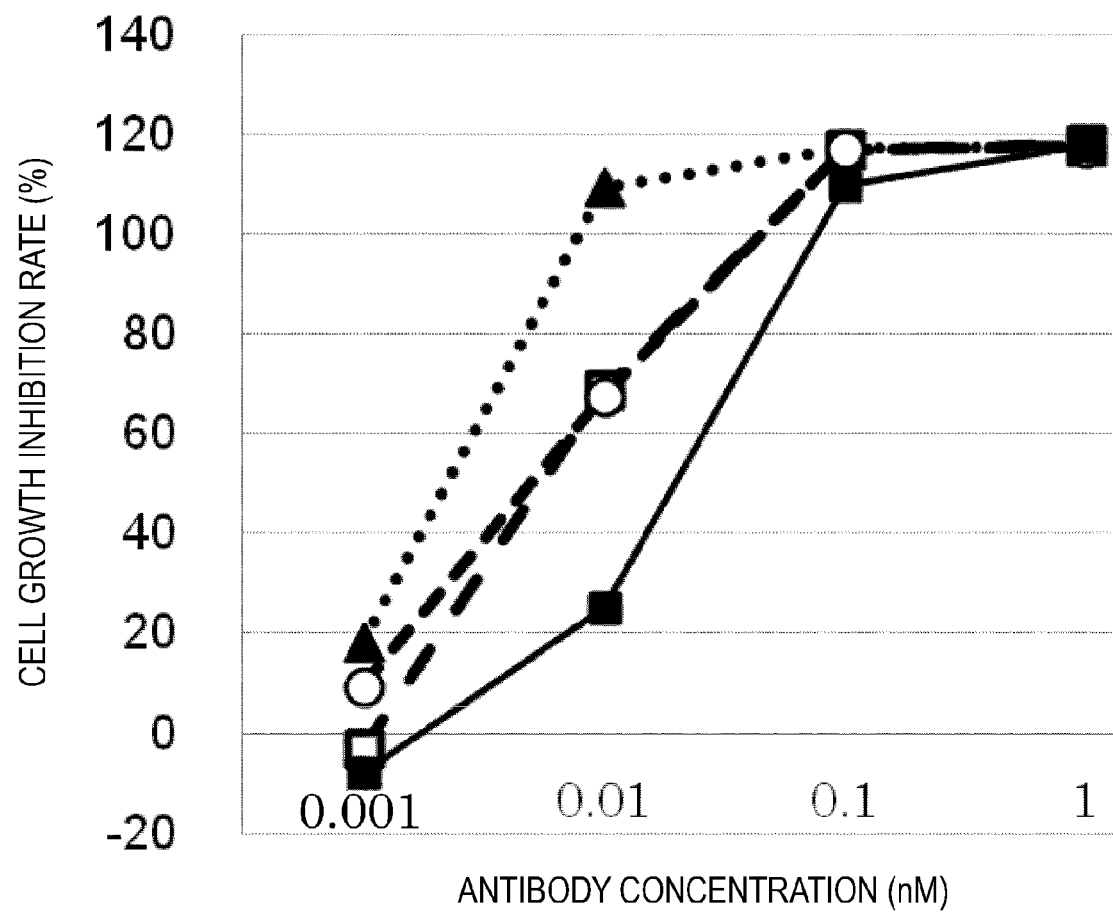
FIG. 20 is a graph showing comparison of the cytotoxic activities of GPC3 BiTE, GPC3 ERY17-2, GPC3 ERY17-3, and GPC3 ERY10-1. Closed square (■), closed triangle (▲), open circle (○), and open square (□) represent the cytotoxic activities of GPC3 BiTE, GPC3 ERY17-2, GPC3 ERY17-3, and GPC3 ERY10-1, respectively.

GPC3 ERY 17-2 and GPC3 ERY 17-3 were assessed for the in vitro cytotoxic activity (FIG. 20). The result showed that both molecules clearly exhibited a greater cytotoxic activity than GPC3 BiTE. Thus, the present invention for the first time demonstrates that molecules in which an anti-cancer antigen IgG is used as a backbone and one of the Fabs is substituted with a CD3 epsilon-binding domain exhibit a cytotoxic activity comparable to or greater than that of BiTE.

(4) Efficacy Test for GPC3 ERY17-2 using PC-10 T Cell Transfer Model

GPC3 ERY17-2, which was demonstrated to have a cytotoxic activity comparable to or greater than that of GPC3 BiTE in the in vitro assay, was assessed for the in vivo efficacy using the PC-10 T cell transfer model. Specifically, the efficacy test of GPC3 ERY17-2 using the PC-10 T cell transfer model was carried out as follows. T cell expansion culture was carried out using T cell activation/expansion kit/human (MACS Miltenyi biotec) and PBMCs isolated from blood collected from healthy volunteers. Human lung squamous carcinoma cell line PC-10 cells (Immuno-Biological Laboratories Co., Ltd.) ($1 \times 10^7$ cells) were mixed with Matrigel Basement Membrane Matrix (BD), and then transplanted subcutaneously to the inguinal region of NOD scid mice (CLEA Japan Inc.; female, 7W). The day of transplantation was designated day 0. On the day before transplantation and days 13, 17, 21, and 25, an anti-asialo-GM1 antibody (Wako Pure Chemical Industries) was intraperitoneally administered to the mice at 0.2 mg/head. On day 13 after transplantation, the mice were grouped by the tumor size and body weight. On day 14 after transplantation, T cells prepared by expansion culture as described above were transplanted at $3 \times 10^7$ cells/head to the peritoneal cavity. After two hours of transplantation, GPC ERY17-2 was intravenously administered at 30 µg/head. GPC ERY17-2 was administered five times in total on days 14, 15, 16, 17, and 18.

Figure 21:
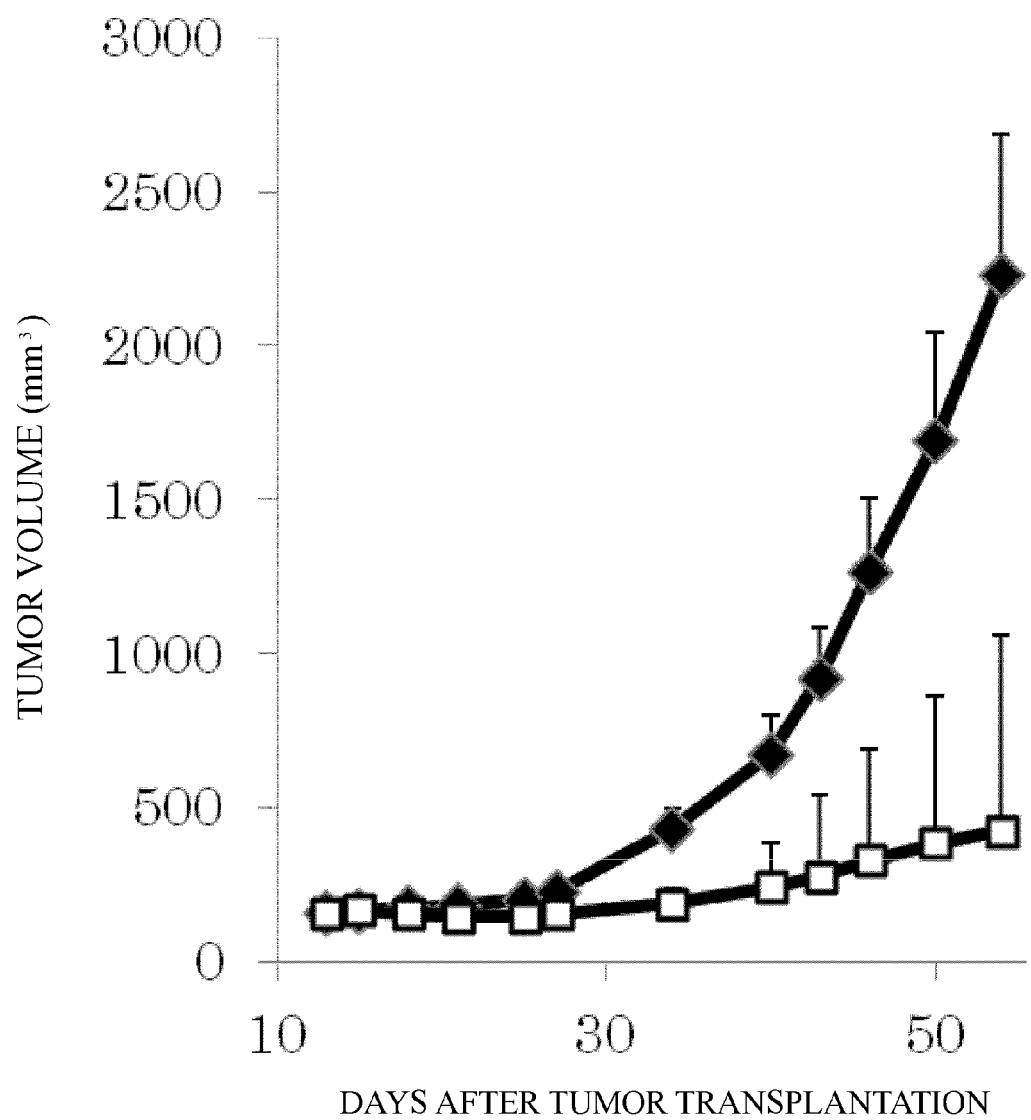
FIG. 21 is a graph showing the in vivo anti-tumor effect of GPC3 ERY17-2 in the PC-10 T cell transfer model. Open square (□) and closed diamond (♦) indicate changes in the tumor volume of the GPC3 ERY17-2 administration group and control (PBS administration) group, respectively.

The result showed that a clear anti-tumor effect was also observed in the GPC3 ERY17-2 administration group of this model, as compared to the solvent administration group (FIG. 21).

The finding described above demonstrates that molecules in which an anti-cancer antigen IgG is used as a backbone and one of the Fabs is substituted with a CD3 epsilon-binding domain produce a clear anti-tumor effect in vivo.

[Example 8] Construction and Assessment of GPC3 ERY17-2-M20

(1) Construction of GPC3 ERY17-2-M20

Next, a molecule retaining the desired activity even after alterations to the CD3 epsilon-binding domain was constructed. GPC3 ERY17-2-M20 (FIG. 19A) was constructed in which the sequence of the CD3 epsilon-binding domain was altered. Specifically, using as a template an expression vector for an anti-CD3 antibody (M20), a method known to a person skilled in the art such as PCR using primers containing the same appropriate sequences as in the above-described methods was performed to produce a series of expression vectors into which a polynucleotide encoding ERY17-2-M20_Hh (SEQ ID NO: 77; the mature sequence does not contain the amino terminal 19 amino acids, which serve as a signal sequence) or ERY17-2-M20_L (SEQ ID NO: 78; the mature sequence does not contain the amino terminal 19 amino acids, which serve as a signal sequence) was inserted.

(2) Purification of GPC3 ERY17-2-M20

The expression vectors for GPC3 ERY8-2_Hk, GPC3 ERY7_L, ERY17-2-M20_Hh (SEQ ID NO: 77), and ERY17-2-M20_L (SEQ ID NO: 78) were co-introduced into FreeStyle293-F cells to express GPC3 ERY17-2-M20 transiently. The resulting culture supernatant was filtered through a φ0.22-µm filter, and then loaded onto an equilibrated rProtein A Sepharose Fast Flow column (GE Healthcare). Purified GPC3 ERY17-2-M20 was obtained by washing steps 1 and 2, and elution step 1 using the buffers shown in Table 3.

TABLE 3

| EQUILIBRATION | FreeStyle 293 Expression Medium (Invitrogen), 1% Pen Strep (Invitrogen) |
|---|---|
| WASH 1 | 1 mM sodium acetate, 150 mM NaCl, pH 6.5 |
| WASH 2 | 0.3 mM HCl, 150 mM NaCl, pH 3.7 |
| ELUTION 1 | 2 mM HCl, pH 2.7 |

(3) Cytotoxic Activity of GPC3 ERY17-2-M20

Figure 22:
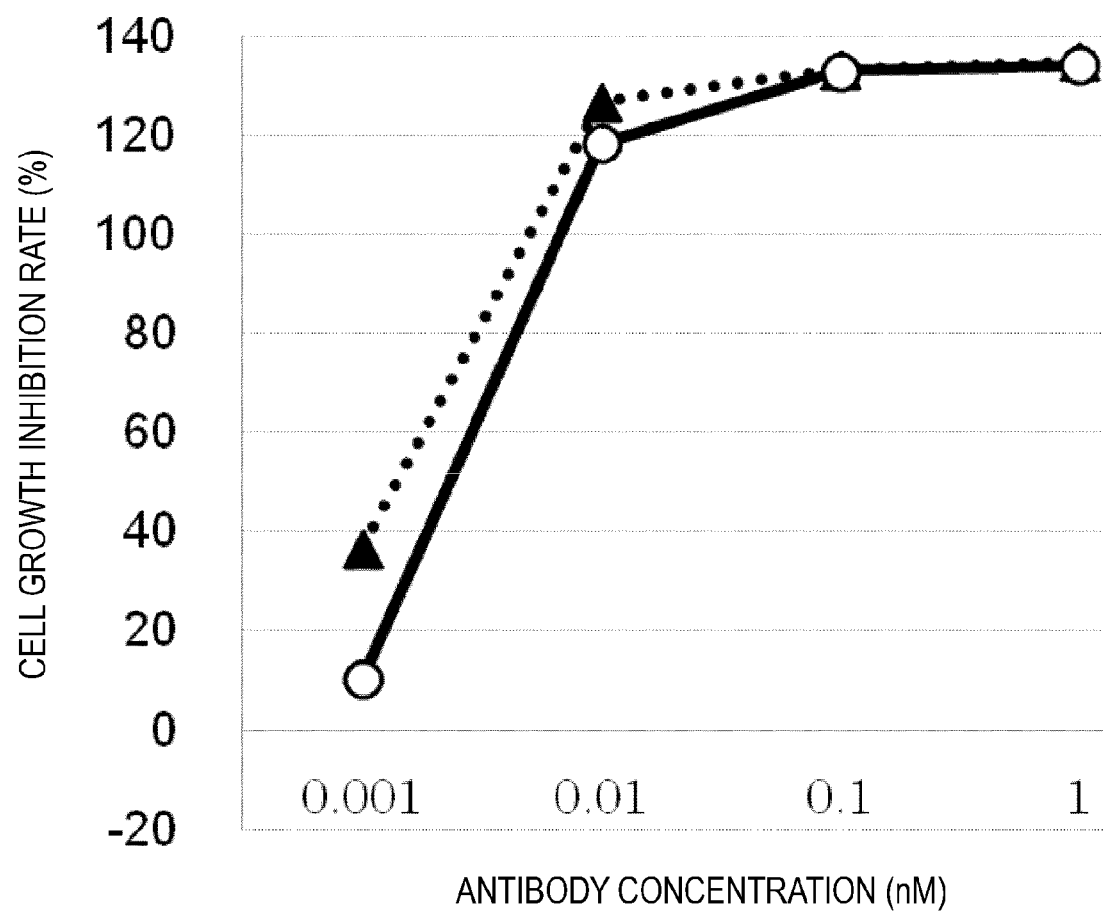
FIG. 22 is a graph showing comparison of the cytotoxic activities of GPC3 ERY17-2 and GPC3 ERY17-2-M20. Closed triangle (▲) and open circle (○) represent the cytotoxic activities of GPC3 ERY17-2 and GPC3 ERY17-2-M20, respectively.

GPC3 ERY17-2-M20 was tested for the in vitro cytotoxic activity, and showed a cytotoxic activity comparable to that of GPC3 ERY17-2 (FIG. 22). This finding demonstrates that even molecules having an altered sequence in the CD3 epsilon-binding domain have a comparable cytotoxic activity.

[Example 9] Construction and Assessment of EpCAM ERY17-2 and EpCAM ERY17-3

(1) Construction of EpCAM ERY17-2 and EpCAM ERY17-3

Next, molecules targeting a different cancer antigen but retaining the desired activity were constructed. EpCAM ERY17-2 (FIG. 19A), in which the anti-GPC3 Fab in GPC3 ERY17-2 was replaced with an anti-EpCAM Fab, and EpCAM ERY17-3 (FIG. 19B), in which the anti-GPC3 Fab in GPC3 ERY17-3 was replaced with an anti-EpCAM Fab, were produced. Specifically, using as a template an expression vector for an anti-EpCAM antibody, a method known to those skilled in the art such as PCR using primers containing the same appropriate sequences as in the above-described method was performed to produce a series of expression vectors into which a polynucleotide encoding EpCAM ERY17_Hk (SEQ ID NO: 79; the mature sequence does not contain the amino terminal 19 amino acids, which serve as a signal sequence) or EpCAM ERY17_L (SEQ ID NO: 80; the mature sequence does not contain the amino terminal 19 amino acids, which serve as a signal sequence) was inserted.

The following combinations of expression vectors were introduced into FreeStyle293-F cells to express each designed molecule transiently.

R. Designed Molecule: EpCAM ERY17-2
Polypeptides encoded by polynucleotides inserted in expression vectors: EpCAM ERY17_Hk (SEQ ID NO: 79; the mature sequence does not contain the amino terminal 19 amino acids, which serve as a signal sequence), EpCAM ERY17_L (SEQ ID NO: 80; the mature sequence does not contain the amino terminal 19 amino acids, which serve as a signal sequence), ERY17-2_Hh, and ERY17-2 L S. Designed Molecule: EpCAM ERY17-3
Polypeptides encoded by polynucleotides inserted in expression vectors: EpCAM ERY17_Hk, EpCAM ERY17_L, ERY17-3_Hh, and ERY17-3_L (2) Purification of EpCAM ERY17-2 and EpCAM ERY17-3

The resulting culture supernatant was loaded onto an Anti FLAG M2 column (Sigma). After washing, the column was eluted with 0.1 mg/ml FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultrafiltration. Then, the fraction was loaded onto a Superdex 200 column (GE Healthcare). Only a monomer fraction was collected from the eluate to obtain each purified designed molecule.

(3) Cytotoxic Activity of EpCAM ERY17-2 and EpCAM ERY17-3

Figure 23:
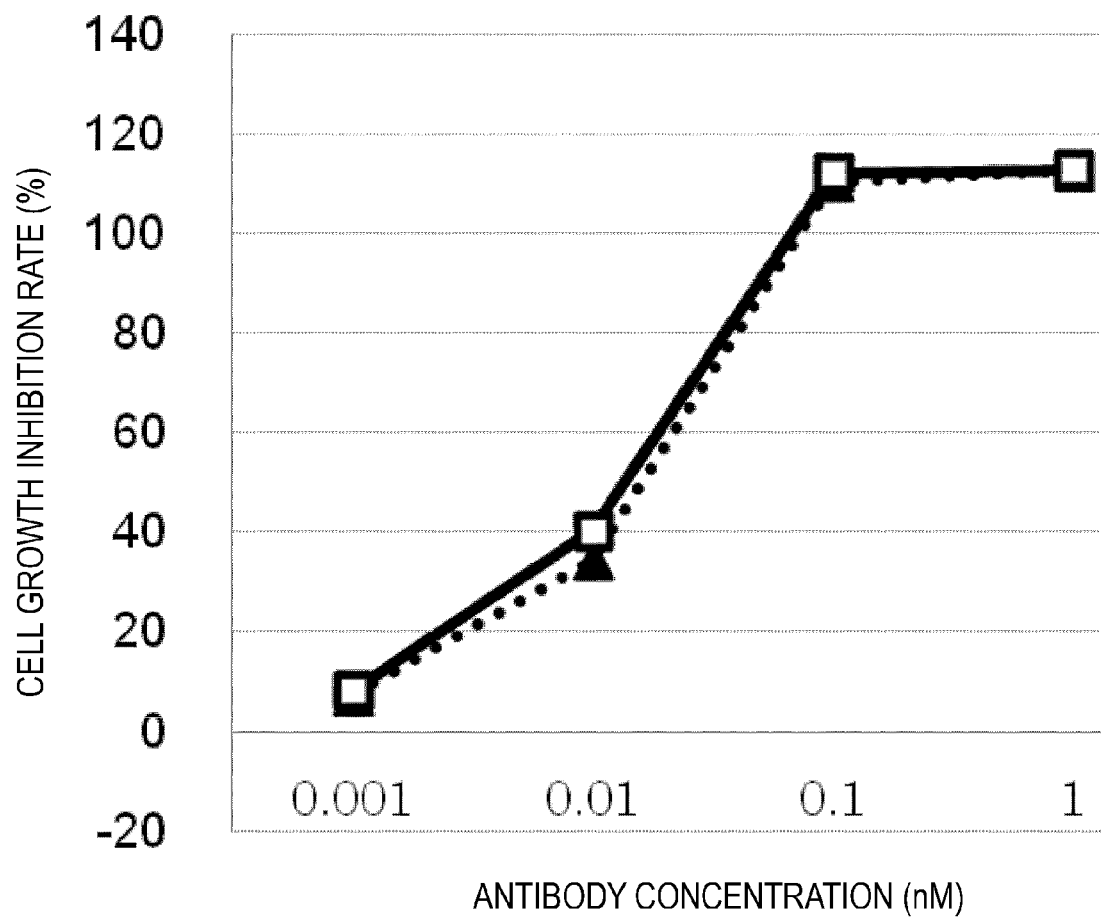
FIG. 23 is a graph showing comparison of the cytotoxic activities of EpCAM ERY17-2 and EpCAM ERY17-3. Closed triangle (▲) and open square (□) represent the cytotoxic activities of EpCAM ERY17-2 and EpCAM ERY17-3, respectively.

EpCAM ERY17-2 and EpCAM ERY17-3 were tested for the in vitro cytotoxic activity, and both showed a strong cytotoxic activity (FIG. 23). Thus, the present invention demonstrates that molecules in which an anti-cancer antigen IgG is used as a backbone and one of the Fabs is substituted with a CD3 epsilon-binding domain have a cytotoxic activity even when the type of cancer antigen has been changed.

[Example 10] Construction and Assessment of Bispecific Antibodies with Modulated CH1/CL Interfacial Association (1) Design of Bispecific Antibody By introducing mutations into each of the CH1 and CL domains of an bispecific antibody and thereby modulating the CH1/CL interfacial association with the use of electric charge repulsion at the CH1/CL interface, specific association may be allowed to occur between the anti-GPC3 H chain and L chain and between the anti-CD3 H chain and L chain. In order to modulate the CH1/CL interfacial association using electric charge repulsion, amino acid residues in CH1 of the H chains or CL of the L chains were substituted with Lys, which is positively charged, or with Glu, which is negatively charged.

(2) Construction of Expression Vectors for Antibody Genes and Expression of Respective Antibodies A bispecific antibody (FIG. 24A) was created by modulating the CH1/CL interfacial association of anti-CD3 antibody M12 (H chain, SEQ ID NO: 81; L chain, SEQ ID NO: 82) and anti-GPC3 antibody GC33(2) (H chain, SEQ ID NO: 83; L chain, SEQ ID NO: 84) and further introducing Knobs-into-Holes (K₁H) modifications (WO 1996/027011; Ridgway J B et al. (Protein Engineering (1996) 9, 617-621), Merchant A M et al. (Nat. Biotechnol. (1998) 16, 677-681)) into them to avoid the H chains from associating with each other. A control bispecific antibody (FIG. 24B), in which neither the CH1/CL interfacial association modulation nor the Knobs-into-Holes (K₁H) modifications were introduced, was also constructed. Specifically, expression vectors having as an insert a polynucleotide encoding M12_TH2h (SEQ ID NO: 85), in which several amino acids in CH1 of the H chain of M12 (SEQ ID NO: 81) were substituted with Lys, or M12_TL17 (SEQ ID NO: 86), in which several amino acids in CL of the L chain (SEQ ID NO: 82) were substituted with Glu, were constructed by a method known to those skilled in the art. Likewise, expression vectors having as an insert a polynucleotide encoding GC33(2)_TH13k (SEQ ID NO: 87) or GC33(2)_TH15k (SEQ ID NO: 88), in which several amino acids in CH1 of the H chain of GC33(2) (SEQ ID NO: 83) were substituted with Glu, or GC33(2)_TL16 (SEQ ID NO: 89) or GC33(2)_TL19 (SEQ ID NO: 90), in which several amino acids in CL of the L chain (SEQ ID NO: 84) were substituted with Lys, were constructed by a method known to those skilled in the art.

The following combinations of expression vectors were introduced into FreeStyle293-F cells to express each designed molecule transiently.

T. Designed Molecule: GM1
Expression vectors: M12_TH2h (SEQ ID NO: 85), M12_TL17 (SEQ ID NO: 86), GC33(2)_TH13k (SEQ ID NO: 87), and GC33(2)_TL16 (SEQ ID NO: 89)

U. Designed Molecule: GM2
Expression vectors: M12_TH2h (SEQ ID NO: 85), M12_TL17 (SEQ ID NO: 86), GC33(2)_TH15k (SEQ ID NO: 88), and GC33(2)_TL19 (SEQ ID NO: 90)

V. Designed Molecule: GM0
Expression vectors: H chain of M12 (SEQ ID NO: 81), L chain of M12 (SEQ ID NO: 82), H chain of GC33(2) (SEQ ID NO: 83), and L chain of GC33(2) (SEQ ID NO: 84)

From the resulting culture supernatant, antibodies were purified by a method known to those skilled in the art using rProtein A Sepharose™ Fast Flow (GE Healthcare).

(3) Cytotoxic Activity of GM1, GM2, and GM0

Figure 25:
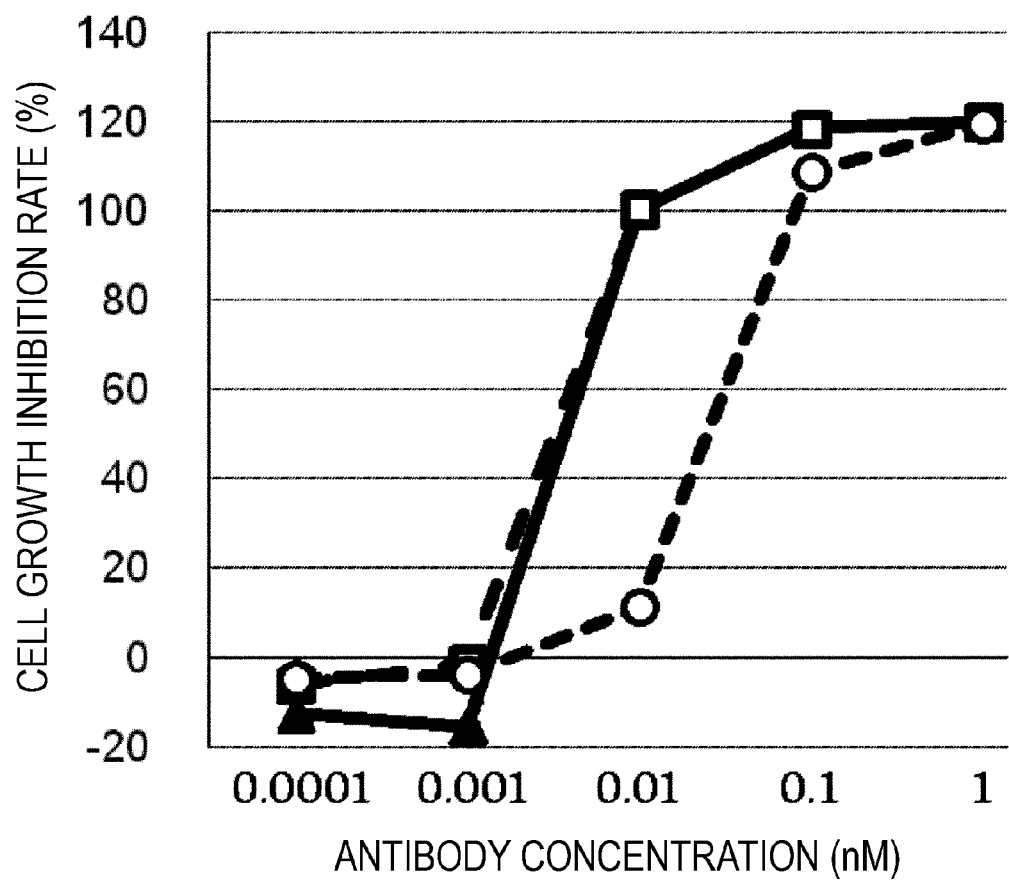
FIG. 25 is a graph showing comparison of the cytotoxic activities of GM1, GM2, and GM0. Closed triangle (▲), open square (□), and open circle (○) represent the cytotoxic activities of GM1, GM2, and GM3, respectively.

Polypeptide complexes GM1, GM2, and GM0 were assessed for the in vitro cytotoxic activity. The result showed that GM1 and GM2 exhibited a comparable cytotoxic activity, and this activity was clearly greater than that of GM0 (FIG. 25). Thus, the present invention demonstrates that the combination of the modulation of CH1/CL interfacial association and the KiH modifications allows efficient production of bispecific antibodies.

[Example 11] Construction and Assessment of EGFR ERY17-2

(1) Construction of EGFR ERY17-2

Furthermore, a molecule having the desired activity that targets another cancer antigen was prepared. EGFR ERY17-2 (FIG. 19A) was constructed by replacing the anti-GPC3 Fab of GPC3 ERY17-2 with the anti-EGFR Fab. Specifically, using as a template an expression vector for an anti-EGFR antibody, a method known to those skilled in the art such as PCR using primers containing the same appropriate sequences as in the above-described method was performed to produce a series of expression vectors into which the polynucleotide encoding EGFR ERY17 Hk (SEQ ID NO: 91: the mature sequence does not contain the amino terminal 19 amino acids, which serve as a signal sequence) or EGFR ERY17_L (SEQ ID NO: 92: the mature sequence does not contain the amino terminal 19 amino acids, which serve as a signal sequence) was inserted.

The following combinations of expression vectors were introduced into FreeStyle293-F cells to express each designed molecule transiently.

W. Designed Molecule: EGFR ERY17-2
Polypeptides encoded by polynucleotides inserted in expression vectors: EGFR ERY17_Hk (SEQ ID NO: 91: the mature sequence does not contain the amino terminal 19 amino acids, which serve as a signal sequence), EGFR ERY17_L (SEQ ID NO: 92: the mature sequence does not contain the amino terminal 19 amino acids, which serve as a signal sequence), ERY17-2_Hh, and ERY17-2_L.

(2) Purification of EGFR ERY17-2

The resulting culture supernatants were loaded onto an Anti FLAG M2 column (Sigma). After washing, the column was eluted with 0.1 mg/mL FLAG peptide (Sigma). A fraction containing the designed molecule was loaded onto a HisTrap HP column (GE Healthcare). After washing, the column was eluted with an imidazole concentration gradient. A fraction containing the designed molecule was concentrated by ultrafiltration. Then, the fraction was loaded onto a Superdex 200 column (GE Healthcare). Only a monomer fraction was collected from the eluate to obtain each purified designed molecule.

(3) Cytotoxic Activity of EGFR ERY17-2

Figure 26:
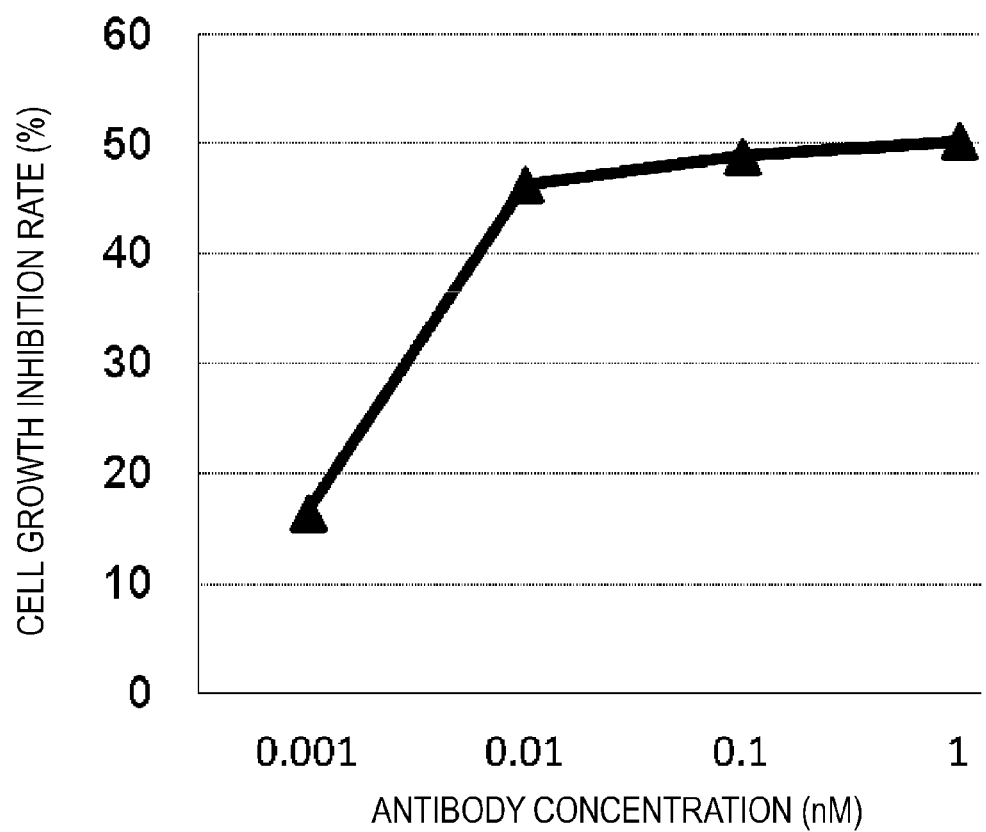
FIG. 26 is a graph showing the cytotoxic activity of EGFR ERY17-2. Closed triangle (▲) represents the cytotoxic activity of EGFR ERY17-2.

EGFR ERY17-2 was tested for the in vitro cytotoxic activity, and it showed a strong cytotoxic activity (FIG. 26). Thus, the present invention demonstrates that molecules in which an anti-cancer antigen IgG is used as a backbone and one of the Fabs is substituted with a CD3 epsilon-binding domain have a cytotoxic activity even when the cancer antigen is GPC3 or EpCAM or the type of cancer antigen has been further changed.

INDUSTRIAL APPLICABILITY

The present invention provides novel polypeptide complexes that retain the strong anti-tumor activity of BiTE and have a long half-life in blood, as well as excellent safety properties that result in no induction of cancer antigen-independent cytokine storm or such. When the antigen-binding domain of a polypeptide complex of the present invention is substituted, therapeutic agents that comprise the polypeptide complex as an active ingredient for inducing cellular cytotoxicity, can target and damage various cells including cancer cells. Thus, various cancers can be treated or prevented. This allows desirable treatments that are highly safe and convenient, and reduce the physical burden for patients.

The invention claimed is:

1. A bispecific antibody that comprises:
a first light chain comprising a first VL domain and a first CL domain;
a second light chain comprising a second VL domain and a second CL domain;
a first heavy chain comprising a first heavy chain variable region and a first heavy chain constant region, wherein the first heavy chain constant region is a non-wild-type heavy chain constant region comprising the sequence of one of SEQ ID NOs: 23, 24, 25 and 26, with one or more amino acid substitutions and optionally a deletion of the amino acids at EU numbering positions 446 and 447; and
a second heavy chain comprising a second heavy chain variable region and a second heavy chain constant region, wherein the second heavy chain constant region is a non-wild-type heavy chain constant region comprising the sequence of one of SEQ ID NOs: 23, 24, 25 and 26, with one or more amino acid substitutions and optionally a deletion of the amino acids at EU numbering positions 446 and 447, wherein the amino acid sequence of the second heavy chain constant region is the same as or different from the amino acid sequence of the first heavy chain constant region, and is of the same isotype as the first heavy chain constant region;
wherein the first light chain and the first heavy chain associate to form a first antigen- binding domain that binds to CD3,
wherein the second light chain and the second heavy chain associate to form a second antigen-binding domain that does not bind to CD3, and that does bind to a cancer antigen that is not CD3,
wherein the first heavy chain constant region associates with the second heavy chain constant region,
wherein, when assessed by a surface plasmon resonance technique, the ability of the associated first and second heavy chain constant regions to bind to a given human Fcγ receptor is reduced, compared to the ability of a wild-type human IgG antibody of the same isotype as the bispecific antibody to bind to the human Fcγ receptor, as a result of at least one of the one or more amino acid substitutions within the first and second heavy chain constant regions,
wherein the at least one substitution in the first and second heavy chain constant regions represents a change in amino acid sequence compared to the amino acid sequence of the heavy chain constant regions of the wild-type human IgG antibody, and
wherein at least one of the amino acid substitutions that result in the reduced ability to bind to the human Fcγ receptor is at a position selected from the following EU numbering positions in each of the first and second heavy chain constant regions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332.

2. The bispecific antibody of claim 1, wherein
the amino acid sequence from position 118 to position 260 (EU numbering) of the first heavy chain constant region and of the second heavy chain constant region is the sequence from the corresponding portion of SEQ ID NO: 24; or
the amino acid sequence from position 261 to position 447 (EU numbering) of the first heavy chain constant region and of the second heavy chain constant region is the sequence from the corresponding portion of SEQ ID NO: 26.

3. The bispecific antibody of claim 1, wherein the first heavy chain constant region and the second heavy chain constant region each comprises the sequence of SEQ ID NO: 23 with one or more substitutions and optionally a deletion of the two residues at the carboxyl terminus of SEQ ID NO: 23.

4. The bispecific antibody of claim 3, wherein the one or more substitutions include a substitution in both the first and the second heavy chain constant regions at a position selected from positions 233, 234, 235, 236, 327, 330, and 331 (EU numbering), the substitution at the selected position being by an amino acid from a corresponding position in IgG2 or IgG4.

5. The bispecific antibody of claim 3, wherein the one or more substitutions include a substitution in both the first and the second heavy chain constant regions at position 234, 235, or 297 (EU numbering).

6. The bispecific antibody of claim 5, wherein the one or more substitutions include a substitution by alanine.

7. The bispecific antibody of claim 1, wherein the amino acid sequence of the second heavy chain constant region is different from the amino acid sequence of the first heavy chain constant region.

8. The bispecific antibody of claim 7, wherein
in one of the two heavy chain constant regions of the bispecific antibody, the amino acids at positions 349 and 366 (EU numbering) are cysteine and tryptophan, respectively; and
in the other heavy chain constant region of the bispecific antibody, the amino acids at positions 356, 366, 368, and 407 (EU numbering) are cysteine, serine, alanine, and valine, respectively.

9. The bispecific antibody of claim 7, wherein:
in one of the two heavy chain constant regions of the bispecific antibody, the amino acid at position 356 is lysine,
in the other heavy chain constant region of the bispecific antibody, the amino acid at position 439 is glutamic acid; and
in one but not both of the two heavy chain constant regions of the bispecific antibody, the amino acid at position 435 is arginine (all positions being by EU numbering).

10. The bispecific antibody of claim 8, wherein the amino acids at EU numbering positions 446 and 447 are deleted in both heavy chain constant regions of the bispecific antibody.

11. The bispecific antibody of claim 1, wherein the human Fcγ receptor is selected from Fcγl, FcγIIA, FcγIIB, FcγIIIA, and FcγIIIB.

12. The bispecific antibody of claim 1, wherein the amino acid sequence of the second heavy chain constant region is the same as the amino acid sequence of the first heavy chain constant region.

13. The bispecific antibody of claim 1, wherein the amino acid sequence of the second heavy chain constant region is different from the amino acid sequence of the first heavy chain constant region, and wherein the percentage of heterodimers formed in a mixture of the first and second heavy chains is higher than the percentage of heterodimers that would be formed if the two heavy chain constant regions were identical and matched one of SEQ ID NO: 23-26.

14. The bispecific antibody of claim 13, wherein the difference between the sequences of the first and second heavy chain constant regions comprises a difference at one or more CH3 domain positions.

15. The bispecific antibody of claim 14, wherein the difference between the sequences of the first and second heavy chain constant regions further comprises a difference at one or more CH1 domain positions, wherein the one or more CH1 domain positions interface with a CL domain.

16. The bispecific antibody of claim 1, wherein the amino acid sequence of the second heavy chain constant region is different from the amino acid sequence of the frst heavy chain constant region, and this difference in sequences comprises a difference at one or more CH1 domain positions of the two heavy chain constant regions, wherein the one or more CH1 domain positions interface with a CL domain.

17. The bispecific antibody of claim 1, wherein the human Fcγ receptor is selected from Fcγl, FcγIIIA, and FcγIIIB.

18. The bispecific antibody of claim 1, wherein, when assessed by a surface plasmon resonance technique, the bispecific antibody's ability to bind to each of human Fcγ receptors Fcγl, FcγIIIA, and FcγIIIB is reduced compared to the ability of a wild-type human IgG antibody of the same isotype as the bispecific antibody to bind to the same human Fcγ receptors.

19. The bispecific antibody of claim 1, wherein, when assessed by a surface plasmon resonance technique, the bispecific antibody's ability to bind to each of human Fcγ receptors Fcγl, FcγIIA, FcγIIB, FcγIIIA, and FcγIIIB is reduced compared to the ability of a wild-type human IgG antibody of the same isotype as the bispecific antibody to bind to the same human Fcγ receptor.

20. The bispecific antibody of claim 1, wherein the first and second heavy chain constant regions are human heavy chain constant regions.

21. The bispecific antibody of claim 1, wherein the associated first and second heavy chain constant regions have essentially no detectable ability to bind to the given human Fcγ receptor, when assessed by a surface plasmon resonance technique.

22. The bispecific antibody of claim 1, wherein the associated first and second heavy chain constant regions have essentially no detectable ability to bind to human Fcγ receptors Fcγl, FcγIIA, FcγIIB, FcγIIIA, and FcγIIIB, when assessed by a surface plasmon resonance technique.

23. The bispecific antibody of claim 3, wherein the one or more substitutions include one of the following sets of substitutions in both the first and second heavy chain constant regions (all positions by EU numbering):
(a) L234F, L235E, P331S;
(b) C226S, C229S, P238S;
(c) C226S, C229S;
(d) C226S, C229S, E233P, L234V, L235A.

24. The bispecific antibody of claim 1, wherein each of the first and second heavy chain constant regions comprises the sequence of SEQ ID NO: 24 with one or more substitutions and optionally a deletion of the two residues at the carboxyl terminus of SEQ ID NO: 24.

25. The bispecific antibody of claim 24, wherein the one or more substitutions include one of the following sets of substitutions in both the first and second heavy chain constant regions (all positions by EU numbering):
(a) H268Q, V309L, A330S, and P331S;
(b) V234A;
(c) G237A;
(d) V234A and G237A;
(e) A235E and G237A; or
(f) V234A, A235E, and G237A.

26. The bispecific antibody of claim 1, wherein the first heavy chain constant region and the second heavy chain constant region comprise the sequence of SEQ ID NO: 25 with one or more substitutions and optionally a deletion of the two residues at the carboxyl terminus of SEQ ID NO: 25.

27. The bispecific antibody of claim 16, wherein the one or more substitutions include one of the following substitutions in both the first and second heavy chain constant regions (all positions by EU numbering):
(a) F241A;
(b) D265A; or
(c) V264A.

28. The bispecific antibody of claim 1, wherein the first heavy chain constant region and the second heavy chain constant region comprise the sequence of SEQ ID NO: 26 with one or more substitutions and optionally a deletion of the two residues at the carboxyl terminus of SEQ ID NO: 26.

29. The bispecific antibody of claim 28, wherein the one or more substitutions include one of the following sets of substitutions in both the first and second heavy chain constant regions (all positions by EU numbering):
(a) L235A, G237A, and E318A;
(b) L235E; or
(c) F234A and L235A.

30. The bispecific antibody of claim 1, wherein the one or more substitutions include a substitution at position 234 (EU numbering) in both the first and second heavy chain constant regions.

31. The bispecific antibody of claim 1, wherein the one or more substitutions include a substitution at position 235 (EU numbering) in both the first and second heavy chain constant regions.

32. The bispecific antibody of claim 1, wherein the one or more substitutions include a substitution at position 239 (EU numbering) in both the first and second heavy chain constant regions.

33. The bispecific antibody of claim 1, wherein the one or more substitutions include a substitution at position 297 (EU numbering) in both the first and second heavy chain constant regions.

34. The bispecific antibody of claim 1, wherein the residues at positions 234 and 235 (both positions by EU numbering) are both alanine in both the first and second heavy chain constant regions.

35. The bispecific antibody of claim 1, wherein the residues at positions 234, 235 and 297 (all positions by EU numbering) are all alanine in both the first and second heavy chain constant regions.

36. The bispecific antibody of claim 1, wherein positions 446 and 447 (EU numbering) are deleted in the sequence of each of the first and second heavy chain constant regions.

37. The bispecific antibody of claim 1, wherein the only substitution(s) in the amino acid sequence of one or both of the first and second heavy chain constant regions, compared to the amino acid sequence of SEQ ID NO: 23, is/are at a position or positions independently selected from the following EU numbering positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332.

38. The bispecific antibody of claim 1, wherein the only substitution(s) in the amino acid sequence of one or both of the first and second heavy chain constant regions, compared to the amino acid sequence of SEQ ID NO: 24, is/are at a position or positions independently selected from the following EU numbering positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332.

39. The bispecific antibody of claim 1, wherein the only substitution(s) in the amino acid sequence of one or both of the first and second heavy chain constant regions, compared to the amino acid sequence of SEQ ID NO: 25, is/are at a position or positions independently selected from the following EU numbering positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332.

40. The bispecific antibody of claim 1, wherein the only substitution(s) in the amino acid sequence of one or both of the first and second heavy chain constant regions, compared to the amino acid sequence of SEQ ID NO: 26, is/are at a position or positions independently selected from the following EU numbering positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332.

41. The bispecific antibody of claim 1, wherein the amino acid sequence of one or both of the first and second heavy chain constant regions has a substitution, compared to the amino acid sequence of SEQ ID NO: 23, at a position or positions independently selected from the following EU numbering positions: 229, 239, 240, 264, 265, 267, 297, 298, 299, 329, 331, and 332.

42. The bispecific antibody of claim 1, wherein the amino acid sequence of one or both of the first and second heavy chain constant regions has a substitution, compared to the amino acid sequence of SEQ ID NO: 24, at a position or positions independently selected from the following EU numbering positions: 229, 239, 240, 264, 265, 267, 297, 298, 299, 329, 331, and 332.

43. The bispecific antibody of claim 1, wherein the amino acid sequence of one or both of the first and second heavy chain constant regions has a substitution, compared to the amino acid sequence of SEQ ID NO: 25, at a position or positions independently selected from the following EU numbering positions: 229, 239, 240, 264, 265, 267, 297, 298, 299, 329, 331, and 332.

44. The bispecific antibody of claim 1, wherein the amino acid sequence of one or both of the first and second heavy chain constant regions has a substitution, compared to the amino acid sequence of SEQ ID NO: 26, at a position or positions independently selected from the following EU numbering positions: 229, 239, 240, 264, 265, 267, 297, 298, 299, 329, and 332.

45. The bispecific antibody of claim 1, wherein the bispecific antibody is a human or humanized antibody.

46. The bispecific antibody of claim 1, wherein the isotype of the bispecific antibody is human IgG1, human IgG2, human IgG3, or human IgG4.

47. The bispecific antibody of claim 1, wherein the isotype of each of the first and second heavy chain constant regions is independently selected from human IgG1, human IgG2, human IgG3, and human IgG4.

48. A pharmaceutical composition, wherein the pharmaceutical composition comprises as an active ingredient the bispecific antibody of claim 1.

\* \* \* \* \*

SEQUENCE LISTING

```
<160> NUMBER OF SEQ ID NOS: 92

<210> SEQ ID NO 1
<211> LENGTH: 1812
<212> TYPE: DNA
<213> ORGANISM: Homo sapiens

<400> SEQUENCE: 1
atggccggga ccgtgcgcac cgcgtgcttg gtggtggcga tgctgctcag cttggacttc      60
ccgggacagg cgcagccccc gccgccgccg ccggacgcca cctgtcacca agtccgctcc     120
ttcttccaga gactgcagcc cggactcaag tgggtgccag aaactcccgt gccaggatca     180
gatttgcaag tatgtctccc taagggccca acatgctgct caagaaagat ggaagaaaaa     240
taccaactaa cagcacgatt gaacatggaa cagctgcttc agtctgcaag tatggagctc     300
aagttcttaa ttattcagaa tgctgcggtt ttccaagagg cctttgaaat tgttgttcgc     360
catgccaaga actacaccaa tgccatgttc aagaacaact acccaagcct gactccacaa     420
gcttttgagt tgtgggtga attttcaca gatgtgtctc tctacatctt gggttctgac     480
atcaatgtag atgacatggt caatgaattg tttgacagcc tgtttccagt catctatacc     540
cagctaatga acccaggcct gcctgattca gccttggaca tcaatgagtg cctccgagga     600
gcaagacgtg acctgaaagt atttgggaat ttccccaagc ttattatgac ccaggtttcc     660
aagtcactgc aagtcactag gatcttcctt caggctctga tcttggaat tgaagtgatc     720 aacacaactg atcacctgaa gttcagtaag gactgtggcc gaatgctcac cagaatgtgg     780
tactgctctt actgccaggg actgatgatg gttaaaccct gtggcggtta ctgcaatgtg     840
gtcatgcaag gctgtatggc aggtgtggtg gagattgaca agtactggag agaatacatt     900
ctgtcccttg aagaacttgt gaatgcatg tacagaatct atgacatgga gaacgtactg     960
cttggtctct tttcaacaat ccatgattct atccagtatg tccagaagaa tgcaggaaag    1020
ctgaccacca ctgaaactga gaagaaaata tggcacttca aatatcctat cttcttcctg    1080 tgtataggc tagacttaca gattggcaag ttatgtgccc attctcaaca acgccaatat    1140
agatctgctt attatcctga agatctcttt attgacaaga agtattaaa agttgctcat    1200 gtagaacatg aagaaacctt atccagccga agaagggaac taattcagaa gttgaagtct    1260
```

-continued

```
ttcatcagct tctatagtgc tttgcctggc tacatctgca gccatagccc tgtggcggaa    1320
aacgacaccc tttgctggaa tggacaagaa ctcgtggaga gatacagcca aaaggcagca    1380
aggaatggaa tgaaaaacca gttcaatctc catgagctga aaatgaaggg ccctgagcca    1440
gtggtcagtc aaattattga caaactgaag cacattaacc agctcctgag aaccatgtct    1500
atgcccaaag gtagagttct ggataaaaac ctggatgagg aagggtttga agtggagac    1560 tgcggtgatg atgaagatga gtgcattgga ggctctggtg atggaatgat aaaagtgaag    1620
aatcagctcc gcttccttgc agaactggcc tatgatctgg atgtggatga tgcgcctgga    1680
aacagtcagc aggcaactcc gaaggacaac gagataagca cctttcacaa cctcgggaac    1740
gttcattccc cgctgaagct tctcaccagc atggccatct cggtggtgtg cttcttcttc    1800
ctggtgcact ga                                                        1812
```

<210> SEQ ID NO 2
<211> LENGTH: 603
<212> TYPE: PRT
<213> ORGANISM: Homo sapiens

<400> SEQUENCE: 2

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270
```

```
Pro Cys Gly Gly Tyr Cys Asn Val Met Gln Gly Cys Met Ala Gly
            275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Glu Thr Lys Lys Ile Trp His
            340                 345                 350

Phe Lys Tyr Pro Ile Phe Phe Leu Cys Ile Gly Leu Asp Leu Gln Ile
            355                 360                 365

Gly Lys Leu Cys Ala His Ser Gln Gln Arg Gln Tyr Arg Ser Ala Tyr
    370                 375                 380

Tyr Pro Glu Asp Leu Phe Ile Asp Lys Lys Val Leu Lys Val Ala His
385                 390                 395                 400

Val Glu His Glu Glu Thr Leu Ser Ser Arg Arg Arg Glu Leu Ile Gln
                405                 410                 415

Lys Leu Lys Ser Phe Ile Ser Phe Tyr Ser Ala Leu Pro Gly Tyr Ile
            420                 425                 430

Cys Ser His Ser Pro Val Ala Glu Asn Asp Thr Leu Cys Trp Asn Gly
    435                 440                 445

Gln Glu Leu Val Glu Arg Tyr Ser Gln Lys Ala Ala Arg Asn Gly Met
    450                 455                 460

Lys Asn Gln Phe Asn Leu His Glu Leu Lys Met Lys Gly Pro Glu Pro
465                 470                 475                 480

Val Val Ser Gln Ile Ile Asp Lys Leu Lys His Ile Asn Gln Leu Leu
                485                 490                 495

Arg Thr Met Ser Met Pro Lys Gly Arg Val Leu Asp Lys Asn Leu Asp
            500                 505                 510

Glu Glu Gly Phe Glu Ser Gly Asp Cys Gly Asp Glu Asp Glu Cys
            515                 520                 525

Ile Gly Gly Ser Gly Asp Gly Met Ile Lys Val Lys Asn Gln Leu Arg
    530                 535                 540

Phe Leu Ala Glu Leu Ala Tyr Asp Leu Asp Val Asp Asp Ala Pro Gly
545                 550                 555                 560

Asn Ser Gln Gln Ala Thr Pro Lys Asp Asn Glu Ile Ser Thr Phe His
                565                 570                 575

Asn Leu Gly Asn Val His Ser Pro Leu Lys Leu Leu Thr Ser Met Ala
            580                 585                 590

Ile Ser Val Val Cys Phe Phe Phe Leu Val His
    595                 600

<210> SEQ ID NO 3
<211> LENGTH: 945
<212> TYPE: DNA
<213> ORGANISM: Homo sapiens

<400> SEQUENCE: 3
atggcgcccc cgcaggtcct cgcgttcggg cttctgcttg ccgcggcgac ggcgactttt    60
gccgcagctc aggaagaatg tgtctgtgaa aactacaagc tggccgtaaa ctgctttgtg   120
aataataatc gtcaatgcca gtgtacttca gttggtgcac aaaatactgt catttgctca   180
aagctggctg ccaaatgttt ggtgatgaag gcagaaatga atggctcaaa acttgggaga   240
```

-continued

```
agagcaaaac ctgaaggggc cctccagaac aatgatgggc tttatgatcc tgactgcgat    300
gagagcgggc tctttaaggc caagcagtgc aacggcacct ccatgtgctg gtgtgtgaac    360
actgctgggg tcagaagaac agacaaggac actgaaataa cctgctctga gcgagtgaga    420
acctactgga tcatcattga actaaaacac aaagcaagag aaaaacctta tgatagtaaa    480
agtttgcgga ctgcacttca gaaggagatc acaacgcgtt atcaactgga tccaaaattt    540
atcacgagta ttttgtatga gaataatgtt atcactattg atctggttca aaattcttct    600 caaaaactc agaatgatgt ggacatagct gatgtggctt attattttga aaagatgtt     660 aaaggtgaat ccttgtttca ttctaagaaa atggacctga cagtaaatgg ggaacaactg    720
gatctggatc ctggtcaaac tttaattat tatgttgatg aaaaagcacc tgaattctca    780
atgcagggtc taaaagctgg tgttattgct gttattgtgg ttgtggtgat agcagttgtt    840
gctggaattg ttgtgctggt tatttccaga agaagagaa tggcaaagta tgagaaggct    900
gagataaagg agatgggtga gatgcatagg gaactcaatg cataa                   945
```

<210> SEQ ID NO 4
<211> LENGTH: 314
<212> TYPE: PRT
<213> ORGANISM: Homo sapiens

<400> SEQUENCE: 4

```
Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255
```

Pro Glu Phe Ser Met Gln Gly Leu Lys Ala Gly Val Ile Ala Val Ile
            260                 265                 270

Val Val Val Val Ile Ala Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 5
<211> LENGTH: 4
<212> TYPE: PRT
<213> ORGANISM: Artificial
<220> FEATURE:
<223> OTHER INFORMATION: an artificially synthesized sequence

<400> SEQUENCE: 5

Gly Gly Gly Ser
1

<210> SEQ ID NO 6
<211> LENGTH: 4
<212> TYPE: PRT
<213> ORGANISM: Artificial
<220> FEATURE:
<223> OTHER INFORMATION: an artificially synthesized sequence

<400> SEQUENCE: 6

Ser Gly Gly Gly
1

<210> SEQ ID NO 7
<211> LENGTH: 5
<212> TYPE: PRT
<213> ORGANISM: Artificial
<220> FEATURE:
<223> OTHER INFORMATION: an artificially synthesized sequence

<400> SEQUENCE: 7

Gly Gly Gly Gly Ser
1               5

<210> SEQ ID NO 8
<211> LENGTH: 5
<212> TYPE: PRT
<213> ORGANISM: Artificial
<220> FEATURE:
<223> OTHER INFORMATION: an artificially synthesized sequence

<400> SEQUENCE: 8

Ser Gly Gly Gly Gly
1               5

<210> SEQ ID NO 9
<211> LENGTH: 6
<212> TYPE: PRT
<213> ORGANISM: Artificial
<220> FEATURE:
<223> OTHER INFORMATION: an artificially synthesized sequence

<400> SEQUENCE: 9

Gly Gly Gly Gly Gly Ser
1               5

<210> SEQ ID NO 10
<211> LENGTH: 6
<212> TYPE: PRT
<213> ORGANISM: Artificial
<220> FEATURE:
<223> OTHER INFORMATION: an artificially synthesized sequence

<400> SEQUENCE: 10

Ser Gly Gly Gly Gly Gly
1               5

<210> SEQ ID NO 11
<211> LENGTH: 7
<212> TYPE: PRT
<213> ORGANISM: Artificial
<220> FEATURE:
<223> OTHER INFORMATION: an artificially synthesized sequence

<400> SEQUENCE: 11

Gly Gly Gly Gly Gly Gly Ser
1               5

<210> SEQ ID NO 12
<211> LENGTH: 7
<212> TYPE: PRT
<213> ORGANISM: Artificial
<220> FEATURE:
<223> OTHER INFORMATION: an artificially synthesized sequence

<400> SEQUENCE: 12

Ser Gly Gly Gly Gly Gly Gly
1               5

<210> SEQ ID NO 13
<211> LENGTH: 1125
<212> TYPE: DNA
<213> ORGANISM: Homo sapiens

<400> SEQUENCE: 13

```
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg aaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agcttactt ctccttctac atgggcagca gaccctgcg aggcaggaac     720
acatcctctg aataccaaat actaactgct agaagagaag actctggtt atactggtgc     780
gaggctgcca cagaggatgg aaatgtcctt aagcgcagcc ctgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
```

```
cttcaagaag acagacattt agaagaagag ctgaaatgtc aggaacaaaa agaagaacag   1080
ctgcaggaag gggtgcaccg gaaggagccc caggggggcca cgtag                 1125
```

<210> SEQ ID NO 14
<211> LENGTH: 374
<212> TYPE: PRT
<213> ORGANISM: Homo sapiens

<400> SEQUENCE: 14

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350
```

Cys Gln Glu Gln Lys Glu Gln Leu Gln Glu Gly Val His Arg Lys
            355                 360                 365

Glu Pro Gln Gly Ala Thr
    370

<210> SEQ ID NO 15
<211> LENGTH: 951
<212> TYPE: DNA
<213> ORGANISM: Homo sapiens

<400> SEQUENCE: 15

```
atgactatgg agacccaaat gtctcagaat gtatgtccca gaaacctgtg gctgcttcaa      60
ccattgacag ttttgctgct gctggcttct gcagacagtc aagctgctcc cccaaaggct     120
gtgctgaaac ttgagccccc gtggatcaac gtgctccagg aggactctgt gactctgaca     180
tgccagggg ctcgcagccc tgagagcgac tccattcagt ggttccacaa tgggaatctc     240
attcccaccc acacgcagcc cagctacagg ttcaaggcca caacaatga cagcggggag     300
tacacgtgcc agactggcca gaccagcctc agcgaccctg tgcatctgac tgtgctttcc     360
gaatggctgg tgctccagac ccctcacctg gagttccagg agggagaaac catcatgctg     420
aggtgccaca gctggaagga caagcctctg gtcaaggtca cattcttcca gaatggaaaa     480
tcccagaaat tctcccattt ggatcccacc ttctccatcc acaagcaaa ccacagtcac     540
agtggtgatt accactgcac aggaaacata ggctacacgc tgttctcatc aagcctgtg     600
accatcactg tccaagtgcc agcatgggc agctcttcac caatgggggt cattgtggct     660
gtggtcattg cgactgctgt agcagccatt gttgctgctg tagtggcctt gatctactgc     720
aggaaaaagc ggatttcagc caattccact gatcctgtga aggctgccca atttgagcca     780
cctgacgtc aaatgattgc catcagaaag agacaacttg aagaaccaa caatgactat     840
gaaacagctg acggcggcta catgactctg aaccccaggg cacctactga cgatgataaa     900
aacatctacc tgactcttcc tcccaacgac catgtcaaca gtaataacta a              951
```

<210> SEQ ID NO 16
<211> LENGTH: 316
<212> TYPE: PRT
<213> ORGANISM: Homo sapiens

<400> SEQUENCE: 16

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser

```
                130                 135                 140
Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Pro Met Gly Val Ile Val Ala Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 17
<211> LENGTH: 876
<212> TYPE: DNA
<213> ORGANISM: Homo sapiens

<400> SEQUENCE: 17
atgggaatcc tgtcattctt acctgtcctt gccactgaga gtgactgggc tgactgcaag      60
tccccccagc cttggggtca tatgcttctg tggacagctg tgctattcct ggctcctgtt     120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attccaccc acacgcagcc agctacagg      300 ttcaaggcca acaacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca ctggaaggga caagcctctg     480
gtcaaggtca cattcttcca gaatggaaaa tccaagaaat tttcccgttc ggatcccaac     540
ttctccatcc acaagcaaa ccacagtcac agtggtgatt accactgcac aggaaacata     600
ggctacacgc tgtactcatc caagcctgtg accatcactg tccaagctcc agctcttca     660 ccgatgggga tcattgtggc tgtggtcact gggattgctg tagcggccat tgttgctgct     720
gtagtggcct tgatctactg caggaaaaag cggatttcag ccaatcccac taatcctgat     780
gaggctgaca agttggggc tgagaacaca atcacctatt cacttctcat gcacccggat     840
gctctggaag agcctgatga ccagaaccgt atttag                                876

<210> SEQ ID NO 18
<211> LENGTH: 291
<212> TYPE: PRT
<213> ORGANISM: Homo sapiens
```

<400> SEQUENCE: 18

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 19
<211> LENGTH: 765
<212> TYPE: DNA
<213> ORGANISM: Homo sapiens

<400> SEQUENCE: 19
atgtggcagc tgctcctccc aactgctctg ctacttctag tttcagctgg catgcggact    60
gaagatctcc caaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gttgacgaca gtggagagta caggtgccag acaaacctct ccaccctcag tgacccggtg   300
cagctagaag tccatatcgg ctggctgttg ctccaggccc ctcggtgggt gttcaaggag   360

| | | |
|---|---|---|
| gaagacccta ttcacctgag gtgtcacagc tggaagaaca ctgctctgca taaggtcaca | | 420 |
| tatttacaga atggcaaagg caggaagtat tttcatcata attctgactt ctacattcca | | 480 |
| aaagccacac tcaaagacag cggctcctac ttctgcaggg ggcttgttgg gagtaaaaat | | 540 |
| gtgtcttcag agactgtgaa catcaccatc actcaaggtt tgtcagtgtc aaccatctca | | 600 |
| tcattctttc cacctgggta ccaagtctct ttctgcttgg tgatggtact ccttttttgca | | 660 |
| gtggacacag gactatattt ctctgtgaag acaaacattc gaagctcaac aagagactgg | | 720 |
| aaggaccata aatttaaatg gagaaaggac cctcaagaca aatga | | 765 |

<210> SEQ ID NO 20
<211> LENGTH: 254
<212> TYPE: PRT
<213> ORGANISM: Homo sapiens

<400> SEQUENCE: 20

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 21
<211> LENGTH: 702
<212> TYPE: DNA
<213> ORGANISM: Homo sapiens

<400> SEQUENCE: 21
atgtggcagc tgctcctccc aactgctctg ctacttctag tttcagctgg catgcggact        60

-continued

```
gaagatctcc caaaggctgt ggtgttcctg gagcctcaat ggtacagcgt gcttgagaag    120
gacagtgtga ctctgaagtg ccagggagcc tactcccctg aggacaattc cacacagtgg    180
tttcacaatg agagcctcat ctcaagccag gcctcgagct acttcattga cgctgccaca    240
gtcaacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga atggcaaaga caggaagtat tttcatcata attctgactt ccacattcca    480
aaagccacac tcaaagatag cggctcctac ttctgcaggg ggcttgttgg gagtaaaaat    540
gtgtcttcag agactgtgaa catcaccatc actcaaggtt tggcagtgtc aaccatctca    600
tcattctctc cacctgggta ccaagtctct ttctgcttgg tgatggtact cctttttgca    660
gtggacacag gactatattt ctctgtgaag acaaacattt ga                      702
```

<210> SEQ ID NO 22
<211> LENGTH: 233
<212> TYPE: PRT
<213> ORGANISM: Homo sapiens

<400> SEQUENCE: 22

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 23
<211> LENGTH: 330

<212> TYPE: PRT
<213> ORGANISM: Artificial
<220> FEATURE:
<223> OTHER INFORMATION: an artificially synthesized sequence

<400> SEQUENCE: 23

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 24
<211> LENGTH: 326
<212> TYPE: PRT
<213> ORGANISM: Artificial
<220> FEATURE:
<223> OTHER INFORMATION: an artificially synthesized sequence

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65              70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 25
<211> LENGTH: 377
<212> TYPE: PRT
<213> ORGANISM: Artificial
<220> FEATURE:
<223> OTHER INFORMATION: an artificially synthesized sequence

<400> SEQUENCE: 25

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 26
<211> LENGTH: 327
<212> TYPE: PRT
<213> ORGANISM: Artificial
<220> FEATURE:
<223> OTHER INFORMATION: an artificially synthesized sequence

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 27
<211> LENGTH: 549
<212> TYPE: DNA
<213> ORGANISM: Homo sapiens

<400> SEQUENCE: 27
atggaacagg ggaagggcct ggctgtcctc atcctggcta tcattcttct tcaaggtact    60
ttggcccagt caatcaaagg aaaccacttg gttaaggtgt atgactatca agaagatggt   120
tcggtacttc tgacttgtga tgcagaagcc aaaaatatca catggtttaa agatgggaag   180
atgatcggct tcctaactga agataaaaaa aatggaatc tgggaagtaa tgccaaggac   240
cctcgaggga tgtatcagtg taaaggatca cagaacaagt caaaaccact ccaagtgtat   300

-continued

```
tacagaatgt gtcagaactg cattgaacta aatgcagcca ccatatctgg ctttctcttt    360
gctgaaatcg tcagcatttt cgtccttgct gttggggtct acttcattgc tggacaggat    420
ggagttcgcc agtcgagagc ttcagacaag cagactctgt tgcccaatga ccagctctac    480
cagcccctca aggatcgaga agatgaccag tacagccacc ttcaaggaaa ccagttgagg    540
aggaattga                                                            549
```

<210> SEQ ID NO 28
<211> LENGTH: 182
<212> TYPE: PRT
<213> ORGANISM: Homo sapiens

<400> SEQUENCE: 28

```
Met Glu Gln Gly Lys Gly Leu Ala Val Leu Ile Leu Ala Ile Ile Leu
 1               5                  10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
        50                  55                  60

Leu Thr Glu Asp Lys Lys Lys Trp Asn Leu Gly Ser Asn Ala Lys Asp
    65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 29
<211> LENGTH: 516
<212> TYPE: DNA
<213> ORGANISM: Homo sapiens

<400> SEQUENCE: 29

```
atggaacata gcacgtttct ctctggcctg gtactggcta cccttctctc gcaagtgagc     60
cccttcaaga tacctataga ggaacttgag gacagagtgt ttgtgaattg caataccagc    120
atcacatggg tagagggaac ggtgggaaca ctgctctcag acattacaag actggacctg    180
ggaaaacgca tcctggaccc acgaggaata tataggtgta atgggacaga tatatacaag    240
gacaaagaat ctaccgtgca agttcattat cgaatgtgcc agagctgtgt ggagctggat    300
ccagccaccg tggctggcat cattgtcact gatgtcattg ccactctgct ccttgctttg    360
ggagtcttct gctttgctgg acatgagact ggaaggctgt ctgggctgc cgacacacaa    420 gctctgttga ggaatgacca ggtctatcag cccctccgag atcgagatga tgctcagtac    480
agccaccttg gaggaaactg ggctcggaac aagtga                              516
```

<210> SEQ ID NO 30
<211> LENGTH: 171
<212> TYPE: PRT
<213> ORGANISM: Homo sapiens

<400> SEQUENCE: 30

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 31
<211> LENGTH: 624
<212> TYPE: DNA
<213> ORGANISM: Homo sapiens

<400> SEQUENCE: 31

```
atgcagtcgg gcactcactg gagagttctg ggcctctgcc tcttatcagt tggcgtttgg      60
gggcaagatg gtaatgaaga atgggtggt attacacaga caccatataa agtctccatc     120
tctggaacca cagtaatatt gacatgccct cagtatcctg gatctgaaat actatggcaa    180
cacaatgata aaacatagg cggtgatgag gatgataaaa acataggcag tgatgaggat    240 caccctgtcac tgaaggaatt ttcagaattg gagcaaagtg gttattatgt ctgctacccc    300
agaggaagca aaccagaaga tgcgaacttt tatctctacc tgagggcaag agtgtgtgag    360
aactgcatgg agatggatgt gatgtcggtg ccacaattg tcatagtgga catctgcatc    420
actgggggct tgctgctgct ggtttactac tggagcaaga atagaaaggc caaggccaag    480
cctgtgacac gaggagcggg tgctggcggc aggcaaaggg gacaaaacaa ggagaggcca    540
ccacctgttc ccaacccaga ctatgagccc atccggaaag gccagcggga cctgtattct    600
ggcctgaatc agagacgcat ctga                                            624
```

<210> SEQ ID NO 32
<211> LENGTH: 207
<212> TYPE: PRT
<213> ORGANISM: Homo sapiens

<400> SEQUENCE: 32

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Ile Thr
            20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205
```

<210> SEQ ID NO 33
<211> LENGTH: 523
<212> TYPE: PRT
<213> ORGANISM: Artificial
<220> FEATURE:
<223> OTHER INFORMATION: an artificially synthesized sequence

<400> SEQUENCE: 33

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Asp Tyr Glu Met His Trp Ile Arg Gln Pro Pro Gly Gln Gly Leu
50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
                100                 105                 110

Tyr Tyr Cys Thr Arg Phe Tyr Ser Tyr Thr Tyr Trp Gly Gln Gly Thr
            115                 120                 125

Leu Val Thr Val Ser Ser Gly Gly Gly Ser Gly Gly Gly Gly Ser
130                 135                 140

Gly Gly Gly Gly Ser Asp Ile Val Met Thr Gln Ser Pro Leu Ser Leu
145                 150                 155                 160
```

```
Pro Val Thr Pro Gly Glu Pro Ala Ser Ile Ser Cys Arg Ser Ser Gln
            165                 170                 175

Ser Leu Val His Ser Asn Arg Asn Thr Tyr Leu His Trp Tyr Gln Gln
        180                 185                 190

Lys Pro Gly Gln Ala Pro Arg Leu Leu Ile Tyr Lys Val Ser Asn Arg
            195                 200                 205

Phe Ser Gly Val Pro Asp Arg Phe Ser Gly Ser Gly Ser Gly Thr Asp
    210                 215                 220

Phe Thr Leu Lys Ile Ser Arg Val Glu Ala Glu Asp Val Gly Val Tyr
225                 230                 235                 240

Tyr Cys Ser Gln Asn Thr His Val Pro Pro Thr Phe Gly Gln Gly Thr
                245                 250                 255

Lys Leu Glu Ile Lys Gly Gly Gly Ser Gln Ala Val Val Thr Gln
            260                 265                 270

Glu Ser Ala Leu Thr Thr Ser Pro Gly Glu Thr Val Thr Leu Thr Cys
    275                 280                 285

Arg Ser Ser Thr Gly Ala Val Thr Thr Ser Asn Tyr Ala Asn Trp Val
    290                 295                 300

Gln Glu Lys Pro Asp His Leu Phe Thr Gly Leu Ile Gly Gly Thr Asn
305                 310                 315                 320

Lys Arg Ala Pro Gly Val Pro Ala Arg Phe Ser Gly Ser Leu Ile Gly
                325                 330                 335

Asp Lys Ala Ala Leu Thr Ile Thr Gly Ala Gln Thr Glu Asp Glu Ala
                340                 345                 350

Ile Tyr Phe Cys Ala Leu Trp Tyr Ser Asn Leu Trp Val Phe Gly Gly
            355                 360                 365

Gly Thr Lys Leu Thr Val Leu Gly Gly Gly Ser Gly Gly Gly Gly
            370                 375                 380

Ser Gly Gly Gly Gly Ser Glu Val Lys Leu Leu Glu Ser Gly Gly Gly
385                 390                 395                 400

Leu Val Gln Pro Lys Gly Ser Leu Lys Leu Ser Cys Ala Ala Ser Gly
            405                 410                 415

Phe Thr Phe Asn Thr Tyr Ala Met Asn Trp Val Arg Gln Ala Pro Gly
            420                 425                 430

Lys Gly Leu Glu Trp Val Ala Arg Ile Arg Ser Lys Tyr Asn Asn Tyr
            435                 440                 445

Ala Thr Tyr Tyr Ala Asp Ser Val Lys Asp Arg Phe Thr Ile Ser Arg
    450                 455                 460

Asp Asp Ser Gln Ser Ile Leu Tyr Leu Gln Met Asn Asn Leu Lys Thr
465                 470                 475                 480

Glu Asp Thr Ala Met Tyr Tyr Cys Val Arg His Gly Asn Phe Gly Asn
                485                 490                 495

Ser Tyr Val Ser Trp Phe Ala Tyr Trp Gly Gln Gly Thr Leu Val Thr
            500                 505                 510

Val Ser Ala His His His His His His
            515                 520

<210> SEQ ID NO 34
<211> LENGTH: 753
<212> TYPE: PRT
<213> ORGANISM: Artificial
<220> FEATURE:
<223> OTHER INFORMATION: an artificially synthesized sequence

<400> SEQUENCE: 34
```

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Glu Met His Trp Ile Arg Gln Pro Pro Gly Gln Gly Leu
        50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Gly Gly Gly Ser Gly Gly Gly Gly Ser
        130                 135                 140

Gly Gly Gly Ser Asp Ile Val Met Thr Gln Ser Pro Leu Ser Leu
145                 150                 155                 160

Pro Val Thr Pro Gly Glu Pro Ala Ser Ile Ser Cys Arg Ser Ser Gln
                165                 170                 175

Ser Leu Val His Ser Asn Arg Asn Thr Tyr Leu His Trp Tyr Gln Gln
            180                 185                 190

Lys Pro Gly Gln Ala Pro Arg Leu Leu Ile Tyr Lys Val Ser Asn Arg
        195                 200                 205

Phe Ser Gly Val Pro Asp Arg Phe Ser Gly Ser Gly Ser Gly Thr Asp
210                 215                 220

Phe Thr Leu Lys Ile Ser Arg Val Glu Ala Glu Asp Val Gly Val Tyr
225                 230                 235                 240

Tyr Cys Ser Gln Asn Thr His Val Pro Pro Thr Phe Gly Gln Gly Thr
            245                 250                 255

Lys Leu Glu Ile Lys Gly Gly Gly Gly Ser Gln Ala Val Val Thr Gln
        260                 265                 270

Glu Ser Ala Leu Thr Thr Ser Pro Gly Glu Thr Val Thr Leu Thr Cys
    275                 280                 285

Arg Ser Ser Thr Gly Ala Val Thr Thr Ser Asn Tyr Ala Asn Trp Val
290                 295                 300

Gln Glu Lys Pro Asp His Leu Phe Thr Gly Leu Ile Gly Gly Thr Asn
305                 310                 315                 320

Lys Arg Ala Pro Gly Val Pro Ala Arg Phe Ser Gly Ser Leu Ile Gly
            325                 330                 335

Asp Lys Ala Ala Leu Thr Ile Thr Gly Ala Gln Thr Glu Asp Glu Ala
        340                 345                 350

Ile Tyr Phe Cys Ala Leu Trp Tyr Ser Asn Leu Trp Val Phe Gly Gly
        355                 360                 365

Gly Thr Lys Leu Thr Val Leu Gly Gly Gly Ser Gly Gly Gly Gly
        370                 375                 380

Ser Gly Gly Gly Gly Ser Glu Val Lys Leu Leu Glu Ser Gly Gly Gly
385                 390                 395                 400

Leu Val Gln Pro Lys Gly Ser Leu Lys Leu Ser Cys Ala Ala Ser Gly
                405                 410                 415
```

Phe Thr Phe Asn Thr Tyr Ala Met Asn Trp Val Arg Gln Ala Pro Gly
              420                 425                 430

Lys Gly Leu Glu Trp Val Ala Arg Ile Arg Ser Lys Tyr Asn Asn Tyr
          435                 440                 445

Ala Thr Tyr Tyr Ala Asp Ser Val Lys Asp Arg Phe Thr Ile Ser Arg
      450                 455                 460

Asp Asp Ser Gln Ser Ile Leu Tyr Leu Gln Met Asn Asn Leu Lys Thr
465                 470                 475                 480

Glu Asp Thr Ala Met Tyr Tyr Cys Val Arg His Gly Asn Phe Gly Asn
              485                 490                 495

Ser Tyr Val Ser Trp Phe Ala Tyr Trp Gly Gln Gly Thr Leu Val Thr
          500                 505                 510

Val Ser Ala Glu Pro Lys Ser Ser Asp Lys Thr His Thr Cys Pro Pro
      515                 520                 525

Cys Pro Ala Pro Glu Ala Ala Gly Gly Pro Ser Val Phe Leu Phe Pro
530                 535                 540

Pro Lys Pro Lys Asp Thr Leu Met Ile Ser Arg Thr Pro Glu Val Thr
545                 550                 555                 560

Cys Val Val Val Asp Val Ser His Glu Asp Pro Glu Val Lys Phe Asn
              565                 570                 575

Trp Tyr Val Asp Gly Val Glu Val His Asn Ala Lys Thr Lys Pro Arg
          580                 585                 590

Glu Glu Gln Tyr Ala Ser Thr Tyr Arg Val Val Ser Val Leu Thr Val
      595                 600                 605

Leu His Gln Asp Trp Leu Asn Gly Lys Glu Tyr Lys Cys Lys Val Ser
610                 615                 620

Asn Lys Ala Leu Pro Ala Pro Ile Glu Lys Thr Ile Ser Lys Ala Lys
625                 630                 635                 640

Gly Gln Pro Arg Glu Pro Gln Val Cys Thr Leu Pro Pro Ser Arg Asp
              645                 650                 655

Glu Leu Thr Lys Asn Gln Val Ser Leu Trp Cys Leu Val Lys Gly Phe
          660                 665                 670

Tyr Pro Ser Asp Ile Ala Val Glu Trp Glu Ser Asn Gly Gln Pro Glu
      675                 680                 685

Asn Asn Tyr Lys Thr Thr Pro Pro Val Leu Asp Ser Asp Gly Ser Phe
690                 695                 700

Phe Leu Tyr Ser Lys Leu Thr Val Asp Lys Ser Arg Trp Gln Gln Gly
705                 710                 715                 720

Asn Val Phe Ser Cys Ser Val Met His Glu Ala Leu His Asn His Tyr
              725                 730                 735

Thr Gln Lys Ser Leu Ser Leu Ser Pro His His His His His His
          740                 745                 750

His

<210> SEQ ID NO 35
<211> LENGTH: 257
<212> TYPE: PRT
<213> ORGANISM: Artificial
<220> FEATURE:
<223> OTHER INFORMATION: an artificially synthesized sequence

<400> SEQUENCE: 35

Met Gly Trp Ser Cys Ile Ile Leu Phe Leu Val Ala Thr Ala Thr Gly
1               5                   10                  15

Val His Ser Glu Pro Lys Ser Ser Asp Lys Thr His Thr Cys Pro Pro

```
                 20                  25                  30
Cys Pro Ala Pro Glu Ala Gly Gly Pro Ser Val Phe Leu Phe Pro
             35                  40                  45
Pro Lys Pro Lys Asp Thr Leu Met Ile Ser Arg Thr Pro Glu Val Thr
 50                  55                  60
Cys Val Val Val Asp Val Ser His Glu Asp Pro Glu Val Lys Phe Asn
 65                  70                  75                  80
Trp Tyr Val Asp Gly Val Glu Val His Asn Ala Lys Thr Lys Pro Arg
                 85                  90                  95
Glu Glu Gln Tyr Ala Ser Thr Tyr Arg Val Val Ser Val Leu Thr Val
            100                 105                 110
Leu His Gln Asp Trp Leu Asn Gly Lys Glu Tyr Lys Cys Lys Val Ser
            115                 120                 125
Asn Lys Ala Leu Pro Ala Pro Ile Glu Lys Thr Ile Ser Lys Ala Lys
            130                 135                 140
Gly Gln Pro Arg Glu Pro Gln Val Tyr Thr Leu Pro Pro Ser Arg Cys
145                 150                 155                 160
Glu Leu Thr Lys Asn Gln Val Ser Leu Ser Cys Ala Val Lys Gly Phe
                165                 170                 175
Tyr Pro Ser Asp Ile Ala Val Glu Trp Glu Ser Asn Gly Gln Pro Glu
                180                 185                 190
Asn Asn Tyr Lys Thr Thr Pro Pro Val Leu Asp Ser Asp Gly Ser Phe
            195                 200                 205
Phe Leu Val Ser Lys Leu Thr Val Asp Lys Ser Arg Trp Gln Gln Gly
210                 215                 220
Asn Val Phe Ser Cys Ser Val Met His Glu Ala Leu His Asn His Tyr
225                 230                 235                 240
Thr Gln Lys Ser Leu Ser Leu Ser Pro Asp Tyr Lys Asp Asp Asp Asp
                245                 250                 255
Lys

<210> SEQ ID NO 36
<211> LENGTH: 514
<212> TYPE: PRT
<213> ORGANISM: Artificial
<220> FEATURE:
<223> OTHER INFORMATION: an artificially synthesized sequence

<400> SEQUENCE: 36

Met Gly Trp Ser Cys Ile Ile Leu Phe Leu Val Ala Thr Ala Thr Gly
 1               5                  10                  15
Val His Ser Gln Val Gln Leu Val Gln Ser Gly Ala Glu Val Lys Lys
             20                  25                  30
Pro Gly Ala Ser Val Lys Val Ser Cys Lys Ala Ser Gly Tyr Thr Phe
             35                  40                  45
Thr Asp Tyr Glu Met His Trp Ile Arg Gln Pro Pro Gly Gln Gly Leu
         50                  55                  60
Glu Trp Ile Gly Ala Ile Asp Pro Lys Thr Gly Asp Thr Ala Tyr Ser
 65                  70                  75                  80
Gln Lys Phe Lys Gly Arg Val Thr Leu Thr Ala Asp Lys Ser Thr Ser
                 85                  90                  95
Thr Ala Tyr Met Glu Leu Ser Ser Leu Thr Ser Glu Asp Thr Ala Val
            100                 105                 110
Tyr Tyr Cys Thr Arg Phe Tyr Ser Tyr Tyr Trp Gly Gln Gly Thr
            115                 120                 125
```

Leu Val Thr Val Ser Ser Gly Gly Gly Gly Gly Gly Ser
130                 135                 140

Gly Gly Gly Gly Ser Asp Ile Val Met Thr Gln Ser Pro Leu Ser Leu
145                 150                 155                 160

Pro Val Thr Pro Gly Glu Pro Ala Ser Ile Ser Cys Arg Ser Ser Gln
                165                 170                 175

Ser Leu Val His Ser Asn Arg Asn Thr Tyr Leu His Trp Tyr Gln Gln
            180                 185                 190

Lys Pro Gly Gln Ala Pro Arg Leu Leu Ile Tyr Lys Val Ser Asn Arg
        195                 200                 205

Phe Ser Gly Val Pro Asp Arg Phe Ser Gly Ser Gly Ser Gly Thr Asp
210                 215                 220

Phe Thr Leu Lys Ile Ser Arg Val Glu Ala Glu Asp Val Gly Val Tyr
225                 230                 235                 240

Tyr Cys Ser Gln Asn Thr His Val Pro Pro Thr Phe Gly Gln Gly Thr
                245                 250                 255

Lys Leu Glu Ile Lys Gly Gly Gly Gly Ser Gly Gly Gly Gly Ser Gly
            260                 265                 270

Gly Gly Ser Glu Pro Lys Ser Ser Asp Lys Thr His Thr Cys Pro
        275                 280                 285

Pro Cys Pro Ala Pro Glu Ala Ala Gly Gly Pro Ser Val Phe Leu Phe
290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Ala Ser Thr Tyr Arg Val Val Ser Val Leu Thr
        355                 360                 365

Val Leu His Gln Asp Trp Leu Asn Gly Lys Glu Tyr Lys Cys Lys Val
370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Cys Glu Leu Thr Lys Asn Gln Val Ser Leu Ser Cys Ala Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
450                 455                 460

Phe Phe Leu Val Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Asp Tyr Lys Asp Asp Asp
            500                 505                 510

Asp Lys

<210> SEQ ID NO 37
<211> LENGTH: 629
<212> TYPE: PRT

<213> ORGANISM: Artificial
<220> FEATURE:
<223> OTHER INFORMATION: an artificially synthesized sequence

<400> SEQUENCE: 37

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Gly Gly Gly Gly Ser Gly Gly Gly Gly Ser
    130                 135                 140

Gly Gly Gly Gly Ser Asp Ile Val Met Thr Gln Ser Pro Leu Ser Leu
145                 150                 155                 160

Pro Val Thr Pro Gly Glu Pro Ala Ser Ile Ser Cys Arg Ser Ser Gln
                165                 170                 175

Ser Leu Val His Ser Asn Arg Asn Thr Tyr Leu His Trp Tyr Gln Gln
            180                 185                 190

Lys Pro Gly Gln Ala Pro Arg Leu Leu Ile Tyr Lys Val Ser Asn Arg
        195                 200                 205

Phe Ser Gly Val Pro Asp Arg Phe Ser Gly Ser Gly Ser Gly Thr Asp
    210                 215                 220

Phe Thr Leu Lys Ile Ser Arg Val Glu Ala Glu Asp Val Gly Val Tyr
225                 230                 235                 240

Tyr Cys Ser Gln Asn Thr His Val Pro Pro Thr Phe Gly Gln Gly Thr
                245                 250                 255

Lys Leu Glu Ile Lys Gly Gly Gly Ser Glu Val Lys Leu Leu Glu
            260                 265                 270

Ser Gly Gly Gly Leu Val Gln Pro Lys Gly Ser Leu Lys Leu Ser Cys
        275                 280                 285

Ala Ala Ser Gly Phe Thr Phe Asn Thr Tyr Ala Met Asn Trp Val Arg
    290                 295                 300

Gln Ala Pro Gly Lys Gly Leu Glu Trp Val Ala Arg Ile Arg Ser Lys
305                 310                 315                 320

Tyr Asn Asn Tyr Ala Thr Tyr Tyr Ala Asp Ser Val Lys Asp Arg Phe
                325                 330                 335

Thr Ile Ser Arg Asp Asp Ser Gln Ser Ile Leu Tyr Leu Gln Met Asn
            340                 345                 350

Asn Leu Lys Thr Glu Asp Thr Ala Met Tyr Tyr Cys Val Arg His Gly
        355                 360                 365

Asn Phe Gly Asn Ser Tyr Val Ser Trp Phe Ala Tyr Trp Gly Gln Gly
    370                 375                 380

Thr Leu Val Thr Val Ser Ala Glu Pro Lys Ser Ser Asp Lys Thr His
```

```
                385                 390                 395                 400
        Thr Cys Pro Pro Cys Pro Ala Pro Glu Ala Ala Gly Gly Pro Ser Val
                        405                 410                 415

Phe Leu Phe Pro Pro Lys Pro Lys Asp Thr Leu Met Ile Ser Arg Thr
                        420                 425                 430

Pro Glu Val Thr Cys Val Val Val Asp Val Ser His Glu Asp Pro Glu
                        435                 440                 445

Val Lys Phe Asn Trp Tyr Val Asp Gly Val Glu Val His Asn Ala Lys
                        450                 455                 460

Thr Lys Pro Arg Glu Glu Gln Tyr Ala Ser Thr Tyr Arg Val Val Ser
        465                 470                 475                 480

Val Leu Thr Val Leu His Gln Asp Trp Leu Asn Gly Lys Glu Tyr Lys
                        485                 490                 495

Cys Lys Val Ser Asn Lys Ala Leu Pro Ala Pro Ile Glu Lys Thr Ile
                        500                 505                 510

Ser Lys Ala Lys Gly Gln Pro Arg Glu Pro Gln Val Cys Thr Leu Pro
                        515                 520                 525

Pro Ser Arg Asp Glu Leu Thr Lys Asn Gln Val Ser Leu Trp Cys Leu
                530                 535                 540

Val Lys Gly Phe Tyr Pro Ser Asp Ile Ala Val Glu Trp Glu Ser Asn
        545                 550                 555                 560

Gly Gln Pro Glu Asn Asn Tyr Lys Thr Thr Pro Pro Val Leu Asp Ser
                        565                 570                 575

Asp Gly Ser Phe Phe Leu Tyr Ser Lys Leu Thr Val Asp Lys Ser Arg
                        580                 585                 590

Trp Gln Gln Gly Asn Val Phe Ser Cys Ser Val Met His Glu Ala Leu
                        595                 600                 605

His Asn His Tyr Thr Gln Lys Ser Leu Ser Leu Ser Pro His His His
                        610                 615                 620

His His His His His
        625

<210> SEQ ID NO 38
<211> LENGTH: 613
<212> TYPE: PRT
<213> ORGANISM: Artificial
<220> FEATURE:
<223> OTHER INFORMATION: an artificially synthesized sequence

<400> SEQUENCE: 38

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Asp Tyr Glu Met His Trp Ile Arg Gln Pro Pro Gly Gln Gly Leu
            50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                        85                  90                  95

Thr Ala Tyr Met Glu Leu Ser Ser Leu Thr Ser Glu Asp Thr Ala Val
                    100                 105                 110

Tyr Tyr Cys Thr Arg Phe Tyr Ser Tyr Thr Tyr Trp Gly Gln Gly Thr
```

```
            115                 120                 125
Leu Val Thr Val Ser Ser Gly Gly Gly Gly Ser Gly Gly Gly Ser
            130                 135                 140
Gly Gly Gly Gly Ser Asp Ile Val Met Thr Gln Ser Pro Leu Ser Leu
145                 150                 155                 160
Pro Val Thr Pro Gly Glu Pro Ala Ser Ile Ser Cys Arg Ser Ser Gln
                    165                 170                 175
Ser Leu Val His Ser Asn Arg Asn Thr Tyr Leu His Trp Tyr Gln Gln
                180                 185                 190
Lys Pro Gly Gln Ala Pro Arg Leu Leu Ile Tyr Lys Val Ser Asn Arg
            195                 200                 205
Phe Ser Gly Val Pro Asp Arg Phe Ser Gly Ser Gly Ser Gly Thr Asp
            210                 215                 220
Phe Thr Leu Lys Ile Ser Arg Val Glu Ala Glu Asp Val Gly Val Tyr
225                 230                 235                 240
Tyr Cys Ser Gln Asn Thr His Val Pro Pro Thr Phe Gly Gln Gly Thr
                245                 250                 255
Lys Leu Glu Ile Lys Gly Gly Gly Gly Ser Gln Ala Val Val Thr Gln
                260                 265                 270
Glu Ser Ala Leu Thr Thr Ser Pro Gly Glu Thr Val Thr Leu Thr Cys
            275                 280                 285
Arg Ser Ser Thr Gly Ala Val Thr Thr Ser Asn Tyr Ala Asn Trp Val
290                 295                 300
Gln Glu Lys Pro Asp His Leu Phe Thr Gly Leu Ile Gly Gly Thr Asn
305                 310                 315                 320
Lys Arg Ala Pro Gly Val Pro Ala Arg Phe Ser Gly Ser Leu Ile Gly
                325                 330                 335
Asp Lys Ala Ala Leu Thr Ile Thr Gly Ala Gln Thr Glu Asp Glu Ala
                340                 345                 350
Ile Tyr Phe Cys Ala Leu Trp Tyr Ser Asn Leu Trp Val Phe Gly Gly
            355                 360                 365
Gly Thr Lys Leu Thr Val Leu Glu Pro Lys Ser Ser Asp Lys Thr His
            370                 375                 380
Thr Cys Pro Pro Cys Pro Ala Pro Glu Ala Ala Gly Gly Pro Ser Val
385                 390                 395                 400
Phe Leu Phe Pro Pro Lys Pro Lys Asp Thr Leu Met Ile Ser Arg Thr
                405                 410                 415
Pro Glu Val Thr Cys Val Val Val Asp Val Ser His Glu Asp Pro Glu
                420                 425                 430
Val Lys Phe Asn Trp Tyr Val Asp Gly Val Glu Val His Asn Ala Lys
            435                 440                 445
Thr Lys Pro Arg Glu Glu Gln Tyr Ala Ser Thr Tyr Arg Val Val Ser
            450                 455                 460
Val Leu Thr Val Leu His Gln Asp Trp Leu Asn Gly Lys Glu Tyr Lys
465                 470                 475                 480
Cys Lys Val Ser Asn Lys Ala Leu Pro Ala Pro Ile Glu Lys Thr Ile
                485                 490                 495
Ser Lys Ala Lys Gly Gln Pro Arg Glu Pro Gln Val Tyr Thr Leu Pro
                500                 505                 510
Pro Ser Arg Cys Glu Leu Thr Lys Asn Gln Val Ser Leu Ser Cys Ala
            515                 520                 525
Val Lys Gly Phe Tyr Pro Ser Asp Ile Ala Val Glu Trp Glu Ser Asn
            530                 535                 540
```

```
Gly Gln Pro Glu Asn Asn Tyr Lys Thr Thr Pro Pro Val Leu Asp Ser
545                 550                 555                 560

Asp Gly Ser Phe Phe Leu Val Ser Lys Leu Thr Val Asp Lys Ser Arg
            565                 570                 575

Trp Gln Gln Gly Asn Val Phe Ser Cys Ser Val Met His Glu Ala Leu
        580                 585                 590

His Asn His Tyr Thr Gln Lys Ser Leu Ser Leu Ser Pro Asp Tyr Lys
    595                 600                 605

Asp Asp Asp Asp Lys
    610

<210> SEQ ID NO 39
<211> LENGTH: 470
<212> TYPE: PRT
<213> ORGANISM: Artificial
<220> FEATURE:
<223> OTHER INFORMATION: an artificially synthesized sequence

<400> SEQUENCE: 39

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285
```

```
Glu Val Lys Phe Asn Trp Tyr Val Asp Gly Val Glu Val His Asn Ala
            290                 295                 300
Lys Thr Lys Pro Arg Glu Gln Tyr Ala Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
            355                 360                 365
Pro Pro Ser Arg Cys Glu Leu Thr Lys Asn Gln Val Ser Leu Ser Cys
370                 375                 380
Ala Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Val Ser Lys Leu Thr Val Asp Lys Ser
                420                 425                 430
Arg Trp Gln Gln Gly Asn Val Phe Ser Cys Ser Val Met His Glu Ala
            435                 440                 445
Leu His Asn His Tyr Thr Gln Lys Ser Leu Ser Leu Ser Pro Asp Tyr
450                 455                 460
Lys Asp Asp Asp Lys
465                 470

<210> SEQ ID NO 40
<211> LENGTH: 238
<212> TYPE: PRT
<213> ORGANISM: Artificial
<220> FEATURE:
<223> OTHER INFORMATION: an artificially synthesized sequence

<400> SEQUENCE: 40

Met Gly Trp Ser Cys Ile Ile Leu Phe Leu Val Ala Thr Ala Thr Gly
1               5                   10                  15
Val His Ser Asp Ile Val Met Thr Gln Ser Pro Leu Ser Leu Pro Val
                20                  25                  30
Thr Pro Gly Glu Pro Ala Ser Ile Ser Cys Arg Ser Ser Gln Ser Leu
            35                  40                  45
Val His Ser Asn Arg Asn Thr Tyr Leu His Trp Tyr Gln Gln Lys Pro
        50                  55                  60
Gly Gln Ala Pro Arg Leu Leu Ile Tyr Lys Val Ser Asn Arg Phe Ser
65                  70                  75                  80
Gly Val Pro Asp Arg Phe Ser Gly Ser Gly Ser Gly Thr Asp Phe Thr
                85                  90                  95
Leu Lys Ile Ser Arg Val Glu Ala Glu Asp Val Gly Val Tyr Tyr Cys
                100                 105                 110
Ser Gln Asn Thr His Val Pro Pro Thr Phe Gly Gln Gly Thr Lys Leu
            115                 120                 125
Glu Ile Lys Arg Thr Val Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
```

```
Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 41
<211> LENGTH: 470
<212> TYPE: PRT
<213> ORGANISM: Artificial
<220> FEATURE:
<223> OTHER INFORMATION: an artificially synthesized sequence

<400> SEQUENCE: 41

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300
```

-continued

```
Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Cys Thr Leu
        355                 360                 365

Pro Pro Ser Arg Asp Glu Leu Thr Lys Asn Gln Val Ser Leu Trp Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro His His
    450                 455                 460

His His His His His His
465                 470

<210> SEQ ID NO 42
<211> LENGTH: 734
<212> TYPE: PRT
<213> ORGANISM: Artificial
<220> FEATURE:
<223> OTHER INFORMATION: an artificially synthesized sequence

<400> SEQUENCE: 42

Met Gly Trp Ser Cys Ile Ile Leu Phe Leu Val Ala Thr Ala Thr Gly
1               5                   10                  15

Val His Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Lys Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Leu Trp Val Phe Gly Gly Gly Thr Lys Leu Thr Val Leu
        115                 120                 125

Gly Gly Gly Gly Ser Gly Gly Gly Gly Ser Gly Gly Gly Gly Ser Glu
    130                 135                 140

Val Lys Leu Leu Glu Ser Gly Gly Gly Leu Val Gln Pro Lys Gly Ser
145                 150                 155                 160

Leu Lys Leu Ser Cys Ala Ala Ser Gly Phe Thr Phe Asn Thr Tyr Ala
                165                 170                 175

Met Asn Trp Val Arg Gln Ala Pro Gly Lys Gly Leu Glu Trp Val Ala
            180                 185                 190
```

-continued

Arg Ile Arg Ser Lys Tyr Asn Asn Tyr Ala Thr Tyr Ala Asp Ser
            195                 200                 205

Val Lys Asp Arg Phe Thr Ile Ser Arg Asp Asp Ser Gln Ser Ile Leu
    210                 215                 220

Tyr Leu Gln Met Asn Asn Leu Lys Thr Glu Asp Thr Ala Met Tyr Tyr
225                 230                 235                 240

Cys Val Arg His Gly Asn Phe Gly Asn Ser Tyr Val Ser Trp Phe Ala
                245                 250                 255

Tyr Trp Gly Gln Gly Thr Leu Val Thr Val Ser Ala Gly Gly Gly Gly
            260                 265                 270

Ser Gly Gly Gly Gly Ser Gly Gly Gly Ser Gln Val Gln Leu Val
        275                 280                 285

Gln Ser Gly Ala Glu Val Lys Lys Pro Gly Ala Ser Val Lys Val Ser
290                 295                 300

Cys Lys Ala Ser Gly Tyr Thr Phe Thr Asp Tyr Glu Met His Trp Ile
305                 310                 315                 320

Arg Gln Pro Pro Gly Gln Gly Leu Glu Trp Ile Gly Ala Ile Asp Pro
            325                 330                 335

Lys Thr Gly Asp Thr Ala Tyr Ser Gln Lys Phe Lys Gly Arg Val Thr
                340                 345                 350

Leu Thr Ala Asp Lys Ser Thr Ser Thr Ala Tyr Met Glu Leu Ser Ser
            355                 360                 365

Leu Thr Ser Glu Asp Thr Ala Val Tyr Tyr Cys Thr Arg Phe Tyr Ser
        370                 375                 380

Tyr Thr Tyr Trp Gly Gln Gly Thr Leu Val Thr Val Ser Ser Ala Ser
385                 390                 395                 400

Thr Lys Gly Pro Ser Val Phe Pro Leu Ala Pro Ser Ser Lys Ser Thr
            405                 410                 415

Ser Gly Gly Thr Ala Ala Leu Gly Cys Leu Val Lys Asp Tyr Phe Pro
                420                 425                 430

Glu Pro Val Thr Val Ser Trp Asn Ser Gly Ala Leu Thr Ser Gly Val
            435                 440                 445

His Thr Phe Pro Ala Val Leu Gln Ser Ser Gly Leu Tyr Ser Leu Ser
    450                 455                 460

Ser Val Val Thr Val Pro Ser Ser Ser Leu Gly Thr Gln Thr Tyr Ile
465                 470                 475                 480

Cys Asn Val Asn His Lys Pro Ser Asn Thr Lys Val Asp Lys Lys Val
                485                 490                 495

Glu Pro Lys Ser Cys Asp Lys Thr His Thr Cys Pro Pro Cys Pro Ala
            500                 505                 510

Pro Glu Ala Ala Gly Gly Pro Ser Val Phe Leu Phe Pro Pro Lys Pro
    515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Ala Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
    595                 600                 605

Leu Pro Ala Pro Ile Glu Lys Thr Ile Ser Lys Ala Lys Gly Gln Pro
610                 615                 620

Arg Glu Pro Gln Val Tyr Thr Leu Pro Pro Ser Arg Cys Glu Leu Thr
625                 630                 635                 640

Lys Asn Gln Val Ser Leu Ser Cys Ala Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Val
                675                 680                 685

Ser Lys Leu Thr Val Asp Lys Ser Arg Trp Gln Gln Gly Asn Val Phe
690                 695                 700

Ser Cys Ser Val Met His Glu Ala Leu His Asn His Tyr Thr Gln Lys
705                 710                 715                 720

Ser Leu Ser Leu Ser Pro Asp Tyr Lys Asp Asp Asp Lys
                725                 730

<210> SEQ ID NO 43
<211> LENGTH: 462
<212> TYPE: PRT
<213> ORGANISM: Artificial
<220> FEATURE:
<223> OTHER INFORMATION: an artificially synthesized sequence

<400> SEQUENCE: 43

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Glu Met His Trp Ile Arg Gln Pro Pro Gly Gln Gly Leu
        50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
                100                 105                 110

Tyr Tyr Cys Thr Arg Phe Tyr Ser Tyr Thr Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser His Glu Asp Pro
    275                 280                 285

Glu Val Lys Phe Asn Trp Tyr Val Asp Gly Val Glu Val His Asn Ala
290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
        340                 345                 350

Ile Ser Lys Ala Lys Gly Gln Pro Arg Glu Pro Gln Val Tyr Thr Leu
    355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
        420                 425                 430

Arg Trp Gln Gln Gly Asn Val Phe Ser Cys Ser Val Met His Glu Ala
    435                 440                 445

Leu His Asn His Tyr Thr Gln Lys Ser Leu Ser Leu Ser Pro
450                 455                 460

<210> SEQ ID NO 44
<211> LENGTH: 246
<212> TYPE: PRT
<213> ORGANISM: Artificial
<220> FEATURE:
<223> OTHER INFORMATION: an artificially synthesized sequence

<400> SEQUENCE: 44

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Val His Ser Asn Arg Asn Thr Tyr Leu His Trp Tyr Gln Gln Lys Pro
        50                  55                  60

Gly Gln Ala Pro Arg Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Asn Thr His Val Pro Pro Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

```
Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys His His
225                 230                 235                 240

His His His His His His
            245

<210> SEQ ID NO 45
<211> LENGTH: 505
<212> TYPE: PRT
<213> ORGANISM: Artificial
<220> FEATURE:
<223> OTHER INFORMATION: an artificially synthesized sequence

<400> SEQUENCE: 45

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Arg Asn Thr Tyr Leu His Trp Tyr Gln Gln Lys Pro
    50                  55                  60

Gly Gln Ala Pro Arg Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Asn Thr His Val Pro Pro Thr Phe Gly Gln Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Gly Gly
225                 230                 235                 240

Gly Gly Ser Gly Gly Gly Ser Gln Ala Val Val Thr Gln Glu Ser
            245                 250                 255
```

```
Ala Leu Thr Thr Ser Pro Gly Glu Thr Val Thr Leu Thr Cys Arg Ser
            260                 265                 270

Ser Thr Gly Ala Val Thr Thr Ser Asn Tyr Ala Asn Trp Val Gln Glu
        275                 280                 285

Lys Pro Asp His Leu Phe Thr Gly Leu Ile Gly Gly Thr Asn Lys Arg
    290                 295                 300

Ala Pro Gly Val Pro Ala Arg Phe Ser Gly Ser Leu Ile Gly Asp Lys
305                 310                 315                 320

Ala Ala Leu Thr Ile Thr Gly Ala Gln Thr Glu Asp Glu Ala Ile Tyr
                325                 330                 335

Phe Cys Ala Leu Trp Tyr Ser Asn Leu Trp Val Phe Gly Gly Gly Thr
            340                 345                 350

Lys Leu Thr Val Leu Gly Gly Gly Ser Gly Gly Gly Gly Ser Gly
        355                 360                 365

Gly Gly Gly Ser Glu Val Lys Leu Leu Glu Ser Gly Gly Gly Leu Val
    370                 375                 380

Gln Pro Lys Gly Ser Leu Lys Leu Ser Cys Ala Ala Ser Gly Phe Thr
385                 390                 395                 400

Phe Asn Thr Tyr Ala Met Asn Trp Val Arg Gln Ala Pro Gly Lys Gly
                405                 410                 415

Leu Glu Trp Val Ala Arg Ile Arg Ser Lys Tyr Asn Asn Tyr Ala Thr
            420                 425                 430

Tyr Tyr Ala Asp Ser Val Lys Asp Arg Phe Thr Ile Ser Arg Asp Asp
        435                 440                 445

Ser Gln Ser Ile Leu Tyr Leu Gln Met Asn Asn Leu Lys Thr Glu Asp
    450                 455                 460

Thr Ala Met Tyr Tyr Cys Val Arg His Gly Asn Phe Gly Asn Ser Tyr
465                 470                 475                 480

Val Ser Trp Phe Ala Tyr Trp Gly Gln Gly Thr Leu Val Thr Val Ser
                485                 490                 495

Ala Asp Tyr Lys Asp Asp Asp Lys
            500                 505

<210> SEQ ID NO 46
<211> LENGTH: 729
<212> TYPE: PRT
<213> ORGANISM: Artificial
<220> FEATURE:
<223> OTHER INFORMATION: an artificially synthesized sequence

<400> SEQUENCE: 46

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110
```

-continued

```
Tyr Tyr Cys Thr Arg Phe Tyr Ser Tyr Thr Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Cys Glu Leu Thr Lys Asn Gln Val Ser Leu Ser Cys
370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Gly
    450                 455                 460

Gly Gly Ser Gly Gly Gly Ser Gln Ala Val Val Thr Gln Glu Ser
465                 470                 475                 480

Ala Leu Thr Thr Ser Pro Gly Glu Thr Val Thr Leu Thr Cys Arg Ser
                485                 490                 495

Ser Thr Gly Ala Val Thr Thr Ser Asn Tyr Ala Asn Trp Val Gln Glu
            500                 505                 510

Lys Pro Asp His Leu Phe Thr Gly Leu Ile Gly Gly Thr Asn Lys Arg
        515                 520                 525

Ala Pro Gly Val Pro Ala Arg Phe Ser Gly Ser Leu Ile Gly Asp Lys
```

```
                530                 535                 540
Ala Ala Leu Thr Ile Thr Gly Ala Gln Thr Glu Asp Glu Ala Ile Tyr
545                 550                 555                 560

Phe Cys Ala Leu Trp Tyr Ser Asn Leu Trp Val Phe Gly Gly Gly Thr
                565                 570                 575

Lys Leu Thr Val Leu Gly Gly Gly Ser Gly Gly Gly Gly Ser Gly
                580                 585                 590

Gly Gly Gly Ser Glu Val Lys Leu Leu Glu Ser Gly Gly Gly Leu Val
                595                 600                 605

Gln Pro Lys Gly Ser Leu Lys Leu Ser Cys Ala Ala Ser Gly Phe Thr
                610                 615                 620

Phe Asn Thr Tyr Ala Met Asn Trp Val Arg Gln Ala Pro Gly Lys Gly
625                 630                 635                 640

Leu Glu Trp Val Ala Arg Ile Arg Ser Lys Tyr Asn Asn Tyr Ala Thr
                645                 650                 655

Tyr Tyr Ala Asp Ser Val Lys Asp Arg Phe Thr Ile Ser Arg Asp Asp
                660                 665                 670

Ser Gln Ser Ile Leu Tyr Leu Gln Met Asn Asn Leu Lys Thr Glu Asp
                675                 680                 685

Thr Ala Met Tyr Tyr Cys Val Arg His Gly Asn Phe Gly Asn Ser Tyr
                690                 695                 700

Val Ser Trp Phe Ala Tyr Trp Gly Gln Gly Thr Leu Val Thr Val Ser
705                 710                 715                 720

Ala Asp Tyr Lys Asp Asp Asp Lys
                725

<210> SEQ ID NO 47
<211> LENGTH: 729
<212> TYPE: PRT
<213> ORGANISM: Artificial
<220> FEATURE:
<223> OTHER INFORMATION: an artificially synthesized sequence

<400> SEQUENCE: 47

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Asp Tyr Glu Met His Trp Ile Arg Gln Pro Pro Gly Gln Gly Leu
                50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
                100                 105                 110

Tyr Tyr Cys Thr Arg Phe Tyr Ser Tyr Thr Tyr Trp Gly Gln Gly Thr
                115                 120                 125

Leu Val Thr Val Ser Ser Ala Ser Thr Lys Gly Pro Ser Val Phe Pro
                130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
```

```
                165                 170                 175
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Cys Glu Leu Thr Lys Asn Gln Val Ser Leu Ser Cys
    370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Gly
    450                 455                 460

Gly Gly Ser Gly Gly Gly Ser Gln Ala Val Val Thr Gln Glu Ser
465                 470                 475                 480

Ala Leu Thr Thr Ser Pro Gly Glu Thr Val Thr Leu Thr Cys Arg Ser
                485                 490                 495

Ser Thr Gly Ala Val Thr Thr Ser Asn Tyr Ala Asn Trp Val Gln Glu
            500                 505                 510

Lys Pro Asp His Leu Phe Thr Gly Leu Ile Gly Gly Thr Asn Lys Arg
        515                 520                 525

Ala Pro Gly Val Pro Ala Arg Phe Ser Gly Ser Leu Ile Gly Asp Lys
    530                 535                 540

Ala Ala Leu Thr Ile Thr Gly Ala Gln Thr Glu Asp Glu Ala Ile Tyr
545                 550                 555                 560

Phe Cys Ala Leu Trp Tyr Ser Asn Leu Trp Val Phe Gly Gly Gly Thr
                565                 570                 575

Lys Leu Thr Val Leu Gly Gly Gly Gly Ser Gly Gly Gly Gly Ser Gly
            580                 585                 590
```

-continued

```
Gly Gly Gly Ser Glu Val Lys Leu Leu Glu Ser Gly Gly Gly Leu Val
            595                 600                 605
Gln Pro Lys Gly Ser Leu Lys Leu Ser Cys Ala Ala Ser Gly Phe Thr
        610                 615                 620
Phe Asn Thr Tyr Ala Met Asn Trp Val Arg Gln Ala Pro Gly Lys Gly
625                 630                 635                 640
Leu Glu Trp Val Ala Arg Ile Arg Ser Lys Tyr Asn Asn Tyr Ala Thr
                645                 650                 655
Tyr Tyr Ala Asp Ser Val Lys Asp Arg Phe Thr Ile Ser Arg Asp Asp
            660                 665                 670
Ser Gln Ser Ile Leu Tyr Leu Gln Met Asn Asn Leu Lys Thr Glu Asp
        675                 680                 685
Thr Ala Met Tyr Tyr Cys Val Arg His Gly Asn Phe Gly Asn Ser Tyr
690                 695                 700
Val Ser Trp Phe Ala Tyr Trp Gly Gln Gly Thr Leu Val Thr Val Ser
705                 710                 715                 720
Ala Asp Tyr Lys Asp Asp Asp Lys
            725

<210> SEQ ID NO 48
<211> LENGTH: 470
<212> TYPE: PRT
<213> ORGANISM: Artificial
<220> FEATURE:
<223> OTHER INFORMATION: an artificially synthesized sequence

<400> SEQUENCE: 48

Met Gly Trp Ser Cys Ile Ile Leu Phe Leu Val Ala Thr Ala Thr Gly
1               5                   10                  15
Val His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
            35                  40                  45
Thr Asp Tyr Glu Met His Trp Ile Arg Gln Pro Pro Gly Gln Gly Leu
        50                  55                  60
Glu Trp Ile Gly Ala Ile Asp Pro Lys Thr Gly Asp Thr Ala Tyr Ser
65                  70                  75                  80
Gln Lys Phe Lys Gly Arg Val Thr Leu Thr Ala Asp Lys Ser Thr Ser
                85                  90                  95
Thr Ala Tyr Met Glu Leu Ser Ser Leu Thr Ser Glu Asp Thr Ala Val
            100                 105                 110
Tyr Tyr Cys Thr Arg Phe Tyr Ser Tyr Thr Tyr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
```

```
Asn Thr Lys Val Asp Lys Val Glu Pro Lys Ser Cys Asp Lys Thr
225                 230                 235                 240

His Thr Cys Pro Pro Cys Pro Ala Pro Glu Leu Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Trp Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro His His
            450                 455                 460

His His His His His His
465                 470

<210> SEQ ID NO 49
<211> LENGTH: 600
<212> TYPE: PRT
<213> ORGANISM: Artificial
<220> FEATURE:
<223> OTHER INFORMATION: an artificially synthesized sequence

<400> SEQUENCE: 49

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110
```

```
Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Cys Glu Leu Thr Lys Asn Gln Val Ser Leu Ser Cys
    370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Gly
    450                 455                 460

Gly Gly Ser Glu Val Lys Leu Leu Glu Ser Gly Gly Gly Leu Val Gln
465                 470                 475                 480

Pro Lys Gly Ser Leu Lys Leu Ser Cys Ala Ala Ser Gly Phe Thr Phe
                485                 490                 495

Asn Thr Tyr Ala Met Asn Trp Val Arg Gln Ala Pro Gly Lys Gly Leu
            500                 505                 510

Glu Trp Val Ala Arg Ile Arg Ser Lys Tyr Asn Asn Tyr Ala Thr Tyr
        515                 520                 525
```

Tyr Ala Asp Ser Val Lys Asp Arg Phe Thr Ile Ser Arg Asp Asp Ser
                530                 535                 540

Gln Ser Ile Leu Tyr Leu Gln Met Asn Asn Leu Lys Thr Glu Asp Thr
545                 550                 555                 560

Ala Met Tyr Tyr Cys Val Arg His Gly Asn Phe Gly Asn Ser Tyr Val
                565                 570                 575

Ser Trp Phe Ala Tyr Trp Gly Gln Gly Thr Leu Val Thr Val Ser Ala
                580                 585                 590

Asp Tyr Lys Asp Asp Asp Lys
                595                 600

<210> SEQ ID NO 50
<211> LENGTH: 584
<212> TYPE: PRT
<213> ORGANISM: Artificial
<220> FEATURE:
<223> OTHER INFORMATION: an artificially synthesized sequence

<400> SEQUENCE: 50

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Glu Met His Trp Ile Arg Gln Pro Pro Gly Gln Gly Leu
        50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
                100                 105                 110

Tyr Tyr Cys Thr Arg Phe Tyr Ser Tyr Thr Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
            275                 280                 285

-continued

Glu Val Lys Phe Asn Trp Tyr Val Asp Gly Val Glu Val His Asn Ala
290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
        340                 345                 350

Ile Ser Lys Ala Lys Gly Gln Pro Arg Glu Pro Gln Val Cys Thr Leu
    355                 360                 365

Pro Pro Ser Arg Asp Glu Leu Thr Lys Asn Gln Val Ser Leu Trp Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
        420                 425                 430

Arg Trp Gln Gln Gly Asn Val Phe Ser Cys Ser Val Met His Glu Ala
    435                 440                 445

Leu His Asn His Tyr Thr Gln Lys Ser Leu Ser Leu Ser Pro Gly Gly
450                 455                 460

Gly Gly Ser Gln Ala Val Val Thr Gln Glu Ser Ala Leu Thr Thr Ser
465                 470                 475                 480

Pro Gly Glu Thr Val Thr Leu Thr Cys Arg Ser Ser Thr Gly Ala Val
            485                 490                 495

Thr Thr Ser Asn Tyr Ala Asn Trp Val Gln Glu Lys Pro Asp His Leu
        500                 505                 510

Phe Thr Gly Leu Ile Gly Gly Thr Asn Lys Arg Ala Pro Gly Val Pro
    515                 520                 525

Ala Arg Phe Ser Gly Ser Leu Ile Gly Asp Lys Ala Ala Leu Thr Ile
530                 535                 540

Thr Gly Ala Gln Thr Glu Asp Glu Ala Ile Tyr Phe Cys Ala Leu Trp
545                 550                 555                 560

Tyr Ser Asn Leu Trp Val Phe Gly Gly Gly Thr Lys Leu Thr Val Leu
            565                 570                 575

His His His His His His His
            580

<210> SEQ ID NO 51
<211> LENGTH: 605
<212> TYPE: PRT
<213> ORGANISM: Artificial
<220> FEATURE:
<223> OTHER INFORMATION: an artificially synthesized sequence

<400> SEQUENCE: 51

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

```
Glu Trp Ile Gly Ala Ile Asp Pro Lys Thr Gly Asp Thr Ala Tyr Ser
 65                  70                  75                  80
Gln Lys Phe Lys Gly Arg Val Thr Leu Thr Ala Asp Lys Ser Thr Ser
                 85                  90                  95
Thr Ala Tyr Met Glu Leu Ser Ser Leu Thr Ser Glu Asp Thr Ala Val
            100                 105                 110
Tyr Tyr Cys Thr Arg Phe Tyr Ser Tyr Thr Tyr Trp Gly Gln Gly Thr
        115                 120                 125
Leu Val Thr Val Ser Ser Ala Ser Thr Lys Gly Pro Ser Val Phe Pro
130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Ala Ala Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
        275                 280                 285
Glu Val Lys Phe Asn Trp Tyr Val Asp Gly Val Glu Val His Asn Ala
290                 295                 300
Lys Thr Lys Pro Arg Glu Glu Gln Tyr Ala Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Arg Cys Glu Leu Thr Lys Asn Gln Val Ser Leu Ser Cys
370                 375                 380
Ala Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Val Ser Lys Leu Thr Val Asp Lys Ser
            420                 425                 430
Arg Trp Gln Gln Gly Asn Val Phe Ser Cys Ser Val Met His Glu Ala
        435                 440                 445
Leu His Asn His Tyr Thr Gln Lys Ser Leu Ser Leu Ser Pro Gly Gly
450                 455                 460
Gly Gly Ser Gly Gly Gly Gly Ser Glu Val Lys Leu Leu Glu Ser Gly
465                 470                 475                 480
Gly Gly Leu Val Gln Pro Lys Gly Ser Leu Lys Leu Ser Cys Ala Ala
```

485                 490                 495
Ser Gly Phe Thr Phe Asn Thr Tyr Ala Met Asn Trp Val Arg Gln Ala
                500                 505                 510

Pro Gly Lys Gly Leu Glu Trp Val Ala Arg Ile Arg Ser Lys Tyr Asn
            515                 520                 525

Asn Tyr Ala Thr Tyr Tyr Ala Asp Ser Val Lys Asp Arg Phe Thr Ile
        530                 535                 540

Ser Arg Asp Asp Ser Gln Ser Ile Leu Tyr Leu Gln Met Asn Asn Leu
545                 550                 555                 560

Lys Thr Glu Asp Thr Ala Met Tyr Tyr Cys Val Arg His Gly Asn Phe
                565                 570                 575

Gly Asn Ser Tyr Val Ser Trp Phe Ala Tyr Trp Gly Gln Gly Thr Leu
            580                 585                 590

Val Thr Val Ser Ala Asp Tyr Lys Asp Asp Asp Lys
        595                 600                 605

<210> SEQ ID NO 52
<211> LENGTH: 589
<212> TYPE: PRT
<213> ORGANISM: Artificial
<220> FEATURE:
<223> OTHER INFORMATION: an artificially synthesized sequence

<400> SEQUENCE: 52

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser

```
            245                 250                 255
Val Phe Leu Phe Pro Lys Pro Lys Asp Thr Leu Met Ile Ser Arg
            260                 265                 270

Thr Pro Glu Val Thr Cys Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Trp Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Gly
        450                 455                 460

Gly Gly Ser Gly Gly Gly Gly Ser Gln Ala Val Val Thr Gln Glu Ser
465                 470                 475                 480

Ala Leu Thr Thr Ser Pro Gly Glu Thr Val Thr Leu Thr Cys Arg Ser
                485                 490                 495

Ser Thr Gly Ala Val Thr Thr Ser Asn Tyr Ala Asn Trp Val Gln Glu
            500                 505                 510

Lys Pro Asp His Leu Phe Thr Gly Leu Ile Gly Gly Thr Asn Lys Arg
            515                 520                 525

Ala Pro Gly Val Pro Ala Arg Phe Ser Gly Ser Leu Ile Gly Asp Lys
            530                 535                 540

Ala Ala Leu Thr Ile Thr Gly Ala Gln Thr Glu Asp Glu Ala Ile Tyr
545                 550                 555                 560

Phe Cys Ala Leu Trp Tyr Ser Asn Leu Trp Val Phe Gly Gly Gly Thr
                565                 570                 575

Lys Leu Thr Val Leu His His His His His His
            580                 585
```

<210> SEQ ID NO 53
<211> LENGTH: 610
<212> TYPE: PRT
<213> ORGANISM: Artificial
<220> FEATURE:
<223> OTHER INFORMATION: an artificially synthesized sequence

<400> SEQUENCE: 53

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
```

```
                 20                  25                  30
Pro Gly Ala Ser Val Lys Val Ser Cys Lys Ala Ser Gly Tyr Thr Phe
             35                  40                  45
Thr Asp Tyr Glu Met His Trp Ile Arg Gln Pro Gly Gln Gly Leu
         50                  55                  60
Glu Trp Ile Gly Ala Ile Asp Pro Lys Thr Gly Asp Thr Ala Tyr Ser
 65                  70                  75                  80
Gln Lys Phe Lys Gly Arg Val Thr Leu Thr Ala Asp Lys Ser Thr Ser
                 85                  90                  95
Thr Ala Tyr Met Glu Leu Ser Ser Leu Thr Ser Glu Asp Thr Ala Val
                100                 105                 110
Tyr Tyr Cys Thr Arg Phe Tyr Ser Tyr Thr Tyr Trp Gly Gln Gly Thr
            115                 120                 125
Leu Val Thr Val Ser Ser Ala Ser Thr Lys Gly Pro Ser Val Phe Pro
            130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
            195                 200                 205
Ser Leu Gly Thr Gln Thr Tyr Ile Cys Asn Val Asn His Lys Pro Ser
            210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Ala Ala Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
            275                 280                 285
Glu Val Lys Phe Asn Trp Tyr Val Asp Gly Val Glu Val His Asn Ala
            290                 295                 300
Lys Thr Lys Pro Arg Glu Glu Gln Tyr Ala Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
            355                 360                 365
Pro Pro Ser Arg Cys Glu Leu Thr Lys Asn Gln Val Ser Leu Ser Cys
            370                 375                 380
Ala Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Val Ser Lys Leu Thr Val Asp Lys Ser
            420                 425                 430
Arg Trp Gln Gln Gly Asn Val Phe Ser Cys Ser Val Met His Glu Ala
            435                 440                 445
```

-continued

```
Leu His Asn His Tyr Thr Gln Lys Ser Leu Ser Leu Ser Pro Gly Gly
    450                 455                 460

Gly Gly Ser Gly Gly Gly Ser Gly Gly Gly Ser Glu Val Lys
465                 470                 475                 480

Leu Leu Glu Ser Gly Gly Leu Val Gln Pro Lys Gly Ser Leu Lys
                485                 490                 495

Leu Ser Cys Ala Ala Ser Gly Phe Thr Phe Asn Thr Tyr Ala Met Asn
            500                 505                 510

Trp Val Arg Gln Ala Pro Gly Lys Gly Leu Glu Trp Val Ala Arg Ile
        515                 520                 525

Arg Ser Lys Tyr Asn Asn Tyr Ala Thr Tyr Tyr Ala Asp Ser Val Lys
    530                 535                 540

Asp Arg Phe Thr Ile Ser Arg Asp Asp Ser Gln Ser Ile Leu Tyr Leu
545                 550                 555                 560

Gln Met Asn Asn Leu Lys Thr Glu Asp Thr Ala Met Tyr Tyr Cys Val
                565                 570                 575

Arg His Gly Asn Phe Gly Asn Ser Tyr Val Ser Trp Phe Ala Tyr Trp
            580                 585                 590

Gly Gln Gly Thr Leu Val Thr Val Ser Ala Asp Tyr Lys Asp Asp Asp
        595                 600                 605

Asp Lys
    610

<210> SEQ ID NO 54
<211> LENGTH: 594
<212> TYPE: PRT
<213> ORGANISM: Artificial
<220> FEATURE:
<223> OTHER INFORMATION: an artificially synthesized sequence

<400> SEQUENCE: 54

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190
```

```
Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Trp Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Gly
            450                 455                 460

Gly Gly Ser Gly Gly Gly Gly Ser Gly Gly Gly Gly Ser Gln Ala Val
465                 470                 475                 480

Val Thr Gln Glu Ser Ala Leu Thr Thr Ser Pro Gly Glu Thr Val Thr
                485                 490                 495

Leu Thr Cys Arg Ser Ser Thr Gly Ala Val Thr Thr Ser Asn Tyr Ala
                500                 505                 510

Asn Trp Val Gln Glu Lys Pro Asp His Leu Phe Thr Gly Leu Ile Gly
                515                 520                 525

Gly Thr Asn Lys Arg Ala Pro Gly Val Pro Ala Arg Phe Ser Gly Ser
            530                 535                 540

Leu Ile Gly Asp Lys Ala Ala Leu Thr Ile Thr Gly Ala Gln Thr Glu
545                 550                 555                 560

Asp Glu Ala Ile Tyr Phe Cys Ala Leu Trp Tyr Ser Asn Leu Trp Val
                565                 570                 575

Phe Gly Gly Gly Thr Lys Leu Thr Val Leu His His His His His His
            580                 585                 590

His His
```

```
<210> SEQ ID NO 55
<211> LENGTH: 615
<212> TYPE: PRT
<213> ORGANISM: Artificial
<220> FEATURE:
<223> OTHER INFORMATION: an artificially synthesized sequence

<400> SEQUENCE: 55
```

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Cys Glu Leu Thr Lys Asn Gln Val Ser Leu Ser Cys

```
                    370                 375                 380
Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Gly
    450                 455                 460

Gly Gly Ser Gly Gly Gly Ser Gly Gly Gly Ser Gly Gly
465                 470                 475                 480

Gly Ser Glu Val Lys Leu Leu Glu Ser Gly Gly Leu Val Gln Pro
                485                 490                 495

Lys Gly Ser Leu Lys Leu Ser Cys Ala Ala Ser Gly Phe Thr Phe Asn
                500                 505                 510

Thr Tyr Ala Met Asn Trp Val Arg Gln Ala Pro Gly Lys Gly Leu Glu
            515                 520                 525

Trp Val Ala Arg Ile Arg Ser Lys Tyr Asn Asn Tyr Ala Thr Tyr Tyr
    530                 535                 540

Ala Asp Ser Val Lys Asp Arg Phe Thr Ile Ser Arg Asp Asp Ser Gln
545                 550                 555                 560

Ser Ile Leu Tyr Leu Gln Met Asn Asn Leu Lys Thr Glu Asp Thr Ala
                565                 570                 575

Met Tyr Tyr Cys Val Arg His Gly Asn Phe Gly Asn Ser Tyr Val Ser
            580                 585                 590

Trp Phe Ala Tyr Trp Gly Gln Gly Thr Leu Val Thr Val Ser Ala Asp
        595                 600                 605

Tyr Lys Asp Asp Asp Asp Lys
    610                 615

<210> SEQ ID NO 56
<211> LENGTH: 599
<212> TYPE: PRT
<213> ORGANISM: Artificial
<220> FEATURE:
<223> OTHER INFORMATION: an artificially synthesized sequence

<400> SEQUENCE: 56

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
```

-continued

```
            115                 120                 125
Leu Val Thr Val Ser Ser Ala Ser Thr Lys Gly Pro Ser Val Phe Pro
        130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
                180                 185                 190
Ser Ser Gly Leu Tyr Ser Leu Ser Ser Val Val Thr Val Pro Ser Ser
                195                 200                 205
Ser Leu Gly Thr Gln Thr Tyr Ile Cys Asn Val Asn His Lys Pro Ser
        210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Ala Ala Gly Gly Pro Ser
                245                 250                 255
Val Phe Leu Phe Pro Pro Lys Pro Lys Asp Thr Leu Met Ile Ser Arg
                260                 265                 270
Thr Pro Glu Val Thr Cys Val Val Val Asp Val Ser His Glu Asp Pro
                275                 280                 285
Glu Val Lys Phe Asn Trp Tyr Val Asp Gly Val Glu Val His Asn Ala
                290                 295                 300
Lys Thr Lys Pro Arg Glu Glu Gln Tyr Ala Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
                340                 345                 350
Ile Ser Lys Ala Lys Gly Gln Pro Arg Glu Pro Gln Val Cys Thr Leu
                355                 360                 365
Pro Pro Ser Arg Asp Glu Leu Thr Lys Asn Gln Val Ser Leu Trp Cys
        370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
                420                 425                 430
Arg Trp Gln Gln Gly Asn Val Phe Ser Cys Ser Val Met His Glu Ala
                435                 440                 445
Leu His Asn His Tyr Thr Gln Lys Ser Leu Ser Leu Ser Pro Gly Gly
        450                 455                 460
Gly Gly Ser Gly Gly Gly Gly Ser Gly Gly Gly Gly Ser Gly Gly Gly
465                 470                 475                 480
Gly Ser Gln Ala Val Val Thr Gln Glu Ser Ala Leu Thr Thr Ser Pro
                485                 490                 495
Gly Glu Thr Val Thr Leu Thr Cys Arg Ser Ser Thr Gly Ala Val Thr
                500                 505                 510
Thr Ser Asn Tyr Ala Asn Trp Val Gln Glu Lys Pro Asp His Leu Phe
                515                 520                 525
Thr Gly Leu Ile Gly Gly Thr Asn Lys Arg Ala Pro Gly Val Pro Ala
        530                 535                 540
```

```
Arg Phe Ser Gly Ser Leu Ile Gly Asp Lys Ala Ala Leu Thr Ile Thr
545                 550                 555                 560

Gly Ala Gln Thr Glu Asp Glu Ala Ile Tyr Phe Cys Ala Leu Trp Tyr
                565                 570                 575

Ser Asn Leu Trp Val Phe Gly Gly Gly Thr Lys Leu Thr Val Leu His
            580                 585                 590

His His His His His His His
            595

<210> SEQ ID NO 57
<211> LENGTH: 610
<212> TYPE: PRT
<213> ORGANISM: Artificial
<220> FEATURE:
<223> OTHER INFORMATION: an artificially synthesized sequence

<400> SEQUENCE: 57

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300
```

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
        340                 345                 350

Ile Ser Lys Ala Lys Gly Gln Pro Arg Glu Pro Gln Val Tyr Thr Leu
    355                 360                 365

Pro Pro Ser Arg Cys Glu Leu Thr Lys Asn Gln Val Ser Leu Ser Cys
370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Val Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Gly
    450                 455                 460

Gly Gly Ser Gly Gly Gly Ser Gly Gly Gly Ser Glu Val Lys
465                 470                 475                 480

Leu Leu Glu Ser Gly Gly Gly Leu Val Gln Pro Lys Gly Ser Leu Lys
                485                 490                 495

Leu Ser Cys Ala Ala Ser Gly Phe Thr Phe Asn Thr Tyr Ala Met Asn
            500                 505                 510

Trp Val Arg Gln Ala Pro Gly Lys Cys Leu Glu Trp Val Ala Arg Ile
        515                 520                 525

Arg Ser Lys Tyr Asn Asn Tyr Ala Thr Tyr Tyr Ala Asp Ser Val Lys
    530                 535                 540

Asp Arg Phe Thr Ile Ser Arg Asp Asp Ser Gln Ser Ile Leu Tyr Leu
545                 550                 555                 560

Gln Met Asn Asn Leu Lys Thr Glu Asp Thr Ala Met Tyr Tyr Cys Val
                565                 570                 575

Arg His Gly Asn Phe Gly Asn Ser Tyr Val Ser Trp Phe Ala Tyr Trp
            580                 585                 590

Gly Gln Gly Thr Leu Val Thr Val Ser Ala Tyr Lys Asp Asp Asp Asp
        595                 600                 605

Asp Lys
    610

<210> SEQ ID NO 58
<211> LENGTH: 594
<212> TYPE: PRT
<213> ORGANISM: Artificial
<220> FEATURE:
<223> OTHER INFORMATION: an artificially synthesized sequence

<400> SEQUENCE: 58

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

```
Thr Asp Tyr Glu Met His Trp Ile Arg Gln Pro Pro Gly Gln Gly Leu
 50                  55                  60

Glu Trp Ile Gly Ala Ile Asp Pro Lys Thr Gly Asp Thr Ala Tyr Ser
 65                  70                  75                  80

Gln Lys Phe Lys Gly Arg Val Thr Leu Thr Ala Asp Lys Ser Thr Ser
                 85                  90                  95

Thr Ala Tyr Met Glu Leu Ser Ser Leu Thr Ser Glu Asp Thr Ala Val
                100                 105                 110

Tyr Tyr Cys Thr Arg Phe Tyr Ser Tyr Thr Tyr Trp Gly Gln Gly Thr
            115                 120                 125

Leu Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Trp Cys
            370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Gly
    450                 455                 460
```

Gly Gly Ser Gly Gly Gly Ser Gly Gly Gly Ser Gln Ala Val
465                 470                 475                 480

Val Thr Gln Glu Ser Ala Leu Thr Thr Ser Pro Gly Glu Thr Val Thr
            485                 490                 495

Leu Thr Cys Arg Ser Ser Thr Gly Ala Val Thr Thr Ser Asn Tyr Ala
            500                 505                 510

Asn Trp Val Gln Glu Lys Pro Asp His Leu Phe Thr Gly Leu Ile Gly
        515                 520                 525

Gly Thr Asn Lys Arg Ala Pro Gly Val Pro Ala Arg Phe Ser Gly Ser
        530                 535                 540

Leu Ile Gly Asp Lys Ala Ala Leu Thr Ile Thr Gly Ala Gln Thr Glu
545                 550                 555                 560

Asp Glu Ala Ile Tyr Phe Cys Ala Leu Trp Tyr Ser Asn Leu Trp Val
                565                 570                 575

Phe Gly Cys Gly Thr Lys Leu Thr Val Leu His His His His His His
            580                 585                 590

His His

<210> SEQ ID NO 59
<211> LENGTH: 704
<212> TYPE: PRT
<213> ORGANISM: Artificial
<220> FEATURE:
<223> OTHER INFORMATION: an artificially synthesized sequence

<400> SEQUENCE: 59

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Thr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr

```
                225                 230                 235                 240
His Thr Cys Pro Pro Cys Pro Ala Pro Glu Ala Ala Gly Gly Pro Ser
                    245                 250                 255

Val Phe Leu Phe Pro Lys Pro Lys Asp Thr Leu Met Ile Ser Arg
                260                 265                 270

Thr Pro Glu Val Thr Cys Val Val Val Asp Val Ser His Glu Asp Pro
                275                 280                 285

Glu Val Lys Phe Asn Trp Tyr Val Asp Gly Val Glu Val His Asn Ala
                290                 295                 300

Lys Thr Lys Pro Arg Glu Glu Gln Tyr Ala Ser Thr Tyr Arg Val Val
305                 310                 315                 320

Ser Val Leu Thr Val Leu His Gln Asp Trp Leu Asn Gly Lys Glu Tyr
                    325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
                355                 360                 365

Pro Pro Ser Arg Cys Glu Leu Thr Lys Asn Gln Val Ser Leu Ser Cys
            370                 375                 380

Ala Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                    405                 410                 415

Ser Asp Gly Ser Phe Phe Leu Val Ser Lys Leu Thr Val Asp Lys Ser
                420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Gly
        450                 455                 460

Gly Gly Ser Gly Gly Gly Ser Gly Gly Gly Ser Glu Val Lys
465                 470                 475                 480

Leu Leu Glu Ser Gly Gly Gly Leu Val Gln Pro Lys Gly Ser Leu Lys
                485                 490                 495

Leu Ser Cys Ala Ala Ser Gly Phe Thr Phe Asn Thr Tyr Ala Met Asn
                500                 505                 510

Trp Val Arg Gln Ala Pro Gly Lys Gly Leu Glu Trp Val Ala Arg Ile
                515                 520                 525

Arg Ser Lys Tyr Asn Asn Tyr Ala Thr Tyr Tyr Ala Asp Ser Val Lys
            530                 535                 540

Asp Arg Phe Thr Ile Ser Arg Asp Asp Ser Gln Ser Ile Leu Tyr Leu
545                 550                 555                 560

Gln Met Asn Asn Leu Lys Thr Glu Asp Thr Ala Met Tyr Tyr Cys Val
                    565                 570                 575

Arg His Gly Asn Phe Gly Asn Ser Tyr Val Ser Trp Phe Ala Tyr Trp
                580                 585                 590

Gly Gln Gly Thr Leu Val Thr Val Ser Ala Ala Ser Thr Lys Gly Pro
            595                 600                 605

Ser Val Phe Pro Leu Ala Pro Ser Ser Lys Ser Thr Ser Gly Gly Thr
        610                 615                 620

Ala Ala Leu Gly Cys Leu Val Lys Asp Tyr Phe Pro Glu Pro Val Thr
625                 630                 635                 640

Val Ser Trp Asn Ser Gly Ala Leu Thr Ser Gly Val His Thr Phe Pro
                    645                 650                 655
```

```
Ala Val Leu Gln Ser Ser Gly Leu Tyr Ser Leu Ser Ser Val Val Thr
            660                 665                 670

Val Pro Ser Ser Ser Leu Gly Thr Gln Thr Tyr Ile Cys Asn Val Asn
            675                 680                 685

His Lys Pro Ser Asn Thr Lys Val Asp Lys Lys Val Glu Pro Lys Ser
            690                 695                 700

<210> SEQ ID NO 60
<211> LENGTH: 692
<212> TYPE: PRT
<213> ORGANISM: Artificial
<220> FEATURE:
<223> OTHER INFORMATION: an artificially synthesized sequence

<400> SEQUENCE: 60

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Glu Met His Trp Ile Arg Gln Pro Gly Gln Gly Leu
    50                  55                  60

Glu Trp Ile Gly Ala Ile Asp Pro Lys Thr Gly Asp Thr Ala Tyr Ser
65                  70                  75                  80

Gln Lys Phe Lys Gly Arg Val Thr Leu Thr Ala Asp Lys Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Arg Phe Tyr Ser Tyr Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Ala Ser Thr Tyr Arg Val Val
305                 310                 315                 320
```

-continued

```
Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Cys Thr Leu
            355                 360                 365

Pro Pro Ser Arg Asp Glu Leu Thr Lys Asn Gln Val Ser Leu Trp Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Gly
            450                 455                 460

Gly Gly Ser Gly Gly Gly Ser Gly Gly Gly Ser Gln Ala Val
465                 470                 475                 480

Val Thr Gln Glu Ser Ala Leu Thr Thr Ser Pro Gly Glu Thr Val Thr
            485                 490                 495

Leu Thr Cys Arg Ser Ser Thr Gly Ala Val Thr Thr Ser Asn Tyr Ala
            500                 505                 510

Asn Trp Val Gln Glu Lys Pro Asp His Leu Phe Thr Gly Leu Ile Gly
            515                 520                 525

Gly Thr Asn Lys Arg Ala Pro Gly Val Pro Ala Arg Phe Ser Gly Ser
530                 535                 540

Leu Ile Gly Asp Lys Ala Ala Leu Thr Ile Thr Gly Ala Gln Thr Glu
545                 550                 555                 560

Asp Glu Ala Ile Tyr Phe Cys Ala Leu Trp Tyr Ser Asn Leu Trp Val
            565                 570                 575

Phe Gly Gly Gly Thr Lys Leu Thr Val Leu Arg Thr Val Ala Ala Pro
            580                 585                 590

Ser Val Phe Ile Phe Pro Pro Ser Asp Glu Gln Leu Lys Ser Gly Thr
            595                 600                 605

Ala Ser Val Val Cys Leu Leu Asn Asn Phe Tyr Pro Arg Glu Ala Lys
            610                 615                 620

Val Gln Trp Lys Val Asp Asn Ala Leu Gln Ser Gly Asn Ser Gln Glu
625                 630                 635                 640

Ser Val Thr Glu Gln Asp Ser Lys Asp Ser Thr Tyr Ser Leu Ser Ser
            645                 650                 655

Thr Leu Thr Leu Ser Lys Ala Asp Tyr Glu Lys His Lys Val Tyr Ala
            660                 665                 670

Cys Glu Val Thr His Gln Gly Leu Ser Ser Pro Val Thr Lys Ser Phe
            675                 680                 685

Asn Arg Gly Glu
    690
```

<210> SEQ ID NO 61
<211> LENGTH: 115
<212> TYPE: PRT
<213> ORGANISM: Artificial
<220> FEATURE:

<223> OTHER INFORMATION: an artificially synthesized sequence

<400> SEQUENCE: 61

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Glu Met His Trp Ile Arg Gln Pro Pro Gly Gln Gly Leu Glu Trp Ile
        35                  40                  45
Gly Ala Ile Asp Pro Lys Thr Gly Asp Thr Ala Tyr Ser Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Phe Tyr Ser Tyr Thr Tyr Trp Gly Gln Gly Thr Leu Val Thr
            100                 105                 110
Val Ser Ser
        115

<210> SEQ ID NO 62
<211> LENGTH: 219
<212> TYPE: PRT
<213> ORGANISM: Artificial
<220> FEATURE:
<223> OTHER INFORMATION: an artificially synthesized sequence

<400> SEQUENCE: 62

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Arg Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Pro Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 63
<211> LENGTH: 328
<212> TYPE: PRT
<213> ORGANISM: Artificial
<220> FEATURE:
<223> OTHER INFORMATION: an artificially synthesized sequence

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 64
<211> LENGTH: 587
<212> TYPE: PRT
<213> ORGANISM: Artificial

```
<220> FEATURE:
<223> OTHER INFORMATION: an artificially synthesized sequence

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Gly Gly Gly Ser Gly Gly Gly
                325                 330                 335

Gly Ser Gln Ala Val Val Thr Gln Glu Ser Ala Leu Thr Thr Ser Pro
            340                 345                 350

Gly Glu Thr Val Thr Leu Thr Cys Arg Ser Ser Thr Gly Ala Val Thr
        355                 360                 365

Thr Ser Asn Tyr Ala Asn Trp Val Gln Glu Lys Pro Asp His Leu Phe
    370                 375                 380

Thr Gly Leu Ile Gly Gly Thr Asn Lys Arg Ala Pro Gly Val Pro Ala
385                 390                 395                 400
```

```
Arg Phe Ser Gly Ser Leu Ile Gly Asp Lys Ala Ala Leu Thr Ile Thr
                405                 410                 415

Gly Ala Gln Thr Glu Asp Glu Ala Ile Tyr Phe Cys Ala Leu Trp Tyr
            420                 425                 430

Ser Asn Leu Trp Val Phe Gly Gly Gly Thr Lys Leu Thr Val Leu Gly
        435                 440                 445

Gly Gly Gly Ser Gly Gly Gly Gly Ser Gly Gly Gly Gly Ser Glu Val
450                 455                 460

Lys Leu Leu Glu Ser Gly Gly Gly Leu Val Gln Pro Lys Gly Ser Leu
465                 470                 475                 480

Lys Leu Ser Cys Ala Ala Ser Gly Phe Thr Phe Asn Thr Tyr Ala Met
                485                 490                 495

Asn Trp Val Arg Gln Ala Pro Gly Lys Gly Leu Glu Trp Val Ala Arg
            500                 505                 510

Ile Arg Ser Lys Tyr Asn Asn Tyr Ala Thr Tyr Tyr Ala Asp Ser Val
        515                 520                 525

Lys Asp Arg Phe Thr Ile Ser Arg Asp Asp Ser Gln Ser Ile Leu Tyr
530                 535                 540

Leu Gln Met Asn Asn Leu Lys Thr Glu Asp Thr Ala Met Tyr Tyr Cys
545                 550                 555                 560

Val Arg His Gly Asn Phe Gly Asn Ser Tyr Val Ser Trp Phe Ala Tyr
                565                 570                 575

Trp Gly Gln Gly Thr Leu Val Thr Val Ser Ala
            580                 585

<210> SEQ ID NO 65
<211> LENGTH: 328
<212> TYPE: PRT
<213> ORGANISM: Artificial
<220> FEATURE:
<223> OTHER INFORMATION: an artificially synthesized sequence

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Arg Tyr Thr
305                 310                 315                 320

Gln Glu Ser Leu Ser Leu Ser Pro
                325

<210> SEQ ID NO 66
<211> LENGTH: 587
<212> TYPE: PRT
<213> ORGANISM: Artificial
<220> FEATURE:
<223> OTHER INFORMATION: an artificially synthesized sequence

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Gly Gly Gly Ser Gly Gly Gly
                325                 330                 335

Gly Ser Gln Ala Val Val Thr Gln Glu Ser Ala Leu Thr Thr Ser Pro
                340                 345                 350

Gly Glu Thr Val Thr Leu Thr Cys Arg Ser Ser Thr Gly Ala Val Thr
            355                 360                 365

Thr Ser Asn Tyr Ala Asn Trp Val Gln Glu Lys Pro Asp His Leu Phe
370                 375                 380

Thr Gly Leu Ile Gly Gly Thr Asn Lys Arg Ala Pro Gly Val Pro Ala
385                 390                 395                 400

Arg Phe Ser Gly Ser Leu Ile Gly Asp Lys Ala Ala Leu Thr Ile Thr
                405                 410                 415

Gly Ala Gln Thr Glu Asp Glu Ala Ile Tyr Phe Cys Ala Leu Trp Tyr
                420                 425                 430

Ser Asn Leu Trp Val Phe Gly Gly Thr Lys Leu Thr Val Leu Gly
            435                 440                 445

Gly Gly Gly Ser Gly Gly Gly Ser Gly Gly Gly Ser Glu Val
450                 455                 460

Lys Leu Leu Glu Ser Gly Gly Gly Leu Val Gln Pro Lys Gly Ser Leu
465                 470                 475                 480

Lys Leu Ser Cys Ala Ala Ser Gly Phe Thr Phe Asn Thr Tyr Ala Met
                485                 490                 495

Asn Trp Val Arg Gln Ala Pro Gly Lys Gly Leu Glu Trp Val Ala Arg
                500                 505                 510

Ile Arg Ser Lys Tyr Asn Asn Tyr Ala Thr Tyr Tyr Ala Asp Ser Val
            515                 520                 525

Lys Asp Arg Phe Thr Ile Ser Arg Asp Asp Ser Gln Ser Ile Leu Tyr
530                 535                 540

Leu Gln Met Asn Asn Leu Lys Thr Glu Asp Thr Ala Met Tyr Tyr Cys
545                 550                 555                 560

Val Arg His Gly Asn Phe Gly Asn Ser Tyr Val Ser Trp Phe Ala Tyr
                565                 570                 575

Trp Gly Gln Gly Thr Leu Val Thr Val Ser Ala
            580                 585

<210> SEQ ID NO 67
<211> LENGTH: 141
<212> TYPE: PRT
<213> ORGANISM: Homo sapiens

```
<400> SEQUENCE: 67

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
130                 135                 140

<210> SEQ ID NO 68
<211> LENGTH: 179
<212> TYPE: PRT
<213> ORGANISM: Homo sapiens

<400> SEQUENCE: 68

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 69
<211> LENGTH: 173
<212> TYPE: PRT
<213> ORGANISM: Homo sapiens

<400> SEQUENCE: 69
```

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
                20                  25                  30

Leu Leu Glu Lys Phe Phe Pro Asp Val Ile Lys Ile His Trp Gln Glu
            35                  40                  45

Lys Lys Ser Asn Thr Ile Leu Gly Ser Gln Glu Gly Asn Thr Met Lys
        50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
            115                 120                 125

Leu Leu Leu Gln Leu Thr Asn Thr Ser Ala Tyr Tyr Met Tyr Leu Leu
130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 70
<211> LENGTH: 204
<212> TYPE: PRT
<213> ORGANISM: Homo sapiens

<400> SEQUENCE: 70

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
                20                  25                  30

Leu Glu Lys Phe Phe Pro Asp Ile Ile Lys Ile His Trp Gln Glu Lys
            35                  40                  45

Lys Ser Asn Thr Ile Leu Gly Ser Gln Glu Gly Asn Thr Met Lys Thr
        50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
            115                 120                 125

Thr Val Asp Pro Lys Tyr Asn Tyr Ser Lys Asp Ala Asn Asp Val Ile
            130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                165                 170                 175

Leu Leu Lys Ser Val Val Tyr Phe Ala Ile Ile Thr Cys Cys Leu Leu
            180                 185                 190

Gly Arg Thr Ala Phe Cys Cys Asn Gly Glu Lys Ser
```

<210> SEQ ID NO 71
<211> LENGTH: 177
<212> TYPE: PRT
<213> ORGANISM: Homo sapiens

<400> SEQUENCE: 71

Pro Ser Tyr Thr Gly Gly Tyr Ala Asp Lys Leu Ile Phe Gly Lys Gly
1               5                   10                  15

Thr Arg Val Thr Val Glu Pro Arg Ser Gln Pro His Thr Lys Pro Ser
            20                  25                  30

Val Phe Val Met Lys Asn Gly Thr Asn Val Ala Cys Leu Val Lys Glu
        35                  40                  45

Phe Tyr Pro Lys Asp Ile Arg Ile Asn Leu Val Ser Ser Lys Lys Ile
    50                  55                  60

Thr Glu Phe Asp Pro Ala Ile Val Ile Ser Pro Ser Gly Lys Tyr Asn
65                  70                  75                  80

Ala Val Lys Leu Gly Lys Tyr Glu Asp Ser Asn Ser Val Thr Cys Ser
                85                  90                  95

Val Gln His Asp Asn Lys Thr Val His Ser Thr Asp Phe Glu Val Lys
            100                 105                 110

Thr Asp Ser Thr Asp His Val Lys Pro Lys Glu Thr Glu Asn Thr Lys
        115                 120                 125

Gln Pro Ser Lys Ser Cys His Lys Pro Lys Ala Ile Val His Thr Glu
    130                 135                 140

Lys Val Asn Met Met Ser Leu Thr Val Leu Gly Leu Arg Met Leu Phe
145                 150                 155                 160

Ala Lys Thr Val Ala Val Asn Phe Leu Leu Thr Ala Lys Leu Phe Phe
                165                 170                 175

Leu

<210> SEQ ID NO 72
<211> LENGTH: 19
<212> TYPE: PRT
<213> ORGANISM: Artificial
<220> FEATURE:
<223> OTHER INFORMATION: signal sequence

<400> SEQUENCE: 72

Met Gly Trp Ser Cys Ile Ile Leu Phe Leu Val Ala Thr Ala Thr Gly
1               5                   10                  15

Val His Ser

<210> SEQ ID NO 73
<211> LENGTH: 466
<212> TYPE: PRT
<213> ORGANISM: Artificial Sequence
<220> FEATURE:
<223> OTHER INFORMATION: an artificially synthesized sequence

<400> SEQUENCE: 73

Met Gly Trp Ser Cys Ile Ile Leu Phe Leu Val Ala Thr Ala Thr Gly
1               5                   10                  15

Val His Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

```
Thr Thr Ser Asn Tyr Ala Asn Trp Val Gln Glu Lys Pro Asp His Leu
    50                  55                  60

Phe Thr Gly Leu Ile Gly Gly Thr Asn Lys Arg Ala Pro Gly Val Pro
 65              70                  75                      80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Ala Leu Trp
            100                 105                 110

Tyr Ser Asn Leu Trp Val Phe Gly Gly Thr Lys Leu Thr Val Leu
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Ala Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Ala Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Cys Glu Leu Thr Lys Asn Gln Val Ser Leu Ser Cys Ala Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Val Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Asp Tyr Lys Asp Asp Asp
450                 455                 460

Asp Lys
```

<210> SEQ ID NO 74
<211> LENGTH: 251
<212> TYPE: PRT
<213> ORGANISM: Artificial Sequence
<220> FEATURE:
<223> OTHER INFORMATION: an artificially synthesized sequence

<400> SEQUENCE: 74

Met Gly Trp Ser Cys Ile Ile Leu Phe Leu Val Ala Thr Ala Thr Gly
1               5                   10                  15

Val His Ser Glu Val Lys Leu Leu Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Tyr Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Ile Leu Tyr Leu Gln Met Asn Asn Leu Lys Thr Glu Asp Thr
            100                 105                 110

Ala Met Tyr Tyr Cys Val Arg His Gly Asn Phe Gly Asn Ser Tyr Val
        115                 120                 125

Ser Trp Phe Ala Tyr Trp Gly Gln Gly Thr Leu Val Thr Val Ser Ala
    130                 135                 140

Ala Ser Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 75
<211> LENGTH: 484
<212> TYPE: PRT
<213> ORGANISM: Artificial Sequence
<220> FEATURE:
<223> OTHER INFORMATION: an artificially synthesized sequence

<400> SEQUENCE: 75

Met Gly Trp Ser Cys Ile Ile Leu Phe Leu Val Ala Thr Ala Thr Gly
1               5                   10                  15

Val His Ser Glu Val Lys Leu Leu Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

```
Asn Thr Tyr Ala Met Asn Trp Val Arg Gln Ala Pro Gly Lys Gly Leu
 50                  55                  60

Glu Trp Val Ala Arg Ile Arg Ser Lys Tyr Asn Asn Tyr Ala Thr Tyr
 65                  70                  75                  80

Tyr Ala Asp Ser Val Lys Asp Arg Phe Thr Ile Ser Arg Asp Asp Ser
                 85                  90                  95

Gln Ser Ile Leu Tyr Leu Gln Met Asn Asn Leu Lys Thr Glu Asp Thr
            100                 105                 110

Ala Met Tyr Tyr Cys Val Arg His Gly Asn Phe Gly Asn Ser Tyr Val
        115                 120                 125

Ser Trp Phe Ala Tyr Trp Gly Gln Gly Thr Leu Val Thr Val Ser Ala
130                 135                 140

Ala Ser Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys Asp Lys Thr His Thr
                245                 250                 255

Cys Pro Pro Cys Pro Ala Pro Glu Ala Ala Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Ala Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Ser Arg Cys Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Asp Tyr Lys Asp
```

-continued

```
465                 470                 475                 480

Asp Asp Asp Lys

<210> SEQ ID NO 76
<211> LENGTH: 233
<212> TYPE: PRT
<213> ORGANISM: Artificial Sequence
<220> FEATURE:
<223> OTHER INFORMATION: an artificially synthesized sequence

<400> SEQUENCE: 76

Met Gly Trp Ser Cys Ile Ile Leu Phe Leu Val Ala Thr Ala Thr Gly
1               5                   10                  15

Val His Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
            35                  40                  45

Thr Thr Ser Asn Tyr Ala Asn Trp Val Gln Glu Lys Pro Asp His Leu
        50                  55                  60

Phe Thr Gly Leu Ile Gly Gly Thr Asn Lys Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Leu Trp Val Phe Gly Gly Gly Thr Lys Leu Thr Val Leu
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys
225                 230

<210> SEQ ID NO 77
<211> LENGTH: 466
<212> TYPE: PRT
<213> ORGANISM: Artificial Sequence
<220> FEATURE:
<223> OTHER INFORMATION: an artificially synthesized sequence

<400> SEQUENCE: 77

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
                20                  25                  30

Pro Gly Gly Thr Val Thr Leu Thr Cys Gly Ser Ser Thr Gly Ala Val
            35                  40                  45

Thr Ser Gly Asn Tyr Pro Asn Trp Val Gln Gln Lys Pro Gly Gln Ala
```

```
            50                  55                  60
Pro Arg Gly Leu Ile Gly Gly Thr Lys Phe Leu Ala Pro Gly Thr Pro
65                  70                  75                  80

Ala Arg Phe Ser Gly Ser Leu Leu Gly Gly Lys Ala Ala Leu Thr Leu
                85                  90                  95

Ser Gly Val Gln Pro Glu Asp Glu Ala Glu Tyr Tyr Cys Val Leu Trp
                100                 105                 110

Tyr Ser Asn Arg Trp Val Phe Gly Gly Gly Thr Lys Leu Thr Val Leu
                115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Leu Gly Thr
                195                 200                 205

Gln Thr Tyr Ile Cys Asn Val Asn His Lys Pro Ser Asn Thr Lys Val
                210                 215                 220

Asp Lys Lys Val Glu Pro Lys Ser Cys Asp Lys Thr His Thr Cys Pro
225                 230                 235                 240

Pro Cys Pro Ala Pro Glu Ala Ala Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
                275                 280                 285

Asn Trp Tyr Val Asp Gly Val Glu Val His Asn Ala Lys Thr Lys Pro
                290                 295                 300

Arg Glu Glu Gln Tyr Ala Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
                340                 345                 350

Lys Gly Gln Pro Arg Glu Pro Gln Val Tyr Thr Leu Pro Pro Ser Arg
                355                 360                 365

Cys Glu Leu Thr Lys Asn Gln Val Ser Leu Ser Cys Ala Val Lys Gly
                370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Val Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Asp Tyr Lys Asp Asp Asp
                450                 455                 460

Asp Lys
465
```

<210> SEQ ID NO 78
<211> LENGTH: 251
<212> TYPE: PRT
<213> ORGANISM: Artificial Sequence
<220> FEATURE:
<223> OTHER INFORMATION: an artificially synthesized sequence

<400> SEQUENCE: 78

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Asn Lys Tyr Ala Met Asn Trp Val Arg Gln Ala Pro Gly Lys Gly Leu
    50                  55                  60

Glu Trp Val Ala Arg Ile Arg Ser Lys Tyr Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Lys Asn Thr Ala Tyr Leu Gln Met Asn Asn Leu Lys Thr Glu Asp Thr
            100                 105                 110

Ala Val Tyr Tyr Cys Val Arg His Gly Asn Phe Gly Asn Ser Tyr Ile
        115                 120                 125

Ser Tyr Trp Ala Tyr Trp Gly Gln Gly Thr Leu Val Thr Val Ser Ser
    130                 135                 140

Ala Ser Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 79
<211> LENGTH: 475
<212> TYPE: PRT
<213> ORGANISM: Artificial Sequence
<220> FEATURE:
<223> OTHER INFORMATION: an artificially synthesized sequence

<400> SEQUENCE: 79

Met Gly Trp Ser Cys Ile Ile Leu Phe Leu Val Ala Thr Ala Thr Gly
1               5                   10                  15

Val His Ser Glu Val Gln Leu Leu Glu Gln Ser Gly Ala Glu Leu Val
            20                  25                  30

Arg Pro Gly Thr Ser Val Lys Ile Ser Cys Lys Ala Ser Gly Tyr Ala
        35                  40                  45

Phe Thr Asn Tyr Trp Leu Gly Trp Val Lys Gln Arg Pro Gly His Gly

-continued

```
            50                  55                  60
Leu Glu Trp Ile Gly Asp Ile Phe Pro Gly Ser Gly Asn Ile His Tyr
 65                  70                  75                  80
Asn Glu Lys Phe Lys Gly Lys Ala Thr Leu Thr Ala Asp Lys Ser Ser
                 85                  90                  95
Ser Thr Ala Tyr Met Gln Leu Ser Ser Leu Thr Phe Glu Asp Ser Ala
                100                 105                 110
Val Tyr Phe Cys Ala Arg Leu Arg Asn Trp Asp Glu Pro Met Asp Tyr
            115                 120                 125
Trp Gly Gln Gly Thr Thr Val Thr Val Ser Ser Ala Ser Thr Lys Gly
            130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Gln Thr Tyr Ile Cys Asn Val
            210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Ala
                245                 250                 255
Ala Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Asp Val
            275                 280                 285
Ser His Glu Asp Pro Glu Val Lys Phe Asn Trp Tyr Val Asp Gly Val
            290                 295                 300
Glu Val His Asn Ala Lys Thr Lys Pro Arg Glu Glu Gln Tyr Ala Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
                340                 345                 350
Pro Ile Glu Lys Thr Ile Ser Lys Ala Lys Gly Gln Pro Arg Glu Pro
            355                 360                 365
Gln Val Cys Thr Leu Pro Pro Ser Arg Asp Glu Leu Thr Lys Asn Gln
            370                 375                 380
Val Ser Leu Trp Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
            435                 440                 445
Val Met His Glu Ala Leu His Asn His Tyr Thr Gln Lys Ser Leu Ser
            450                 455                 460
Leu Ser Pro His His His His His His
465                 470                 475
```

```
<210> SEQ ID NO 80
<211> LENGTH: 239
<212> TYPE: PRT
<213> ORGANISM: Artificial Sequence
<220> FEATURE:
<223> OTHER INFORMATION: an artificially synthesized sequence

<400> SEQUENCE: 80

Met Gly Trp Ser Cys Ile Ile Leu Phe Leu Val Ala Thr Ala Thr Gly
1               5                   10                  15

Val His Ser Glu Leu Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Gly Asn Gln Lys Asn Tyr Leu Thr Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Tyr Pro Leu Thr Phe Gly Ala Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 81
<211> LENGTH: 453
<212> TYPE: PRT
<213> ORGANISM: Artificial Sequence
<220> FEATURE:
<223> OTHER INFORMATION: an artificially synthesized sequence

<400> SEQUENCE: 81

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
```

```
                65                  70                  75                  80
Leu Tyr Leu Gln Met Asn Asn Leu Lys Thr Glu Asp Thr Ala Met Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala Ala Ser Thr
                115                 120                 125

Lys Gly Pro Ser Val Phe Pro Leu Ala Pro Ser Ser Lys Ser Thr Ser
                130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro
            450

<210> SEQ ID NO 82
<211> LENGTH: 216
<212> TYPE: PRT
<213> ORGANISM: Artificial Sequence
```

```
<220> FEATURE:
<223> OTHER INFORMATION: an artificially synthesized sequence

<400> SEQUENCE: 82

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 83
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
```

```
            115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 84
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
```

```
            35                  40                  45
Pro Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Tyr Tyr Cys Ser Gln Asn
                 85                  90                  95

Thr His Val Pro Pro Thr Phe Gly Gln Gly Thr Lys Leu Glu Ile Lys
                    100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 85
<211> LENGTH: 453
<212> TYPE: PRT
<213> ORGANISM: Artificial Sequence
<220> FEATURE:
<223> OTHER INFORMATION: an artificially synthesized sequence

<400> SEQUENCE: 85

Glu Val Lys Leu Leu Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Gln Ser Ile
 65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Lys Ser Ser Gly Leu Tyr Ser Leu Ser Ser
```

```
                180             185             190
Val Val Thr Val Pro Ser Ser Leu Gly Thr Gln Thr Tyr Ile Cys
                195             200             205
Asn Val Asn His Lys Pro Ser Asn Thr Lys Val Asp Lys Val Glu
                210             215             220
Pro Lys Ser Cys Asp Lys Thr His Thr Cys Pro Pro Cys Ala Pro
225             230             235             240
Glu Ala Ala Gly Gly Pro Ser Val Phe Leu Phe Pro Pro Lys Pro
                245             250             255
Lys Asp Thr Leu Met Ile Ser Arg Thr Pro Glu Val Thr Cys Val
                260             265             270
Val Val Asp Val Ser His Glu Asp Pro Glu Val Lys Phe Asn Trp
                275             280             285
Tyr Val Asp Gly Val Glu Val His Asn Ala Lys Thr Lys Pro Arg
                290             295             300
Glu Glu Gln Tyr Ala Ser Thr Tyr Arg Val Val Ser Val Leu Thr
305             310             315             320
Val Leu His Gln Asp Trp Leu Asn Gly Lys Glu Tyr Lys Cys Lys
                325             330             335
Val Ser Asn Lys Ala Leu Pro Ala Pro Ile Glu Lys Thr Ile Ser
                340             345             350
Lys Ala Lys Gly Gln Pro Arg Glu Pro Gln Val Tyr Thr Leu Pro
                355             360             365
Pro Ser Arg Cys Glu Leu Thr Lys Asn Gln Val Ser Leu Ser Cys
                370             375             380
Ala Val Lys Gly Phe Tyr Pro Ser Asp Ile Ala Val Glu Trp Glu
385             390             395             400
Ser Asn Gly Gln Pro Glu Asn Asn Tyr Lys Thr Thr Pro Pro Val
                405             410             415
Leu Asp Ser Asp Gly Ser Phe Phe Leu Val Ser Lys Leu Thr Val
                420             425             430
Asp Lys Ser Arg Trp Gln Gln Gly Asn Val Phe Ser Cys Ser Val
                435             440             445
Met His Glu Ala Leu His Asn His Tyr Thr Gln Lys Ser Leu Ser
                                                450

Leu Ser Pro
450

<210> SEQ ID NO 86
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 86

Gln Ala Val Val Thr Gln Glu Ser Ala Leu Thr Thr Ser Pro Gly Glu
1               5                   10                  15
Thr Val Thr Leu Thr Cys Arg Ser Ser Thr Gly Ala Val Thr Thr Ser
                20                  25                  30
Asn Tyr Ala Asn Trp Val Gln Glu Lys Pro Asp His Leu Phe Thr Gly
                35                  40                  45
Leu Ile Gly Gly Thr Asn Lys Arg Ala Pro Gly Val Pro Ala Arg Phe
            50                  55                  60
Ser Gly Ser Leu Ile Gly Asp Lys Ala Ala Leu Thr Ile Thr Gly Ala
65                  70                  75                  80
Gln Thr Glu Asp Glu Ala Ile Tyr Phe Cys Ala Leu Trp Tyr Ser Asn
```

```
                85                  90                  95
Leu Trp Val Phe Gly Gly Gly Thr Lys Leu Thr Val Leu Arg Thr Val
            100                 105                 110
Ala Ala Pro Ser Val Phe Ile Phe Pro Pro Ser Asp Glu Gln Leu Lys
            115                 120                 125
Ser Gly Thr Ala Glu Val Val Cys Leu Leu Asn Asn Phe Tyr Pro Arg
        130                 135                 140
Glu Ala Lys Val Gln Trp Lys Val Asp Asn Ala Leu Gln Ser Gly Asn
145                 150                 155                 160
Ser Glu Glu Ser Val Thr Glu Gln Asp Ser Lys Asp Ser Thr Tyr Ser
                165                 170                 175
Leu Ser Ser Thr Leu Glu Leu Ser Lys Ala Asp Tyr Glu Lys His Lys
            180                 185                 190
Val Tyr Ala Cys Glu Val Thr His Gln Gly Leu Ser Ser Pro Val Thr
            195                 200                 205
Lys Ser Phe Asn Arg Gly Glu Cys
        210                 215

<210> SEQ ID NO 87
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 87

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Glu Met His Trp Ile Arg Gln Pro Pro Gly Gln Gly Leu Glu Trp Ile
        35                  40                  45
Gly Ala Ile Asp Pro Lys Thr Gly Asp Thr Ala Tyr Ser Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Phe Tyr Ser Tyr Thr Tyr Trp Gly Gln Gly Thr Leu Val Thr
            100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Glu Asp Tyr Phe Pro Glu Pro Val Thr Val Ser Trp Asn Ser Gly Ala
145                 150                 155                 160
Leu Thr Ser Gly Val His Thr Phe Pro Ala Val Leu Glu Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
        210                 215                 220
Pro Pro Cys Pro Ala Pro Glu Ala Ala Gly Gly Pro Ser Val Phe Leu
```

```
                225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Ala Ser Thr Tyr Arg Val Val Ser Val Leu
                        290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Cys Thr Leu Pro Pro Ser
                        340                 345                 350

Arg Asp Glu Leu Thr Lys Asn Gln Val Ser Leu Trp Cys Leu Val Lys
                        355                 360                 365

Gly Phe Tyr Pro Ser Asp Ile Ala Val Glu Trp Glu Ser Asn Gly Gln
                        370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro
                        435                 440

<210> SEQ ID NO 88
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 88

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Asp Tyr
                        20                  25                  30

Glu Met His Trp Ile Arg Gln Pro Pro Gly Gln Gly Leu Glu Trp Ile
                        35                  40                  45

Gly Ala Ile Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
        65                  70                  75                  80

Met Glu Leu Ser Ser Leu Thr Ser Glu Asp Thr Ala Val Tyr Tyr Cys
                        85                  90                  95

Thr Arg Phe Tyr Ser Tyr Thr Tyr Trp Gly Gln Gly Thr Leu Val Thr
                        100                 105                 110

Val Ser Ser Ala Ser Thr Lys Gly Pro Ser Val Phe Pro Leu Ala Pro
                        115                 120                 125

Ser Ser Lys Ser Thr Ser Gly Gly Thr Ala Ala Leu Gly Cys Leu Val
                        130                 135                 140

Glu Asp Tyr Phe Pro Glu Pro Val Thr Val Ser Trp Asn Ser Gly Ala
```

```
              145                 150                 155                 160
         Leu Thr Ser Gly Val His Thr Phe Pro Ala Val Leu Glu Ser Ser Gly
                         165                 170                 175

Leu Tyr Ser Leu Ser Ser Val Val Thr Val Pro Ser Ser Ser Leu Gly
                         180                 185                 190

Thr Gln Thr Tyr Ile Cys Asn Val Asn His Lys Pro Ser Asn Thr Lys
                         195                 200                 205

Val Asp Glu Lys Val Glu Pro Lys Ser Cys Asp Lys Thr His Thr Cys
             210                 215                 220

Pro Pro Cys Pro Ala Pro Glu Ala Ala Gly Gly Pro Ser Val Phe Leu
         225                 230                 235                 240

Phe Pro Pro Lys Pro Lys Asp Thr Leu Met Ile Ser Arg Thr Pro Glu
                         245                 250                 255

Val Thr Cys Val Val Val Asp Val Ser His Glu Asp Pro Glu Val Lys
                         260                 265                 270

Phe Asn Trp Tyr Val Asp Gly Val Glu Val His Asn Ala Lys Thr Lys
                         275                 280                 285

Pro Arg Glu Glu Gln Tyr Ala Ser Thr Tyr Arg Val Val Ser Val Leu
             290                 295                 300

Thr Val Leu His Gln Asp Trp Leu Asn Gly Lys Glu Tyr Lys Cys Lys
         305                 310                 315                 320

Val Ser Asn Lys Ala Leu Pro Ala Pro Ile Glu Lys Thr Ile Ser Lys
                         325                 330                 335

Ala Lys Gly Gln Pro Arg Glu Pro Gln Val Cys Thr Leu Pro Pro Ser
                         340                 345                 350

Arg Asp Glu Leu Thr Lys Asn Gln Val Ser Leu Trp Cys Leu Val Lys
                         355                 360                 365

Gly Phe Tyr Pro Ser Asp Ile Ala Val Glu Trp Glu Ser Asn Gly Gln
                         370                 375                 380

Pro Glu Asn Asn Tyr Lys Thr Thr Pro Pro Val Leu Asp Ser Asp Gly
         385                 390                 395                 400

Ser Phe Phe Leu Tyr Ser Lys Leu Thr Val Asp Lys Ser Arg Trp Gln
                         405                 410                 415

Gln Gly Asn Val Phe Ser Cys Ser Val Met His Glu Ala Leu His Asn
                         420                 425                 430

His Tyr Thr Gln Lys Ser Leu Ser Leu Ser Pro
                         435                 440

<210> SEQ ID NO 89
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 89

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ser Gln Asn
                    85                  90                  95

Thr His Val Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Lys Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Lys Glu Ser Val Thr Glu Gln Asp Ser Lys Asp Ser
                165                 170                 175

Thr Tyr Ser Leu Ser Ser Thr Leu Lys Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 90
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 90

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
                35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Lys
                115                 120                 125

Gln Leu Lys Ser Gly Thr Ala Lys Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Lys Glu Ser Val Thr Glu Gln Asp Ser Lys Asp Ser
                165                 170                 175

Thr Tyr Ser Leu Ser Ser Thr Leu Lys Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
```

-continued

```
          210                 215

<210> SEQ ID NO 91
<211> LENGTH: 474
<212> TYPE: PRT
<213> ORGANISM: Artificial Sequence
<220> FEATURE:
<223> OTHER INFORMATION: an artificially synthesized sequence

<400> SEQUENCE: 91

Met Gly Trp Ser Cys Ile Ile Leu Phe Leu Val Ala Thr Ala Thr Gly
1               5                   10                  15

Val His Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Ala Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
```

```
                355                 360                 365
Val Cys Thr Leu Pro Pro Ser Arg Asp Glu Leu Thr Lys Asn Gln Val
    370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro His His His His His His His His
465                 470
```

```
<210> SEQ ID NO 92
<211> LENGTH: 233
<212> TYPE: PRT
<213> ORGANISM: Artificial Sequence
<220> FEATURE:
<223> OTHER INFORMATION: an artificially synthesized sequence

<400> SEQUENCE: 92

Met Gly Trp Ser Cys Ile Ile Leu Phe Leu Val Ala Thr Ala Thr Gly
1               5                   10                  15

Val His Ser Asp Ile Leu Leu Thr Gln Ser Pro Val Ile Leu Ser Val
            20                  25                  30

Ser Pro Gly Glu Arg Val Ser Phe Ser Cys Arg Ala Ser Gln Ser Ile
        35                  40                  45

Gly Thr Asn Ile His Trp Tyr Gln Gln Arg Thr Asn Gly Ser Pro Arg
    50                  55                  60

Leu Leu Ile Lys Tyr Ala Ser Glu Ser Ile Ser Gly Ile Pro Ser Arg
65                  70                  75                  80

Phe Ser Gly Ser Gly Ser Gly Thr Asp Phe Thr Leu Ser Ile Asn Ser
                85                  90                  95

Val Glu Ser Glu Asp Ile Ala Asp Tyr Tyr Cys Gln Gln Asn Asn Asn
            100                 105                 110

Trp Pro Thr Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

UNITED STATES PATENT AND TRADEMARK OFFICE
CERTIFICATE OF CORRECTION

Page 1 of 1

PATENT NO. : 11,066,483 B2
APPLICATION NO. : 13/990088
DATED : July 20, 2021
INVENTOR(S) : Nezu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 391 days.

Signed and Sealed this
Sixth Day of September, 2022

Katherine Kelly Vidal
*Director of the United States Patent and Trademark Office*